(12) United States Patent
Fleck et al.

(10) Patent No.: US 8,877,741 B2
(45) Date of Patent: Nov. 4, 2014

(54) PYRROLIDINE DERIVATIVES, PHARMACEUTICAL COMPOSITIONS AND USES THEREOF

(71) Applicants: Martin Fleck, Warthausen (DE); Niklas Heine, Biberach an der Riss (DE); Bernd Nosse, Biberach an der Riss (DE); Gerald Juergen Roth, Biberach an der Riss (DE)

(72) Inventors: Martin Fleck, Warthausen (DE); Niklas Heine, Biberach an der Riss (DE); Bernd Nosse, Biberach an der Riss (DE); Gerald Juergen Roth, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/161,256

(22) Filed: Jan. 22, 2014

(65) Prior Publication Data

US 2014/0213568 A1 Jul. 31, 2014

(30) Foreign Application Priority Data

Jan. 25, 2013 (EP) .................................... 13152734

(51) Int. Cl.

| A61K 31/397 | (2006.01) |
|---|---|
| A01N 43/54 | (2006.01) |
| A01N 43/76 | (2006.01) |
| A01N 43/78 | (2006.01) |
| A61K 31/44 | (2006.01) |
| C07D 205/02 | (2006.01) |
| C07D 213/72 | (2006.01) |
| C07D 239/02 | (2006.01) |
| C07D 263/34 | (2006.01) |
| C07D 277/02 | (2006.01) |
| C07D 311/04 | (2006.01) |
| C07D 417/14 | (2006.01) |
| C07D 401/14 | (2006.01) |
| C07D 405/14 | (2006.01) |
| C07D 401/04 | (2006.01) |

(52) U.S. Cl.
CPC ............ *C07D 401/04* (2013.01); *C07D 417/14* (2013.01); *C07D 401/14* (2013.01); *C07D 405/14* (2013.01)

USPC .............. 514/210.01; 514/210.21; 514/210.2; 514/275; 514/352; 514/374; 514/210.19; 544/330; 544/255; 544/298; 544/329; 544/356; 546/297; 546/139; 546/162; 546/268.1; 548/185; 548/201; 548/236; 548/952; 548/133; 548/138; 548/162; 548/194; 548/200; 548/217; 548/222; 548/241; 548/248; 548/364.1; 548/518; 549/404

(58) Field of Classification Search
None
See application file for complete search history.

(56) References Cited

U.S. PATENT DOCUMENTS

2013/0158004 A1* 6/2013 Fleck et al. .............. 514/210.21

FOREIGN PATENT DOCUMENTS

| WO | 9728128 A1 | 8/1997 |
|---|---|---|
| WO | 2012090219 A2 | 7/2012 |

OTHER PUBLICATIONS

International Search Report, form PCT/ISA/220, and written opinion, form PCT/ISA/237, for corresponding application PCT/EP2014/050981 date of mailing Apr. 3, 2014.

* cited by examiner

*Primary Examiner* — Janet L Anders
*Assistant Examiner* — Timothy R Rozof
(74) *Attorney, Agent, or Firm* — Michael P. Morris; Alan R. Stempel

(57) ABSTRACT

The invention relates to new pyrrolidine derivatives of the formula

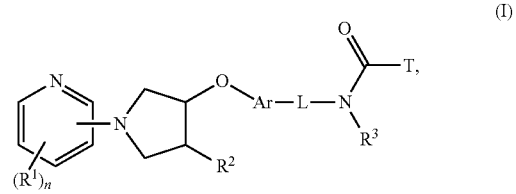

(I)

to their use as medicaments, to methods for their therapeutic use and to pharmaceutical compositions containing them.

14 Claims, No Drawings

PYRROLIDINE DERIVATIVES, PHARMACEUTICAL COMPOSITIONS AND USES THEREOF

FIELD OF THE INVENTION

This invention relates to new compounds, in particular pyrrolidine derivatives, to processes for preparing such compounds, to their use as inhibitors of acetyl-CoA carboxylase(s), to methods for their therapeutic use, in particular in diseases and conditions mediated by the inhibition of acetyl-CoA carboxylase(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairment of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (Saggerson D. Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; Corbett J W, Harwood J H Jr., Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essén-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, JEB. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26).

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (ST Henderson Neurotherapeutics, 2008, 5:470-480; L C Costantini, L J Barr, J L Vogel, S T Henderson BMC Neurosci. 2008, 9 Suppl 2:S16; K W Barañano, Ala. Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. Nat. Biotechnol. 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

Aim of the Present Invention

The aim of the present invention is to provide new compounds, in particular new pyrrolidine derivatives, which are active with regard to acetyl-CoA carboxylase(s).

Another aim of the present invention is to provide new compounds, in particular new pyrrolidine derivatives, which are active with regard to ACC2.

A further aim of the present invention is to provide new compounds, in particular new pyrrolidine derivatives, which have an inhibitory effect on acetyl-CoA carboxylase(s) in vitro and/or in vivo and possess suitable pharmacological and pharmacokinetic properties to use them as medicaments.

A further aim of the present invention is to provide new compounds, in particular new pyrrolidine derivatives, which have an inhibitory effect on ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyrrolidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to acetyl-CoA carboxylase(s).

According to another aspect of the present invention it has been found that the new compounds of general formula (I) as described hereinafter exhibit an inhibiting activity with regard to ACC2.

In a first aspect the present invention provides a compound of general formula

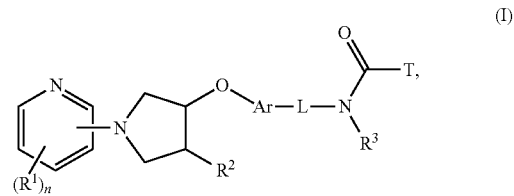

wherein

Ar is selected from the group Ar-G1 consisting of phenylene and pyridinylene, which are each optionally substituted with one or two substituents independently selected from F, Cl, —O—$CH_3$ and $CH_3$;

$R^1$ independently of one another are selected from the group $R^1$-G1 consisting of halogen, CN, $O_{1-6}$-alkyl, $O_{3-6}$-cycloalkyl, —O—($C_{1-6}$-alkyl), —S—($C_{1-3}$-alkyl), —O—($C_{3-6}$-cycloalkyl), —O—($C_{5-6}$-cycloalkenyl), —O—$(OH_2)_{1-2}$-($C_{3-6}$-cycloalkyl), —O—($C_{1-3}$-alkyl)-aryl, —O—$OH_2$-($O_{2-4}$-alkenyl), —O—$OH_2$—($O_{2-4}$-alkinyl), —O—$CH_2$-tetrahydrofuranyl, —O—$CH_2$-heteroaryl, —O-heterocyclyl, —O-aryl, —O-heteroaryl, (C=O)—NH-aryl, —$NR^{N1}R^{N2}$,

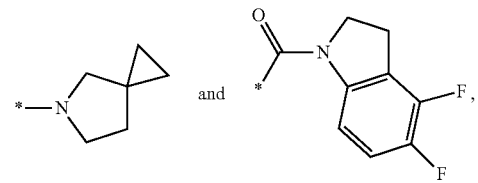

wherein $R^{N1}$ is H or $C_{1-3}$-alkyl, and $R^{N2}$ is H, $C_{1-4}$-alkyl, $C_{3-6}$-cycloalkyl, —$CH_2$—($C_{3-6}$-cycloalkyl), heterocyclyl or —$CH_2$-heterocyclyl, or wherein $R^{N1}$ and $R^{N2}$ are connected and together with the N-atom to which they are attached form an azetidinyl, pyrrolidinyl, piperidinyl, 2,5-dihydro-1H-pyrrolyl, morpholinyl or [1,4]oxazepanyl ring, wherein each of said rings is optionally substituted with one or two F, OH, $C_{1-3}$-alkyl, —O—$C_{1-3}$-alkyl or —($C_{1-3}$-alkyl)-O—($C_{1-3}$-alkyl), said substituents being the same or different, wherein heterocyclyl is tetrahydrofuranyl or tetrahydropyranyl, wherein heteroaryl is selected from the group consisting of pyridinyl, pyrimidinyl, pyridazinyl and pyrazinyl, wherein aryl is selected from the group consisting of phenyl, indanyl and naphthyl, wherein each alkyl is linear or branched and is optionally substituted with 1 to 6 F or with one —OH or —O—($C_{1-3}$-alkyl), wherein each cycloalkyl is optionally substituted with 1 to 4 F or with one CN, OH, $CH_3$, $CF_3$ or —$SO_2$—($C_{1-3}$-alkyl), and wherein each aryl or heteroaryl is optionally substituted with one or two substituents independently selected from F, Cl, $C_{1-3}$-alkyl or —O—$CH_3$;

n is 1, 2 or 3;

$R^2$ is selected from the group $R^2$-G1 consisting of H, F, Cl, CN and —O—($C_{1-3}$-alkyl);

$R^3$ is selected from the group $R^3$-G1 consisting of H and $C_{1-3}$-alkyl;

L is selected from the group L-G1 consisting of straight-chain $C_{1-3}$-alkylene, which is optionally substituted with one or two $C_{1-3}$-alkyl groups; and T is selected from the group T-G1 consisting of: H,
  linear or branched $C_{1-6}$-alkyl which is optionally substituted with one to six F, with one CN, OH, —O—$CH_3$ or —O—C(=O)—$CH_3$, or with a heteroaryl group preferably selected from the group consisting of: oxazolyl, thiazolyl, pyrrolyl, isoxazolyl, pyrimidinyl and pyrazinyl,
    wherein each of said heteroaryl groups is optionally substituted with one or two substituents, which are independently of each other selected from the group consisting of $C_{1-3}$-alkyl, ($C_{1-3}$-alkyl)-O—$CH_3$ and —NH—(C=O)—($C_{1-3}$-alkyl);
  ($C_{2-4}$-alkenyl)-($C_{3-7}$-cycloalkyl);
  $C_{3-6}$-cycloalkyl which is optionally substituted with one or two F, CN, $CH_3$, $CF_3$, OH, —O—($C_{1-3}$-alkyl), $NH_2$, —NH—(C=O)$CH_3$, —C(=O)—$NH_2$, C(=O)—NH ($C_{1-3}$-alkyl) or —C(=O)—N($C_{1-3}$-alkyl)$_2$, wherein the substituents are identical of different;
  —O—($C_{1-2}$-alkyl);
  tetrahydrofuranyl;
  —$NR^4R^5$, wherein $R^4$ is H or $C_{1-3}$-alkyl, and $R^5$ is H, $C_{1-3}$-alkyl, —($C_{1-3}$-alkyl)-O—$CH_3$ or a 5-membered heteroaryl group containing 1 to 3 heteroatoms selected independently from O, S, N and NH, wherein said heteroaryl group is optionally substituted with $C_{1-3}$-alkyl; or wherein $R^4$ and $R^5$ are connected and together with the N to which they are attached form an azetidinyl, pyrrolidinyl, piperidinyl, piperazinyl or morpholinyl ring that is optionally substituted with one or two $C_{1-3}$-alkyl or with one —NH—(C=O)—$CH_3$;
  a 5-membered heteroaryl group containing one to three heteroatoms selected independently from O, S, N and NH, which is optionally substituted with one or two substituents selected independently from the group consisting of: Cl, $C_{1-3}$-alkyl, —NH—C(=O)—($C_{1-3}$-alkyl)-O—$OH_3$, $NH_2$, —NH—C(=O)—$C_{1-3}$-alkyl, —NH—C(=O)—$CH_2$OH, —NH—C(=O)—$CH_2$O—C(=O)$CH_3$, —NH—C(=O)—$CH_2$O$CH_2$-Ph and —O—($C_{1-2}$-alkyl), wherein each alkyl group is optionally substituted with one to three F or with one OH;
  a 6-membered heteroaryl group containing 1 or 2 N, which is optionally substituted with F, CN, —$CH_3$, —C(=O)—NH—(OH$_3$) or —NH—C(=O)—(CH$_3$); and phenyl optionally substituted with F, Cl, CN or —$OCH_3$;
  a tautomer or stereoisomers thereof,
  or a salt thereof,
  or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of acetyl-CoA carboxylase(s).

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly Ar, $R^1$, $R^2$, $R^3$, $R^4$, L, T and n, are defined as above and hereinafter. If residues, substituents, or groups occur several times in a compound, as for example $R^1$, they may have the same or different meanings. Some preferred meanings of individual groups and substituents of the compounds according to the invention will be given hereinafter. Any and each of these definitions may be combined with each other.

Ar:

Ar-G1:

The group Ar is preferably selected from the group Ar-G1 as defined hereinbefore and hereinafter.

Ar-G2:

In another embodiment the group Ar is selected from the group Ar-G2 consisting of: phenylene, which is optionally monosubstituted with F.

Ar-G3:

In another embodiment the group Ar is selected from the group Ar-G3 consisting of: phenylene.

Ar-G4:

In another embodiment the group Ar is selected from the group Ar-G4 consisting of:

wherein the before mentioned group is optionally monosubstituted with F.

Ar-G5:

In another embodiment the group Ar is selected from the group Ar-G5 consisting of:

$R^1$:

$R^1$-G1:

The group $R^1$ is preferably selected from the group $R^1$-G1 as defined hereinbefore and hereinafter.

$R^1$-G2:

In another embodiment the group $R^1$ is independently of one another selected from the group $R^1$-G2 consisting of:

F, Cl, Br, CN, $O_{1-6}$-alkyl, $C_{3-6}$-cycloalkyl, —O—($C_{1-6}$-alkyl), —O—($C_{3-6}$-cycloalkyl), —O—($C_{5-6}$-cycloalkenyl), —O—$(OH_2)_{1-2}$-($C_{3-6}$-cycloalkyl), —O—($C_{1-2}$-alkyl)-phenyl, —O—$CH_2$—($C_{2-4}$-alkenyl), —O—$CH_2$-tetrahydrofuranyl, —O—$CH_2$-pyridinyl, —O-heterocyclyl, —O-phenyl, —O-pyridinyl, —$NR^{N1}R^{N2}$ and

wherein $R^{N1}$ is H or $C_{1-3}$-alkyl, and $R^{N2}$ is $C_{1-4}$-alkyl, $C_{3-6}$-cycloalkyl, —$CH_2$—($C_{3-6}$-cycloalkyl), heterocyclyl or —$CH_2$-heterocyclyl, or wherein $R^{N1}$ and $R^{N2}$ are connected and together with the N-atom to which they are attached form an azetidinyl, pyrrolidinyl, piperidinyl, 2,5-dihydro-1H-pyrrolyl, morpholinyl or [1,4]oxazepanyl ring, wherein each of said rings is optionally substitued with one or two F, OH, $C_{1-3}$-alkyl or —O—$C_{1-3}$-alkyl, said substituents being the same or different, wherein heterocyclyl is tetrahydrofuranyl or tetrahydropyranyl, wherein each alkyl is linear or branched and is optionally substituted with 1 to 4 F or with one —OH or —O—($C_{1-2}$-alkyl), wherein each cycloalkyl is optionally substituted with 1 to 3 F or with one CN, OH, $CH_3$ or —$SO_2$—$OH_3$, and wherein each phenyl is optionally substituted with one F or Cl.

$R^1$-G3:

In another embodiment the group $R^1$ is selected from the group $R^1$-G3 consisting of: F, Cl, CN, $C_{1-4}$-alkyl, $C_{3-5}$-cycloalkyl, —O—($C_{1-5}$-alkyl), —O—($C_{3-6}$-cycloalkyl), —O-cyclopentenyl, —O-tetrahydrofuranyl, —O—$CH_2$—($C_{2-4}$-alkenyl), —O—$CH_2$—($C_{3-4}$-cycloalkyl), —O—$CH_2$-phenyl, —$NR^{N1}R^{N2}$ and

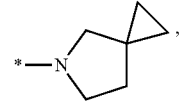

wherein $R^{N1}$ is H or $C_{1-2}$-alkyl, and $R^{N2}$ is $C_{1-4}$-alkyl or —$CH_2$—($C_{3-6}$-cycloalkyl), or wherein $R^{N1}$ and $R^{N2}$ are connected and together with the N-atom to which they are attached form an azetidinyl, pyrrolidinyl, piperidinyl or morpholin ring, wherein each of said rings is optionally substitued with one or two F, OH or $CH_3$, said substituents being the same or different, wherein each alkyl is linear or branched and is optionally substituted with 1 to 3 F or with one —O—$CH_3$ or OH and wherein each $C_{3-6}$-cycloalkyl is optionally substituted with 1 to 2 F or with one CN, OH or $CH_3$, wherein each phenyl is optionally substituted with one F.

$R^1$-G4:

In another embodiment the group $R^1$ is selected from the group $R^1$-G4 consisting of: F, Cl, CN, $CF_3$, $C_{1-4}$-alkyl, $C_{3-5}$-cycloalkyl, —O—($C_{1-5}$-alkyl), —O—($C_{3-6}$-cycloalkyl), —NH—($C_{1-3}$-alkyl), —N($C_{1-3}$-alkyl)$_2$,

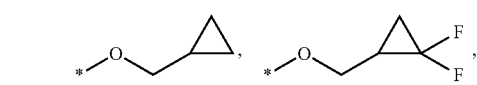

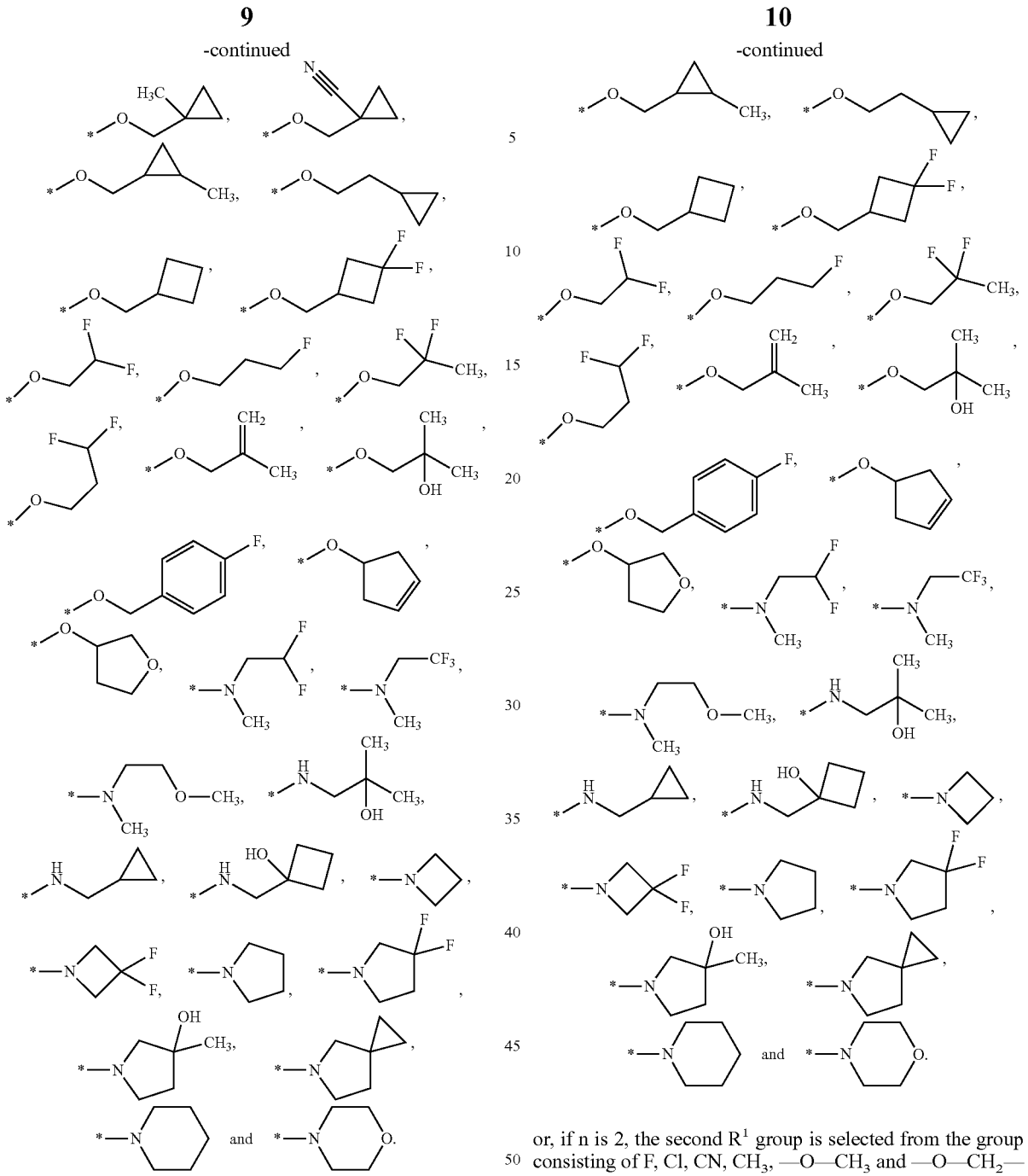

R¹-G4a:

In another embodiment the group R¹ is selected from the group R¹-G4a consisting of: CF₃, C₁₋₄-alkyl, C₃₋₅-cycloalkyl, —O—(C₁₋₅-alkyl), —O—(C₃₋₆-cycloalkyl), —NH—(C₁₋₃-alkyl), —N(C₁₋₃-alkyl)₂, or, if n is 2, the second R¹ group is selected from the group consisting of F, Cl, CN, CH₃, —O—CH₃ and —O—CH₂—CHF₂;

or, if n is 3, the third R¹ group is F.

R¹-G4b:

In another embodiment the group R¹ is selected from the group R¹-G4b consisting of: CF₃, C₁₋₄-alkyl, C₃₋₅-cycloalkyl, —O—(C₁₋₅-alkyl), —O—(C₃₋₆-cycloalkyl), —NH—(C₁₋₃-alkyl), —N(C₁₋₃-alkyl)₂,

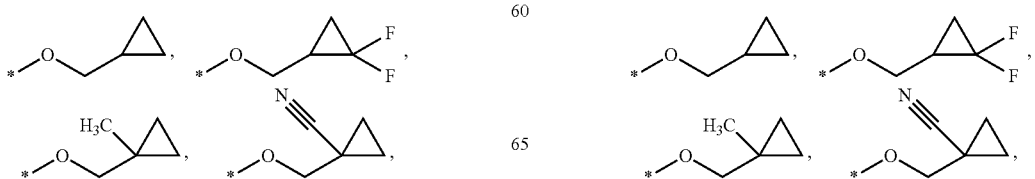

-continued

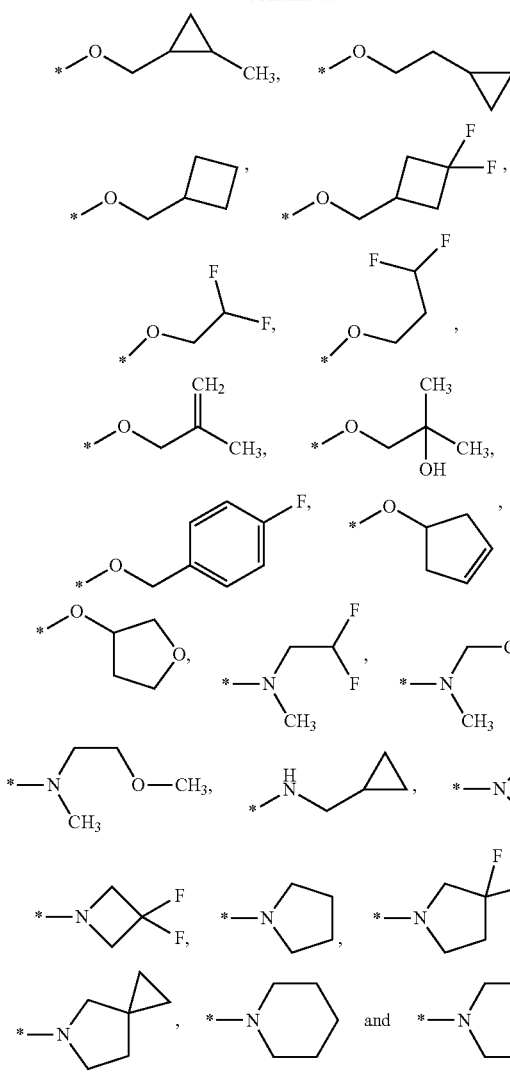

or, if n is 2, the second R¹ group is selected from the group consisting of F, Cl, CH₃ and —O—CH₃;
or, if n is 3, the third R¹ group is F.

R¹-G5:

In another embodiment the group R¹ is selected from the group R¹-G5 consisting of: CF₃, —O—(C₁₋₅-alkyl), —O—(C₃₋₆-cycloalkyl), —NH—(C₁₋₃-alkyl), —N(C₁₋₃-alkyl)₂,

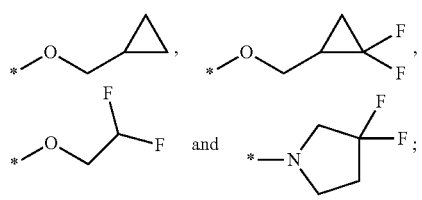

while, if n is 2, the second R¹ group is F, OCH₃ or CH₃.

R¹-G5a:

In another embodiment the group R¹ is selected from the group R¹-G5a consisting of: CF₃, —O—(C₁₋₅-alkyl),

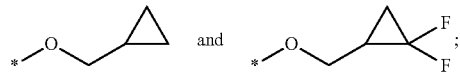 [SMILES: *OCC1CC1 ; *OCC1CC1(F)F]

while, if n is 2, the second R¹ group is F, or OCH₃.

R¹-G6:

In another embodiment the group R¹ is selected from the group R¹-G6 consisting of: —O—(C₁₋₅-alkyl), —O—(C₃₋₆-cycloalkyl), —NH—(C₁₋₃-alkyl), —N(C₁₋₃-alkyl)₂,

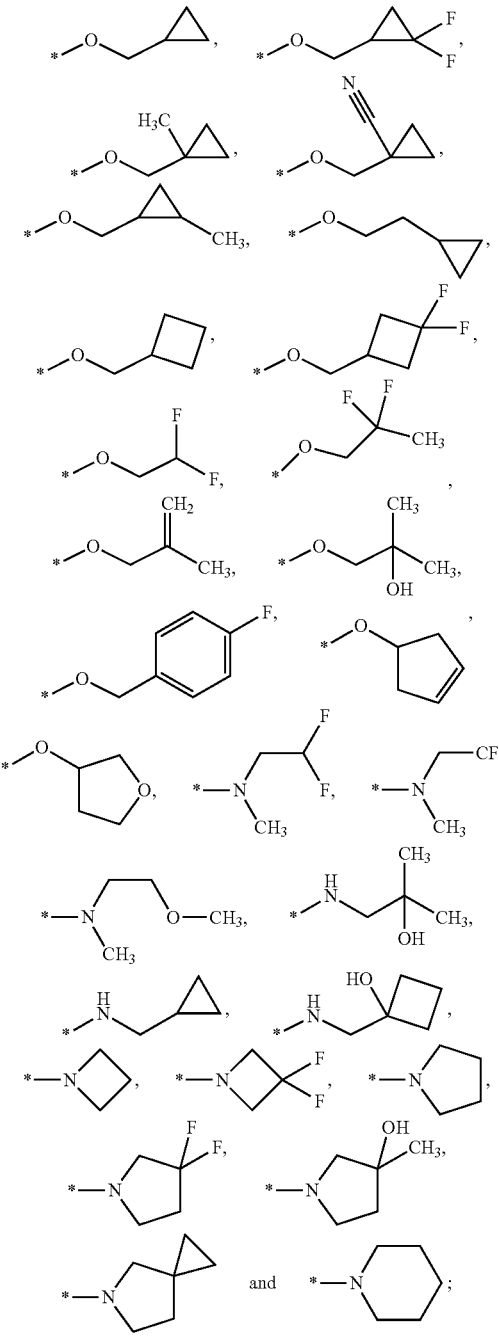

or, if n is 2, the second R¹ group is selected from the group consisting of F, Cl, CH₃ and —O—CH₃;
or, if n is 3, the third R¹ group is F.

$R^1$-G6a:

In another embodiment the group $R^1$ is selected from the group $R^1$-G6a consisting of: —O—($C_{1-5}$-alkyl), —O—($C_{3-6}$-cycloalkyl), —N($C_{1-3}$-alkyl)$_2$, —NH($C_{2-3}$-alkyl),

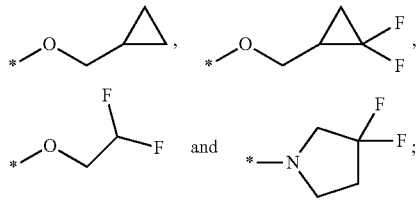

or, if n is 2, the second $R^1$ group is selected from the group consisting of F, $CH_3$ and —O—$CH_3$.

$R^1$-G6b:

In another embodiment the group $R^1$ is selected from the group $R^1$-G6b consisting of: —O—($C_{1-5}$-alkyl),

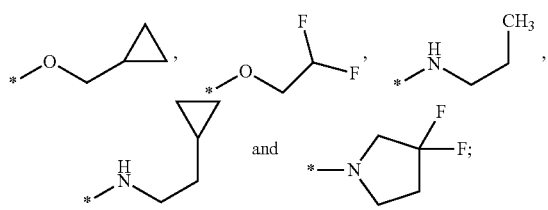

or, if n is 2, the second $R^1$ group is selected from the group consisting of F, Cl, $OCH_3$ and $CH_3$.

$R^1$-G7:

In another embodiment the group $R^1$ is selected from the group $R^1$-G7 consisting of: $CF_3$, $C_{1-4}$-alkyl, $C_{3-5}$-cycloalkyl, —O—($C_{1-5}$-alkyl), —O—($C_{3-6}$-cycloalkyl),

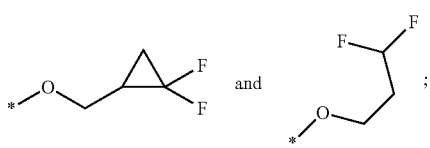 [SMILES: *OCC1CC1(F)F ; *OCCC(F)F]

or, if n is 2, the second $R^1$ group is selected from the group consisting of F and Cl; or, if n is 3, the third $R^1$ group is F.

$R^1$-G7a:

In another embodiment the group $R^1$ is selected from the group $R^1$-G7a consisting of: $CF_3$ and

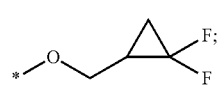 [SMILES: *OCC1CC1(F)F]

or, if n is 2, the second $R^1$ group is selected from the group consisting of F and Cl.

$R^1$-G7b:

In another embodiment the group $R^1$ is selected from the group $R^1$-G7b consisting of:

or, if n is 2, the second $R^1$ group is F.

n n is 1, 2 or 3.

Preferably, n is 1 or 2.

In one embodiment, n is 2.

Most preferably, n is 1.

$R^2$ $R^2$-G1:

The group $R^2$ is preferably selected from the group $R^2$-G1 as defined hereinbefore and hereinafter.

$R^2$-G2:

In another embodiment the group $R^2$ is selected from the group $R^2$-G2 consisting of: H, F and —O—$CH_3$.

$R^2$-G3:

In another embodiment, the group $R^2$ is selected from the group $R^2$-G3 consisting of H.

$R^3$:

$R^3$-G1:

The group $R^3$ is preferably selected from the group $R^3$-G1 as defined hereinbefore and hereinafter.

$R^3$-G2:

In one embodiment the group $R^3$ is selected from the group $R^3$-G2 consisting of H and $CH_3$.

$R^3$-G3:

In another embodiment the group $R^3$ is selected from the group $R^3$-G3 consisting of H.

L:

L-G1:

The group L is preferably selected from the group L-G1 as defined hereinbefore and hereinafter.

L-G2:

In one embodiment the group L is selected from the group L-G2 consisting of: a straight-chain $C_{1-3}$-alkylene group which is optionally substituted with one or two $CH_3$ groups.

L-G3:

In another embodiment the group L is selected from the group L-G3 consisting of: a straight-chain $C_{1-2}$-alkylene group which is optionally substituted with one methyl group.

L-G4:

In another embodiment the group L is selected from the group L-G4 consisting of:

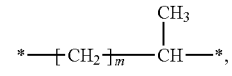

wherein m is 0 or 1, and wherein the asterisk to the left-hand side is connected to Ar and the asterisk to the right-hand side is connected to N atom depicted in formula (I).

L-G5:

In another embodiment the group L is selected from the group L-G5 consisting of: —CH($CH_3$)—.

L-G5a:

In another embodiment the aroup L is selected from the group L-G5a consisting of:

wherein the asterisk to the left-hand side is connected to Ar and the asterisk to the right-hand side is connected to N atom depicted in formula (I).

L-G5b:

In another embodiment the group L is selected from the group L-G5b consisting of:

wherein the asterisk to the left-hand side is connected to Ar and the asterisk to the right-hand side is connected to N atom depicted in formula (I).

T:

T-G1:

The group T is preferably selected from the group T-G1 as defined hereinbefore and hereinafter.

T-G2:

In one embodiment the group T is selected from the group T-G2 consisting of:

H, linear or branched $C_{1-4}$-alkyl which is optionally substituted with one to six F, or with one CN, —O—$CH_3$ or OH or with a heteroaryl group preferably selected from the group consisting of: oxazolyl, thiazolyl, pyrrolyl, isoxazolyl, pyrimidinyl and pyrazinyl, wherein each of said heteroaryl groups is optionally substituted with one or two substituents, which are independently of each other selected from the group consisting of $C_{1-3}$-alkyl, —($C_{1-3}$-alkyl)-O—$CH_3$ and —NH—(C=O)—($C_{1-3}$-alkyl);

($C_{2-4}$-alkenyl)-($C_{3-7}$-cycloalkyl);

$C_{3-6}$-cycloalkyl which is optionally substituted with one or two F, CN, $CH_3$ or $CF_3$, wherein the substituents are identical ror different;

—O—($C_{1-2}$-alkyl);

tetrahydrofuranyl;

—$NR^4R^5$, wherein $R^4$ is H or $C_{1-3}$-alkyl, and $R^5$ is H, $C_{1-3}$-alkyl, —($C_{1-3}$-alkyl)-O—$CH_3$ or a 5-membered heteroaryl group containing 1 to 3 heteroatoms selected independently from O, S, N and NH; or wherein $R^4$ and $R^5$ are connected and together with the N to which they are attached form an azetidinyl, pyrrolidinyl, piperidinyl or morpholinyl ring that is optionally substituted with one or two $C_{1-3}$-alkyl or with one —NH—(C=O)—$CH_3$;

a 5-membered heteroaryl group containing one to three heteroatoms selected independently from O, S, N and NH, which is optionally substituted with one or two substituents selected independently from the group consisting of $C_1$, $C_{1-3}$-alkyl, —O—($C_{1-2}$-alkyl), —NH—C(=O)—($C_{1-3}$-alkyl)-O—$CH_3$, $NH_2$ and —NH—C(=O)—$C_{1-3}$-alkyl; and a 6-membered heteroaryl group containing 1 or 2 N, which is optionally substituted with F, CN, —$CH_3$, —O(=O)—NH—($OH_3$) or —NH—C(=O)—($CH_3$).

T-G3:

In one embodiment the group T is selected from the group T-G3 consisting of:

linear or branched $C_{1-3}$-alkyl which is optionally substituted with one to six F, or with one CN, OH or —O—$CH_3$, or with a heteroaryl group preferably selected from the group consisting of thiazolyl, isoxazolyl and pyrimidinyl, wherein each of said heteroaryl groups is optionally substituted with one or two substituents, which are independently of each other selected from the group consisting of $C_{1-3}$-alkyl, —($C_{1-3}$-alkyl)-O—$OH_3$ and —NH—(C=O)—$CH_3$;

$C_{3-6}$-cycloalkyl which is optionally substituted with one or two F or one CN, $CH_3$ or $CF_3$;

—O—$CH_3$;

tetrahydrofuranyl;

—$NR^4R^5$, wherein $R^4$ is H or $C_{1-3}$-alkyl, and $R^5$ is H, $C_{1-3}$-alkyl, —($C_{1-3}$-alkyl)-O—$OH_3$ or isoxazolyl; or wherein $R^4$ and $R^5$ are connected and together with the N to which they are attached form an azetidinyl, pyrrolidinyl, piperidinyl or morpholinyl ring that is optionally substituted with one or two $C_{1-3}$-alkyl or with one —NH—(C=O)—$CH_3$;

a furanyl, thiazolyl, oxazolyl, pyrazolyl, isoxazolyl, isothiazolyl or thiadiazolyl group, each of which is optionally substituted with one or two substituents selected independently from the group consisting of $C_1$, $C_{1-3}$-alkyl, —NH—C(=O)—($C_{1-3}$-alkyl)-β-$CH_3$, $NH_2$ and —NH—C(=O)—$C_{1-3}$-alkyl; and a pyridinyl, pyridazinyl or pyrimidinyl group, each of which is optionally substituted with F, CN, —$CH_3$, —C(=O)—NH—($CH_3$) or —NH—C(=O)—($CH_3$).

T-G4:

In one embodiment the group T is selected from the group T-G4 consisting of:

linear or branched $C_{1-3}$-alkyl which is optionally substituted with one to three F, cyclopropyl which is optionally substituted with one CN or $CH_3$;

—O—$CH_3$;

—$NR^4R^5$, wherein $R^4$ is H or $C_{1-3}$-alkyl, and $R^5$ is $C_{1-3}$-alkyl; and a thiazolyl, oxazolyl, pyrazolyl, isoxazolyl or isothiazolyl group, each of which is optionally substituted with one or two substituents selected independently from the group consisting of $CH_3$, —NH—C(=O)—$CH_2$—O—$CH_3$ and —NH—C(=O)—$CH_3$.

T-G5:

In one embodiment the group T is selected from the group T-G5 consisting of:

H;

linear or branched $C_{1-4}$-alkyl which is optionally substituted with one to five F or with one CN or OH;

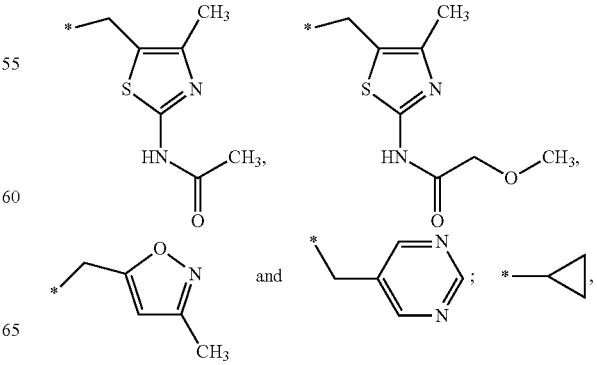

17
-continued
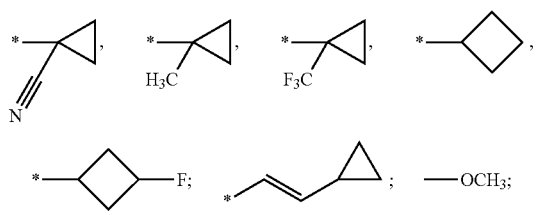
—NH₂, wherein each H is optionally independently of each other replaced with methyl, ethyl or —CH₂—CH₂—O—CH₃;
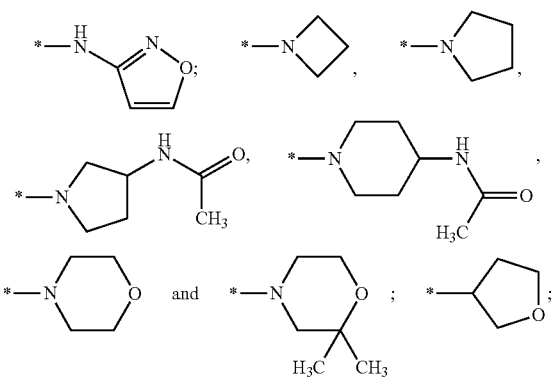
a 5-membered heteroaryl group selected from:
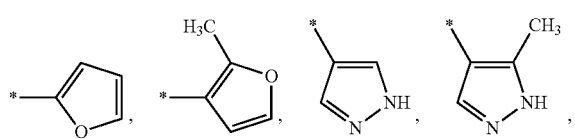
18
-continued
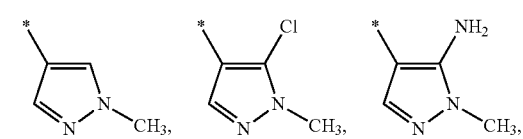
and
a 6-membered heteroaryl group selected from:
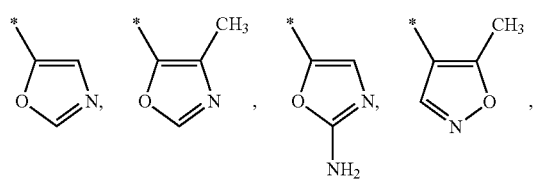
T-G6:
In one embodiment the group T is selected from the group T-G6 consisting of: —CH₃, —CHF₂, —CF₃, —CH₂CH₃, —OCH₃, —NH(CH₃), —N(CH₃)₂, —NH(CH₂CH₃), —N(CH₃)(CH₂CH₃),
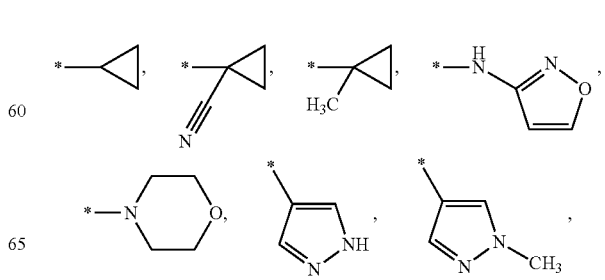

-continued

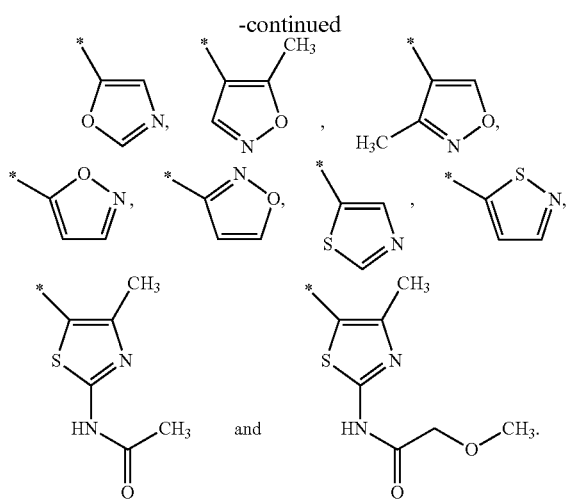

T-G6a:
In one embodiment the group T is selected from the group T-G6a consisting of: —CH₃, —CHF₂, —CF₃, —CH₂CH₃, —OCH₃, —N(CH₃)₂,

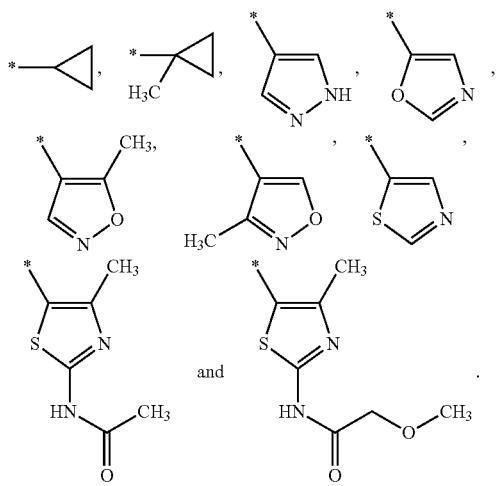

T-G7:
In one embodiment the group T is selected from the group T-G7 consisting of: CH₃.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | R¹ | Ar | R² | L | R³ | T | n |
|---|---|---|---|---|---|---|---|
| E-1 | R¹-G1 | Ar-G2 | R²-G1 | L-G2 | R³-G2 | T-G1 | 1, 2 or 3 |
| E-2 | R¹-G2 | Ar-G2 | R²-G2 | L-G3 | R³-G2 | T-G2 | 1, 2 or 3 |
| E-3 | R¹-G3 | Ar-G3 | R²-G3 | L-G3 | R³-G3 | T-G3 | 1, 2 or 3 |
| E-4 | R¹-G4 | Ar-G3 | R²-G3 | L-G5 | R³-G3 | T-G3 | 1, 2 or 3 |
| E-5 | R¹-G5 | Ar-G3 | R²-G3 | L-G5 | R³-G3 | T-G3 | 1, 2 or 3 |
| E-6 | R¹-G3 | Ar-G4 | R²-G3 | L-G5 | R³-G3 | T-G4 | 1 or 2 |
| E-7 | R¹-G3 | Ar-G4 | R²-G3 | L-G5 | R³-G3 | T-G6 | 1 or 2 |
| E-8 | R¹-G3 | Ar-G4 | R²-G3 | L-G5 | R³-G3 | T-G7 | 1 or 2 |
| E-9 | R¹-G3 | Ar-G5 | R²-G3 | L-G5 | R³-G3 | T-G4 | 1 or 2 |
| E-10 | R¹-G3 | Ar-G5 | R²-G3 | L-G5 | R³-G3 | T-G6 | 1 or 2 |
| E-11 | R¹-G3 | Ar-G5 | R²-G3 | L-G5 | R³-G3 | T-G7 | 1 or 2 |
| E-12 | R¹-G4 | Ar-G4 | R²-G3 | L-G5 | R³-G3 | T-G4 | 1 or 2 |
| E-13 | R¹-G4 | Ar-G4 | R²-G3 | L-G5 | R³-G3 | T-G6 | 1 or 2 |
| E-14 | R¹-G4 | Ar-G4 | R²-G3 | L-G5 | R³-G3 | T-G7 | 1 or 2 |
| E-15 | R¹-G5 | Ar-G5 | R²-G3 | L-G5 | R³-G3 | T-G4 | 1 or 2 |
| E-16 | R¹-G5 | Ar-G5 | R²-G3 | L-G5 | R³-G3 | T-G6 | 1 or 2 |
| E-17 | R¹-G5 | Ar-G5 | R²-G3 | L-G5 | R³-G3 | T-G7 | 1 or 2 |

The following preferred embodiments of compounds of the formula (I) are described using generic formulae (I.1a) to (I.4c), wherein any tautomers and stereoisomers, solvates, hydrates and salts thereof, in particular the pharmaceutically acceptable salts thereof, are encompassed.

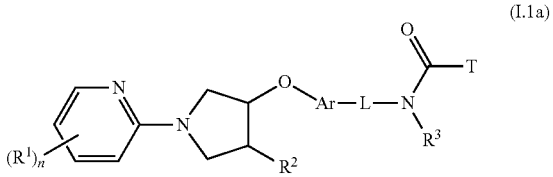
(I.1a)

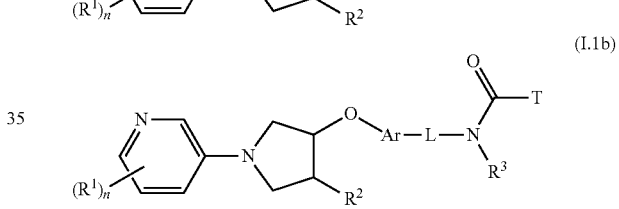
(I.1b)

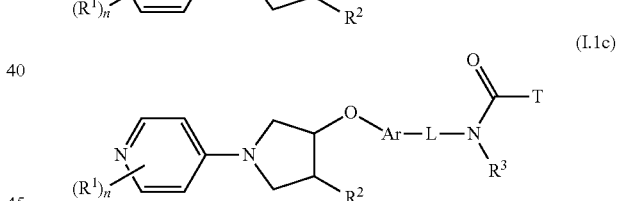
(I.1c)

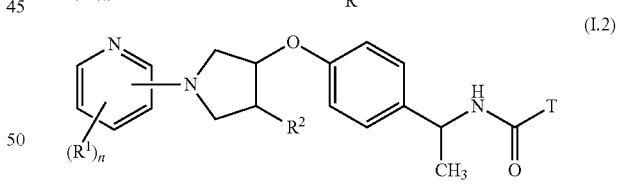
(I.2)

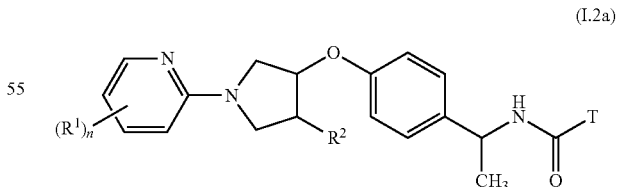
(I.2a)

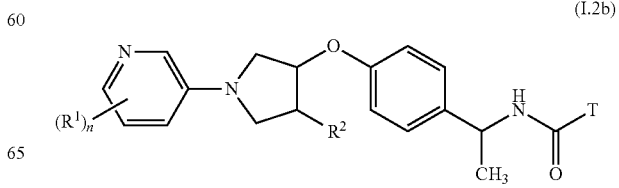
(I.2b)

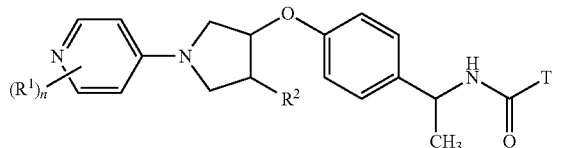 (I.2c)

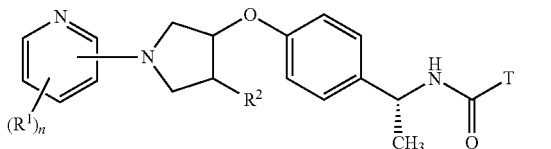 (I.4)

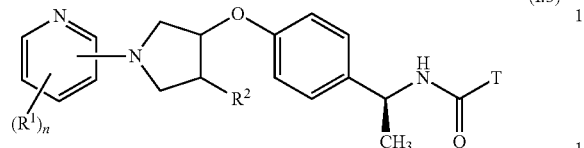 (I.3)

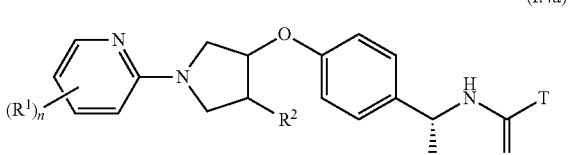 (I.4a)

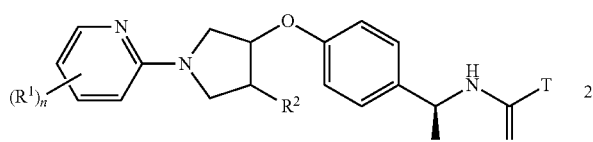 (I.3a)

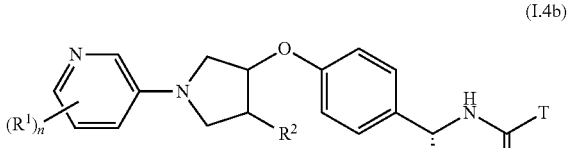 (I.4b)

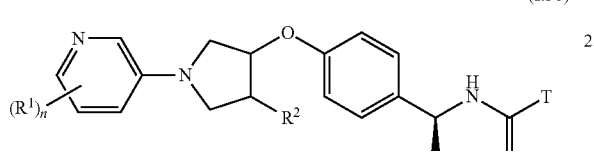 (I.3b)

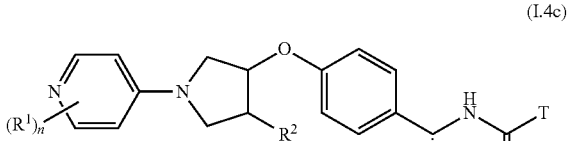 (I.4c)

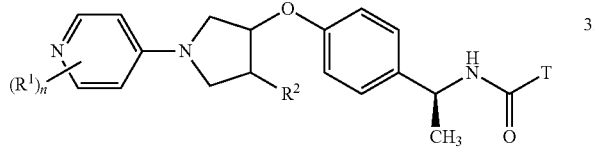 (I.3c)

wherein in each of the above formulae (I.1a) to (I.4c), the groups Ar, $R^1$, $R^2$, $R^3$, L, T and n are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Formula | $R^1$ | Ar | $R^2$ | L | $R^3$ | T | n |
|---|---|---|---|---|---|---|---|---|
| E-18 | (I.1a) | $R^1$-G3 | Ar-G3 | $R^2$-G2 | L-G2 | $R^3$-G2 | T-G2 | 1, 2 or 3 |
| E-19 | (I.1a) | $R^1$-G4 | Ar-G3 | $R^2$-G2 | L-G3 | $R^3$-G2 | T-G5 | 1, 2 or 3 |
| E-20 | (I.1a) | $R^1$-G7 | Ar-G3 | $R^2$-G2 | L-G3 | $R^3$-G2 | T-G5 | 1, 2 or 3 |
| E-21 | (I.1a) | $R^1$-G7a | Ar-G3 | $R^2$-G2 | L-G3 | $R^3$-G2 | T-G5 | 1, 2 or 3 |
| E-22 | (I.1a) | $R^1$-G7b | Ar-G3 | $R^2$-G2 | L-G3 | $R^3$-G2 | T-G5 | 1, 2 or 3 |
| E-23 | (I.1c) | $R^1$-G3 | Ar-G3 | $R^2$-G2 | L-G2 | $R^3$-G2 | T-G3 | 1, 2 or 3 |
| E-24 | (I.1c) | $R^1$-G4 | Ar-G3 | $R^2$-G2 | L-G3 | $R^3$-G2 | T-G5 | 1, 2 or 3 |
| E-25 | (I.1c) | $R^1$-G6 | Ar-G3 | $R^2$-G3 | L-G3 | $R^3$-G2 | T-G5 | 1, 2 or 3 |
| E-26 | (I.1c) | $R^1$-G6a | Ar-G3 | $R^2$-G3 | L-G3 | $R^3$-G2 | T-G5 | 1, 2 or 3 |
| E-27 | (I.1c) | $R^1$-G6b | Ar-G3 | $R^2$-G3 | L-G3 | $R^3$-G2 | T-G5 | 1, 2 or 3 |
| E-28 | (I.2a) | $R^1$-G3 | — | $R^2$-G2 | — | — | T-G2 | 1, 2 or 3 |
| E-29 | (I.2a) | $R^1$-G4 | — | $R^2$-G2 | — | — | T-G5 | 1, 2 or 3 |
| E-30 | (I.2a) | $R^1$-G7 | — | $R^2$-G2 | — | — | T-G5 | 1, 2 or 3 |
| E-31 | (I.2a) | $R^1$-G7a | — | $R^2$-G2 | — | — | T-G5 | 1, 2 or 3 |
| E-32 | (I.2a) | $R^1$-G7b | — | $R^2$-G2 | — | — | T-G5 | 1, 2 or 3 |
| E-33 | (I.2c) | $R^1$-G3 | — | $R^2$-G2 | — | — | T-G3 | 1, 2 or 3 |
| E-34 | (I.2c) | $R^1$-G4 | — | $R^2$-G2 | — | — | T-G5 | 1, 2 or 3 |
| E-35 | (I.2c) | $R^1$-G6 | — | $R^2$-G3 | — | — | T-G5 | 1, 2 or 3 |
| E-36 | (I.2c) | $R^1$-G6a | — | $R^2$-G3 | — | — | T-G5 | 1, 2 or 3 |
| E-37 | (I.2c) | $R^1$-G6b | — | $R^2$-G3 | — | — | T-G5 | 1, 2 or 3 |

A preferred embodiment of the present invention concerns compounds of general formula

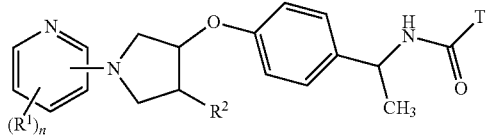

(I.2)

wherein
n is 1, 2 or 3;
$R^1$ is selected from a group consisting of F, Cl, CN, $CF_3$, $C_{1-4}$-alkyl, $C_{3-5}$-cycloalkyl, —O—($C_{1-5}$-alkyl), —O—($C_{3-6}$-cycloalkyl), —NH—($C_{1-3}$-alkyl), —N($C_{1-3}$-alkyl)$_2$,

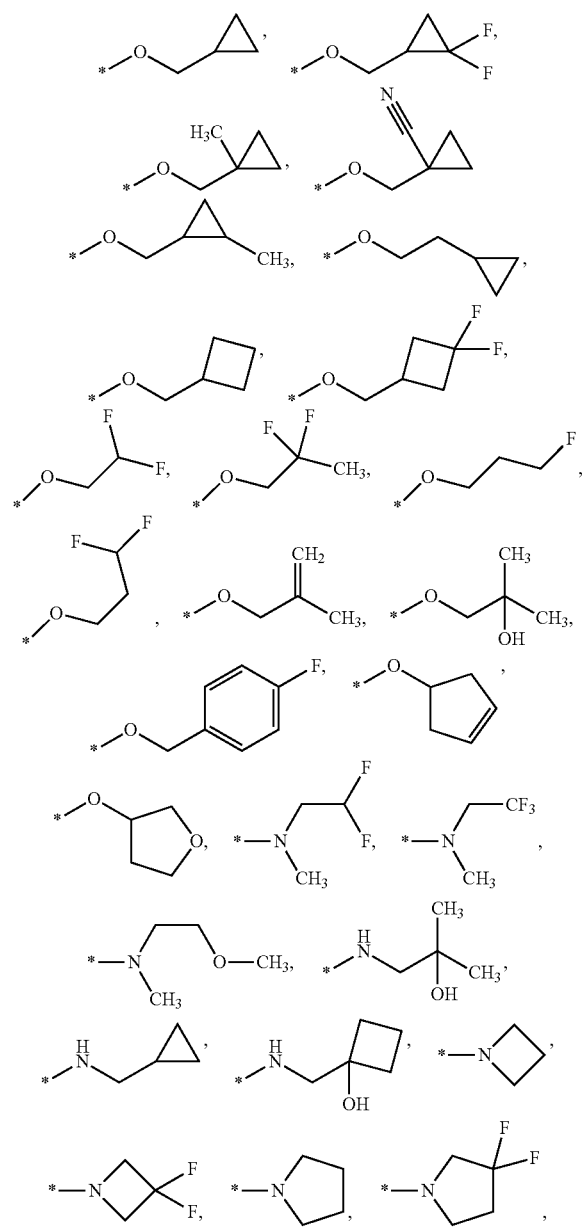

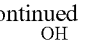

$R^2$ is H, F or —O—$CH_3$; and
T is selected from a group consisting of:
linear or branched $C_{1-3}$-alkyl which is optionally substituted with one to six F, or with one CN, OH or —O—$CH_3$, or with a heteroaryl group preferably selected from the group consisting of: thiazolyl, isoxazolyl and pyrimidinyl,
   wherein each of said heteroaryl groups is optionally substituted with one or two substituents, which are independently of each other selected from the group consisting of $C_{1-3}$-alkyl, —($C_{1-3}$-alkyl)-O—$OH_3$ and —NH—(C=O)—$CH_3$;
$C_{3-6}$-cycloalkyl which is optionally substituted with one or two F or one CN, $CH_3$ or $CF_3$;
—O—$CH_3$;
tetrahydrofuranyl;
—$NR^4R^5$, wherein $R^4$ is H or $C_{1-3}$-alkyl, and $R^5$ is H, $C_{1-3}$-alkyl, —($C_{1-3}$-alkyl)-O—$CH_3$ or isoxazolyl; or wherein $R^4$ and $R^5$ are connected and together with the N to which they are attached form an azetidinyl, pyrrolidinyl, piperidinyl or morpholinyl ring that is optionally substituted with one or two $C_{1-3}$-alkyl or with one —NH—(C=O)—$CH_3$;
a furanyl, thiazolyl, oxazolyl, pyrazolyl, isoxazolyl, isothiazolyl or thiadiazolyl group, each of which is optionally substituted with one or two substituents selected independently from the group consisting of: Cl, $C_{1-3}$-alkyl, —NH—C(=O)—($C_{1-3}$-alkyl)-β-$CH_3$, $NH_2$ and —NH—C(=O)—$C_{1-3}$-alkyl; and
a pyridinyl, pyridazinyl or pyrimidinyl group, each of which is optionally substituted with F, CN, —$CH_3$, —C(=O)—NH—($OH_3$) or —NH—C(=O)—($CH_3$);
or a salt thereof.

A preferred embodiment of the present invention concerns compounds of general formula (I.2), wherein
n is 1, 2 or 3;
$R^1$ is selected from a group consisting of $CF_3$, $C_{1-4}$-alkyl, $C_{3-5}$-cycloalkyl, —O—($C_{1-5}$-alkyl), —O—($C_{3-6}$-cycloalkyl), —NH—($C_{1-3}$-alkyl), —N($C_{1-3}$-alkyl)$_2$,

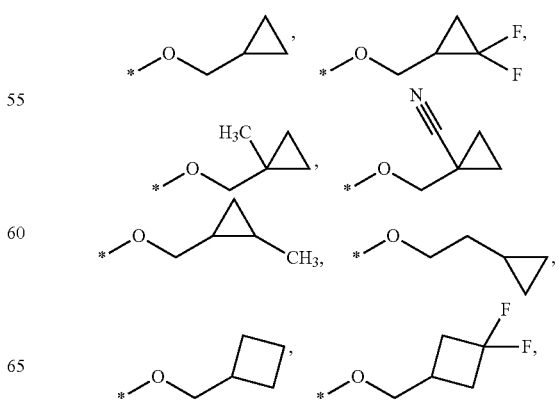

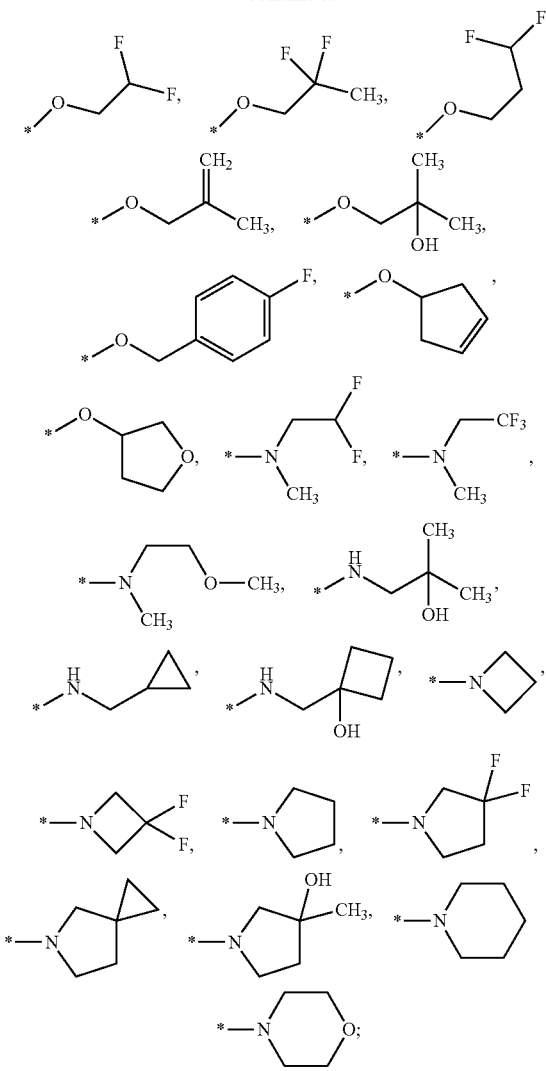

or, if n is 2, the second R¹ group is selected from the group consisting of F, Cl, CH₃ and —O—CH₃;

or, if n is 3, the third R¹ group is F;

R² is H, F or —O—CH₃; and

T is selected from a group consisting of:

linear or branched $C_{1-3}$-alkyl which is optionally substituted with one to three F, cyclopropyl which is optionally substituted with one CN or CH₃;

—O—CH₃;

—NR⁴R⁵, wherein R⁴ is H or $C_{1-3}$-alkyl, and R⁵ is $C_{1-3}$-alkyl; and a thiazolyl, oxazolyl, pyrazolyl, isoxazolyl or isothiazolyl group, each of which is optionally substituted with one or two substituents selected independently from the group consisting of CH₃, —NH—C(=O)—CH₂—O—CH₃ and —NH—C(=O)—CH₃;

or a pharmaceutically acceptable salt thereof.

Another preferred embodiment of the present invention concerns compounds of general formula (I.2a)

[Structure of formula I.2a]

wherein n is 1, 2 or 3;

R¹ is selected from a group consisting of CF₃, $C_{1-4}$-alkyl, $C_{3-5}$-cycloalkyl, —O—($C_{1-5}$-alkyl), —O—($C_{3-6}$-cycloalkyl),

[Two small structures with F substituents]

or, if n is 2, the second R¹ group is selected from the group consisting of F and Cl; or, if n is 3, the third R¹ group is F;

R² is H, F or —O—CH₃; and

T is selected from a group consisting of:

linear or branched $C_{1-3}$-alkyl which is optionally substituted with one to three F, cyclopropyl which is optionally substituted with one CN or CH₃;

—O—CH₃;

—NR⁴R⁵, wherein R⁴ is H or $C_{1-3}$-alkyl, and R⁵ is $C_{1-3}$-alkyl; and a thiazolyl, oxazolyl, pyrazolyl, isoxazolyl or isothiazolyl group, each of which is optionally substituted with one or two substituents selected independently from the group consisting of: CH₃, —NH—C(=O)—CH₂—O—CH₃ and —NH—C(=O)—CH₃;

or a pharmaceutically acceptable salt thereof.

A third preferred embodiment of the present invention concerns compounds of general formula (I.2c)

[Structure of formula I.2c]

wherein n is 1, 2 or 3;

R¹ is selected from a group consisting of —O—($C_{1-5}$-alkyl), —O—($C_{3-6}$-cycloalkyl), —NH—($C_{1-3}$-alkyl), —N($C_{1-3}$-alkyl)₂,

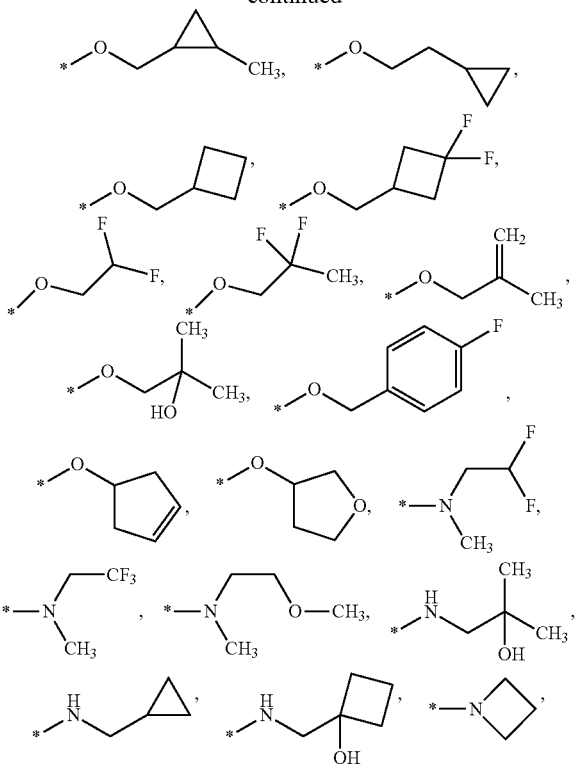

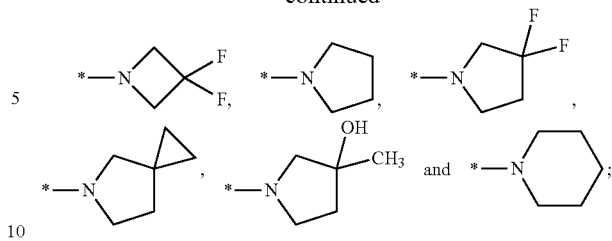

or, if n is 2, the second $R^1$ group is selected from the group consisting of F, Cl, $CH_3$ and —O—$CH_3$;

or, if n is 3, the third $R^1$ group is F;

$R^2$ is H, F or —O—$CH_3$; and

T is selected from a group consisting of:

linear or branched $C_{1-3}$-alkyl which is optionally substituted with one to three F, cyclopropyl which is optionally substituted with one CN or $CH_3$;

—O—$CH_3$;

—$NR^4R^5$, wherein $R^4$ is H or $C_{1-3}$-alkyl, and $R^5$ is $C_{1-3}$-alkyl; and a thiazolyl, oxazolyl, pyrazolyl, isoxazolyl or isothiazolyl group, each of which is optionally substituted with one or two substituents selected independently from the group consisting of $CH_3$, NH—C(=O)—$CH_2$—O—$OH_3$ and —NH—C(=O)—$CH_3$;

or a pharmaceutically acceptable salt thereof.

Preferred compounds of the invention include:

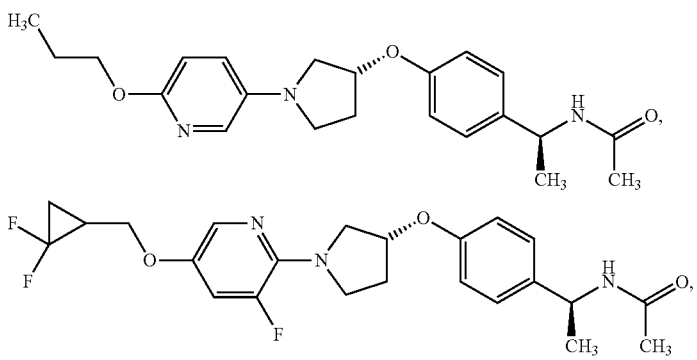

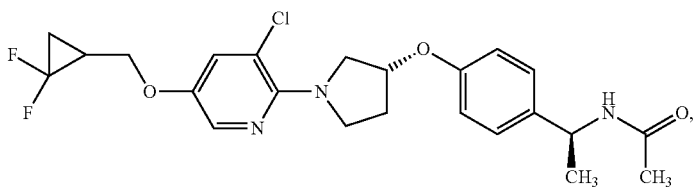

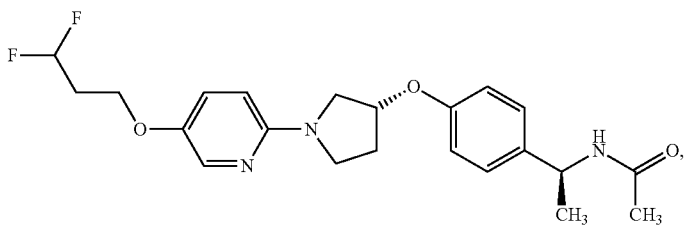

-continued
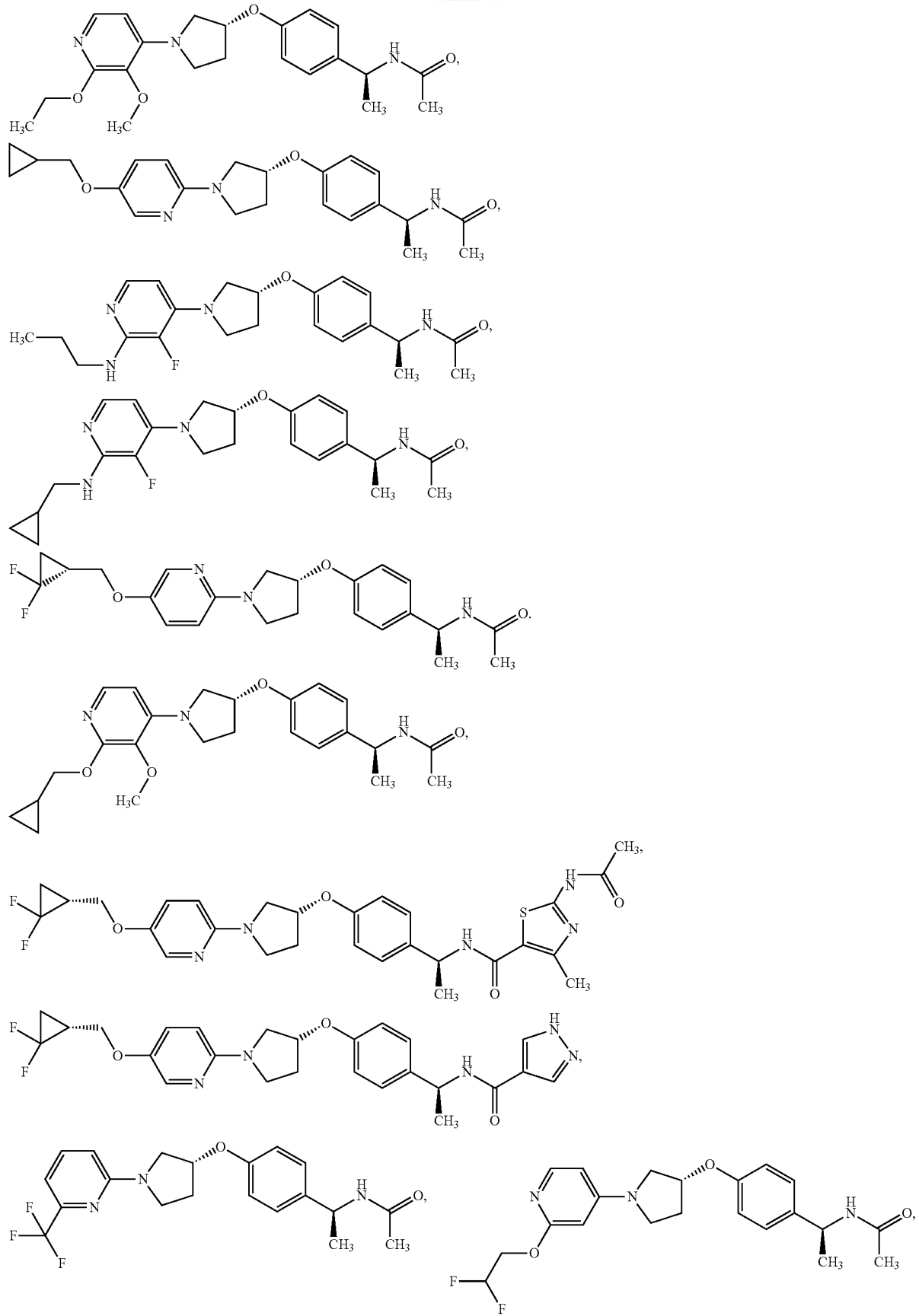

-continued
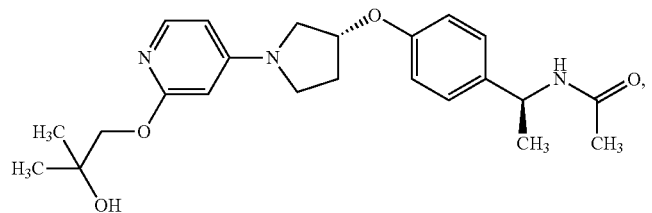
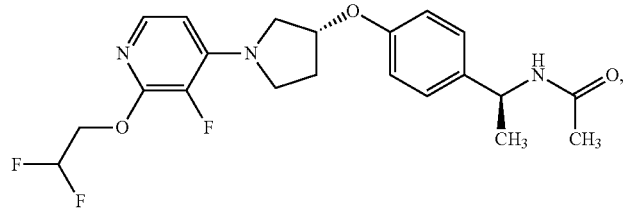
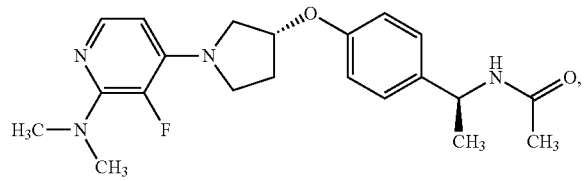
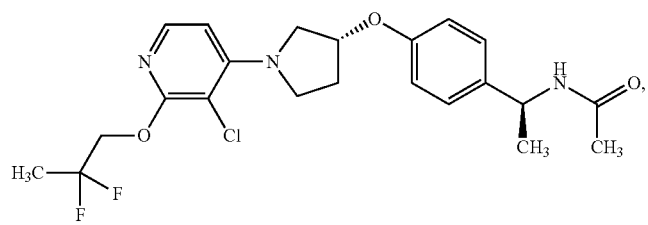
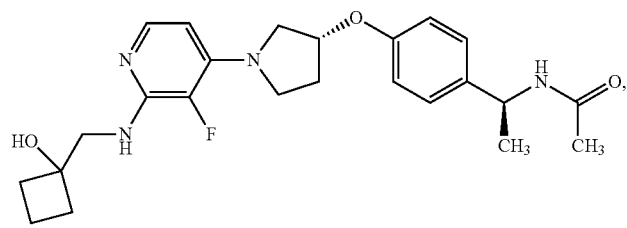
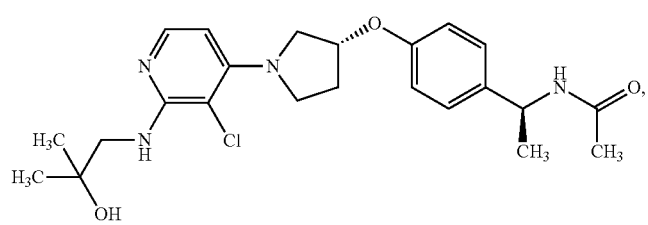
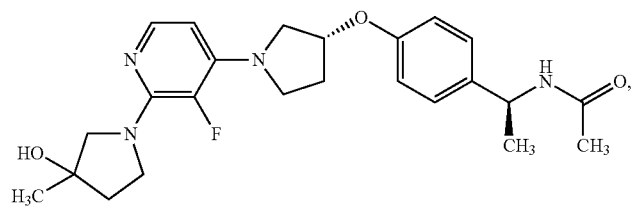
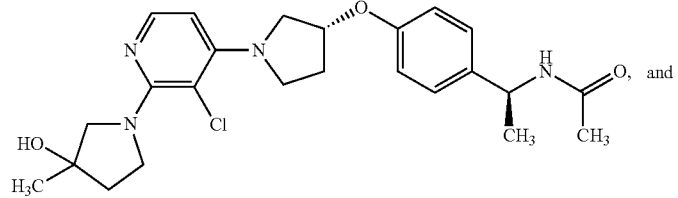

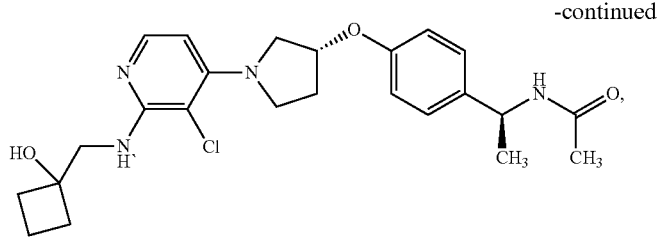

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of acetyl-CoA carboxylase(s) (ACC) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

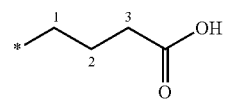

wherein the carboxy group is attached to the third carbon atom of the propyl group. The terms "1-methylpropyl-", "2,2-dimethylpropyl-" or "cyclopropylmethyl-" group represent the following groups:

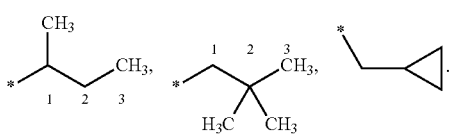 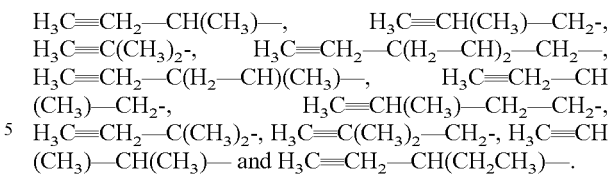

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2-$, $H_3C—CH_2—CH_2-$, $H_3C—CH(CH_3)—$, $H_3C—CH_2—C(H_2—CH)_2—$, $H_3C—CH_2—CH(CH_3)—$, $H_3C—CH(CH_3)—CH_2-$, $H_3C—C(CH_3)_2-$, $H_3C—CH_2—C(H_2—CH)_2—CH_2—$, $H_3C—CH_2—C(H_2—CH)(CH_3)—$, $H_3C—CH_2—CH(CH_3)—CH_2-$, $H_3C—CH(CH_3)—CH_2—CH_2-$, $H_3C—CH_2—C(CH_3)_2-$, $H_3C—C(CH_3)_2—CH_2-$, $H_3C—CH(CH_3)—CH(CH_3)—$ and $H_3C—CH_2—CH(CH_2CH_3)—$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $—(CH_2)—$, $—(CH_2—CH_2)—$, $—(CH(CH_3))—$, $—(CH_2—C(H_2—CH)_2)—$, $—(C(CH_3)_2)—$, $—(CH(CH_2CH_3))—$, $—(CH(CH_3)—CH_2)—$, $—(C(H_2—CH)(CH_3))—$, $—(CH_2—CH_2—C(H_2—CH)_2)—$, $—(CH_2—C(H_2—CH)(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3))—$, $—(CH_2—CH(CH_2CH_3))—$, $—(CH(CH_2CH_3)—CH_2)—$, $—(CH(CH_2CH_2CH_3))—$, $—(CHCH(CH_3)_2)—$ and $—C(CH_3)(CH_2CH_3)—$.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes $—CH=CH_2$, $—CH=CH—CH_3$, $—CH_2—CH=CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes $—CH=CH—$, $—CH=CH—CH_2-$, $—CH_2—CH=CH—$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes $—C≡CH$, $—C≡C—CH_3$, $—CH_2—C≡CH$.

The term "$C_{2-n}$-alkynylene" is used for a group as defined in the definition for "$C_{1-n}$-alkynylene" with at least two carbon atoms, if at least two of those carbon atoms of said group are bonded to each other by a triple bond. For example the term $C_{2-3}$-alkynylene includes $—C≡C—$, $—C≡C≡CH_2-$, $—CH_2—C≡C—$.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cyloalkyl, $C_{3-10}$-cycloalkenyl, octahydro-pentalenyl, octahydroindenyl, decahydronaphthyl, indanyl, tetrahydronaphthyl. Most preferably, the term $C_{3-n}$-carbocyclyl denotes $C_{3-n}$-cyloalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably, the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or $S(O)_r$ with r=0, 1 or 2, which in addition may have a carbonyl group. More preferably, the term "heterocyclyl" as used herein, either alone or in combination with another radical, means a saturated or unsaturated, even more preferably, a saturated mono-, bi- or spirocyclic-ring system containing 1, 2, 3 or 4 heteroatoms selected from N, O or S(O), with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

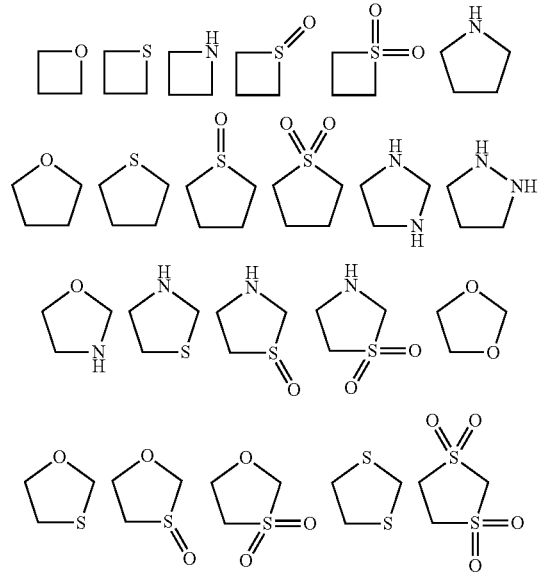

-continued

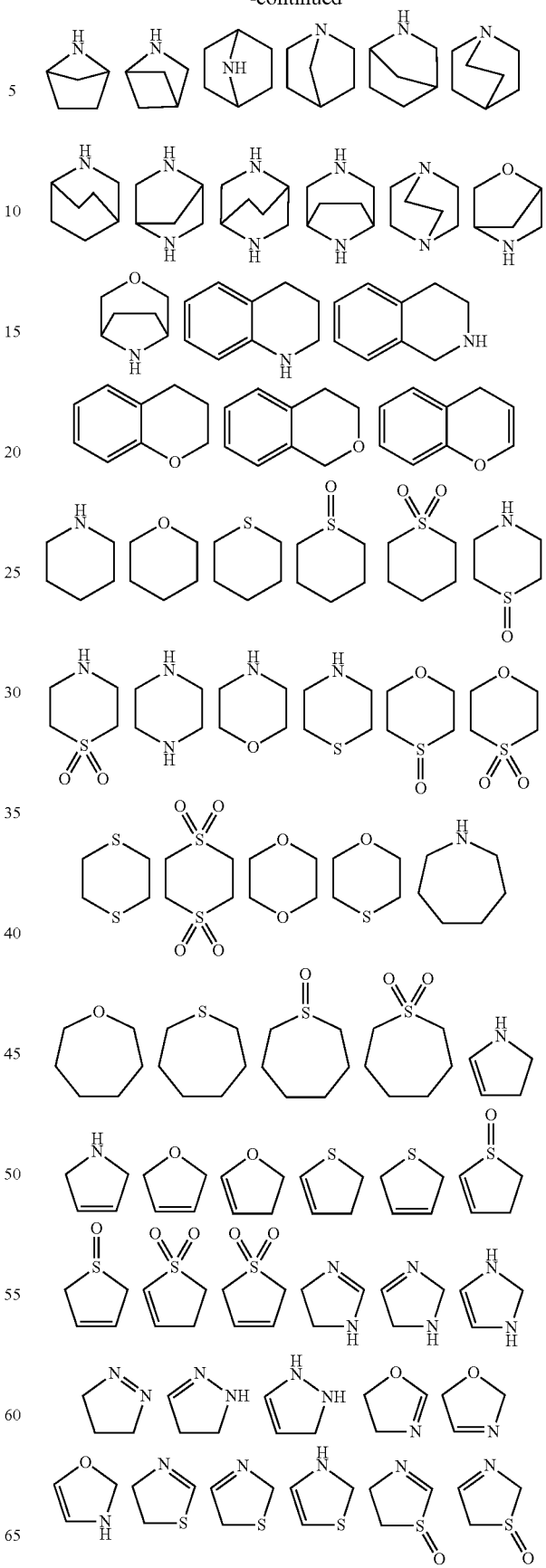

-continued

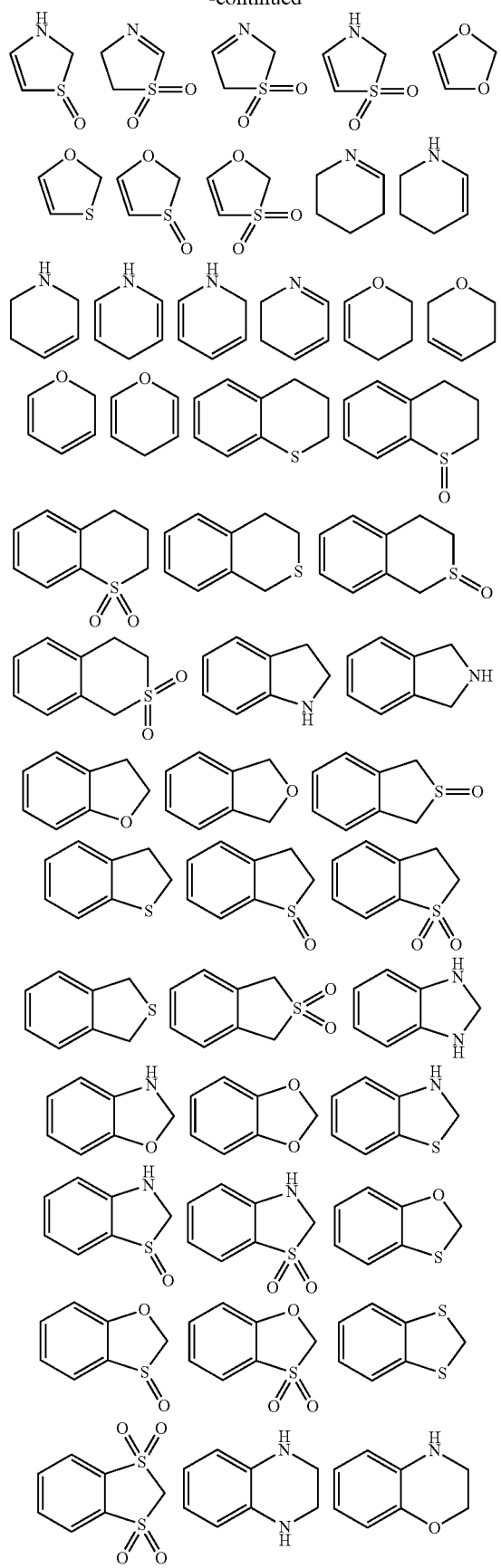

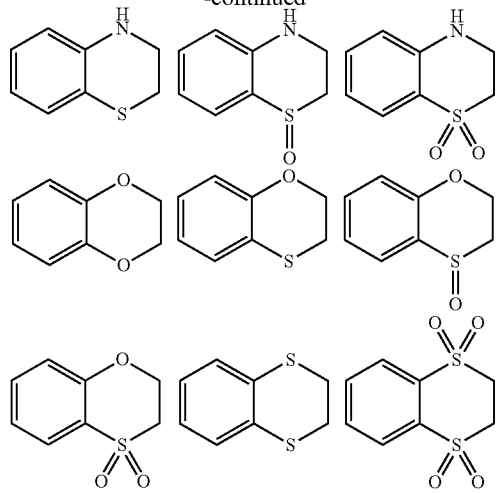

The term "heteroaryl" means a mono- or polycyclic, preferably mono- or bicyclic-ring system containing one or more heteroatoms selected from N, O or $S(O)_r$ with r=0, 1 or 2 wherein at least one of the heteroatoms is part of an aromatic ring, and wherein said ring system may have a carbonyl group. More preferably, the term "heteroaryl" as used herein, either alone or in combination with another radical, means a mono- or bicyclic-ring system containing 1, 2, 3 or 4 heteroatoms selected from N, O or $S(O)_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

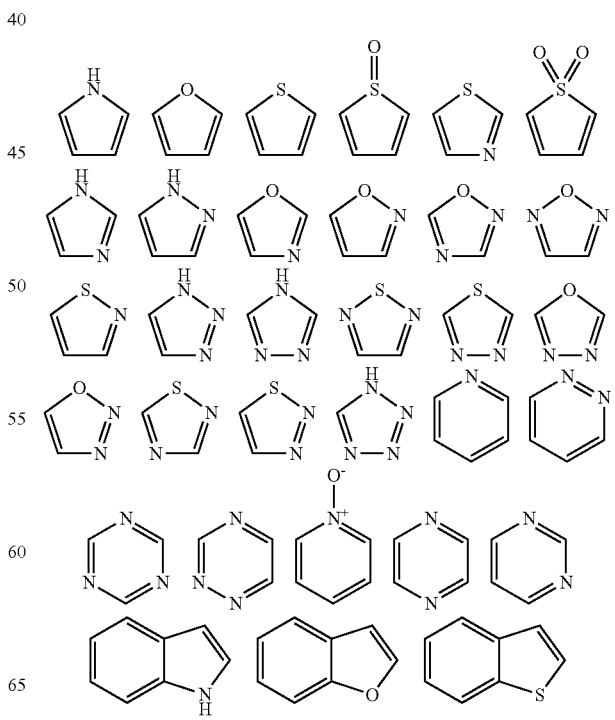

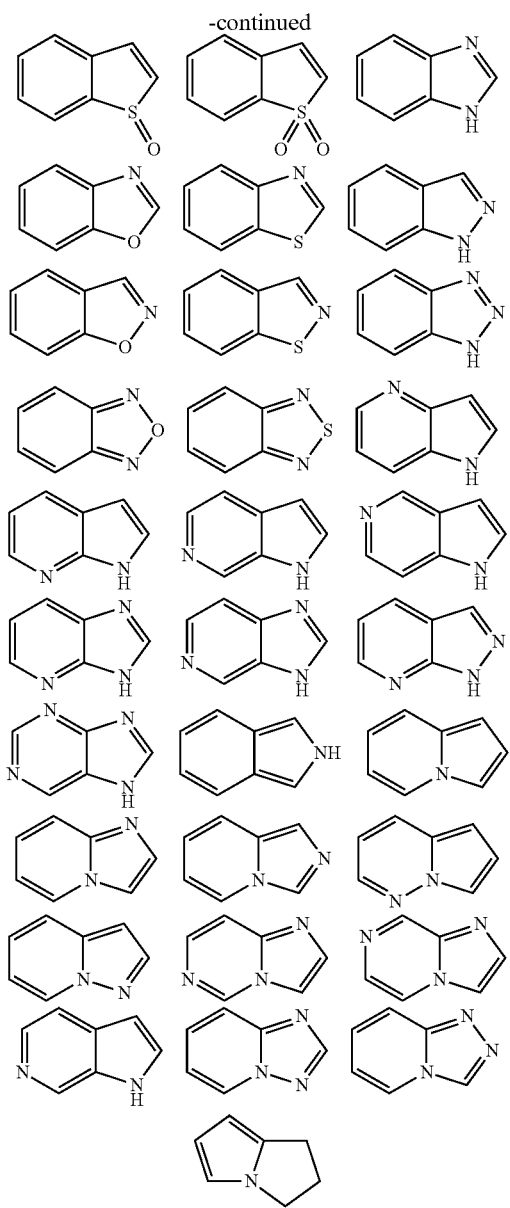

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCO_3$, 10 mM $MgCl_2$, 0.5 mg/ml BSA, 3.75 mM reduced L-glutathione, 15 U/ml lactate dehydrogenase, 0.5 mM phosphoenolpyruvate, 15 U/ml pyruvate kinase, compounds at different concentrations at final DMSO concentrations of 1%.

The enzymatic reaction is then started by addition of a mixture of NADH, acetyl Coenzyme A (both 2000 μM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For $IC_{50}$ value determination, the sample slope in the presence of the test compound after subtraction of the low controls (S(compound)−S('LOW')) are used.

An $IC_{50}$ value is derived from the compound slopes at different dosages after subtraction of the low controls (S(compound)−S('LOW')) by non-linear regression curve fitting (equation $y=(A+((B-A)/(1+((C/x)^D))))$).

The compounds of general formula (I) according to the invention for example have $IC_{50}$ values below 10000 nM, particularly below 1000 nM, preferably below 300 nM.

In the following table the activity expressed as $IC_{50}$ (μM) of compounds according to the invention is presented wherein the $IC_{50}$ values are determined in the ACC2 assay as described hereinbefore. The term "Example" refers to the example numbers according to the following experimental section.

| Example | $IC_{50}$ [μM] |
| --- | --- |
| 1.1 | 0.046 |
| 1.2 | 0.146 |
| 1.3 | 0.134 |
| 1.4 | 0.193 |
| 1.5 | 0.510 |
| 1.6 | 0.306 |
| 1.7 | 0.137 |
| 1.8 | 0.375 |
| 1.9 | 0.556 |
| 1.10 | 0.832 |
| 1.11 | 0.151 |
| 1.12 | 0.265 |
| 1.13 | 0.345 |
| 1.14 | 0.394 |
| 1.15 | 0.060 |
| 1.16 | 0.114 |
| 1.17 | 0.190 |
| 1.18 | 0.167 |
| 1.19 | 0.054 |
| 1.20 | 0.065 |
| 1.21 | 0.335 |
| 1.22 | 0.104 |
| 1.23 | 0.115 |
| 1.24 | 0.447 |
| 1.25 | 0.228 |
| 1.26 | 0.114 |
| 1.27 | 0.070 |
| 1.28 | 0.245 |
| 1.29 | 0.130 |
| 1.30 | 0.117 |

| Example | IC$_{50}$ [μM] | | Example | IC$_{50}$ [μM] |
|---|---|---|---|---|
| 1.31 | 0.139 | | 1.108 | 0.042 |
| 1.32 | 0.050 | | 1.109 | 0.155 |
| 1.33 | 0.504 | | 1.110 | 0.023 |
| 1.34 | 0.434 | | 1.111 | 0.112 |
| 1.35 | 0.414 | | 1.112 | 0.068 |
| 1.36 | 0.168 | | 1.113 | 0.163 |
| 1.37 | 0.360 | | 1.114 | 0.043 |
| 1.38 | 0.095 | | 1.115 | 0.260 |
| 1.39 | 0.379 | | 1.116 | 0.177 |
| 1.40 | 0.775 | | 1.117 | 0.753 |
| 1.41 | 0.154 | | 1.118 | 0.039 |
| 1.42 | 0.219 | | 1.119 | 1.332 |
| 1.43 | 0.059 | | 1.120 | 0.032 |
| 1.44 | 0.256 | | 1.121 | 0.041 |
| 1.45 | 0.064 | | 1.122 | 2.711 |
| 1.46 | 0.149 | | 1.123 | 0.228 |
| 1.47 | 0.120 | | 1.124 | 0.076 |
| 1.48 | 0.352 | | 1.125 | 0.402 |
| 1.49 | 0.179 | | 1.126 | 0.597 |
| 1.50 | 0.170 | | 1.127 | 0.031 |
| 1.51 | 0.401 | | 1.128 | 0.360 |
| 1.52 | 0.474 | | 1.129 | 0.210 |
| 1.53 | 0.085 | | 1.130 | 0.233 |
| 1.54 | 0.140 | | 1.131 | 0.076 |
| 1.55 | 0.154 | | 1.132 | 0.041 |
| 1.56 | 0.585 | | 1.133 | 0.246 |
| 1.57 | 0.678 | | 1.134 | 0.102 |
| 1.58 | 0.055 | | 1.135 | 0.062 |
| 1.59 | 0.150 | | 1.136 | 0.476 |
| 1.60 | 0.202 | | 1.137 | 0.633 |
| 1.61 | 0.340 | | 1.138 | 0.026 |
| 1.62 | 0.802 | | 1.139 | 0.037 |
| 1.63 | 0.055 | | 1.140 | 0.065 |
| 1.64 | 0.154 | | 1.141 | 0.421 |
| 1.65 | 0.107 | | 1.142 | 0.067 |
| 1.66 | 0.384 | | 1.143 | 0.116 |
| 1.67 | 0.463 | | 1.144 | 0.093 |
| 1.68 | 0.354 | | 1.145 | 0.995 |
| 1.69 | 0.387 | | 1.146 | 0.109 |
| 1.70 | 0.722 | | 1.147 | 0.047 |
| 1.71 | 0.088 | | 1.148 | 0.047 |
| 1.72 | 0.070 | | 1.149 | 0.156 |
| 1.73 | 0.059 | | 1.150 | 0.069 |
| 1.74 | 0.100 | | 1.151 | 0.504 |
| 1.75 | 0.030 | | 2.1 | 0.025 |
| 1.76 | 0.063 | | 2.2 | 0.705 |
| 1.77 | 0.029 | | 2.3 | 0.149 |
| 1.78 | 0.198 | | 2.4 | 0.145 |
| 1.79 | 0.950 | | 2.5 | 0.070 |
| 1.80 | 0.484 | | 2.6 | 0.145 |
| 1.81 | 0.425 | | 2.7 | 0.389 |
| 1.82 | 0.110 | | 2.8 | 0.065 |
| 1.83 | 2.987 | | 2.9 | 0.873 |
| 1.84 | 0.115 | | 2.10 | 0.670 |
| 1.85 | 0.107 | | 2.11 | 1.000 |
| 1.86 | 0.089 | | 2.12 | 0.921 |
| 1.87 | 0.677 | | 2.13 | 0.798 |
| 1.88 | 0.423 | | 2.14 | 0.410 |
| 1.89 | 0.278 | | 2.15 | 0.769 |
| 1.90 | 0.379 | | 2.16 | 0.316 |
| 1.91 | 0.661 | | 2.17 | 0.607 |
| 1.92 | 0.524 | | 2.18 | 0.862 |
| 1.93 | 0.107 | | 2.19 | 0.250 |
| 1.94 | 0.094 | | 2.20 | 0.110 |
| 1.95 | 0.082 | | 2.21 | 0.389 |
| 1.96 | 0.114 | | 2.22 | 0.998 |
| 1.97 | 0.970 | | 2.23 | 0.970 |
| 1.98 | 0.967 | | 2.24 | 0.199 |
| 1.99 | 0.201 | | 2.25 | 0.564 |
| 1.100 | 0.385 | | 2.26 | 0.466 |
| 1.101 | 0.092 | | 2.27 | 0.571 |
| 1.102 | 0.061 | | 2.28 | 0.512 |
| 1.103 | 0.070 | | 2.29 | 0.267 |
| 1.104 | 0.024 | | 2.30 | 0.455 |
| 1.105 | 0.059 | | 2.31 | 0.964 |
| 1.106 | 0.069 | | 2.32 | 0.120 |
| 1.107 | 0.052 | | 2.33 | 0.055 |

| Example | IC$_{50}$ [μM] |
|---|---|
| 2.34 | 0.069 |
| 2.35 | 0.276 |
| 2.36 | 0.130 |
| 2.37 | 0.247 |
| 2.38 | 0.869 |
| 2.39 | 0.610 |
| 2.40 | 0.139 |
| 2.41 | 0.315 |
| 2.42 | 0.675 |
| 2.43 | 0.057 |
| 2.44 | 0.991 |
| 2.45 | 0.100 |
| 2.46 | 0.060 |
| 2.47 | 0.320 |
| 2.48 | 0.891 |
| 2.49 | 0.560 |
| 2.50 | 0.895 |
| 2.51 | 0.128 |
| 2.52 | 0.275 |
| 2.53 | 0.314 |
| 2.54 | 0.455 |
| 2.55 | 0.424 |
| 2.56 | 0.175 |
| 2.57 | 0.255 |
| 2.58 | 0.069 |
| 2.59 | 0.055 |
| 2.60 | 0.035 |
| 2.61 | 0.035 |
| 2.62 | 0.175 |
| 2.63 | 0.204 |
| 2.64 | 0.045 |
| 2.65 | 0.085 |
| 2.66 | 0.050 |
| 2.67 | 0.046 |
| 2.68 | 0.265 |
| 2.69 | 0.281 |
| 2.70 | 0.099 |
| 2.71 | 0.110 |
| 2.72 | 0.130 |
| 2.73 | 0.065 |
| 2.74 | 0.359 |
| 2.75 | 0.039 |
| 2.76 | 0.024 |
| 2.77 | 0.069 |
| 2.78 | 0.799 |
| 2.79 | 0.456 |
| 2.80 | 0.122 |
| 2.81 | 0.035 |
| 2.82 | 0.300 |
| 2.83 | 0.210 |
| 2.84 | 0.169 |
| 2.85 | 0.105 |
| 2.86 | 0.063 |
| 2.87 | 0.270 |
| 2.88 | 0.278 |
| 2.89 | 0.285 |
| 2.90 | 0.009 |
| 2.91 | 0.067 |
| 2.92 | 0.110 |
| 2.93 | 0.040 |
| 2.94 | 0.084 |
| 2.95 | 0.049 |
| 2.96 | 0.055 |
| 2.97 | 0.140 |
| 2.98 | 0.282 |
| 2.99 | 0.085 |
| 2.100 | 0.624 |
| 2.101 | 0.076 |
| 2.102 | 0.136 |
| 2.103 | 0.523 |
| 2.104 | 0.658 |
| 2.105 | 0.784 |
| 2.106 | 0.088 |
| 2.107 | 0.389 |
| 2.108 | 0.714 |
| 2.109 | 0.453 |
| 2.110 | 0.263 |
| 2.111 | 0.107 |
| 2.112 | 0.298 |
| 2.113 | 0.077 |
| 2.114 | 0.611 |
| 2.115 | 0.869 |
| 2.116 | 0.362 |
| 2.117 | 0.408 |
| 2.118 | 0.169 |
| 2.119 | 0.235 |
| 2.120 | 0.037 |
| 2.121 | 0.043 |
| 2.122 | 0.085 |
| 2.123 | 0.058 |
| 2.124 | 0.072 |
| 2.125 | 0.060 |
| 2.126 | 0.045 |
| 3.1 | 0.081 |
| 3.2 | 0.065 |
| 3.3 | 0.150 |
| 3.4 | 0.075 |
| 3.5 | 0.050 |
| 3.6 | 0.110 |
| 3.7 | 0.444 |
| 3.8 | 0.090 |
| 3.9 | 0.200 |
| 3.10 | 0.112 |
| 3.11 | 0.314 |
| 3.12 | 0.144 |
| 3.13 | 0.497 |
| 3.14 | 0.238 |
| 3.15 | 0.411 |
| 3.16 | 0.313 |
| 3.17 | 0.138 |
| 3.18 | 0.423 |
| 3.19 | 1.440 |
| 3.20 | 0.092 |
| 3.21 | 0.363 |
| 3.22 | 0.050 |
| 3.23 | 0.205 |
| 4.1 | 0.039 |
| 4.2 | 0.139 |
| 4.3 | 0.059 |
| 4.4 | 0.070 |
| 4.5 | 0.166 |
| 4.6 | 0.068 |
| 4.7 | 0.134 |
| 4.8 | 0.077 |
| 4.9 | 0.163 |
| 5.1 | 0.649 |
| 5.2 | 0.090 |
| 5.3 | 0.034 |
| 5.4 | 0.049 |
| 5.5 | 0.310 |
| 5.6 | 0.036 |
| 5.7 | 0.117 |
| 5.8 | 0.141 |
| 5.9 | 0.073 |
| 6.1 | 0.428 |
| 6.2 | 0.614 |
| 7.1 | 0.400 |
| 7.2 | 0.124 |
| 7.3 | 0.054 |
| 8.1 | 0.062 |
| 8.2 | 0.565 |
| 8.3 | 0.755 |
| 8.4 | 0.438 |
| 8.5 | 0.530 |
| 8.6 | 0.086 |
| 8.7 | 0.910 |
| 8.8 | 0.265 |
| 8.9 | 0.105 |
| 8.10 | 0.693 |
| 8.11 | 1.102 |
| 9.1 | 0.039 |
| 9.2 | 0.041 |
| 9.3 | 0.480 |
| 9.4 | 0.075 |

| Example | IC$_{50}$ [μM] |
|---|---|
| 9.5 | 0.390 |
| 9.6 | 0.090 |
| 9.7 | 0.040 |
| 9.8 | 0.268 |
| 9.9 | 0.140 |
| 9.10 | 0.184 |
| 9.11 | 0.068 |
| 9.12 | 0.534 |
| 9.13 | 0.230 |
| 9.14 | 0.075 |
| 9.15 | 0.040 |
| 9.16 | 0.035 |
| 9.17 | 0.077 |
| 9.18 | 0.482 |
| 9.19 | 0.330 |
| 9.20 | 0.070 |
| 9.21 | 0.477 |
| 9.22 | 0.140 |
| 9.23 | 0.045 |
| 9.24 | 0.055 |
| 9.25 | 0.572 |
| 9.26 | 0.125 |
| 9.27 | 0.055 |
| 9.28 | 0.040 |
| 9.29 | 0.030 |
| 9.30 | 0.402 |
| 9.31 | 0.090 |
| 9.32 | 0.305 |
| 9.33 | 0.535 |
| 9.34 | 0.095 |
| 9.35 | 0.584 |
| 9.36 | 0.209 |
| 9.37 | 0.385 |
| 9.38 | 0.510 |
| 9.39 | 0.149 |
| 9.40 | 0.326 |
| 9.41 | 0.095 |
| 9.42 | 0.402 |
| 9.43 | 0.184 |
| 9.44 | 0.639 |
| 9.45 | 0.500 |
| 9.46 | 0.544 |
| 9.47 | 0.745 |
| 9.48 | 0.495 |
| 9.49 | 0.668 |
| 9.50 | 0.110 |
| 9.51 | 0.042 |
| 9.52 | 0.061 |
| 9.53 | 0.040 |
| 9.54 | 0.115 |
| 9.55 | 0.059 |
| 9.56 | 0.900 |
| 9.57 | 0.055 |
| 9.58 | 0.055 |
| 9.59 | 0.235 |
| 9.60 | 0.040 |
| 9.61 | 0.065 |
| 9.62 | 0.044 |
| 9.63 | 0.055 |
| 9.64 | 0.035 |
| 9.65 | 0.085 |
| 9.66 | 0.615 |
| 9.67 | 0.146 |
| 9.68 | 0.251 |
| 9.69 | 0.603 |
| 9.70 | 0.124 |
| 9.71 | 0.045 |
| 9.72 | 0.079 |
| 9.73 | 0.045 |
| 9.74 | 0.220 |
| 9.75 | 0.881 |
| 9.76 | 0.114 |
| 9.77 | 0.059 |
| 9.78 | 0.057 |
| 9.79 | 0.132 |
| 9.80 | 0.138 |
| 9.81 | 0.053 |
| 9.82 | 0.035 |
| 9.83 | 0.080 |
| 9.84 | 0.045 |
| 9.85 | 0.058 |
| 9.86 | 0.187 |
| 9.87 | 0.280 |
| 9.88 | 0.177 |
| 10.1 | 0.145 |
| 10.2 | 0.208 |
| 10.3 | 0.153 |
| 10.4 | 0.261 |
| 10.5 | 0.182 |
| 10.6 | 0.827 |
| 10.7 | 0.505 |
| 10.8 | 0.594 |
| 10.9 | 0.849 |
| 10.10 | 0.115 |
| 10.11 | 0.209 |
| 10.12 | 0.691 |
| 10.13 | 0.498 |
| 10.14 | 0.045 |
| 10.15 | 0.150 |
| 10.16 | 0.035 |
| 10.17 | 0.097 |
| 10.18 | 0.855 |
| 10.19 | 0.035 |
| 10.20 | 0.167 |
| 10.21 | 0.963 |
| 10.22 | 0.552 |
| 10.23 | 0.087 |
| 10.24 | 0.285 |
| 10.25 | 0.331 |
| 10.26 | 0.755 |
| 10.27 | 0.123 |
| 10.28 | 0.142 |
| 10.29 | 0.170 |
| 10.30 | 0.154 |
| 10.31 | 0.314 |
| 10.32 | 0.245 |
| 10.33 | 0.133 |
| 10.34 | 0.464 |
| 10.35 | 0.853 |
| 10.36 | 0.399 |
| 10.37 | 0.325 |
| 10.38 | 0.369 |
| 10.39 | 0.360 |
| 10.40 | 0.528 |
| 10.41 | 1.020 |
| 10.42 | 0.759 |
| 10.43 | 0.770 |
| 10.44 | 0.665 |
| 10.45 | 0.165 |
| 10.46 | 0.175 |
| 10.47 | 0.455 |
| 10.48 | 0.256 |
| 10.49 | 0.785 |
| 10.50 | 0.053 |
| 10.51 | 0.065 |
| 10.52 | 0.080 |
| 10.53 | 0.215 |
| 10.54 | 0.114 |
| 10.55 | 0.057 |
| 11.1 | 0.510 |
| 11.2 | 0.870 |
| 11.3 | 0.131 |
| 12 | 0.888 |
| 13 | 0.240 |
| 14.1 | 0.058 |
| 14.2 | 0.045 |
| 15 | 0.245 |

In view of their ability to inhibit acetyl-CoA carboxylase(s), the compounds of general formula (I) according to the invention and the corresponding salts thereof are theoretically suitable for the treatment, including preventative treatment of all those diseases or conditions which may be affected or which are mediated by the inhibition of acetyl-CoA carboxylase(s), in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase(s), in particular ACC2, in a patient, preferably in a human.

In yet another aspect the present invention relates a method for treating, including preventing a disease or condition mediated by the inhibition of acetyl-CoA carboxylase(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as ishyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance.

Obesity and overweight are generally defined by body mass index (BMI), which is correlated with total body fat and estimates the relative risk of disease. BMI is calculated by weight in kilograms divided by height in meters squared (kg/m$^2$). Overweight is typically defined as a BMI of 25-29.9 kg/m$^2$, and obesity is typically defined as a BMI of 30 kg/m$^2$ or greater.

According to another aspect the compounds of the present invention are particularly suitable for treating, inclduing preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;
B. hepatic disorders and conditions related thereto, including: fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
   eczema, acne, sebaceous gland diseases, psoriasis, keloid scar formation or prevention, other diseases releated to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
   atherosclerosis such as, for example (but not restricted thereto), coronary sclerosis including angina pectoris or myocardial infarction, stroke, ischemic, stroke and transient ischemic attack (TIA),
   peripheral occlusive disease,
   vascular restenosis or reocclusion,
   chronic inflammatory bowel diseases such as, for example, Crohn's disease and ulcerative colitis,
   pancreatitis,
   sinusitis,
   retinopathy, ischemic retinopathy,
   adipose cell tumors,
   lipomatous carcinomas such as, for example, liposarcomas,
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
   tumors in which ACC is up regulated,
   acute and chronic myeloproliferative disorders and lymphomas, angiogenesis
   neurodegenerative disorders including Alzheimer's disease, multiple sclerosis, Parkinson's disease, epilepsy,
   erythemato-squamous dermatoses such as, for example, psoriasis, acne vulgaris,
other skin disorders and dermatological conditions which are modulated by PPAR,
eczemas and neurodermatitis,
dermatitis such as, for example, seborrheic dermatitis or photodermatitis,
keratitis and keratoses such as, for example, seborrheic keratoses, senile keratoses, actinic keratoses, photo-induced keratoses or keratosis follicularis,
keloids and keloid prophylaxis,
bacterial infections,
fungal infections,
warts, including condylomata or condylomata acuminata
viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia,
papular dermatoses such as, for example, lichen planus,
skin cancer such as, for example, basal-cell carcinomas, melanomas or cutaneous T-cell lymphomas,
localized benign epidermal tumors such as, for example, keratoderma, epidermal naevi,
chilblains;
high blood pressure,
polycystic ovary syndrome (PCOS),
asthma,
cystic fibrosis,
osteoarthritis,
lupus erythematosus (LE) or inflammatory rheumatic disorders such as, for example rheumatoid arthritis,
vasculitis,
wasting (cachexia),
gout,
ischemia/reperfusion syndrome,
acute respiratory distress syndrome (ARDS)
viral diseases and infections
lipodystrophy and lipodystrophic conditions, also for treating adverse drug effect;
myophathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11 beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11 beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the acetyl-CoA carboxylase(s), in particular ACC2, in particular diseases or conditions as described hereinbefore and hereinafter.

In yet another aspect the present invention relates a method for treating, including preventing a disease or condition mediated by the inhibition of acetyl-CoA carboxylase(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

Synthesis Schemes

Compounds of general formula (I) may be prepared by palladium-mediated Buchwald reactions or copper-mediated Ullmann reactions of pyridines (Py-Z, II), which may additionally be substituted with 1 to 3 substitutents $R^1$, with pyrrolidines (III) wherein Z is a leaving group which for example denotes Cl, Br or I.

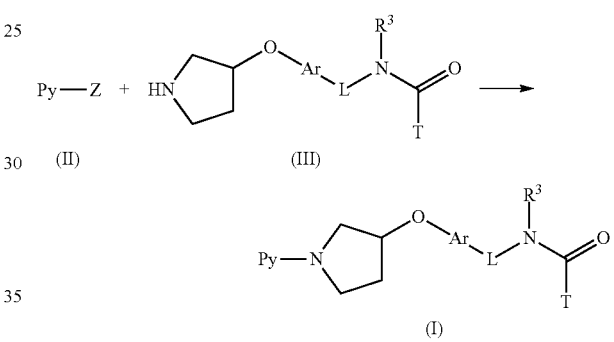

Compounds of general formula (I) may be prepared by amide coupling reactions of amines (IV) with carboxylic acids (V) mediated by coupling reagents such as for example 2-(1H-benzotriazol-1-yl)-1,1,3,3-tetramethyluronium tetrafluoroborat (TBTU), 2-chloro-1,3-dimethyl-2-imidazolinium hexafluorophosphate (CIP), benzotriazole-1-yl-oxy-trispyrrolidinophosphonium hexafluorophosphate (PyBop), and 1-chloro-N,N-2-trimethylpropenylamine.

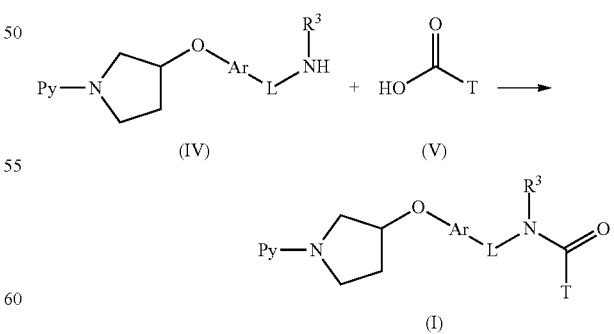

Alternatively, compounds of general formula (I) may be prepared by amide coupling reactions of amines (IV) with carboxylic acids chlorides (VI) or carboxylic acid anhydrides (VII).

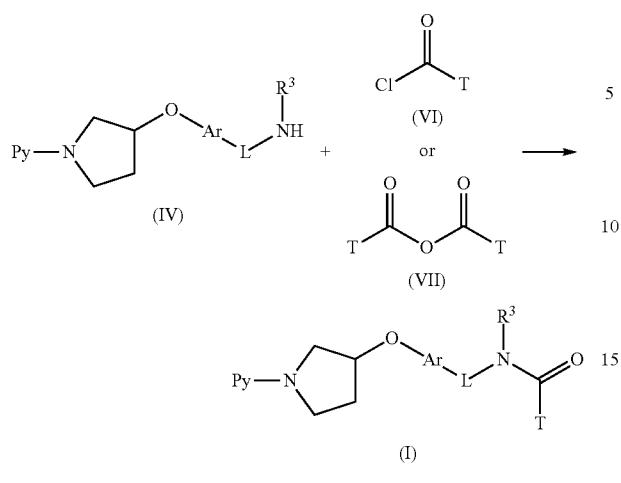

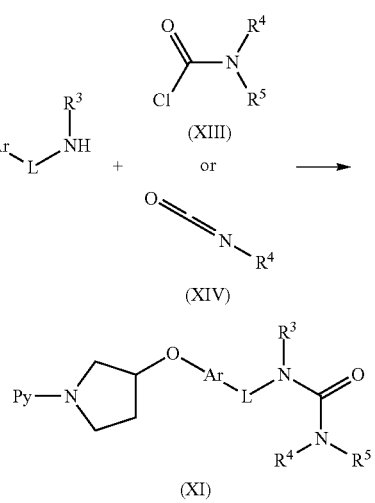

Compounds of general formula (VIII) may be prepared by alkylation reactions of aromatic alcohols (IX) with electrophiles (X) wherein Z is a leaving group which for example denotes Cl, Br, I, mesylate, tosylate or triflate.

Compounds of general formula (XV) may be prepared by urethane forming reactions such as reaction of amines (IV) with alcohols (XVI) after reaction with reagents such as CDT or CDI. Alcohols may be used in their deprotonated form.

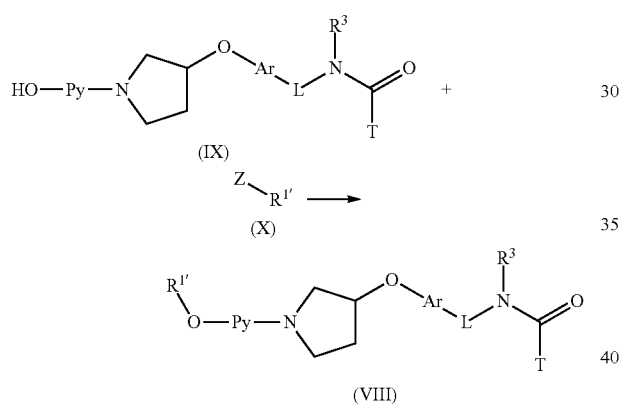

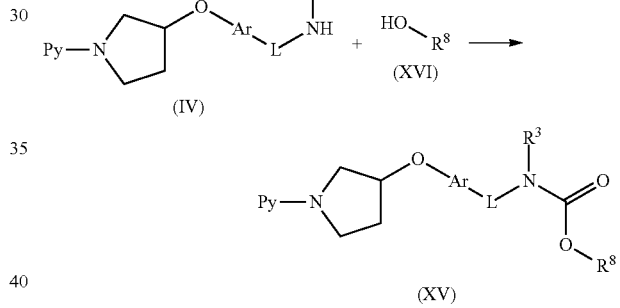

Compounds of general formula (XI) may be prepared by urea forming reactions such as reaction of amines (IV) with amines (XII) after reaction with reagents such as N,N-carbonyldithiazole (CDT) or N,N-carbonyldiimidazole (CDI).

Alternatively, compounds of general formula (XV) may be prepared by urethane forming reactions such as reaction of amines (IV) with chloro formates (XVII).

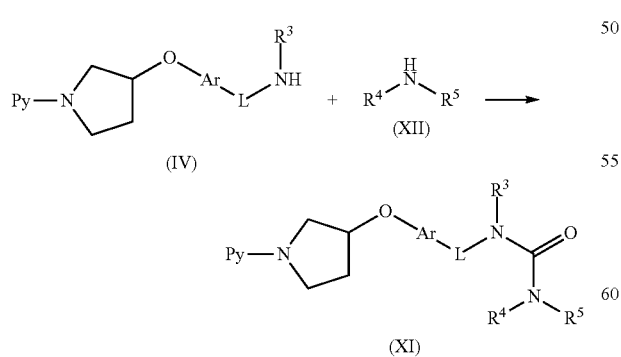

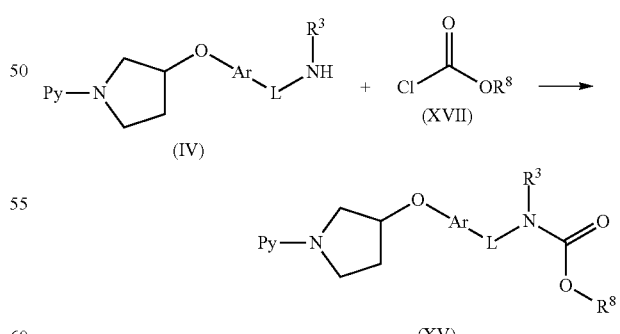

Alternatively, compounds of general formula (XI) may be prepared by urea forming reactions such as reaction of amines (IV) with carbamoyl chlorides (XIII) or isocyanates (XIV).

Compounds of general formula (I) may alternatively be prepared by nucleophilic aromatic substitution reactions ($S_NAr$) of pyridyl halides, pyridyl triflates (XVIII) with pyrrolidines (III), wherein Z is a leaving group which for example denotes F, Cl.

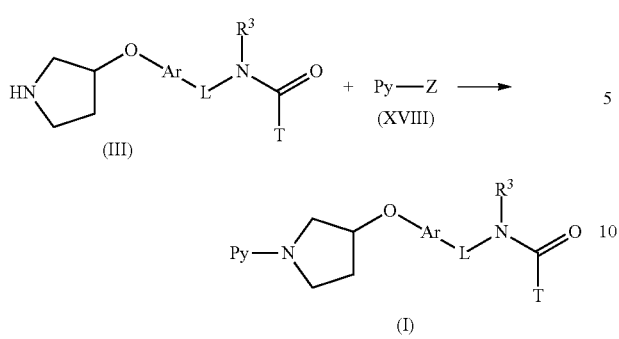

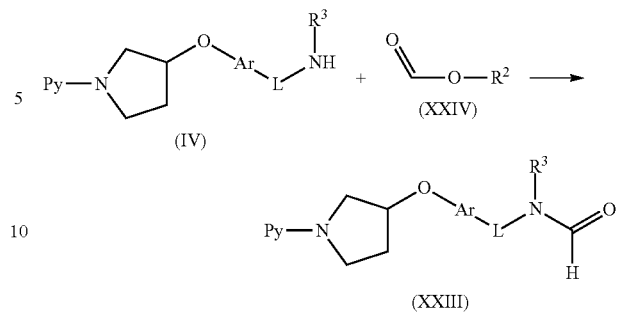

Compounds of general formula (XIX) may be prepared by aromatic subtitution of pyridyl halides (XX) with amines (XII) wherein Z is a leaving group which for example denotes F or Cl.

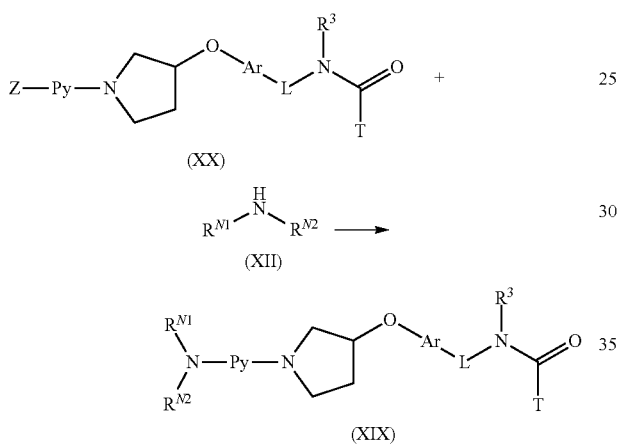

Compounds of general formula (XXI) may be prepared by aromatic subtitution of pyridyl halides (XX) with alcohols (XXII) wherein Z is a leaving group which for example denotes F or Cl. Alcohols are used in their deprotonated form.

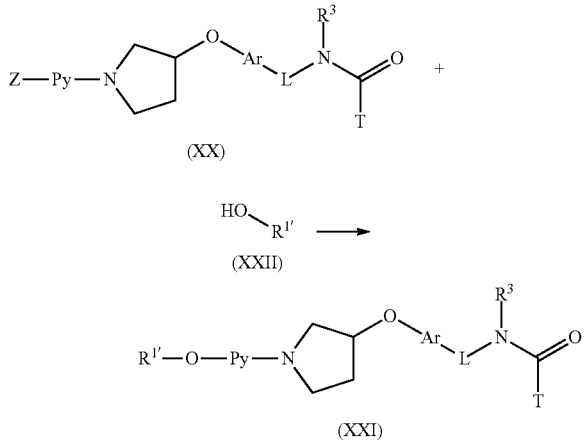

Compounds of general formula (XXIII) may be prepared by reaction of amines (IV) with formates (XXIV).

Experimental Part

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$-values are determined using silica gel plates and UV light at 254 nm.

To describe the relative configuration of stereogenic centers straight bars are used. To describe the relative and absolute configuration, the bars have a wedged shape.

relative configuration:

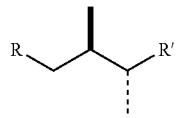

relative and absolute configuration:

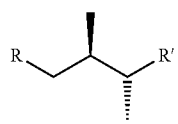

Abbreviations

| | |
|---|---|
| aq. | aqueous |
| ACN | acetonitrile |
| AcOH | acetic acid |
| BOC | tert-butoxy-carbonyl- |
| BuLi | butyl lithium |
| CDI | N,N-carbonyldiimidazole |
| CDT | N,N-carbonylditriazole |
| CIP | 2-chloro-1,3-dimethyl-2-imidazolinium hexafluorophosphate |
| CyH | cyclohexane |
| d | day |
| DCM | dichloromethane |
| DIPE | diisopropyl ether |
| DIPEA | N,N-diisopropylethylamine |
| DMAP | 4-dimethylaminopyridine |
| DMF | N,N-dimethylformamide |
| DMSO | dimethyl sulfoxide |
| dppf | diphenylphosphinoferrocene |
| EtOAc | ethyl acetate |
| EtOH | ethanol |
| eq | equivalent |
| Ex | example |

| | |
|---|---|
| FA | formic acid |
| h | hour |
| MeOH | methanol |
| min | minute |
| MsCl | methanesulfonyl chloride |
| n.d. | not determined |
| NMP | N-methyl-2-pyrrolidone |
| Pd/C | palladium on activated carbon |
| PE | petroleum ether |
| PyBop | (benzotriazol-1-yloxy)tripyrrolidinophosphonium hexafluorophosphate |
| r.t. | room temperature (about 20° C.) |
| sat. | saturated |
| TBME | tert-butyl methyl ether |
| TEA | triethylamine |
| TF/TFA | trifluoroacetic acid |
| THF | tetrahydrofuran |
| TBAF | tetrabutylammonium fluoride |
| TBS | tert-butyl-dimethylsilyl |
| TBTU | 2-(1H-benzotriazol-1-yl)-1,1,3,3-tetramethyluronium tetrafluoroborat |
| TMS | trimethylsilyl |
| Ts | 4-toluenesulfonyl |
| THP | tetrahydropyran |
| X-Phos | 2-dicyclohexylphosphino-2',4',6'-tri-isopropyl-1,1'-biphenyl |

Preparation of Starting Compounds

Example I (S)—N-(1-(4-Bromophenyl)ethyl)acetamide

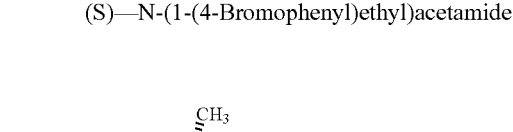

To 200 g (1.00 mol) (S)-1-(4-bromophenyl)ethylamine in 800 mL DCM are slowly added 94.5 mL (1.00 mol) acetic anhydride while cooling the mixture to 20-30° C. Then the cooling is removed and the reaction mixture is stirred at r.t. over night. Afterwards the mixture is consecutively washed with water, sat. aq. NaHCO$_3$ solution, water, diluted aq. citric acid solution and again water. The org. layer is dried over MgSO$_4$, filtered and the solvent is removed in vacuo.

$C_{10}H_{12}BrNO$ (M=242.1 g/mol)
ESI-MS: 242/244 [M+H]$^+$
R$_t$(HPLC):1.67 min (method A)

Example II (S)-tert-Butyl 1-(4-bromophenyl)ethylcarbamate

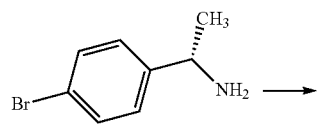

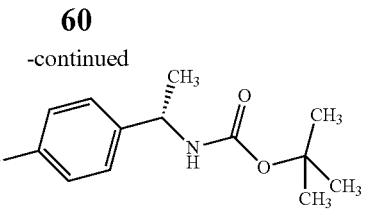

To 150 g (735 mmol) (S)-1-(4-bromophenyl)ethylamine in 2 L DCM are added 459 mL (918 mmol) of an aq. Na$_2$CO$_3$ solution (c=2 mol/L). To this mixture a solution of 164 g (749 mmol) BOC$_2$O in 350 mL THF is added dropwise at r.t. and stirring is continued for 1 h. Then the mixture is poured onto water and stirred for additional 20 min. The layers are separated, the org. layer is washed with water (2×), dried over Na$_2$SO$_4$, filtered and the solvent is removed in vacuo.

$C_{13}H_{18}BrNO_2$ (M=300.2 g/mol)
ESI-MS: 300/302 [M+H]$^+$
R$_f$(TLC): 0.90 (silica gel, DCM/MeOH 9/1)

Example III

Example 111.1

General Route (S)—N-(1-(4-Hydroxyphenyl)ethyl)acetamide

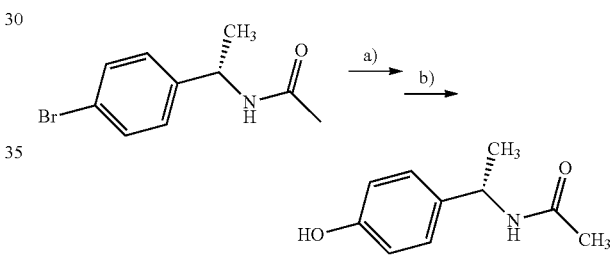

a) To a mixture of 60.0 g (248 mmol) of example 1, 73.0 g (743 mmol) KOAc, 94.4 g (372 mmol) bis(pinakolato)diboron and 3.62 g (4.96 mmol) PdCl$^2$(dppf) in an atmosphere of argon are added 450 mL DMSO and the resulting mixture is degassed twice and stirred at 80° C. for 3 h. Then the reaction mixture is chilled to r.t., diluted with water and EtOAc and the layers are separated. The aq. layer is extracted with EtOAc (2×). The org. layers are combined, washed with water (3×), dried over MgSO$_4$, filtered through a plug of Celite® and the solvent is removed in vacuo.

$C_{16}H_{24}BrNO_3$ (M=289.2 g/mol)
ESI-MS: 290 [M+H]$^+$
R$_t$(HPLC):1.19 min (method B)

b) 80.0 g (180 mmol) of the above mentioned product are added to 500 mL THF and chilled to 0° C. 31.8 mL (360 mmol) H$_2$O$_2$ (35% in water) and subsequently 51.7 mL (155 mmol) 4N aq. NaOH solution are added and the resulting mixture is stirred for 2 h at constant temperature. EtOAc is added and the mixture is extracted with 1N aq. NaOH solution (2×). The aq. layer is washed with EtOAc, acidified with citric acid and extracted with EtOAc (3×). The org. layers are combined, washed with a Na$_2$S$_2$O$_3$ solution (10% in water), dried over Na$_2$SO$_4$, filtered and the solvent is removed in vacuo. The resulting product is triturated with TBME.

$C_{10}H_{13}NO_2$ (M=179.2 g/mol)
ESI-MS: 180 [M+H]$^+$
R$_t$(HPLC):0.30 min (method C)

The following compounds are prepared analogously to example III.1:

| Ex. | Starting material | Product structure | Mass spec result | HPLC retention time (method) |
|---|---|---|---|---|
| III.1 | (S)-N-(1-(4-bromophenyl)ethyl)acetamide | (S)-N-(1-(4-hydroxyphenyl)ethyl)acetamide | 180 [M + H]$^+$ | 0.30 (C) |
| III.2 | tert-butyl (S)-(1-(4-bromophenyl)ethyl)carbamate | tert-butyl (S)-(1-(4-hydroxyphenyl)ethyl)carbamate | 238 [M + H]$^+$ | 1.58 (A) |

Example IV

Example IV.1

General Route (4-Bromo-3-methoxy-pyridin-2-yl)-methyl-propyl-amine

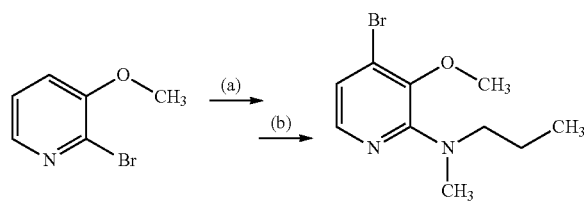

a) To 1.00 g (5.32 mmol) 2-Bromo-3-methoxypyridine in 10 mL NMP are added 0.86 mg (11.7 mmol) N-methyl-N-propylamine and the reaction mixture is stirred at 100° C. over night. Afterwards the reaction mixture is poured onto ice water and stirred for additional 10 min. Then the mixture is extracted with DCM. The org. layer is dried over MgSO$_4$, filtered and the solvent is removed in vacuo. The crude product is purified by HPLC (MeOH/H$_2$O/NH$_4$OH).
$C_{10}H_{16}N_2O$ (M=180.3 g/mol)
ESI-MS:181 [M+H]$^+$
$R_t$(HPLC): 0.73 (method M)

b) To 770 mg (4.27 mmol) of the above mentioned product in 50 mL THF are added dropwise at −70° C. 5.87 mL (9.40 mmol) n-BuLi (c=1.6 mol/L in THF), the mixture is allowed to warm to 0° C. and stirring is continued at 0° C. for 1 h. Then the mixture is chilled to −70° C. before 1.13 g (10.7 mmol) cyanogen bromide (in 5 mL THF) are added. Then the cooling is removed and the resulting mixture is stirred over night while the temperature raises to r.t. Afterwards the solvent is removed in vacuo and the resulting mixture is purified by column chromatography (silica gel, CyH/EtOAc).
$C_{10}H_{15}BrN_2O$ (M=259.1 g/mol)
ESI-MS:259/261 [M+H]$^+$
$R_t$(HPLC): 0.81 (method M)

The following compounds are prepared analogously to example IV.1:

| Ex. | Starting material | Product structure | Mass spec result | HPLC retention time (method) |
|---|---|---|---|---|
| IV.1 | 2-bromo-3-methoxypyridine | 4-bromo-3-methoxy-N-methyl-N-propylpyridin-2-amine | 259/261 [M + H]$^+$ | 0.81 (M) |
| IV.2 | 2-bromo-3-methoxypyridine | 4-bromo-3-methoxy-2-(pyrrolidin-1-yl)pyridine | 257/259 [M + H]$^+$ | 0.94 (K) |

| Ex. | Starting material | Product structure | Mass spec result | HPLC retention time (method) |
|---|---|---|---|---|
| IV.3 | (3-methoxy-2-bromopyridine) | (4-bromo-3-methoxy-2-(dimethylamino)pyridine) | 231/233 [M + H]+ | 0.65 (D) |

Example V

Example V.1

General Route

3-Bromo-6-ethoxy-2-methoxy-pyridine

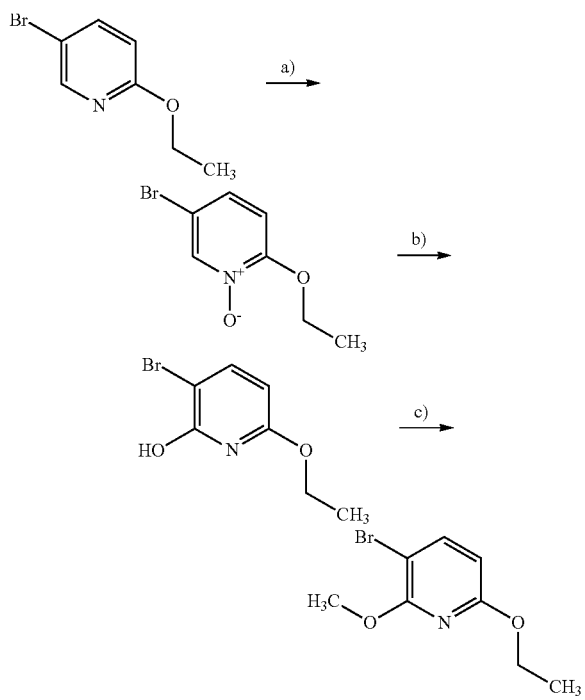

a) To 5.00 g (24.7 mmol) 5-bromo-2-ethoxy-pyridine in 50 mL DCM are added 4.66 g (49.5 mmol) urea hydrogen peroxide. Then the mixture is chilled to 0° C. before 6.88 mL (49.5 mmol) TFA anhydride are added. Afterwards cooling is removed and the resulting mixture is stirred over night while the temperature raises to r.t. The solvent is removed in vacuo, water is added and the resulting mixture is extracted with DCM. The combined org. layers are dried over MgSO$_4$, filtered and the sovent is removed in vacuo. The crude product is purified by column chromatography (silica gel, DCM/MeOH).

$C_7H_8BrNO_2$ (M=218.1 g/mol)
ESI-MS: 218/220 [M+H]+
R$_f$(HPLC): 0.55 (method E)

b) 4.50 g (20.6 mml) of the above mentioned product and 14.3 mL (103 mmol) TEA are added to 50 mL THF and chilled to 0° C. with an ice water bath. 3.59 mL (25.8 mmol) TFA anhydride are added and the reaction mixture is stirred at r.t. for 2 h. Afterwards the reaction mixture is poured into water, the org. layer is separated and washed with aq. sat. NaCl solution. Then the org. layer is dried over MgSO$_4$, filtered and the solvent is removed in vacuo. The crude product is purified by HPLC (ACN/H$_2$O/FA).

$C_7H_8BrNO_2$ (M=218.1 g/mol)
ESI-MS: 218/220 [M+H]+
R$_f$(HPLC): 0.74 (method M)

c) 4.20 g (19.3 mmol) of the above mentioned product, 13.7 g (96.3 mmol) methyliodide and 7.97 g (28.9 mmol) Ag$_2$CO$_3$ are added to 50 mL DCM and stirred at r.t. over night. The resulting precipitate is filtered off and the solvent is removed in vacuo. The crude product is purified by HPLC (ACN/H$_2$O/FA).

$C_8H_{10}BrNO_2$ (M=232.1 g/mol)
ESI-MS: 232/234 [M+H]+
R$_f$(HPLC): 1.14 (method M)

The following compounds are prepared analogously to example V.1:

| Ex. | Starting material | Product structure | Mass spec result | HPLC retention time (method) |
|---|---|---|---|---|
| V.1 | (5-bromo-2-ethoxypyridine) | (3-bromo-2-methoxy-6-ethoxypyridine) | 232/234 [M + H]+ | 1.14 (M) |

| Ex. | Starting material | Product structure | Mass spec result | HPLC retention time (method) |
|---|---|---|---|---|
| V.2 | 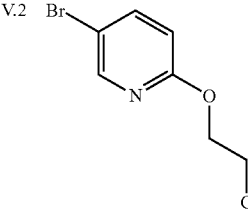 | 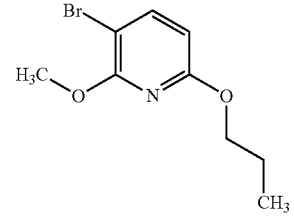 | 246/248 [M + H]⁺ | 1.20 (M) |

Example VI

Example VI.1

General Route

6-Bromo-N-(2,2-difluoroethyl)-N-methylpyridin-2-amine

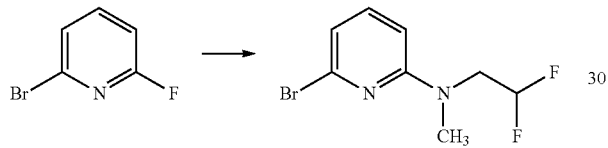

88.0 mg (0.50 mmol) 2-bromo-2-fluoropyridine, 78.9 mg (0.60 mmol) (2,2-difluoro-ethyl)-methyl-amine hydrochloride and 0.17 mL (1.00 mmol) DIPEA are stirred at 90° C. over night. The reaction is quenched by the addition of water and extracted with DCM. The combined org. layers are dried over MgSO$_4$, filtered and the solvent is removend in vacuo.

$C_8H_9BrF_2N_2$ (M=251.1 g/mol)
ESI-MS: 250/252 [M+H]⁺
R$_f$(HPLC): 0.93 (method K)

The following compounds are prepared analogously to example VI.1:

| Ex. | Starting material | Product structure | Mass spec result | HPLC retention time (method) |
|---|---|---|---|---|
| VI.1 |  | 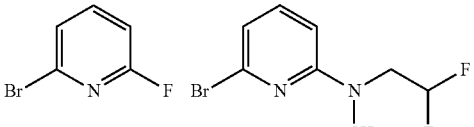 | 250/252 [M + H]⁺ | 0.93 (K) |
| VI.2 | 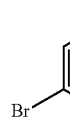 | 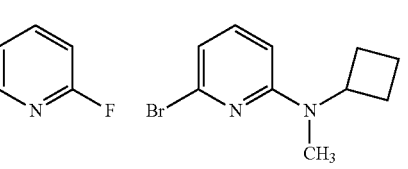 | 241/243 [M + H]⁺ | 1.04 (K) |

Example VII (S)-Benzyl 1-(4-hydroxyphenyl)ethylcarbamate

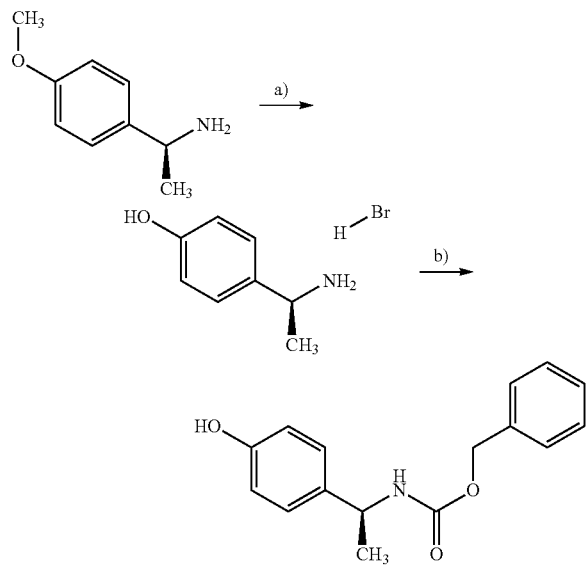

a) 10.0 g (66.1 mmol) (S)-4-methoxy-alpha-methylbenzylamine are added to 30 mL HBr (30% in AcOH) and stirred at 100° C. for 4 h. The reaction mixture is cooled to r.t. and the solvent is removed in vacuo. The crude product is used without further purification.

b) 5.00 g (22.9 mmol) 4-(1-amino-ethyl)-phenol hydrobromide are added to 10 mL THF and 10 mL $H_2O$ before 13.5 g (160 mmol) $NaHCO_3$ are added. Then 3.60 mL (25.2 mmol) benzyl chloroformate are added dropwise and the reaction mixture is stirred at r.t. for 3 h. Afterwards the reaction mixture is quenched by the addition of water and is set to a gentle acidic pH value using citric acid (10% in water). Then the product is extracted with EtOAc, the combined organic layers are dried over $MgSO_4$, filtered and the solvent is removed in vacuo. The crude product is purified by flash chromatography (silica gel, PE/EtOAc).

$C_{16}H_{17}NO_3$ (M=271.3 g/mol)
ESI-MS: 272 [M+H]$^+$
$R_t$(HPLC):1.65 min (method A)

Example VIII (R)-tert-Butyl 3-(4-((S)-1-(benzyloxycarbonylamino)ethyl)phenoxy)pyrrolidine-1-carboxylate

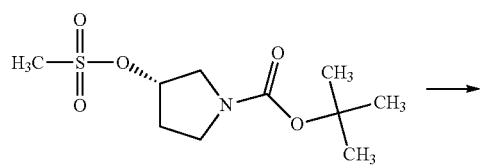

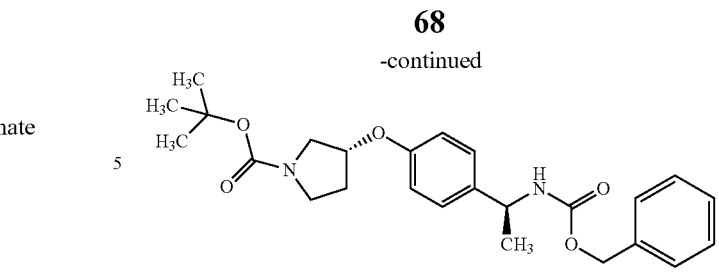

6.00 g (22.6 mmol) 3-methanesulfonyloxy-pyrrolidine-1-carboxylic acid tert-butyl ester*, 6.14 g (22.6 mmol) of example VII and 14.7 g (45.2 mmol) $Cs_2CO_3$ are added to 80 mL DMF and stirred at 80° C. over night. The reaction mixture is filtered, washed with MeOH and the solvent is removed in vacuo. The crude product is purified by HPLC (MeOH/$H_2O$/$NH_4OH$).

$C_{25}H_{32}N_2O_5$ (M=440.5 g/mol)
ESI-MS: 439 [M–H]$^-$
$R_t$(HPLC):1.22 min (method C)

*A representative procedure for the preparation of N-protected 3-methylsulfonyloxy-pyrrolidines can be found in Zersh et al. Synthesis 2011, 22, 3669-3674

Example IX

Example IX.1

General Route (R)-tert Butyl-3-(4-((S)-1-acetamidoethyl)phenoxy)pyrrolidine-1-carboxylate

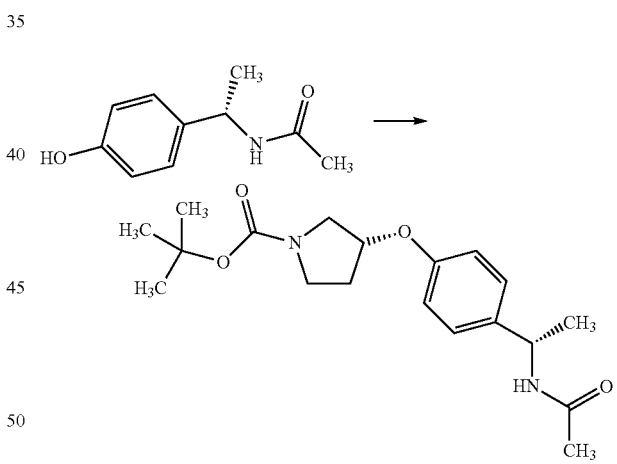

20.0 g (75.4 mmol) (S)-tert butyl 3-(methylsulfonyloxy)-pyrrolidine-1-carboxylate*, 13.5 g (75.4 mmol) of example 111.1 and 49.1 g (151 mmol) $Cs_2CO_3$ are added to 150 mL DMF and stirred for 16 h at 80° C. Then the reaction mixture is chilled to r.t., diluted with water and extracted with EtOAc (2×). The org. layers are combined, washed with aq. $NaHCO_3$ solution (3×) and dried over $MgSO_4$. After filtration the solvent is removed in vacuo and the crude product is purified by flash chromatography (silica gel, DCM/MeOH 93/7).

$C_{19}H_{28}N_2O_4$ (M=348.4 g/mol)
ESI-MS: 349 [M+H]$^+$
$R_t$(HPLC):1.02 min (method C)

The following compounds are prepared analogously to example IX.1:

| Ex. | Starting material (s) | Product structure | Mass spec result | HPLC retention time (method) |
|---|---|---|---|---|
| IX.1 | III.1 + (S)-tert Butyl 3-(methylsulfonyloxy)-pyrrolidine-1-carboxylate* | | 349 [M + H]⁺ | 1.02 (C) |
| IX.2 | III.1 + (R)-tert Butyl 3-(methysulfonyloxy)-pyrrolidine-1-carboxylate* | | 349 [M + H]⁺ | 2.15 (A) |
| IX.3 | III.2 + (S)-Benzyl 3-(methylsulfonyloxy)-pyrrolidine-1-carboxylate* | | 441 [M + H]⁺ | 1.22 (C) |

*A representative procedure for the preparation of N-protected 3-methylsulfonyloxy-pyrrolidines can be found in Zersh et al. Synthesis 2011, 22, 3669-3674;

Example X (trans)-tert-Butyl-3-(4-((1S)-1-acetamidoethyl)phenoxy)-4-hydroxypyrrolidine-1-carboxylate

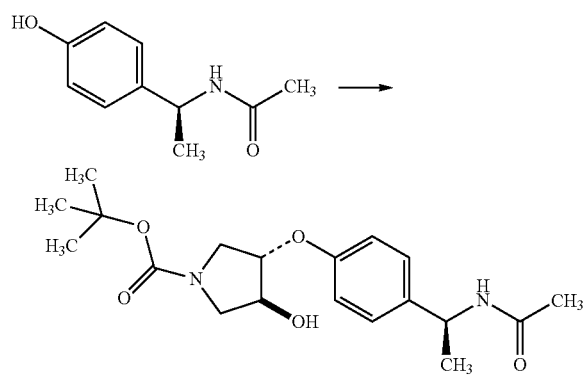

1.00 g (5.58 mmol) of example 111.1, 1.14 g (6.14 mmol) tert-butyl 6-oxa-3-azabicyclo-[3.1.0]hexane-3-carboxylate and 2.73 g (8.37 mmol) $Cs_2CO_3$ are added to 14 mL DMF and stirred at 80° C. over night. The reaction is quenched by the addition of water and extracted with EtOAc. The org. layers are combined, washed with aq. NaOH solution (c=1 mol/L) and dried over $MgSO_4$. After filtration the solvent is removed in vacuo.

$C_{19}H_{28}N_2O_5$ (M=364.4 g/mol)
ESI-MS: 365 [M+H]⁺
$R_t$(HPLC):0.94 min (method C)

Example XI (cis)-tert-Butyl-3-(4-((1S)-1-acetamidoethyl)phenoxy)-4-methoxypyrrolidine-1-carboxylate

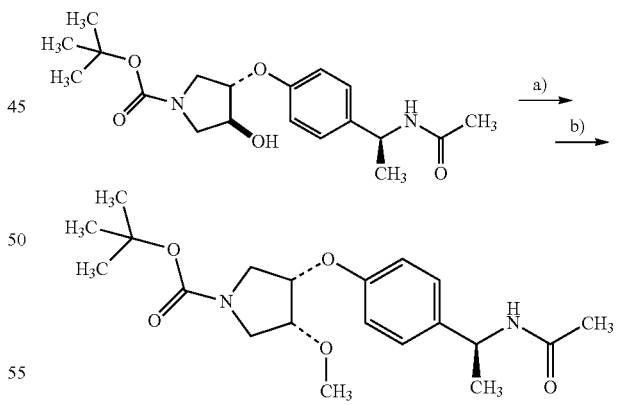

a) 0.50 g (1.37 mmol) of example X are added to 4 mL THF before 0.23 mL (1.65 mmol) TEA and 0.14 mL (1.65 mmol) MsCl are added and the resulting mixture is stirred at r.t. over night. The reaction is quenched by the addition of water and extracted with EtOAc. The org. layers are combined, dried over $MgSO_4$, filtered and the solvent is removed in vacuo.

b) 200 mg (0.45 mmol) of the above mentioned product is added to 1 mL DMF, then 21.7 mg (0.68 mmol) methanol and 16.3 mg (0.68 mmol) NaH are added and stirred at r.t. for 3 h.

The reaction is quenched by the addition of water and extracted with EtOAc. The org. layers are combined, dried over MgSO$_4$, filtered and the solvent is removed in vacuo. The crude product is purified by HPLC (MeOH/H$_2$O/NH$_4$OH).

C$_{20}$H$_{30}$N$_2$O$_5$ (M=378.5 g/mol)
ESI-MS: 379 [M+H]$^+$
R$_t$(HPLC):1.10 min (method L)

Example XII (cis)-tert-Butyl 3-(4-((S)-1-acetamidoethyl)phenoxy)-4-fluoropyrrolidine-1-carboxylate

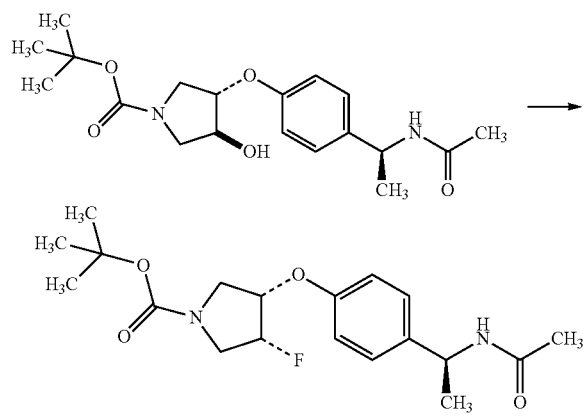

0.15 mL (0.41 mmol) of a Deoxo-Fluor® solution (50% in toluene) and 15.0 μL MeOH are added to 3 mL DCM in a closed vessel. Then 100 mg (0.27 mmol) of example X are added and stirred at r.t. over night. Afterwards the reaction is quenched by the addition of aq. sat.NaHCO$_3$ solution and extracted with EtOAc. The org. layers are combined, dried over MgSO$_4$, filtered and the solvent is removed in vacuo.

C$_{19}$H$_{27}$FN$_2$O$_5$ (M=366.4 g/mol)
R$_t$(HPLC):1.43 min (method M)

Example XIII

Example XIII.1

General Route

N—((S)-1-(4-((R)-Pyrrolidin-3-yloxy)phenyl)ethyl)acetamide hydrochloride

To 20.5 g (58.8 mmol) of example IX.1 in 200 mL dioxane are added 29.4 mL (118 mmol) HCl in dioxane (c=4 mol/L) and the resulting mixture is stirred at r.t. over night. Additional 15 mL (60 mmol) HCl in dioxane (c=4 mol/L) are added and stirring is continued for 1 d. Then the reaction mixture is treated with TBME and the precipitate is filtered off, washed with TBME and dried at 40° C. in vacuo.

C$_{14}$H$_{20}$N$_2$O$_2$*HCl (M=284.8 g/mol)
ESI-MS: 249 [M+H]$^+$
R$_t$(HPLC):0.63 min (method C)

The following compounds are prepared analogously to example XIII.1: For example XIII.3 the resulting product is transferred into the free base using an aq. NaOH solution (c=1 mol/L).

| Ex. | Starting material | Product structure | Mass spec result | HPLC retention time (method) |
|---|---|---|---|---|
| XIII.1 | IX.1 | | 249 [M + H]$^+$ | 0.63 (C) |
| XIII.2 | IX.2 | | 249 [M + H]$^+$ | 1.30 (A) |

-continued

| Ex. | Starting material | Product structure | Mass spec result | HPLC retention time (method) |
|---|---|---|---|---|
| XIII.3 | IX.1 | | 249 [M + H]+ | 0.54 (B) |
| XIII.4 | VIII | | 341 [M + H]+ | 1.00 (C) |
| XIII.5 | XI | | 279 [M + H]+ | 0.66 (C) |
| XIII.6 | XII | | 267 [M + H]+ | 0.62 (M) |

Example XIV (R)-Benzyl 3-(4-((S)-1-aminoethyl)phenoxy)pyrrolidine-1-carboxylate hydrochloride

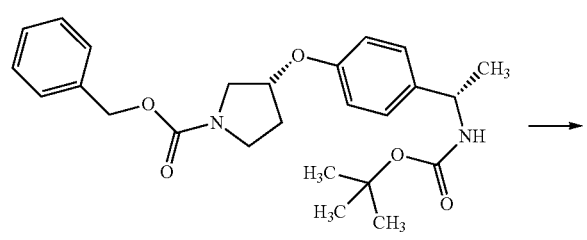

→

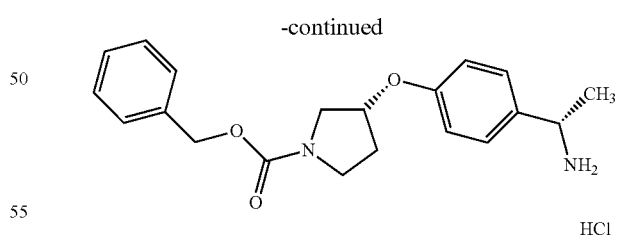

HCl 4.70 g (10.7 mmol) of example IX.3 in 25 mL dioxane are charged with 5.33 mL (21.3 mmol) of a HCl solution in dioxane (c=4 mol/L) and stirred at r.t. over night. The solvent is removed in vacuo and the residue is taken up in ethanol and the solvent is removed again. The resulting product is triturated with DIPE and dried at 50° C.

$C_{20}H_{24}N_2O_3$*HCl (M=376.9 g/mol)

ESI-MS: 324 [M+H−NH$_3$]+

R$_f$(HPLC):1.07 min (method C)

Example XV

Example XV.1

General Route (R)-Benzyl 3-(4-((S)-1-(thiazole-5-carboxamido)ethyl)phenoxy)pyrrolidine-1-carboxylate

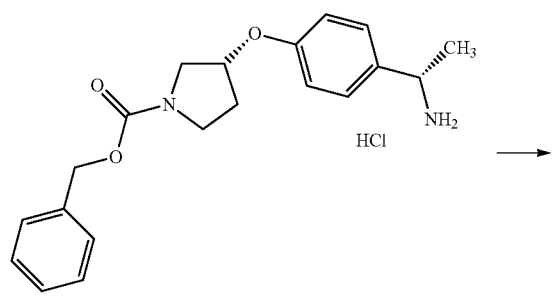

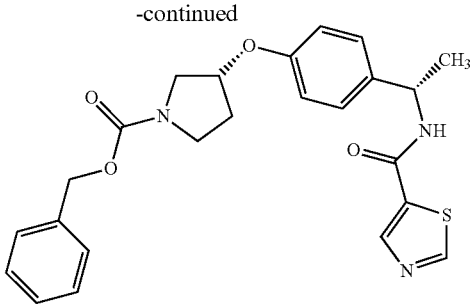

3.80 g (10.1 mmol) of example XIV in 20 mL DMF are charged with 5.15 mL (29.9 mmol) DIPEA, 3.80 g (11.5 mmol) TBTU and 1.29 g (9.99 mmol) thiazole-5-carboxylic acid and the resulting mixture is stirred at r.t. over night. Water is added and the mixture is extracted with EtOAc (3×). The organic layers are combined, dried over MgSO$_4$, filtered and the solvent is removed in vacuo. The crude product is purified by flash chromatography (silica gel, EtOAc). The product is added to EtOAc and washed with a saturated aq. NaHCO$_3$ solution (3×), dried over MgSO$_4$, filtered and the solvent is removed in vacuo.

$C_{24}H_{25}N_3O_4S$ (M=451.5 g/mol)
ESI-MS: 452 [M+H]$^+$
R$_t$(HPLC):0.92 min (method D)

The following compounds are prepared analogously to example XV.1:

| Ex. | Starting material | Product structure | Mass spec result | HPLC retention time (method) |
|---|---|---|---|---|
| XV.1 | XIV | | 452 [M + H]$^+$ | 0.92 (D) |
| XV.2 | XIV | | 523 [M + H]$^+$ | 1.08 (C) |
| XV.3 | XIV | | 537 [M + H]$^+$ | 0.72 (D) |

Example XVI (R)-Benzyl 3-(4-((S)-1-(cyclopropanecarboxamido)ethyl)phenoxy)pyrrolidine-1-carboxylate

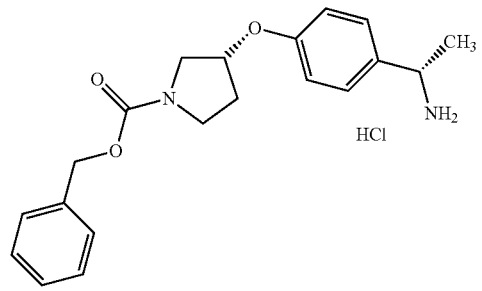

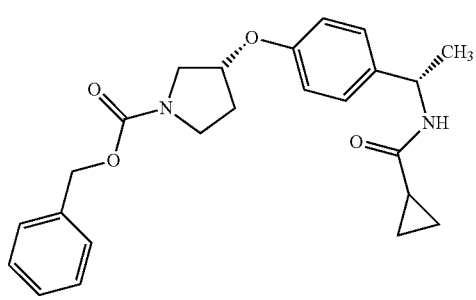

To 3.79 g (10.1 mmol) of example XIV and 5.00 mL (35.9 mmol) TEA in 50 mL DCM are slowly added 1.10 mL (11.9 mmol) cyclopropanecarbonyl chloride dissolved in 10 mL DCM. After stirring the mixture at r.t. for 3 h, the mixture is washed with water, dried over MgSO$_4$, filtered and the solvent is removed in vacuo. The resulting product is triturated with DIPE and dried at 50° C.

$C_{24}H_{28}N_2O_4$ (M=408.5 g/mol)
ESI-MS: 409 [M+H]$^+$
R$_f$(HPLC):1.25 min (method E)

Example XVII (R)-Benzyl 3-(4-((S)-1-(3,3-dimethylureido)ethyl)phenoxy)pyrrolidine-1-carboxylate

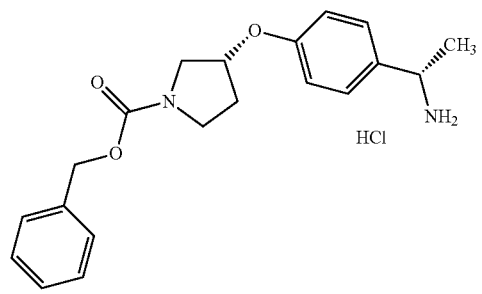

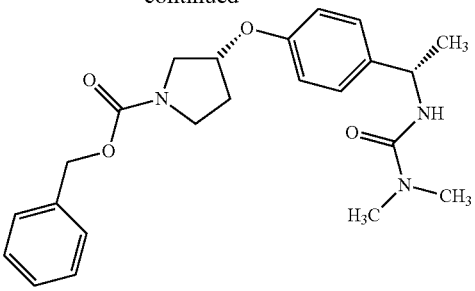

To 2.00 g (5.31 mmol) of example XIV and 1.86 mL (13.3 mmol) TEA in 40 mL DCM are added 0.91 g (5.57 mmol) CDT and the resulting mixture is stirred at r.t. for 15 min. Then 0.72 g (15.9 mmol) dimethylamine are added and stirring is continued over night. The solvent is removed in vacuo and the crude product is purified by HPLC (MeOH/H$_2$O/NH$_3$).

$C_{23}H_{29}N_3O_4$ (M=411.5 g/mol)
ESI-MS: 412 [M+H]$^+$
R$_f$(HPLC):1.05 min (method C)

Example XVIII

Example XVIII.1

General Route tert-Butyl (S)-1-(4-((R)-pyrrolidin-3-yloxy)phenyl)ethyl)carbamate

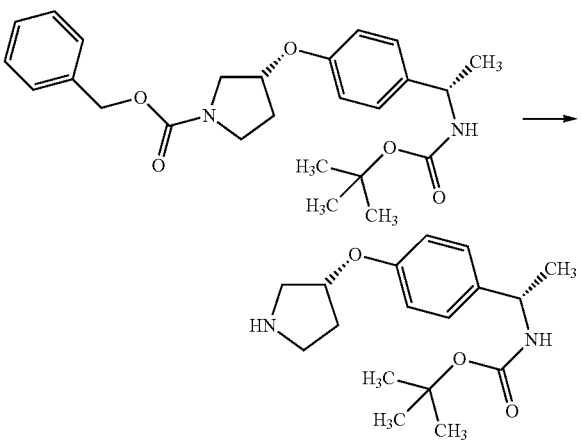

15.0 g (34.1 mmol) of example IX.3 in 200 mL methanol are hydrogenated at r.t. using 1.50 g Pd/C (10%) and a hydrogen pressure of 3 bar. After completion the reaction mixture is filtered and the solvent is removed in vacuo.

$C_{17}H_{26}N_2O_3$ (M=306.4 g/mol)
ESI-MS: 307 [M+H]$^+$
R$_f$(HPLC):1.01 min (method C)

The following compounds are prepared analogously to example XVIII.1: For example XVIII.2 the resulting product is transferred into the hydrochloride salt using a methanolic HCl solution (c=1.25 mol/L).

| Ex. | Starting material | Product structure | Mass spec result | HPLC retention time (method) |
|---|---|---|---|---|
| XVIII.1 | IX.3 | | 307 [M + H]+ | 1.01 (C) |
| XVIII.2 | XVI | | 275 [M + H]+ | 0.68 (E) |
| XVIII.3 | XVII | | 278 [M + H]+ | 0.68 (C) |

Example XIX

Example XIX.1

General Route

2-Acetamido-4-methyl-N—((S)-1-(4-((R)-pyrrolidin-3-yloxy)phenyl)ethyl)thiazole-5-carboxamide

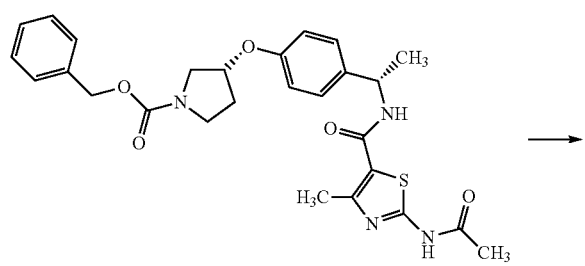

→

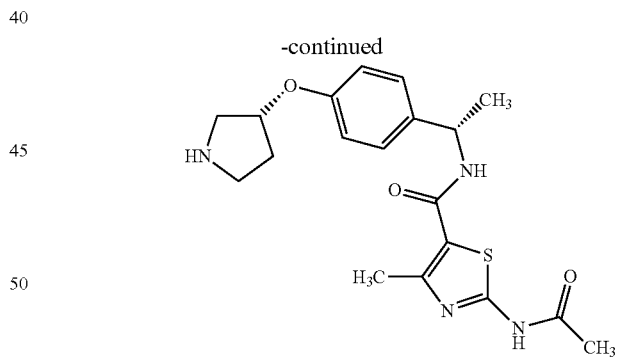

2.00 g (3.83 mmol) of example XV.2 in 50 mL ACN are chilled by using an ice-water bath and charged with 2.60 mL (19.1 mmol) TMSI. The cooling is removed and the mixture is stirred at r.t. for 1 h. The reaction is quenched by the addition of some water. Solvent is removed in vacuo and the crude product is purified by HPLC (MeOH/H₂O/NH₃).

$C_{13}H_{24}N_4O_3S$ (M=388.5 g/mol)

ESI-MS: 389 [M+H]+

R$_t$(HPLC):0.77 min (method C)

The following compounds are prepared analogously to example XIX.1:

| Ex. | Starting material | Product structure | Mass spec result | HPLC retention time (method) |
|---|---|---|---|---|
| XIX.1 | XV.2 | | 389 [M + H]+ | 0.77 (C) |
| XIX.2 | XV.1 | | 318 [M + H]+ | 0.55 (D) |
| XIX.3 | XV.3 | | 403 [M + H]+ | 0.72 (D) |

Example XX

Example XX.1

General Route

N—((S)-1-(4-((R)-1-(2-Chloro-3-fluoropyridin-4-yl) pyrrolidin-3-yloxy)phenyl)ethyl)acetamide

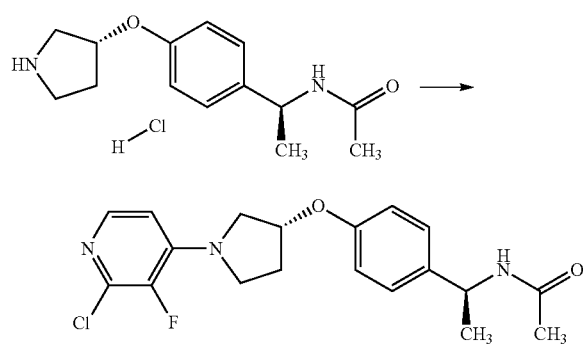

0.95 g (3.34 mmol) of example XII.1, 0.59 g (3.52 mmol) 2,4-dichloro-3-fluoro-pyridine and 1.90 g (13.7 mmol) $K_2CO_3$ are added to 6 mL NMP and stirred at 80° C. over night. The reaction is quenched by the addition water and extracted with EtOAc (3×). The combined organic layers are dried over $MgSO_4$, filtered and the solvent is removed in vacuo. The crude product is purified by HPLC (ACN/$H_2O$/FA).

$C_{19}H_{21}ClFN_3O_2$ (M=377.8 g/mol)

ESI-MS: 378 [M+H]+

$R_t$(HPLC):0.93 min (method D)

The following compounds are prepared analogously to example XX.1:

For the examples XX.7, XX.10 and XX.13 the reaction is done in THF/DMF (10/1), with TEA as base and the reaction temperature is 0° C. for 5 h and at r.t. over night.

For example XX.8 the reaction is done in THF/DMF (10/1), with DIPEA as base at reflux over night.

For example XX.11 the reaction is done in THF with TEA as base and the reaction conditions are 70° C. for 5 h.

| Ex. | Starting materials | Product structure | Mass spec result | HPLC retention time (method) |
|---|---|---|---|---|
| XX.1 | XIII.1 + 2,4-dichloro-3-fluoro-pyridine | | 378 [M + H]⁺ | 0.93 (D) |
| XX.2 | XIII.1 + 4,6-dichloro nicotinonitrile | | 385 [M + H]⁺ | 1.10 (E) |
| XX.3 | XIII.1 + 2,6-difluoro-pyridine | | 344 [M + H]⁺ | 1.00 (M) |
| XX.4 | XIII.1 + 2,3,6-trifluoro-pyridine | | 362 [M + H]⁺ | 0.88 (K) |
| XX.5 | XIII.1 + 2-chloro-3-fluoro-4-iodopyridine | | 470 [M + H]⁺ | 0.95 (M) |
| XX.6 | XIII.1 + 2,4-dichloro-3-fluoropyridine | | 378 [M + H]⁺ | 0.96 (M) |

-continued

| Ex. | Starting materials | Product structure | Mass spec result | HPLC retention time (method) |
|---|---|---|---|---|
| XX.7 | XIII.1 + 2,4 difluoropyridine | | 344 [M + H]⁺ | 0.79 (M) |
| XX.8 | XIII.1 + 2,3,5,6-tetrafluoropyridine | | 380 [M + H]⁺ | 1.06 (E) |
| XX.9 | XVIII.1 + 2,4-dichloro-3-fluoropyridine | | 436 [M + H]⁺ | 1.02 (K) |
| XX.10 | XVIII.2 + 2,4 difluoropyridine | | 370 [M + H]⁺ | 0.98 (E) |
| XX.11 | XVIII.1 + 2-fluoro-6-trifluoromethyl pyridine | | 452 [M + H]⁺ | 0.95 (K) |

-continued

| Ex. | Starting materials | Product structure | Mass spec result | HPLC retention time (method) |
|---|---|---|---|---|
| XX.12 | XIX.2 + 2,4 difluoro-pyridine | | 413 [M + H]+ | 0.84 (M) |
| XX.13 | XVIII.1 + 2,4 difluoro-pyridine | | 402 [M + H]+ | 0.87 (D) |
| XX.14 | XVIII.3 + 2,4-dichloro-3-fluoro-pyridine | | 407 [M + H]+ | 0.94 (M) |

Example XXI

Example XXI.1

General Route

N—((S)-1-(4-((R)-1-(2-Chloro-3-methylpyridin-4-yl)pyrrolidin-3-yloxy)phenyl)ethyl)acetamide

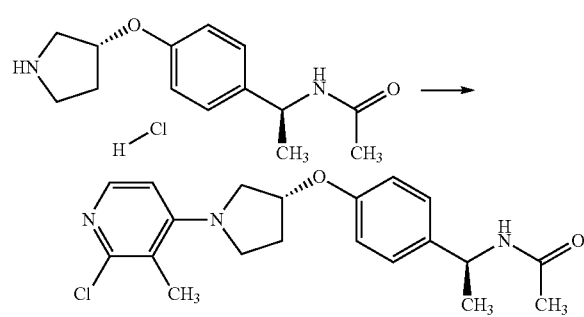

Under inert gas atmosphere 0.80 g (2.53 mmol) of example XIII.1, 0.65 g (2.53 mmol) of 2-chloro-4-iodo-3-methyl-pyridine, 1.00 g (10.4 mmol) NaOtBu and 100 mg (0.14 mmol) chloro(2-dicyclohexylphosphino-2',4',6'-triisopropyl-1,1'-biphenyl)(2-(2-aminoethyl)-phenyl)-palladium (II) are added to 50 mL dioxane and stirred at 45° C. over night. Afterwards the solvent is removed, water is added and the product is extracted with EtOAc. The organic layer is dried over MgSO$_4$, filtered and the solvent is removed in vacuo. The crude product is purified by HPLC (ACN/H$_2$O/TFA).

$C_{20}H_{24}ClN_3O_2$ (M=373.9 g/mol)

ESI-MS: 374 [M+H]+

R$_t$(HPLC):0.77 min (method M)

The following compounds are prepared analogously to example XXI.1:

For example XXI.3 and XXI.10 the reaction temperature is 70-80° C. for 3-4 h.

For example XXI.5 the reaction time is 3 h.

For example XXI.6 the reaction conditions are 80° C. over night,

| Ex. | Starting material | Product structure | Mass spec result | HPLC retention time (method) |
|---|---|---|---|---|
| XXI.1 | XIII.1 + 2,4-dichloro-3-methylpyridine | | 374 [M + H]+ | 0.77 (M) |
| XXI.2 | XIII.1 + 2-bromo-4-hydroxy-pyridine | | 342 [M + H]+ | 0.90 (N) |
| XXI.3 | XIII.1 + 4-chloro-2,5-difluoro-pyridine | | 362 [M + H]+ | 0.80 (K) |
| XXI.4 | XIII.4 + 4-bromo-2-(iso-propoxy)-pyridine | | 476 [M + H]+ | 1.69 (L) |
| XXI.5 | XVIII.1 + XXXII.1 | | 490 [M + H]+ | 1.25 (C) |
| XXI.6 | XVIII.1 + XXIV.27 | | 490 [M + H]+ | 1.16 (E) |
| XXI.7 | XVIII.1 + 1-cyclopropyl-methoxy-4-iodo-benzene | | 453 [M + H]+ | 1.18 (M) |

-continued

| Ex. | Starting material | Product structure | Mass spec result | HPLC retention time (method) |
|---|---|---|---|---|
| XXI.8 | XVIII.1 + XXV.13 | (structure: 2-cyclopropylmethoxy-pyridin-4-yl pyrrolidinyloxy phenyl (S)-ethyl Boc-carbamate) | n.d. | TLC: R$_f$ = 0.80 (silica gel, PE/EtOAc 10/1) |
| XXI.9 | XIII.1 + 2,3-dichloro-4-iodo-pyridine | (structure: 2,3-dichloropyridin-4-yl pyrrolidinyloxy phenyl (S)-ethyl acetamide) | 394 [M + H]$^+$ | 0.93 (M) |
| XXI.10 | XIII.1 + XXV.22 | (structure: 2-chloro-3-methoxy-pyridin-4-yl pyrrolidinyloxy phenyl (S)-ethyl acetamide) | 390 [M + H]$^+$ | 0.81 (M) |
| XXI.11 | XIX.3 + 2,3-dichloro-4-iodo-pyridine | (structure: 2,3-dichloropyridin-4-yl pyrrolidinyloxy phenyl (S)-ethyl methylthiazole propionamide) | 548 [M + H]$^+$ | 1.05 (D) |
| XXI.12 | XIX.3 + 2-chloro-3-fluoro-4-iodo-pyridine | (structure: 2-chloro-3-fluoropyridin-4-yl pyrrolidinyloxy phenyl (S)-ethyl methylthiazole propionamide) | 532 [M + H]$^+$ | 1.02 (D) |

Example XXII

Example XXII.1

General Route (1S)-1-(4-((3R)-1-(5-((2,2-Difluorocyclopropyl)methoxy)pyridin-2-yl)pyrrolidin-3-yloxy)phenyl)ethanamine

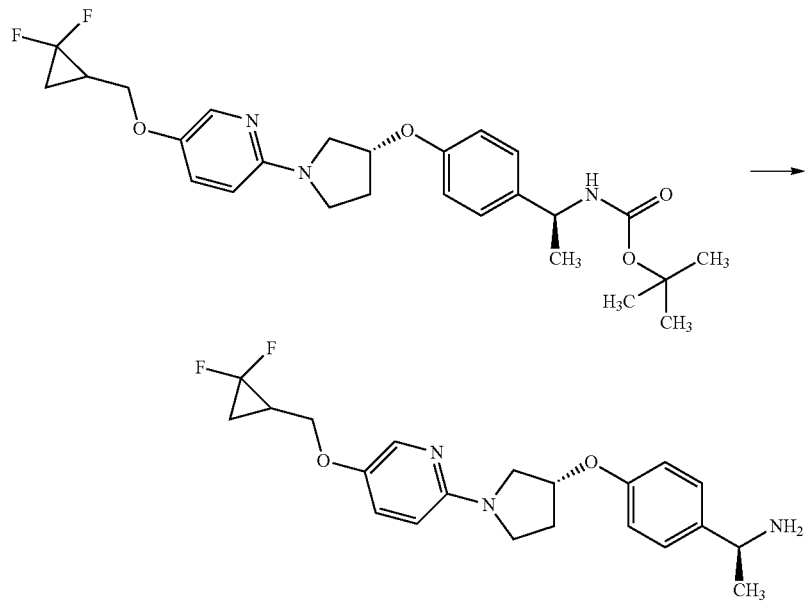

To 0.80 g (1.63 mmol) of example XXI.5 in 2.0 mL dioxane are added 1.23 mL (4.90 mmol) HCl in dioxane (c=4 mol/L) and the resulting mixture is stirred ar r.t. over night. Then the reaction mixture is treated with half sat. aq. NaHCO$_3$ solution and the precipitate is filtered off, washed with H$_2$O and dried at 40° C. in vacuo.

$C_{21}H_{25}F_2N_3O_2$ (M=389.4 g/mol)
ESI-MS: 390 [M+H]$^+$
R$_t$(HPLC):1.16 min (method C)

The following compounds are prepared analogously to example XXII.1:

For example XXII.3 after the reaction the solvent is removed in vacuo and the crude product is purified by HPLC (ACN/H$_2$O/NH$_3$).

For example XXII.5 the solvent of the reaction mixture is removed in vacuo.

| Ex. | Starting material | Product structure | Mass spec result | HPLC retention time (method) |
|---|---|---|---|---|
| XXII.1 | XXI.5 | (structure) | 390 [M + H]$^+$ | 1.16 (C) |
| XXII.2 | XXI.6 | (structure) | 390 [M + H]$^+$ | 0.90 (K) |

-continued

| Ex. | Starting material | Product structure | Mass spec result | HPLC retention time (method) |
|---|---|---|---|---|
| XXII.3 | XX.11 | | 352 [M + H]+ | 1.38 (R) |
| XXII.4 | XXI.7 | | 353 [M + H]+ | 1.22 (C) |
| XXII.5 | XXI.8 | | 354 [M + H]+ | 0.87 (K) |

Example XXIII (S)-1-(4-((R)-1-(2-iso-Propoxypyridin-4-yl)pyrrolidin-3-yloxy)phenyl)ethanamine

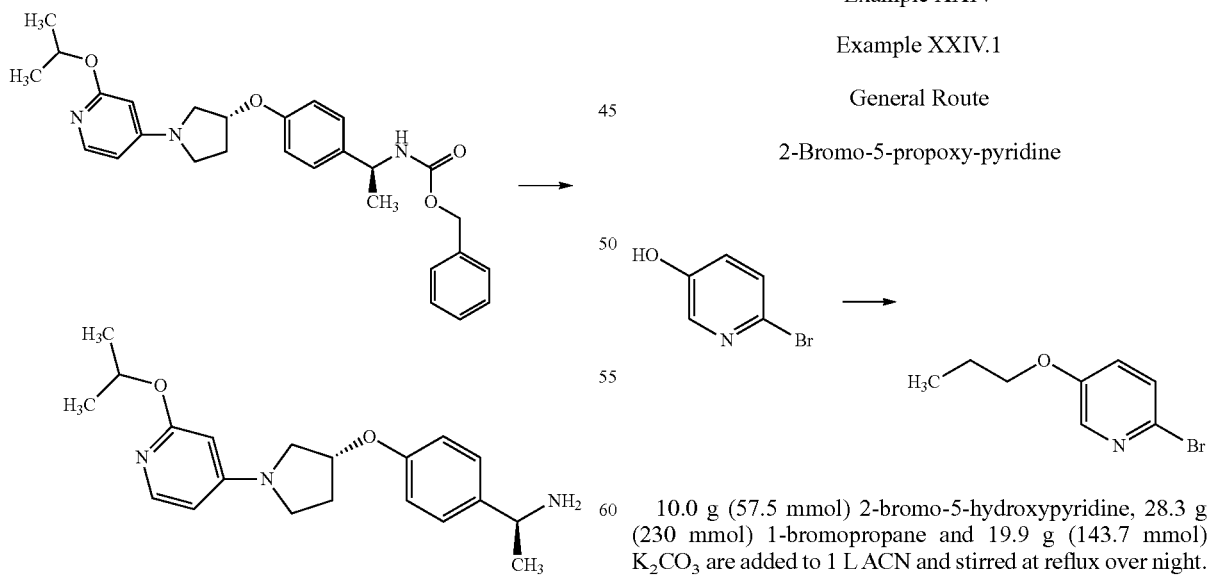

2.50 g (5.26 mmol) of example XXI.4 in 50 mL ACN are chilled by using an ice-water bath and charged with 3.58 mL (26.3 mmol) TMSI. The cooling is removed and the mixture is stirred at r.t. for 20 min. Then the solvent is removed in vacuo and the crude product is purified by HPLC (MeOH/H$_2$O/NH$_3$).
C$_{20}$H$_{27}$N$_3$O$_2$ (M=341.5 g/mol)
ESI-MS: 342 [M+H]+
R$_t$(HPLC):1.11 min (method C)

Example XXIV

Example XXIV.1

General Route

2-Bromo-5-propoxy-pyridine 10.0 g (57.5 mmol) 2-bromo-5-hydroxypyridine, 28.3 g (230 mmol) 1-bromopropane and 19.9 g (143.7 mmol) K$_2$CO$_3$ are added to 1 L ACN and stirred at reflux over night. Afterwards the reaction is quenched by the addition of water and extracted with TBME. The org. layers are combined, dried over MgSO$_4$, filtered and the solvent is removed in vacuo. The crude product is purified by column chromatography (silica gel, PE/EtOAc).

$C_8H_{10}BrNO$ (M=216.1 g/mol)
ESI-MS: 216/218 [M+H]$^+$
R$_t$(HPLC):1.88 min (method C)
The following compounds are prepared analogously to example XXIV.1:
For the examples XXIV.10-XXIV.14, XXIV.16-XXIV.18 and XXIV.23 the reaction is done in DMF.

For the examples XXIV.17-XXIV.18 $Cs_2CO_3$ is used as base.
For the examples XXIV.27 and XXIV.28 a separation of the enantiomers (example XXIV.3) was performed using chiral SFC: column: Daicel ADH (200 mm×25 mm; 5 μm); flow: 55 mL/min; solvent: $CO_2$/MeOH (95/5) with diethylamine (0.2%).

| Ex. | Starting material | Starting material | Product structure | Mass spec result | HPLC retention time (method) |
|---|---|---|---|---|---|
| XXIV.1 | | | | 216/218 [M + H]$^+$ | 1.88 (C) |
| XXIV.2 | | | | 230/232 [M + H]$^+$ | 2.00 (A) |
| XXIV.3 | | | | 264/266 [M + H]$^+$ | 0.95 (K) |
| XXIV.4 | | | | 228/230 [M + H]$^+$ | 1.00 (C) |
| XXIV.5 | | | | 242/244 [M + H]$^+$ | 1.55 (L) |
| XXIV.6 | | | | 230/232 [M + H]$^+$ | 1.04 (C) |
| XXIV.7 | | | | 234/236 [M + H]$^+$ | 0.90 (C) |
| XXIV.8 | | | | 248/250 [M + H]$^+$ | 0.92 (C) |
| XXIV.9 | | | | 252/254 [M + H]$^+$ | 0.86 (K) |
| XXIV.10 | | | | 202 [M + H]$^+$ | 1.20 (H) |

| Ex. | Starting material | Starting material | Product structure | Mass spec result | HPLC retention time (method) |
|---|---|---|---|---|---|
| XXIV.11 | HO-pyridine(F)(Cl) | H₃C-CH₂-Br | H₃C-CH₂-O-pyridine(F)(Cl) | 176 [M + H]⁺ | 1.07 (H) |
| XXIV.12 | HO-pyridine(F)(Cl) | H₃C-CH₂-CH₂-Br | H₃C-CH₂-CH₂-O-pyridine(F)(Cl) | 190 [M + H]⁺ | 1.49 (N) |
| XXIV.13 | HO-pyridine(F)(Cl) | cyclobutyl-Br | cyclobutyl-O-pyridine(F)(Cl) | 202 [M + H]⁺ | 1.07 (C) |
| XXIV.14 | HO-pyridine(F)(Cl) | H₃C-CH(I)-CH₃ | H₃C-CH(CH₃)-O-pyridine(F)(Cl) | 190 [M + H]⁺ | 1.85 (G) |
| XXIV.15 | HO-pyridine(F)(Cl) | 2,2-difluorocyclopropyl-CH₂-OTs | 2,2-difluorocyclopropyl-CH₂-O-pyridine(F)(Cl) | 238 [M + H]⁺ | 1.09 (M) |
| XXIV.16 | HO-pyridine(F)(Cl) | CF₃-CH₂-I | CF₃-CH₂-O-pyridine(F)(Cl) | 229 [M + H]⁺ | 3.07 (F) |
| XXIV.17 | HO-pyridine(Cl) | cyclopropyl-Br | cyclopropyl-O-pyridine(Cl) | 170 [M + H]⁺ | 2.80 (F) |
| XXIV.18 | HO-pyridine(F)(Cl) | cyclopropyl-Br | cyclopropyl-O-pyridine(F)(Cl) | 188 [M + H]⁺ | 1.81 (G) |
| XXIV.19 | HO-pyridine(Cl)(Cl) | H₃C-CH₂-CH₂-Br | H₃C-CH₂-CH₂-O-pyridine(Cl)(Cl) | 206 [M + H]⁺ | 0.97 (K) |
| XXIV.20 | HO-pyridine(Cl)(Cl) | 2,2-difluorocyclopropyl-CH₂-OTs | 2,2-difluorocyclopropyl-CH₂-O-pyridine(Cl)(Cl) | 254 [M + H]⁺ | 1.06 (C) |
| XXIV.21 | HO-pyridine(Cl)(Cl) | H₃C-CH₂-I | H₃C-CH₂-O-pyridine(Cl)(Cl) | 192 [M + H]⁺ | 1.01 (C) |

-continued

| Ex. | Starting material | Starting material | Product structure | Mass spec result | HPLC retention time (method) |
|---|---|---|---|---|---|
| XXIV.22 | 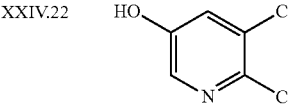 |  | 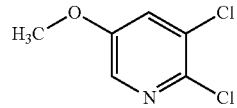 | 178 [M + H]⁺ | 1.06 (E) |
| XXIV.23 | 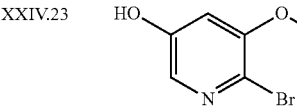 |  | 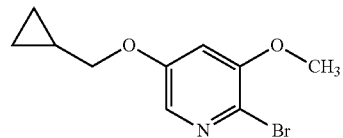 | 258/260 [M + H]⁺ | TLC: $R_f$ = 0.70 (silica gel, PE/EtOAc 5/1) |
| XXIV.24 | 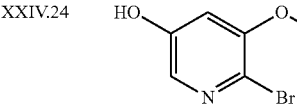 | 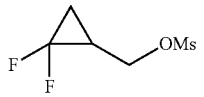 | 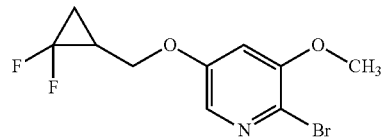 [SMILES: COc1cc(OCC2CC2(F)F)cnc1Br] | 294/296 [M + H]⁺ | TLC: $R_f$ = 0.70 (silica gel, PE/EtOAc 5/1) |
| XXIV.25 | 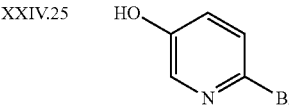 | 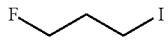 | 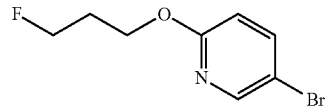 [SMILES: FCCCOc1ccc(Br)cn1] | 234/236 [M + H]⁺ | 0.79 (E) |
| XXIV.26 | 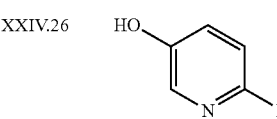 |  | 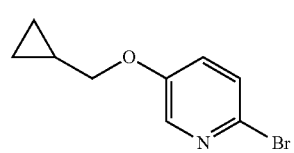 [SMILES: Brc1ccc(OCC2CC2)cn1] | 228/230 [M + H]⁺ | 0.95 (C) |
| XXIV.27 | 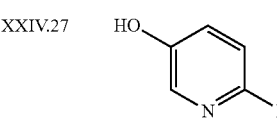 | 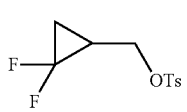 | 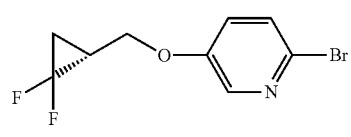 | 264/266 [M + H]⁺ | 1.08 (E) |
| XXIV.28 | 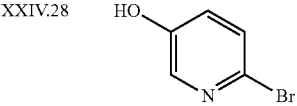 | 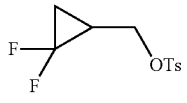 | 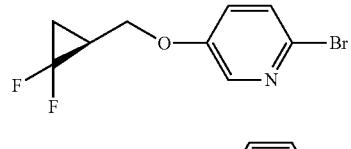 | 264/266 [M + H]⁺ | 1.08 (E) |
| XXIV.29 | 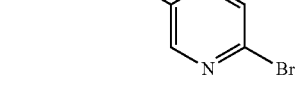 | 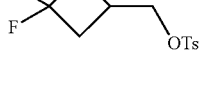 | 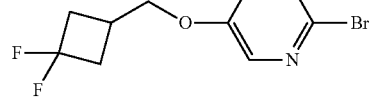 | 278/280 [M + H]⁺ | 1.03 (M) |

Example XXV

Example XXV.1

General Route

5-Bromo-2-cyclopropylmethoxy-pyridine

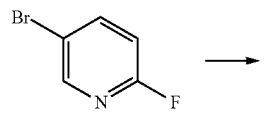

→

-continued

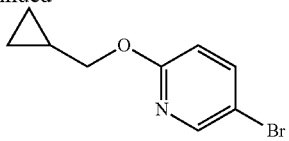

0.49 g (6.82 mmol) cyclopropane methanol in 10 mL THF are charged with 0.42 g (11.4 mmol) NaH and the reaction mixture is stirred at r.t. for 20 min. Then 1.00 g (5.68 mmol) 5-bromo-2-fluoropyridine are added and the mixture is stirred at r.t. over night. The reaction is quenched by the addition of water and extracted with EtOAc. The organic layers are combined, dried over MgSO₄, filtered and the solvent is removed in vacuo. The crude product is purified by HPLC (MeOH/H₂O/FA).

$C_9H_{10}BrNO$ (M=228.1 g/mol)
ESI-MS: 228/229 $[M+H]^+$
$R_t$(HPLC):1.14 min (method C)

The following compounds are prepared analogously to example XXV.1:

For example XXV.4 the reaction conditions are 50° C. for 4 h.

For examples XXV.10-XXV.13 and XXV.19-XXV.21 the reaction time is 2 h.

For example XXV.9 no solvent is used and the reaction temperature is 95° C.

For the examples XXV.4, XXV.10-XXV.12, XXV.15-XXV.16 and XXV.19-XXV.21 the reaction is done in DMF.

For example XXV.18 the reaction is done in DMSO at 100° C.

For example XXV.21 toluene is used as solvent and the reaction conditions are 50° C. for 1 h.

For example XXV.22 methyltetrahydrofurane is used as solvent at 0° C. for the deprotonation and 50° C. for the substitution.

| Ex. | Starting material | Starting material | Product structure | Mass spec result | HPLC retention time (method) |
|---|---|---|---|---|---|
| XXV.1 | 5-bromo-2-fluoropyridine | cyclopropylmethanol | cyclopropylmethoxy-5-bromopyridine | 228/230 $[M + H]^+$ | 1.14 (C) |
| XXV.2 | 4-bromo-2-fluoropyridine | cyclopropylmethanol | cyclopropylmethoxy-4-bromopyridine | 228/230 $[M + H]^+$ | 1.15 (C) |
| XXV.3 | 4-bromo-2-fluoropyridine | propanol | propoxy-4-bromopyridine | 216/218 $[M + H]^+$ | 1.15 (C) |
| XXV.4 | 4-iodo-2-fluoropyridine | phenol | phenoxy-4-iodopyridine | 298 $[M + H]^+$ | 3.64 (F) |
| XXV.5 | 4-bromo-2-fluoropyridine | (2,2-difluorocyclopropyl)methanol | (2,2-difluorocyclopropyl)methoxy-4-bromopyridine | 264/266 $[M + H]^+$ | 1.31 (B) |
| XXV.6 | 4-iodo-5-methyl-2-fluoropyridine | ethanol | ethoxy-4-iodo-5-methylpyridine | 264 $[M + H]^+$ | 1.63 (N) |
| XXV.7 | 4-iodo-5-methyl-2-fluoropyridine | cyclopropylmethanol | cyclopropylmethoxy-4-iodo-5-methylpyridine | 290 $[M + H]^+$ | 1.24 (C) |
| XXV.8 | 3-bromo-6-chloro-2-methylpyridine | propanol | propoxy-3-bromo-6-methylpyridine | 230/232 $[M + H]^+$ | 1.40 (E) |

-continued

| Ex. | Starting material | Starting material | Product structure | Mass spec result | HPLC retention time (method) |
|---|---|---|---|---|---|
| XXV.9 | 5-hydroxy-3-methyl-2-bromopyridine | 1-bromopropane | 5-propoxy-3-methyl-2-bromopyridine | 230/232 [M + H]+ | 1.24 (E) |
| XXV.10 | 5-hydroxy-3-methyl-2-bromopyridine | bromomethylcyclopropane | 5-(cyclopropylmethoxy)-3-methyl-2-bromopyridine | 242/244 [M + H]+ | 1.23 (E) |
| XXV.11 | 5-bromo-4-methyl-2-chloropyridine | (2,2-difluorocyclopropyl)methanol | 2-((2,2-difluorocyclopropyl)methoxy)-4-methyl-5-bromopyridine | 278/280 [M + H]+ | 1.34 (E) |
| XXV.12 | 5-bromo-2-fluoropyridine | (2,2-difluorocyclopropyl)methanol | 2-((2,2-difluorocyclopropyl)methoxy)-5-bromopyridine | 264/266 [M + H]+ | 1.27 (E) |
| XXV.13 | 4-bromo-2-fluoropyridine | cyclopropylmethanol | 2-(cyclopropylmethoxy)-4-bromopyridine | 228/230 [M + H]+ | 1.15 (C) |
| XXV.14 | 5-bromo-4-methyl-2-chloropyridine | 1-propanol | 2-propoxy-4-methyl-5-bromopyridine | 230/232 [M + H]+ | 1.37 (E) |
| XXV.15 | 2-bromo-3-methyl-5-chloropyridine | ethanol | 5-ethoxy-3-methyl-2-bromopyridine | 216/218 [M + H]+ | 1.12 (E) |
| XXV.16 | 5-methyl-4-iodo-2-fluoropyridine | cyclopropylmethanol | 2-(cyclopropylmethoxy)-4-iodo-5-methylpyridine | 290 [M + H]+ | 1.24 (C) |
| XXV.17 | 4-bromo-2-fluoropyridine | 3-hydroxypyridine | 2-(pyridin-3-yloxy)-4-bromopyridine | 251/253 [M + H]+ | 0.98 (N) |

| Ex. | Starting material | Starting material | Product structure | Mass spec result | HPLC retention time (method) |
|---|---|---|---|---|---|
| XXV.18 | | | | 326 [M + H]+ | 0.61 (U) |
| XXV.19 | | | | 278 [M + H]+ | 0.62 (U) |
| XXV.20 | | | | 300 [M + H]+ | 1.11 (K) |
| XXV.21 | | | | 258/260 [M + H]+ | 1.10 (M) |
| XXV.22 | | | | 270 [M + H]+ | 0.82 (K) |

Example XXVI

Example XXVI.1

General Route

2-Bromo-5-(3,3,3-trifluoro-propoxy)-pyridine

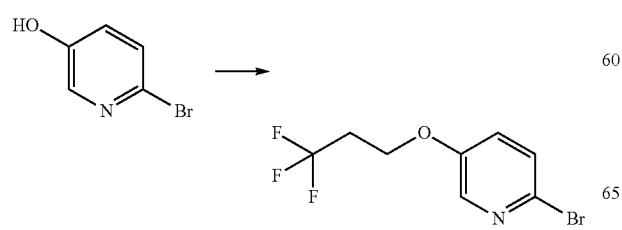

1.00 g (5.75 mmol) 2-bromo-5-hydroxypyridine, 0.66 g (5.75 mmol) 3,3,3-trifluoro-1-propanol and 1.51 g (5.75 mmol) triphenylphosphine are added to 50 mL THF. Then 1.32 g (5.75 mmol) di-tert-butyl azodicarboxylate are added and the reaction mixture is stirred at 60° C. for 3 h. The solvent is removed in vacuo and the crude product is purified by column chromatography (silica gel, PE/EtOAc).

$C_8H_7BrF_3NO$ (M=270.1 g/mol)

ESI-MS: 270/272 [M+H]+

$R_t$(HPLC):0.94 min (method C)

The following compounds are prepared analogously to example XXVI.1:

| Ex. | Starting material | Starting material | Product structure | Mass spec result | HPLC retention time (method) |
|---|---|---|---|---|---|
| XXVI.1 | HO-pyridine-Br | HO-CH2CH2-CF3 | CF3-CH2CH2-O-pyridine-Br | 270/272 [M + H]+ | 0.94 (C) |
| XXVI.2 | HO-pyridine-Br | HO-CH2-cyclopropyl | cyclopropyl-CH2-O-pyridine-Br | 242/244 [M + H]+ | 1.55 (L) |
| XXVI.3 | HO-pyridine(F)-Cl | HO-CH2-cyclopropyl | cyclopropyl-CH2-O-pyridine(F)-Cl | 216 [M + H]+ | 1.14 (C) |
| XXVI.4 | HO-pyridine(F)-Cl | HO-cyclopentyl | cyclopentyl-O-pyridine(F)-Cl | 216/218 [M + H]+ | 3.44 (F) |

Example XXVII

Example XXVII.1

General Route

4-Bromo-2-ethoxy-5-fluoro-pyridine 0.20 g (1.04 mmol) 4-bromo-5-fluoro-pyridin-2-ol, 0.83 mL (10.4 mmol) ethyliodide and 0.43 g (1.56 mmol) $Ag_2CO_3$ are added to 5 mL DCM and stirred at r.t. over night. The reaction is quenched by the addition of water. DCM is added, the resulting mixture is filtered and the organic layer is separated, dried over $MgSO_4$, filtered again and the solvent is removed in vacuo.

$C_7H_7BrFNO$ (M=220.0 g/mol)

ESI-MS: 220/222 [M+H]+

$R_t$(HPLC):1.27 min (method B)

The following compounds are prepared analogously to example XXVII.1:

For example XXVII.6 $K_2CO_3$ and KI are additionally added and the reaction is done at 40° C.

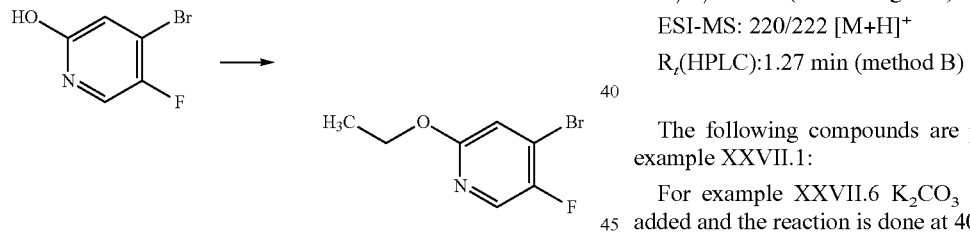

| Ex. | Starting material | Starting material | Product structure | Mass spec result | HPLC retention time (method) |
|---|---|---|---|---|---|
| XXVII.1 | HO-pyridine(Br)-F | I-CH2CH3 | H3C-CH2-O-pyridine(Br)-F | 220/222 [M + H]+ | 1.27 (B) |
| XXVII.2 | HO-pyridine(Br)-F | I-CH2CH2-CH3 | H3C-CH2CH2-O-pyridine(Br)-F | 234/236 [M + H]+ | 0.85 (D) |

| Ex. | Starting material | Starting material | Product structure | Mass spec result | HPLC retention time (method) |
|---|---|---|---|---|---|
| XXVII.3 | HO-pyridine(Br,F) | I-CH2-cyclopropyl | cyclopropyl-CH2-O-pyridine(Br,F) | 246/248 [M + H]+ | 0.89 (D) |
| XXVII.4 | HO-pyridine(Br,F) | I-CH(CH3)2 | (CH3)2CH-O-pyridine(Br,F) | 234/236 [M + H]+ | 0.90 (D) |
| XXVII.5 | HO-pyridine(Br,F) | I-CH2-CH(CH3)2 | (CH3)2CH-CH2-O-pyridine(Br,F) | 248/250 [M + H]+ | 0.93 (D) |
| XXVII.6 | HO-pyridine(Br,F) | Br-CH2-cyclopropyl(F,F) | F2-cyclopropyl-CH2-O-pyridine(Br,F) | 282/284 [M + H]+ | 0.90 (D) |

Example XXVIII

Example XXVIII.1

General Route

3-Bromo-6-propoxy-pyridine-2-carbonitrile

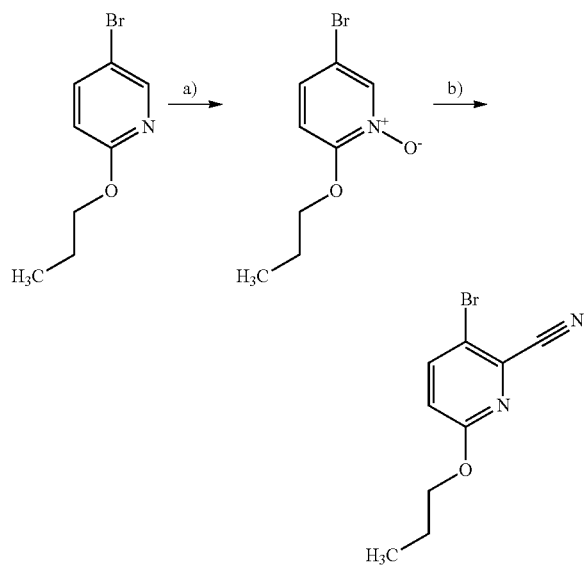

a) To 2.70 g (12.5 mmol) 4-bromo-2-propoxypyridine in 100 mL DCM are added 5.75 g (25.0 mmol) 3-chloroperoxy-benzoic acid and the resulting mixture is stirred at r.t. over night. MgSO$_4$ is added and the mixture is filtered through a plug of aluminium oxide (basic, activated). The solvent of the filtrate is removed in vacuo and the residue is purified by HPLC (acetone/H$_2$O/NH$_3$).

C$_8$H$_{10}$BrN$_2$O (M=232.1 g/mol)
ESI-MS: 232/234 [M+H]$^+$
R$_f$(HPLC): 0.69 (method M)

b) 1.00 g (4.31 mmol) 5-bromo-2-propoxy-pyridine-1-oxide, 2.31 mL (17.2 mmol) TMS cyanide and 1.80 mL (12.9 mmol) TEA in 15 mL ACN are stirred at 100° C. over night in a closed reaction vessel. Then the solvent is removed in vacuo, DCM is added and the resulting mixture is washed with aq. NaHCO$_3$ solution, dried over MgSO$_4$, filtered and the solvent is removed in vacuo.

C$_9$H$_9$BrN$_2$O (M=241.1 g/mol)
ESI-MS: 241/243 [M+H]$^+$
R$_f$(HPLC): 1.09 (method C)

The following compounds are prepared analogously to example XXVIII.1:

| Ex. | Starting material | Product structure | Mass spec result | HPLC retention time (method) |
|---|---|---|---|---|
| XXVIII.1 | | | 241/243 [M + H]+ | 1.09 (C) |
| XXVIII.2 | | | 289/291 [M + H]+ | 3.26 (F) |

Example XXIX

2-Bromo-6-(1-methanesulfonyl-cyclopropyl)-pyridine

Example XXX

2-Bromo-5-(3,3-difluoro-propoxy)-pyridine

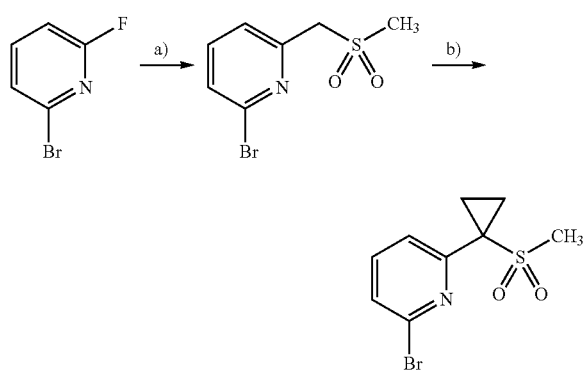

a) Under inert gas atmosphere 28.4 mL (56.8 mmol) of a sodium-bis-(trimethylsilyl)-amide solution in THF (c=2 mol/L) are chilled to −17° C. and dropwise charged with 2.00 g (11.3 mmol) 2-bromo-6-fluoropyridine. Afterwards 2.14 g (22.7 mmol) dimethyl sulfone are added and the reaction mixture is stirred at −17° C. for 1 h. The reaction is quenched by the addition of aq. sat.NaCl solution and extracted with EtOAc. The organic layer is dried over MgSO$_4$, filtered and the solvent is removed in vacuo.

C$_7$H$_8$BrN$_2$O$_2$S (M=250.1 g/mol)

ESI-MS: 250/252 [M+H]+ b) 35 mL aq. NaOH solution (50%) is mixed with 35 mL DCM. Then 0.45 g (1.4 mmol) tetrabutylammonium bromide, 3.46 g (13.8 mmol) 2-bromo-6-methane-sulfonylmethyl-pyridine and 5.96 g (69.2 mmol) 1,2-dibromoethane are added and stirred at r.t. Afterwards the layers of the reaction mixture are separated and the aq. layer is extracted with DCM (2×). The combined organic layers are washed with aq. sat. NaCl solution, dried over MgSO$_4$, filtered and the solvent is removed in vacuo.

C$_9$H$_{10}$BrN$_2$S(M=276.2 g/mol)

ESI-MS: 276/278 [M+H]+ a) Under inert gas atmosphere 0.40 g (17.2 mmol) sodium are added to 10 mL EtOH and stirred until the sodium is dissolved. Then 3.00 g (17.2 mmol) 2-bromo-5-hydroxypyridine are added and stirred for 10 minutes. Finally 1.63 g (17.2 mmol) 3-chloro-1-propanol are added and the resulting mixture is stirred under reflux for 2 h and then at 60° C. for 72 h. The reaction is quenched by the addition of water and diluted with EtOAc. The organic layer is separated, washed with aq. NaOH (c=1 mol/L) solution, dried over MgSO$_4$, filtered and the solvent is removed in vacuo.

C$_8$H$_{10}$BrNO$_2$ (M=232.1 g/mol)

ESI-MS: 232/234 [M+H]+

R$_f$(HPLC): 0.64 (method K)

b) To 3.00 g (12.9 mmol) 3-(6-bromo-pyridin-3-yloxy)-propan-1-ol in 40 mL DCM are added 5.67 g (12.9 mmol) Dess-Martin-periodinane and the resulting mixture is stirred at r.t. over night. The reaction mixture is diluted with DCM, 100 mL aq. half sat. NaHCO$_3$ solution is added and the mixture is filtered through a plug of Celite®. The filtrate is extracted with EtOAc, the organic layers are combined, washed with water, dried over MgSO$_4$, filtered and the solvent is removed in vacuo.

$C_8H_8BrNO_2$ (M=230.1 g/mol)
ESI-MS: 230/232 [M+H]$^+$
$R_t$(HPLC): 0.64 (method K)

c) To 3.50 g (12.9 mmol) 3-(6-bromo-pyridin-3-yloxy)-propionaldehyde in 20 mL DCM are added 2.39 g (18.3 mmol) diethylaminosulfur trifluoride and the resulting mixture is stirred at r.t.over night. Then the reaction mixture is diluted with DCM before aq. half sat. NaHCO$_3$ solution is added. The layers are separated and the aq. layer is extracted with EtOAc. The organic layers are combined, dried over MgSO$_4$, filtered and the solvent is removed in vacuo. The crude product is purified by HPLC (ACN/H$_2$O/NH$_3$).

$C_8H_8BrF_2NO$ (M=252.1 g/mol)
ESI-MS: 252/254 [M+H]$^+$
$R_t$(HPLC): 0.82 (method K)

Example XXXI

Example XXXI.1

General Route (S)-1-(4-((R)-1-(2-(2,2-Difluoroethoxy)pyridin-4-yl)pyrrolidin-3-yloxy)phenyl)ethanamine

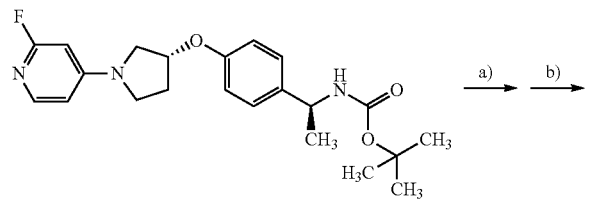

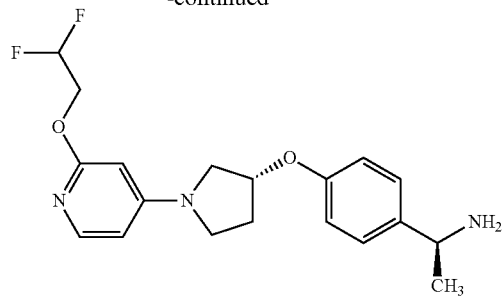

a) 3.15 mL (49.8 mmol) 2,2-difluoroethanol in 100 mL dioxane are charged with 1.26 g (49.8 mmol) NaH and the reaction mixture is stirred at r.t. for 5 min Then 4.00 g (9.96 mmol) of example XX.13 are added and the resulting mixture is stirred at 120° C. over night. The solvent is removed in vacuo, DCM and H$_2$O are added, the layers are separated and the aq. layer is extracted one more time with DCM. The org. layers are combined, dried over MgSO$_4$, filtered and the solvent is removed in vacuo.

$C_{24}H_{31}F_2N_3O_4$ (M=463.5 g/mol)
ESI-MS: 464 [M+H]$^+$
$R_t$(HPLC):1.02 min (method D)

b) To the intermediate described above in 70 mL dioxane are added 20.0 mL (80.0 mmol) HCl (c=4 mol/L in dioxane) and the resulting mixture is stirred at r.t. for 5 h. The precipitate is filtered off and washed with diethylether. The crude product is purified by HPLC (ACN/H$_2$O/TFA). The organic solvent is removed in vacuo and the aq. layer is basified with NH$_3$ (aq) and extracted with DCM. The organic layer is dried over MgSO$_4$, filtered and the solvent is removed in vacuo.

$C_{19}H_{23}F_2N_3O_2$ (M=363.4 g/mol)
ESI-MS: 364 [M+H]$^+$ $R_t$ (HPLC):0.88 min (method D)

The following compounds are prepared analogously to example XXXI.1:

| Ex. | Starting material | Product structure | Mass spec result | HPLC retention time (method) |
|---|---|---|---|---|
| XXXI.1 | XX.13 | | 364 [M + H]$^+$ | 0.88 (D) |
| XXXI.2 | XX.9 | | 408 [M + H]$^+$ | 0.97 (K) |
| XXXI.3 | XX.9 | | 382 [M + H]$^+$ | 0.87 (M) |

Example XXXII

Example XXXII.1

General Route (S)-1-(4-((R)-1-(2-(3,3-Difluoropyrrolidin-1-yl)-3-fluoropyridin-4-yl)pyrrolidin-3-yloxy)phenyl)ethanamine

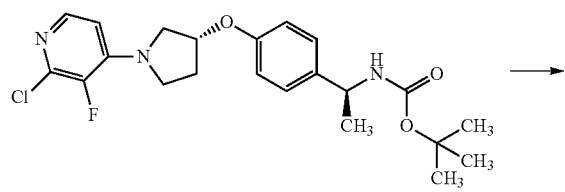

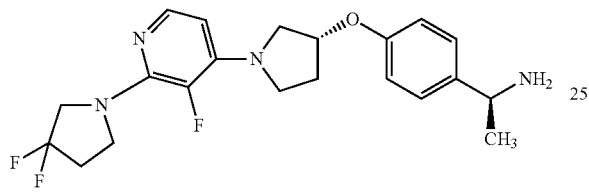

Under inert gas atmosphere 1.00 g (2.07 mmol) of example XX.9, 0.30 g (2.09 mmol) 3,3-difluoropyrrolidine hydrochloride, 0.60 g (6.24 mmol) NaOtBu and 100 mg (0.14 mmol) chloro(2-dicyclohexylphosphino-2',4',6'-triisopropyl-1,1'-biphenyl)(2-(2-aminoethyl)-phenyl)-palladium (II) are added to 15 mL dioxane and stirred at 100° C. for 1.5 h. Afterwards the reaction mixture is cooled to r.t. and filtered. 1.00 mL (13.0 mmol) TFA is added and the resulting mixture is stirred at 45° C. for 4 h. The solvent is removed in vacuo and to the residue is added EtOAc. The mixture is washed with half sat. HCl solution. The aq. layer is basified with 4 N NaOH solution and extracted with DCM. The org. layer is dried over $MgSO_4$, filtered and the solvent is removed in vacuo. The crude product is purified by HPLC (ACN/$H_2O$/$NH_3$).

$C_{21}H_{25}F_3N_4O$ (M=406.4 g/mol)

ESI-MS: 407 $[M+H]^+$ $R_t$(HPLC):0.76 min (method M)

The following compounds are prepared analogously to example XXXII.1:

For example XXXII.2 the reaction is done at 100° C. for 3 h. Afterwards the mixture is treated with water and extracted with EtOAc. After removing of the solvent the crude product is purified by HPLC.

| Ex. | Starting material | Product structure | Mass spec result | HPLC retention time (method) |
|---|---|---|---|---|
| XXXII.1 | XX.9 | | 407 $[M+H]^+$ | 0.76 (M) |
| XXXII.2 | XX.9 | | 359 $[M+H]^+$ | 0.90 (M) |

Example XXXIII

Example XXXIII.1

General Route

4-Bromo-3-methoxy-2-propoxy-pyridine

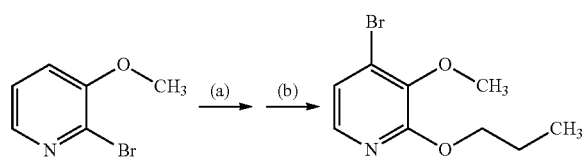

a) 384 mg (6.38 mmol) n-propanol in 10 mL toluene are charged with 255 mg (6.38 mmol) NaH and the reaction mixture is stirred at 60° C. for 10 min Then 1.00 g (5.32 mmol) 2-bromo-3-methoxypyridine are added and stirring is continued at 110° C. over night. Afterwards the reaction mixture is filtered and the crude product is purified by HPLC (ACN/H$_2$O/FA).
$C_9H_{13}NO_2$ (M=167.2 g/mol)
ESI-MS:168 [M+H]$^+$
R$_f$(HPLC): 1.03 (method M)

b) To 830 mg (4.96 mmol) of the above mentioned product in 50 mL THF are added dropwise at −70° C. 6.83 mL (10.9 mmol) n-BuLi (c=1.6 mol/L in THF). The temperature is raised to 0° C. and stirring is continued at 0° C. for 1 h. Then the mixture is chilled to −70° C. again before 1.31 g (12.4 mmol) cyanogen bromide (in 2 mL THF) are added. The cooling is removed and the resulting mixture is stirred over night. The solvent is removed in vacuo and the resulting mixture is poured into H$_2$O and extracted with TBME. The solvent is removed in vacuo and the crude product is purified by column chromatography (silica gel, CyH/EtOAc).
$C_9H_{12}BrNO_2$ (M=246.1 g/mol)
ESI-MS:246/248 [M+H]+
R$_f$(HPLC): 1.14 (method M)

The following compounds are prepared analogously to example XXXIII.1:

For example XXXIII.8 the intermediat product after step a) is TBS protected by using TBS-triflate in DCM with TEA.

| Ex. | Starting material | Product structure | Mass spec result | HPLC retention time (method) |
|---|---|---|---|---|
| XXXIII.1 | | | 246/248 [M + H]$^+$ | 1.14 (M) |
| XXXIII.2 | | | 260/262 [M + H]$^+$ | 1.18 (M) |
| XXXIII.3 | | | 232/234 [M + H]$^+$ | 1.04 (M) |
| XXXIII.4 | | | 258/260 [M + H]$^+$ | 1.11 (M) |
| XXXIII.5 | | | 272/274 [M + H]$^+$ | 1.20 (D) |

-continued

| Ex. | Starting material | Product structure | Mass spec result | HPLC retention time (method) |
|---|---|---|---|---|
| XXXIII.6 | | | 290/292 [M + H]+ | 1.06 (M) |
| XXXIII.7 | | | 246/248 [M + H]+ | 1.13 (D) |
| XXXIII.8 | | | 246/248 [M + H]+ | 1.13 (M) |

Preparation of Final Compounds

General Synthetic Procedures:

Buchwald Couplings

Method A)

To 1.76 mmol of the appropriate amine in 15 mL dioxane are added 1.76 mmol pyridyl halide, 7.02 mmol NaOtBu and 0.18 mmol chloro(2-dicyclohexyl-phosphino-2',4',6'-triisopropyl-1,1'-biphenyl)(2-(2-aminoethyl)-phenyl)-palladium (II). The mixture is degassed thoroughly and stirred at 45° C. for 3 h. A small amount of water and MeOH are added, the mixture is filtered and afterwards purified by HPLC.

Method B)

To 1.76 mmol of the appropriate amine in 10 mL dioxane are added 1.76 mmol pyridyl halide, 7.02 mmol NaOtBu, 0.70 mmol 2-(di-tert-butylphosphino)biphenyl and 0.18 mmol $Pd_2(dba)_3$. The mixture is degassed thoroughly and stirred at 45° C. over night. The reaction mixture is filtered, the solvent removed in vacuo and the residue is purified by HPLC.

Method C)

To 0.28 mmol of the appropriate amine in 1.5 mL toluene and 0.5 mL tert-butanol are added 0.28 mmol pyridyl halide, 0.70 mmol $Cs_2CO_3$, 14 µmol X-Phos and 14 µmol $Pd(OAc)_2$. The mixture is degassed thoroughly and stirred at 120° C. over night. A small amount of water and MeOH are added, the mixture is filtered and afterwards purified by HPLC.

Method D)

To 0.40 mmol of the appropriate amine in 2.5 mL dioxane are added 0.40 mmol pyridyl halide, 1.61 mmol NaOtBu, 0.70 mmol 2-(di-tert-butylphosphino)biphenyl and 0.04 mmol $Pd_2(dba)_3$. The mixture is degassed thoroughly and stirred for 45 min at 80° C. in a microwave oven. A small amount of water and MeOH are added, the mixture is filtered and afterwards purified by HPLC.

Example 1

Example 1.1

General Route

N—((1S)-1-(4-((3R)-1-(5-((2,2-Difluorocyclopropyl)methoxy)pyridin-2-yl)pyrrolidin-3-yloxy)phenyl)ethyl)acetamide

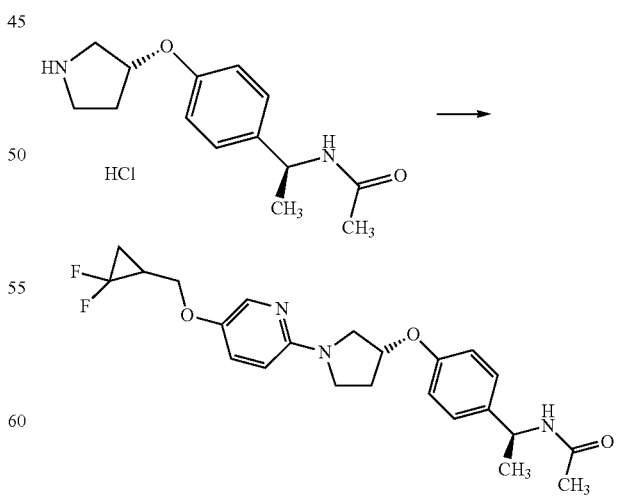

The title compound can be prepared according to the general procedure described in method A with a reaction temperature of 75° C.

$C_{23}H_{27}F_2N_3O_3$ (M=431.5 g/mol)
ESI-MS: 432 [M+H]$^+$
R$_t$(HPLC):1.05 min (method C)

The following compounds are prepared according to the general procedures A-D described above:

For the examples 1.1, 1.3-1.16, 1.66, 1.72, 1.78-1.82, 1.85, 1.87-1.89, 1.94-1.95, 1.99-1.100, 1.110-1.120, 1.123, 1.128, 1.129, 1.132, 1.134-1.151 the reaction conditions are 80-100° C. for 1-16 h.

For the examples 1.23, 1.70, 1.71, 1.73 1.77, 1.83 and 1.86 the reaction is stirred over night.

For the examples 1.105-1.109 Cs$_2$CO$_3$ is used as base.

For the examples 1.124-1.127, 1.129-1.131 and 1.133 the reaction is stirred at 60° C. over night.

For example 1.151 the reaction is done at 70° C. over night. After purification by HPLC the intermediate product is deprotected by using TFA in DCM and purified by HPLC again.

| Ex. | Starting material(s) | Structure | Method | Mass spec result | HPLC retention time (method) |
|---|---|---|---|---|---|
| 1.1 | XIII.1 + XXIV.3 | 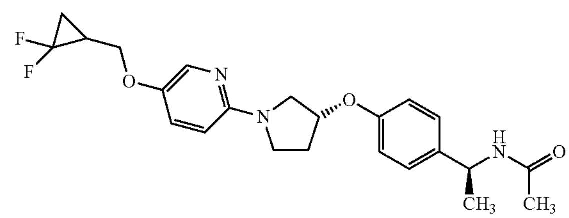 | A | 432 [M + H]$^+$ | 1.05 (C) |
| 1.2 | XIII.3 + XXIV.1 | 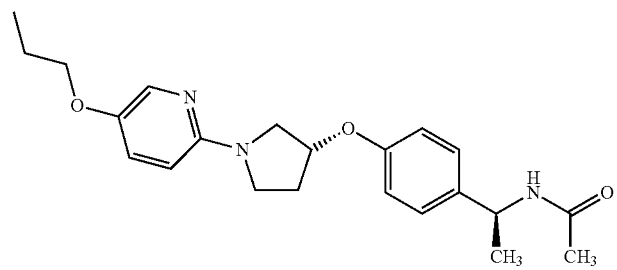 | D | 384 [M + H]$^+$ | 1.12 (C) |
| 1.3 | XIII.3 + 4-bromo-2-(iso-propoxy) pyridine | 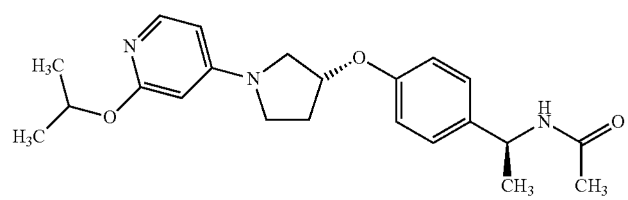 | B | 384 [M + H]$^+$ | 1.07 (C) |
| 1.4 | XIII.3 + 5-bromo-2-propoxy pyridine | 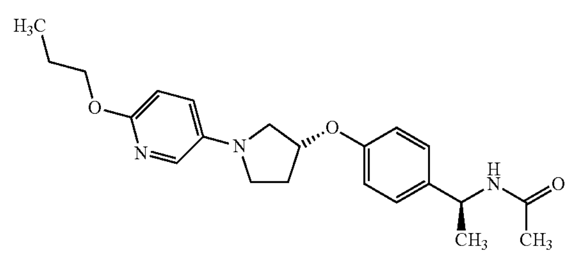 | B | 384 [M + H]$^+$ | 1.14 (C) |
| 1.5 | XIII.3 + 5-bromo-2-ethoxy pyridine | 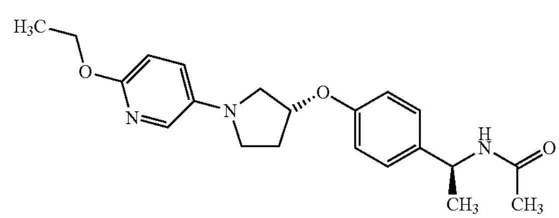 | B | 370 [M + H]$^+$ | 1.04 (C) |

-continued

| Ex. | Starting material(s) | Structure | Method | Mass spec result | HPLC retention time (method) |
|---|---|---|---|---|---|
| 1.6 | XIII.3 + 2-bromo-5-ethoxy pyridine | 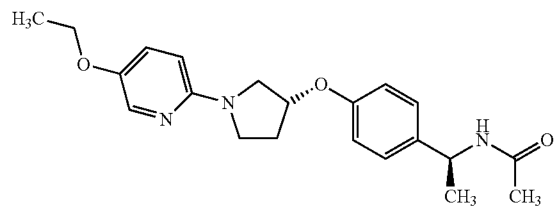 | B | 370 [M + H]⁺ | 1.02 (C) |
| 1.7 | XIII.3 + XXIV.10 | 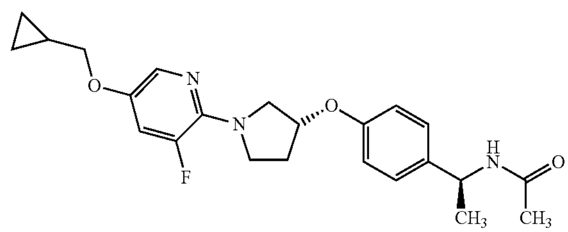 | B | 414 [M + H]⁺ | 1.16 (C) |
| 1.8 | XIII.3 + XXIV.2 | 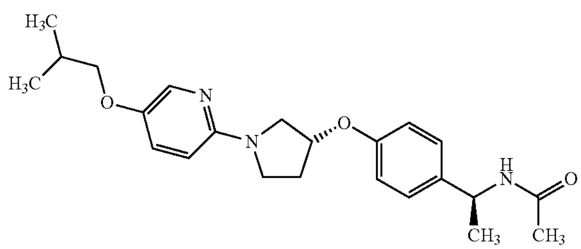 | B | 398 [M + H]⁺ | 1.17 (C) |
| 1.9 | XIII.3 + XXIV.11 | 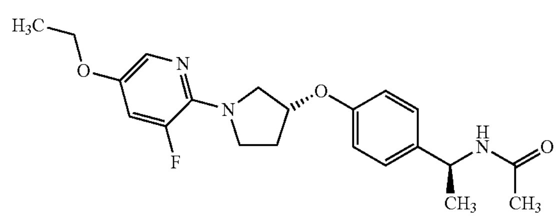 | B | 388 [M + H]⁺ | 1.11 (C) |
| 1.10 | XIII.3 + 5-bromo-2-isopropoxy-isopropoxy-pyridine | 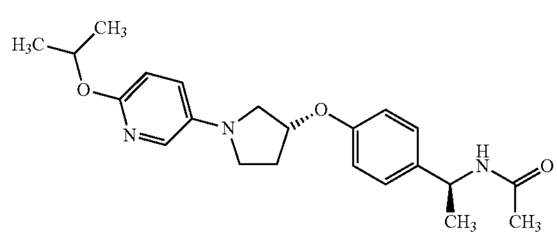 | B | 384 [M + H]⁺ | 1.09 (C) |
| 1.11 | XIII.3 + XXIV.12 | 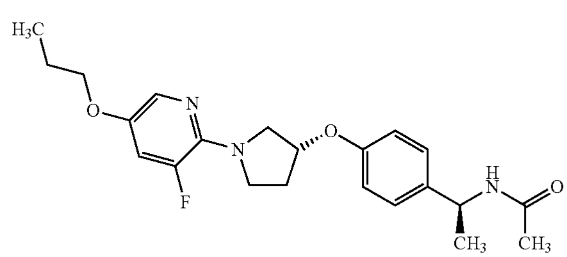 | B | 402 [M + H]⁺ | 1.18 (C) |

-continued

| Ex. | Starting material(s) | Structure | Method | Mass spec result | HPLC retention time (method) |
|---|---|---|---|---|---|
| 1.12 | XIII.3 + 4-bromo-2-ethoxy pyridine | 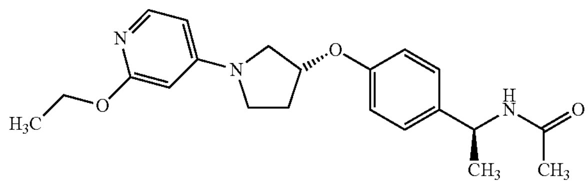 | B | 370 [M + H]⁺ | 1.01 (C) |
| 1.13 | XIII.3 + XXVIII.1 | 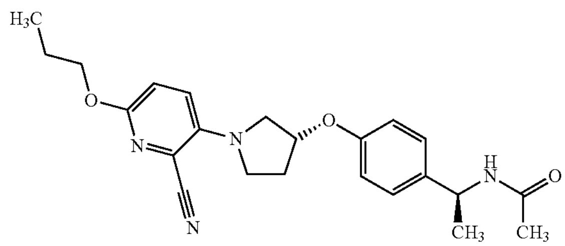 | B | 409 [M + H]⁺ | 1.14 (C) |
| 1.14 | XIII.3 + XXV.1 | 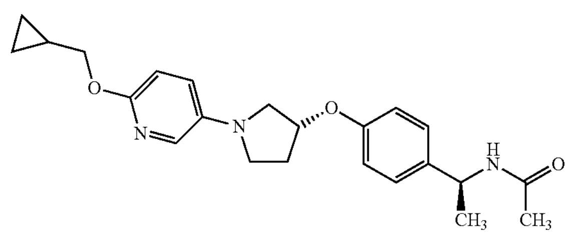 | B | 396 [M + H]⁺ | 1.12 (C) |
| 1.15 | XIII.3 + XXV.2 | 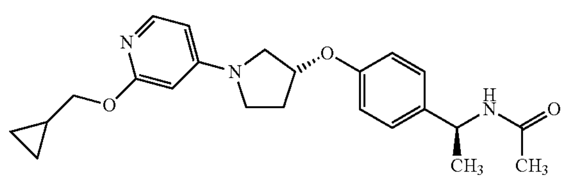 | B | 396 [M + H]⁺ | 1.08 (C) |
| 1.16 | XIII.3 + XXV.3 | 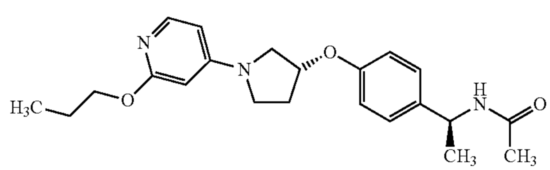 | B | 384 [M + H]⁺ | 1.08 (C) |
| 1.17 | XIII.1 + XXV.4 | 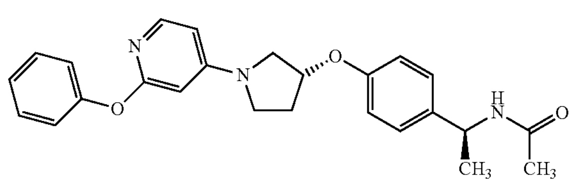 | C | 418 [M + H]⁺ | 1.24 (H) |
| 1.18 | XIII.1 + 2-bromo-6-methyl pyridine | 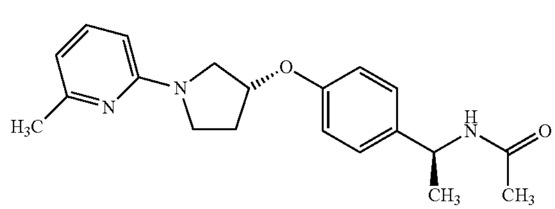 | C | 340 [M + H]⁺ | 1.21 (H) |

-continued

| Ex. | Starting material(s) | Structure | Method | Mass spec result | HPLC retention time (method) |
|---|---|---|---|---|---|
| 1.19 | XIII.1 + XXV.5 | 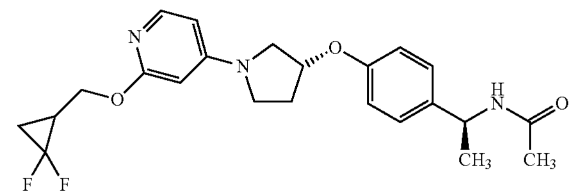 | B | 432 [M + H]+ | 1.07 (C) |
| 1.20 | XIII.1 + XXIV.13 | 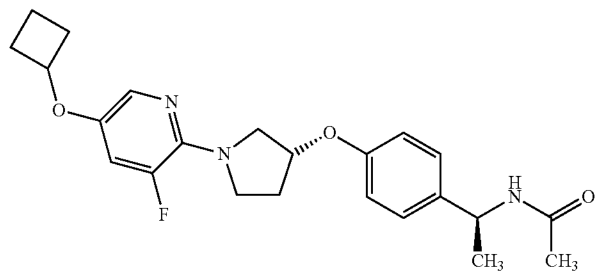 | B | 414 [M + H]+ | 1.20 (C) |
| 1.21 | XIII.1 + 3-bromo-6-(cyclo-botoxy) pyridine | 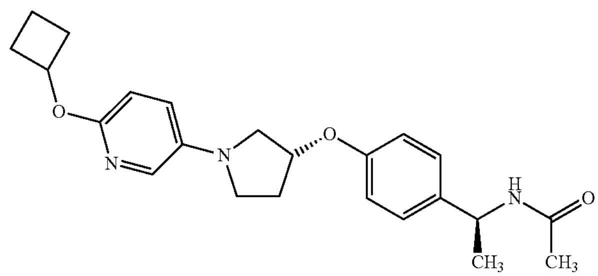 | B | 396 [M + H]+ | 1.64 (L) |
| 1.22 | XIII.1 + XXIV.14 | 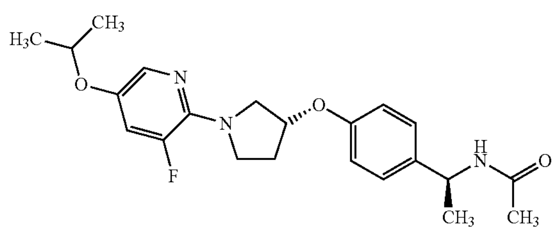 | B | 402 [M + H]+ | 1.69 (L) |
| 1.23 | XIII.1 + XXIV.15 | 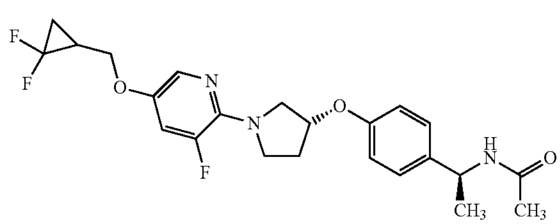 | A | 450 [M + H]+ | 1.58 (L) |
| 1.24 | XIII.1 + XXV.6 | 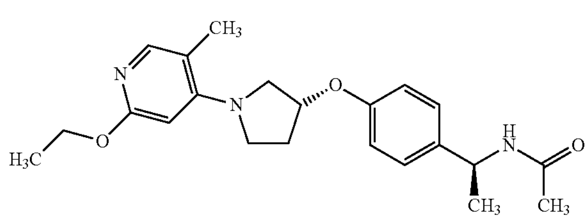 | B | 384 [M + H]+ | 0.62 (T) |

-continued

| Ex. | Starting material(s) | Structure | Method | Mass spec result | HPLC retention time (method) |
|---|---|---|---|---|---|
| 1.25 | XIII.1 + XXV.16 | 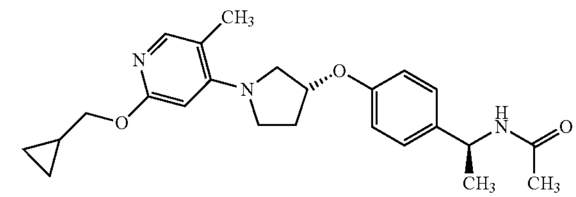 | B | 410 [M + H]⁺ | 1.12 (C) |
| 1.26 | XIII.1 + XXIV.14 | 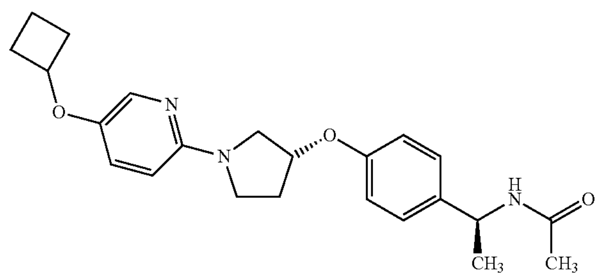 | B | 396 [M + H]⁺ | 1.11 (C) |
| 1.27 | XIII.1 + XXIV.5 | 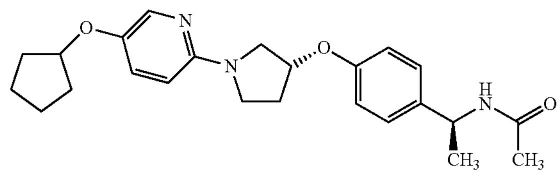 | B | 410 [M + H]⁺ | 1.16 (C) |
| 1.28 | XIII.1 + XXIV.6 | 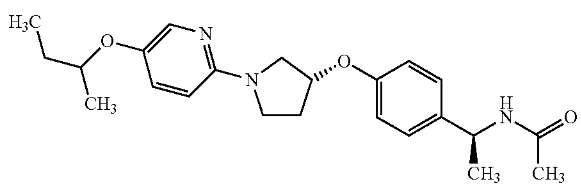 | B | 398 [M + H]⁺ | 1.13 (C) |
| 1.29 | XIII.1 + XXVI.1 | 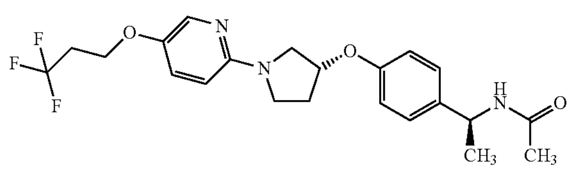 | B | 438 [M + H]⁺ | 1.07 (C) |
| 1.30 | XIII.1 + XXVII.2 | 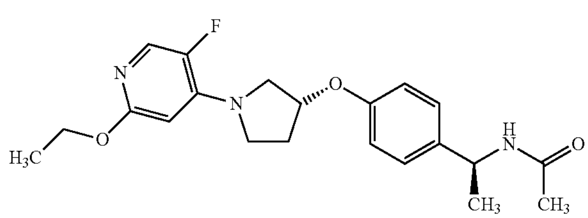 | B | 388 [M + H]⁺ | 1.24 (H) |
| 1.31 | XIII.1 + XXVI.2 | 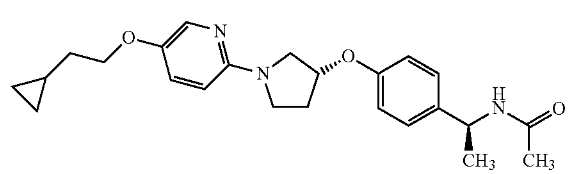 | B | 410 [M + H]⁺ | 1.17 (C) |

-continued

| Ex. | Starting material(s) | Structure | Method | Mass spec result | HPLC retention time (method) |
|---|---|---|---|---|---|
| 1.32 | XIII.1 + XXVI.4 | 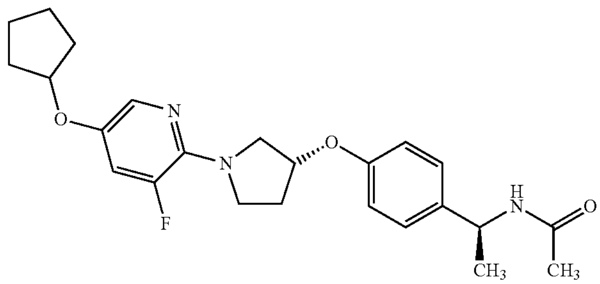 | B | 428 [M + H]⁺ | 1.24 (C) |
| 1.33 | XIII.1 + XXIV.16 | 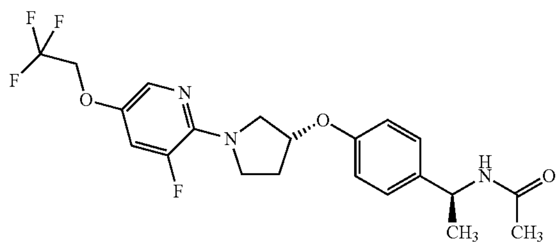 | B | 442 [M + H]⁺ | 1.13 (C) |
| 1.34 | XIII.1 + XXVI.3 | 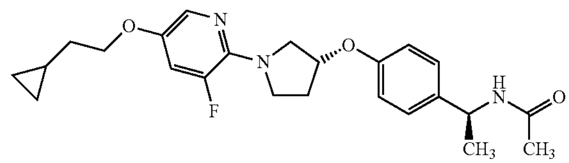 | B | 428 [M + H]⁺ | 1.24 (C) |
| 1.35 | XIII.2 + XXV.2 | 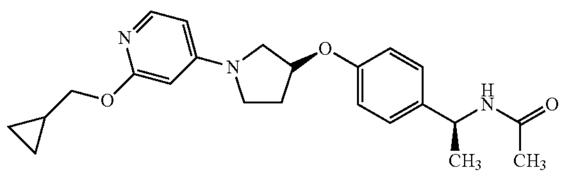 | B | 396 [M + H]⁺ | 1.53 (L) |
| 1.36 | XIII.1 | 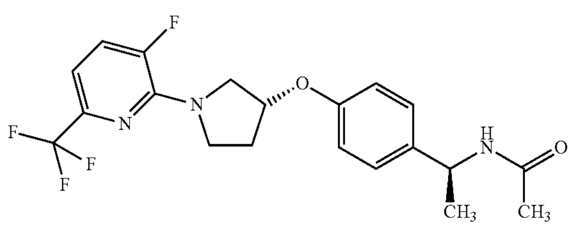 | B | 412 [M + H]⁺ | 1.18 (C) |
| 1.37 | XIII.1 + XXV.8 | 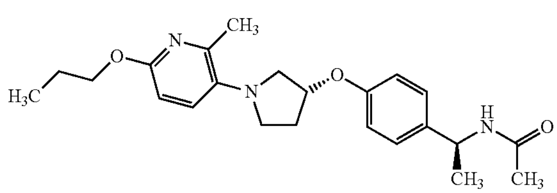 | B | 398 [M + H]⁺ | 1.10 (E) |
| 1.38 | XIII.1 + 2-bromo-6-cyclo-propyl-pyridine | 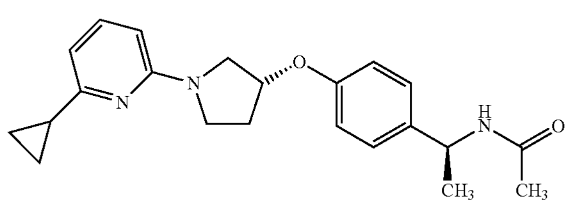 | B | 366 [M + H]⁺ | 0.90 (E) |

-continued

| Ex. | Starting material(s) | Structure | Method | Mass spec result | HPLC retention time (method) |
|---|---|---|---|---|---|
| 1.39 | XIII.1 + XXV.9 | 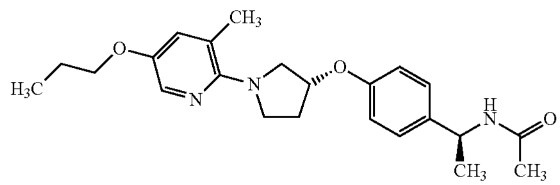 | B | 398 [M + H]+ | 1.02 (E) |
| 1.40 | XIII.1 + XXV.11 | 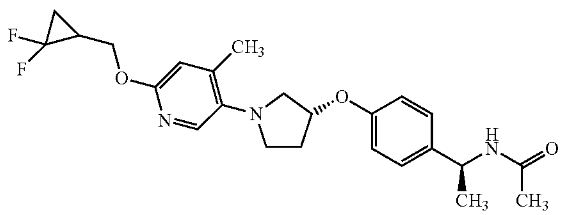 | B | 446 [M + H]+ | 1.20 (E) |
| 1.41 | XIII.1 + XXV.10 | 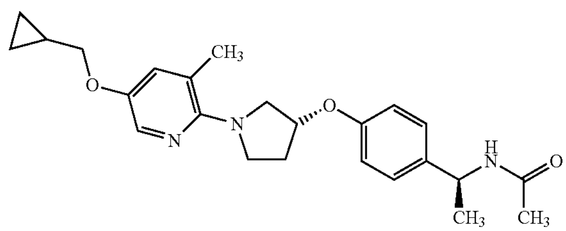 | B | 410 [M + H]+ | 1.03 (E) |
| 1.42 | XIII.1 + XXV.12 | 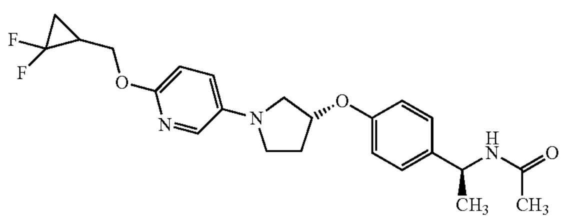 | B | 432 [M + H]+ | 1.15 (E) |
| 1.43 | XIX.1 + XXV.2 | 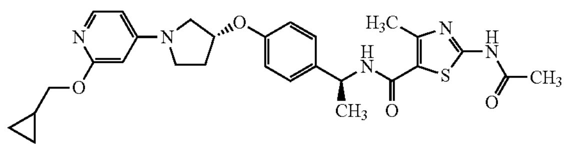 [SMILES: CC(=O)Nc1nc(C)c(C(=O)N[C@@H](C)c2ccc(O[C@@H]3CCN(c4ccnc(OCC5CC5)c4)C3)cc2)s1] | B | 536 [M + H]+ | 1.13 (C) |
| 1.44 | XIII.1 + 2-bromo-3-fluoro-6-methyl-pyridine | 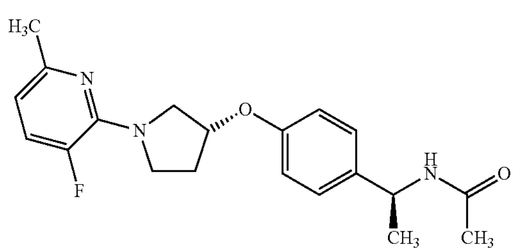 | B | 358 [M + H]+ | 0.90 (E) |
| 1.45 | XIX.1 + 2-chloro-6-(trifluoro-metyhl) pyridine | 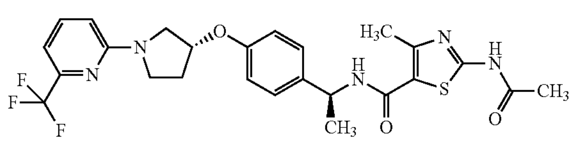 | B | 534 [M + H]+ | 1.16 (C) |

-continued

| Ex. | Starting material(s) | Structure | Method | Mass spec result | HPLC retention time (method) |
|---|---|---|---|---|---|
| 1.46 | XIX.1 + 5-bromo-2-propoxy-pyridine | 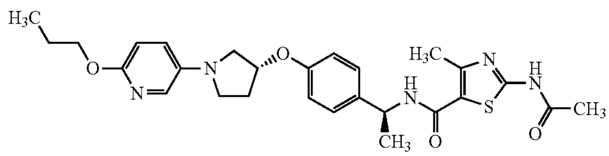 [SMILES: CCCOc1ccc(N2CC[C@@H](Oc3ccc([C@H](C)NC(=O)c4sc(NC(C)=O)nc4C)cc3)C2)cn1] | B | 524 [M + H]⁺ | 1.16 (C) |
| 1.47 | XIX.1 + 4-bromo-2-ethoxy-pyridine | 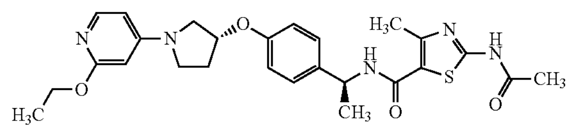 | B | 510 [M + H]⁺ | 1.07 (C) |
| 1.48 | XIX.1 + XXIV.12 | 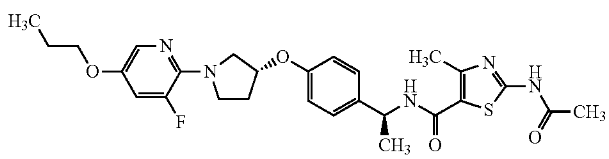 [SMILES: CCCOc1cnc(N2CC[C@@H](Oc3ccc([C@H](C)NC(=O)c4sc(NC(C)=O)nc4C)cc3)C2)c(F)c1] | B | 542 [M + H]⁺ | 1.27 (B) |
| 1.49 | XIX.1 + 4-bromo-2-(iso-propoxy)pyridine | 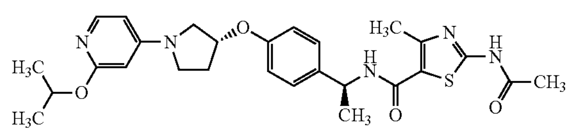 [SMILES: CC(=O)Nc1nc(C)c(C(=O)N[C@@H](C)c2ccc(O[C@@H]3CCN(c4ccnc(OC(C)C)c4)C3)cc2)s1] | B | 524 [M + H]⁺ | 1.11 (C) |
| 1.50 | XIX.1 + XXIV.1 | 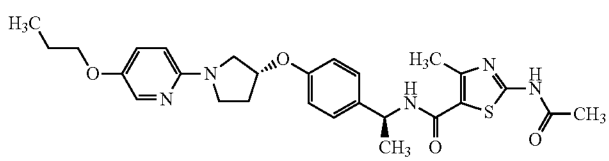 [SMILES: CCCOc1ccc(N2CC[C@@H](Oc3ccc([C@H](C)NC(=O)c4sc(NC(C)=O)nc4C)cc3)C2)nc1] | B | 524 [M + H]⁺ | 1.14 (C) |
| 1.51 | XIII.1 + XXV.14 | 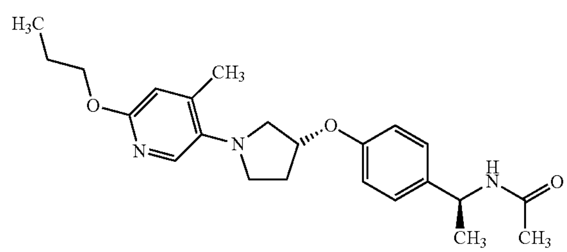 | B | 398 [M + H]⁺ | 1.17 (E) |
| 1.52 | XIII.1 + XXV.15 | 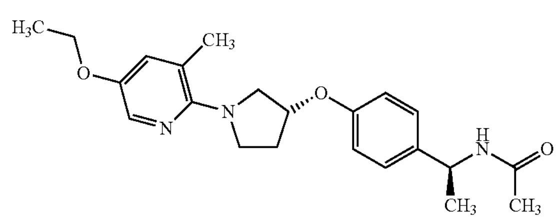 | B | 384 [M + H]⁺ | 0.75 (I) |
| 1.53 | XVIII.3 + XXV.2 | 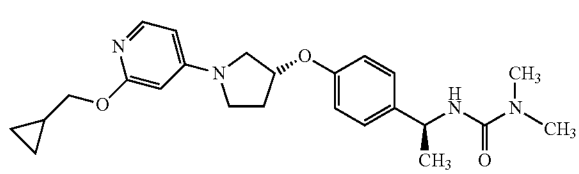 | B | 425 [M + H]⁺ | 1.09 (C) |

-continued

| Ex. | Starting material(s) | Structure | Method | Mass spec result | HPLC retention time (method) |
|---|---|---|---|---|---|
| 1.54 | XVIII.3 + XXIV.3 | 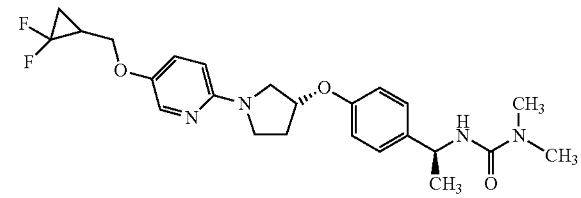 | B | 461 [M + H]+ | 1.08 (C) |
| 1.55 | XVIII.3 + XXIV.10 | 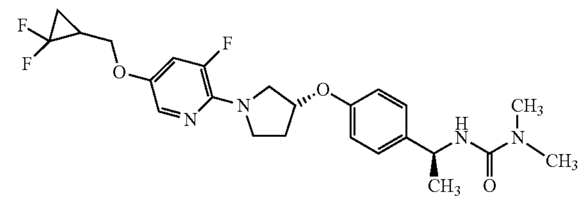 | B | 479 [M + H]+ | 1.14 (C) |
| 1.56 | XVIII.3 + XXV.7 | 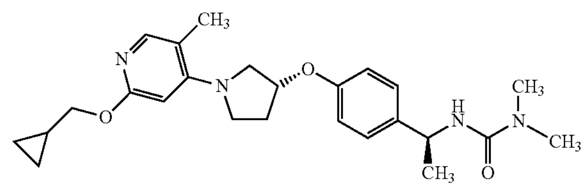 | B | 437 [M − H]− | 1.14 (N) |
| 1.57 | XIII.1 + 2-bromo-6-methoxypyridine | 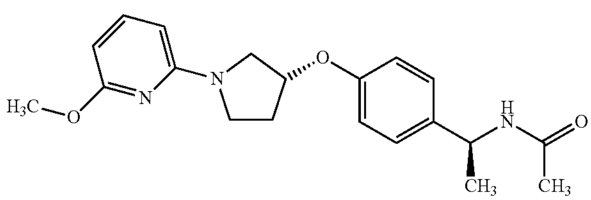 | B | 356 [M + H]+ | 1.24 (H) |
| 1.58 | XVIII.3 + 3,6-difluoro-2-(trifluoromethyl)pyridine | 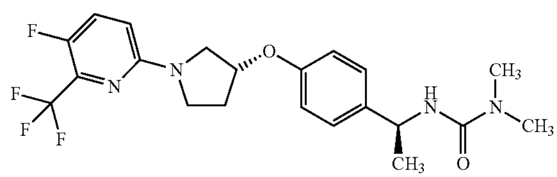 | B | 441 [M − H]− | 1.16 (C) |
| 1.59 | XIII.1 + 2-bromo-6-tert-butyl-pyridine | 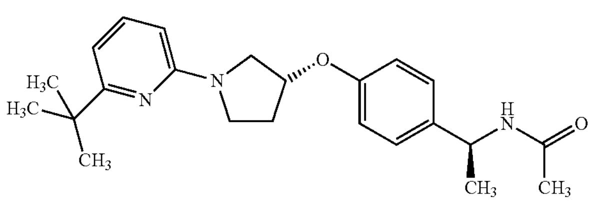 | B | 382 [M + H]+ | 1.44 (H) |
| 1.60 | XIII.1 + 2-bromo-6-ethylpyridine | 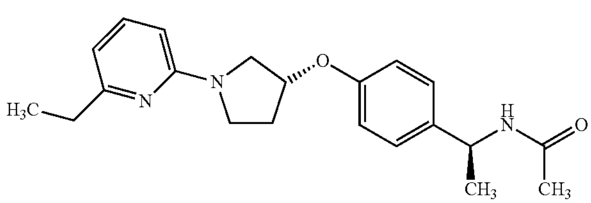 | B | 354 [M + H]+ | 1.28 (H) |

-continued

| Ex. | Starting material(s) | Structure | Method | Mass spec result | HPLC retention time (method) |
|---|---|---|---|---|---|
| 1.61 | XIII.1 + XXVIII.2 | 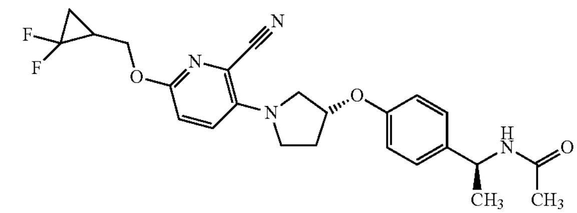 | B | 357 [M + H]+ | 1.25 (H) |
| 1.62 | XIII.1 + 2-bromo-6-ethoxy pyridine | 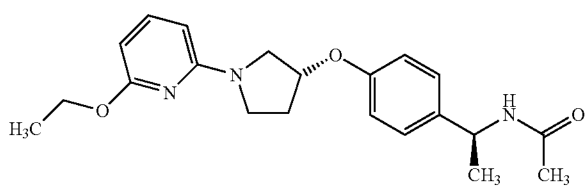 | B | 370 [M + H]+ | 1.29 (H) |
| 1.63 | XIII.1 + 2-bromo-6-isopropyl pyridine | 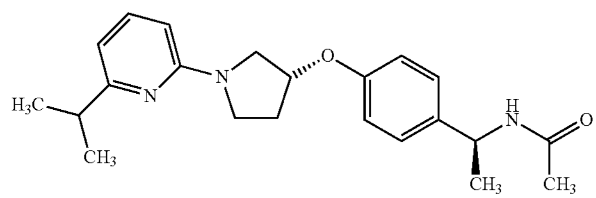 | B | 368 [M + H]+ | 1.37 (H) |
| 1.64 | XIII.1 + 2-bromo-6-(difluoro methyl) pyridine | 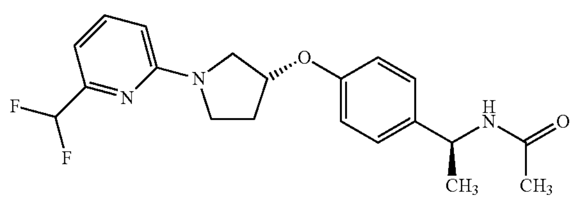 | B | 376 [M + H]+ | 1.22 (H) |
| 1.65 | XIII.1 + 2-bromo-5-fluoro-6-methyl pyridine | 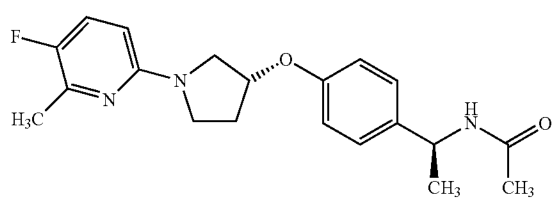 | A | 358 [M + H]+ | 0.83 (B) |
| 1.66 | XIII.1 + XXIV.17 | 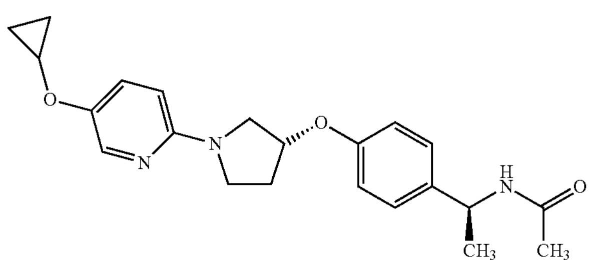 | A | 382 [M + H]+ | 1.05 (C) |
| 1.67 | XIII.1 + XXIV.18 | 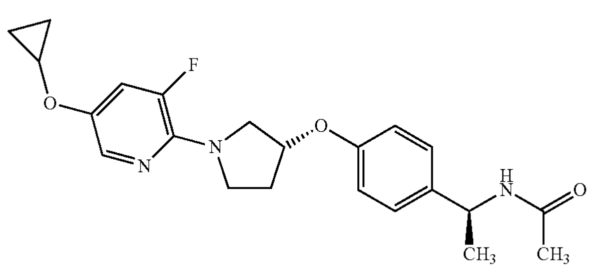 | A | 400 [M + H]+ | 1.14 (C) |

-continued

| Ex. | Starting material(s) | Structure | Method | Mass spec result | HPLC retention time (method) |
|---|---|---|---|---|---|
| 1.68 | XIII.1 + XXV.17 | 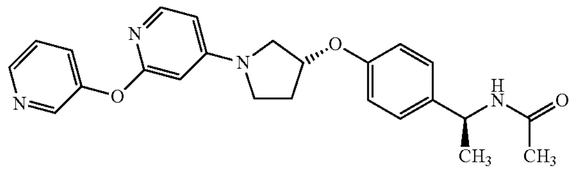 | B | 419 [M + H]+ | 0.96 (B) |
| 1.69 | XIII.1 + 2-bromo-5-methyl sulfanyl-pyridine | 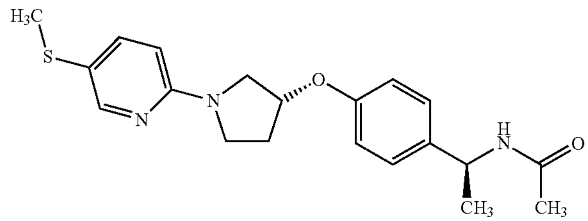 | A | 372 [M + H]+ | 1.04 (C) |
| 1.70 | XIII.1 + 2-bromo-5-(cyclo-propyl)pyridine | 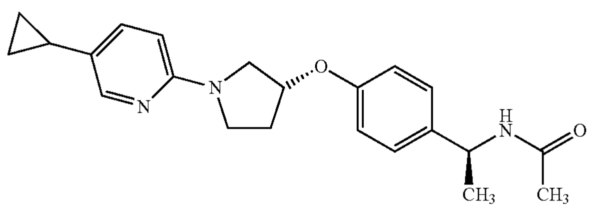 | A | 366 [M + H]+ | 1.10 (C) |
| 1.71 | XIII.1 + XXIV.19 | 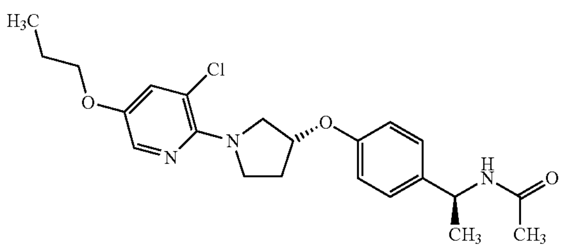 | A | 418 [M + H]+ | 1.30 (C) |
| 1.72 | XIII.1 + XXVII.2 | 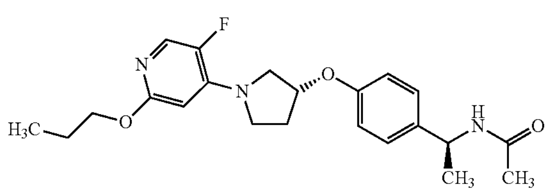 | A | 402 [M + H]+ | 0.92 (B) |
| 1.73 | XIII.1 + XXVII.3 | 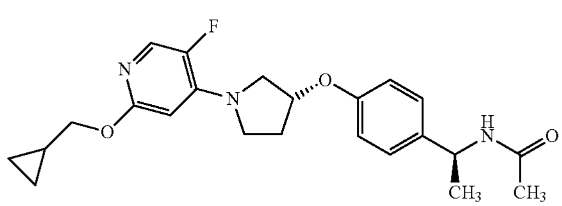 | A | 414 [M + H]+ | 0.94 (B) |
| 1.74 | XIII.1 + XXVII.4 | 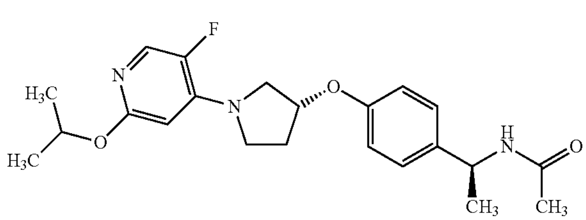 | A | 402 [M + H]+ | 0.90 (B) |

-continued

| Ex. | Starting material(s) | Structure | Method | Mass spec result | HPLC retention time (method) |
|---|---|---|---|---|---|
| 1.75 | XIII.1 + XXVII.5 | 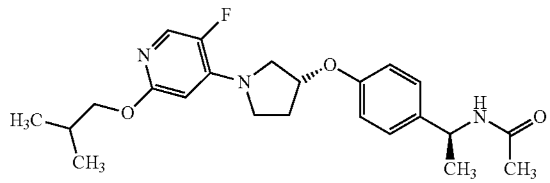 | A | 416 [M + H]+ | 0.99 (B) |
| 1.76 | XIII.1 + XXVII.6 | 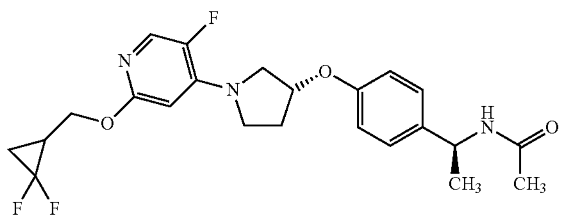 | A | 450 [M + H]+ | 1.00 (B) |
| 1.77 | XIII.1 + XXIV.20 | 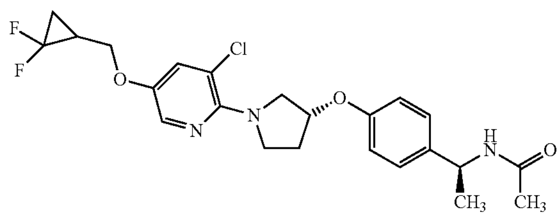 | A | 466 [M + H]+ | 1.18 (C) |
| 1.78 | XIII.1 + XXIV.21 | 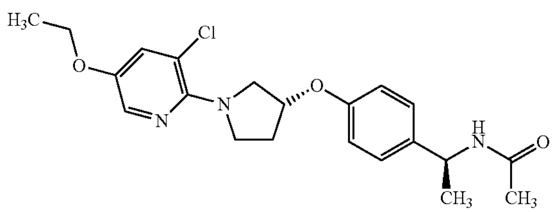 | A | 404 [M + H]+ | 1.29 (E) |
| 1.79 | XIII.1 + XXIX | 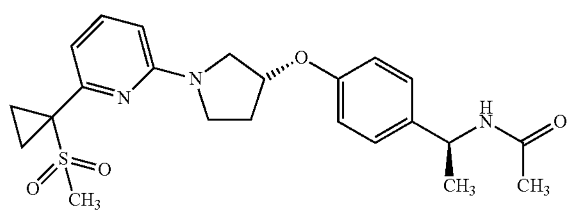 | A | 444 [M + H]+ | 0.89 (B) |
| 1.80 | XIII.1 + XXIV.23 | 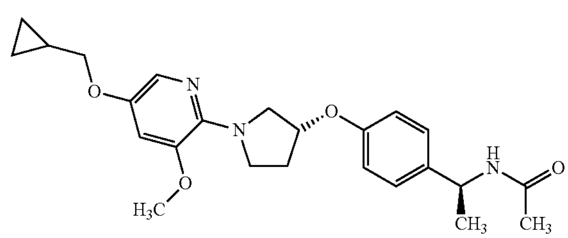 | A | 426 [M + H]+ | 1.23 (C) |
| 1.81 | XIII.1 + XXIV.23 | 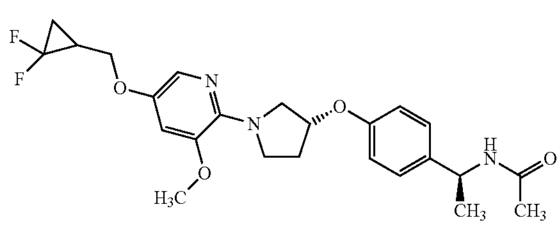 | A | 462 [M + H]+ | 1.10 (C) |

| Ex. | Starting material(s) | Structure | Method | Mass spec result | HPLC retention time (method) |
|---|---|---|---|---|---|
| 1.82 | XIX.2 + XXIV.7 | 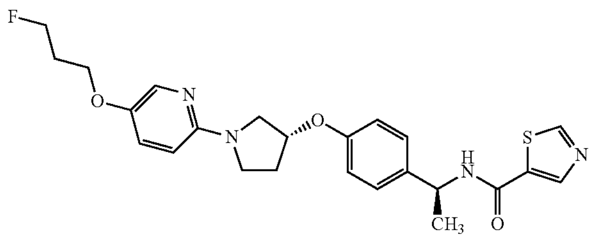 [SMILES: C[C@H](NC(=O)c1cncs1)c1ccc(O[C@@H]2CCN(c3ccc(OCCCF)cn3)C2)cc1] | A | 471 [M + H]⁺ | 0.79 (D) |
| 1.83 | XIII.1 + 5-bromo-2-(methylthio)pyridine | 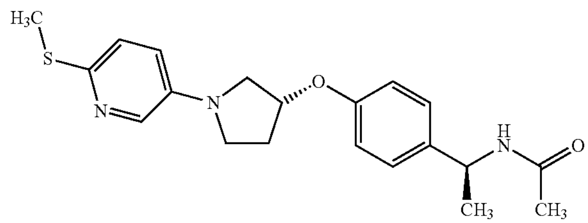 | A | 372 [M + H]⁺ | 0.79 (M) |
| 1.84 | XIII.1 + 2-bromo-6-cyclopentyl-pyridine | 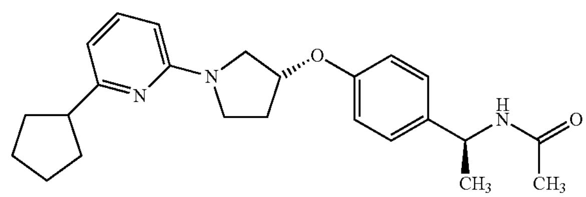 | A | 394 [M + H]⁺ | 1.30 (C) |
| 1.85 | XIX.2 + 2-bromo-6-methyl pyridine | 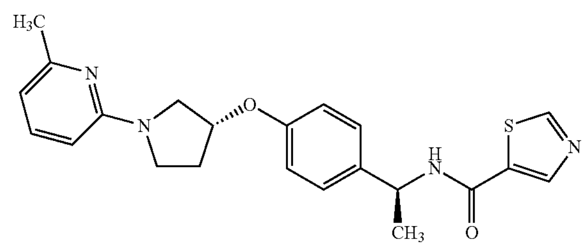 [SMILES: Cc1cccc(N2CC[C@@H](Oc3ccc([C@H](C)NC(=O)c4cncs4)cc3)C2)n1] | A | 409 [M + H]⁺ | 0.81 (B) |
| 1.86 | XIII.1 + 2-bromo-6-cyclobutyl-pyridine | 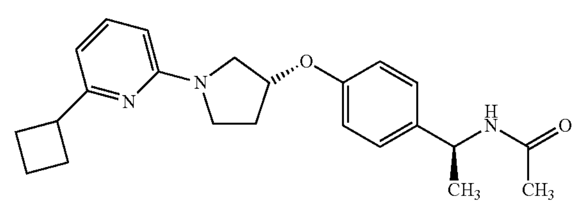 | A | 380 [M + H]⁺ | 1.25 (C) |
| 1.87 | XIII.1 + XXIV.8 | 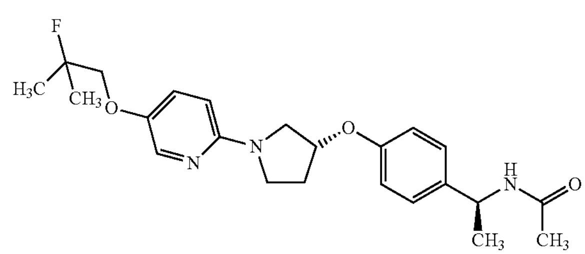 | A | 416 [M + H]⁺ | 1.07 (C) |

-continued

| Ex. | Starting material(s) | Structure | Method | Mass spec result | HPLC retention time (method) |
|---|---|---|---|---|---|
| 1.88 | XIII.1 + XXIV.25 | 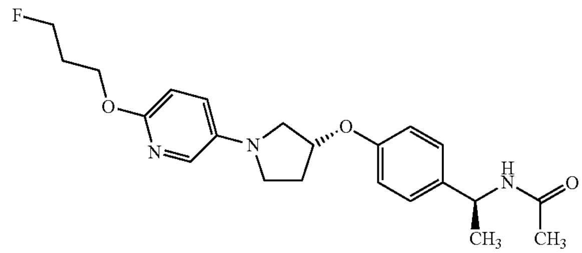 | A | 402 [M + H]⁺ | 1.01 (E) |
| 1.89 | XIII.1 + XXV.18 | 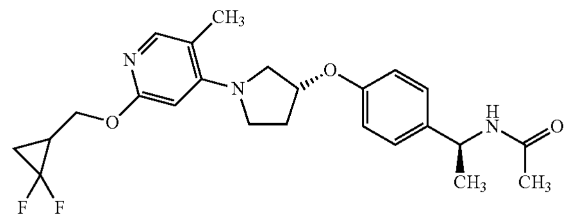 | A | 446 [M + H]⁺ | 0.84 (M) |
| 1.90 | XIII.1 + XXV.19 | 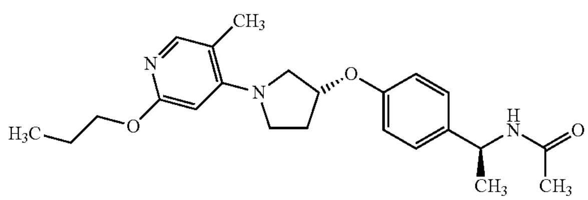 | A | 398 [M + H]⁺ | 0.85 (M) |
| 1.91 | XIII.1 + XXIV.9 | 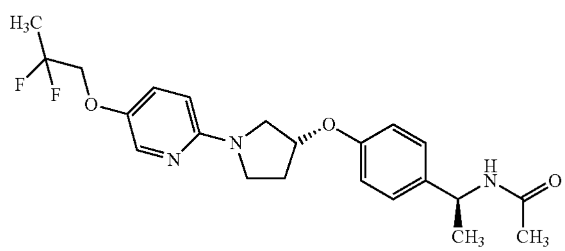 | A | 420 [M + H]⁺ | 0.86 (K) |
| 1.92 | XIII.1 + XXV.20 | 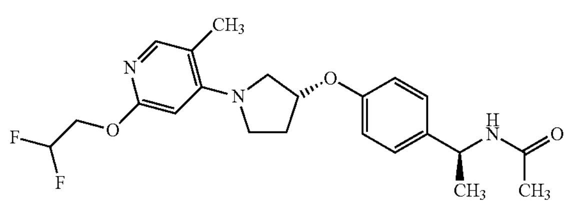 | A | 420 [M + H]⁺ | 0.80 (M) |
| 1.93 | XIII.1 + XXX | 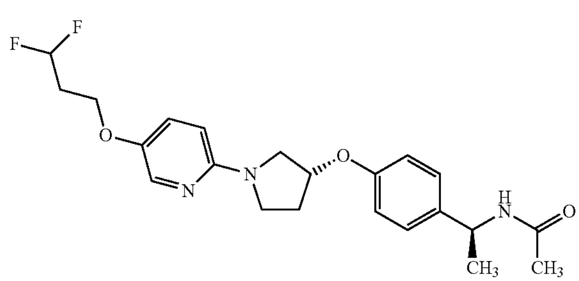 | A | 420 [M + H]⁺ | 1.03 (C) |

-continued

| Ex. | Starting material(s) | Structure | Method | Mass spec result | HPLC retention time (method) |
|---|---|---|---|---|---|
| 1.94 | XIII.6 + XXIV.3 | 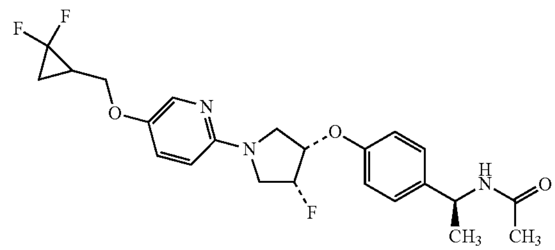 | A | 450 [M + H]+ | 0.84 (M) |
| 1.95 | XIII.3 + XXXIII.3 | 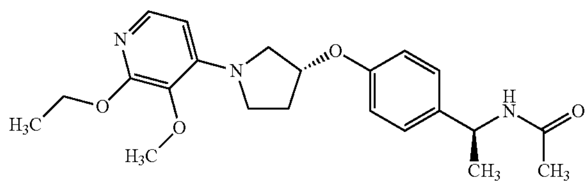 [SMILES: CCOc1nccc(N2CC[C@@H](Oc3ccc([C@H](C)NC(C)=O)cc3)C2)c1OC] | C | 400 [M + H]+ | 0.82 (M) |
| 1.96 | XIII.1 + XXIV.26 | 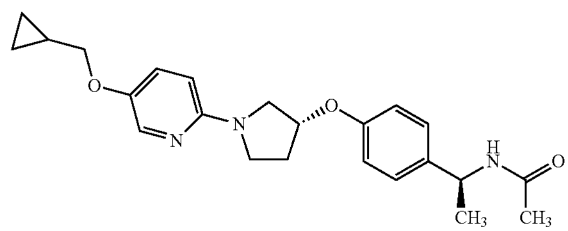 [SMILES: CC(=O)N[C@@H](C)c1ccc(O[C@@H]2CCN(c3ccc(OCC4CC4)cn3)C2)cc1] | A | 396 [M + H]+ | 1.10 (C) |
| 1.97 | XX.5 + N-ethyl-methyl-amine | 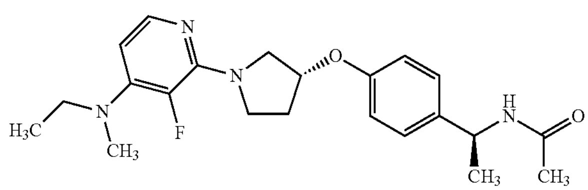 [SMILES: CCN(C)c1ccnc(N2CC[C@@H](Oc3ccc([C@H](C)NC(C)=O)cc3)C2)c1F] | A | 401 [M + H]+ | 1.14 (C) |
| 1.98 | XX.5 + dimethyl-amine | 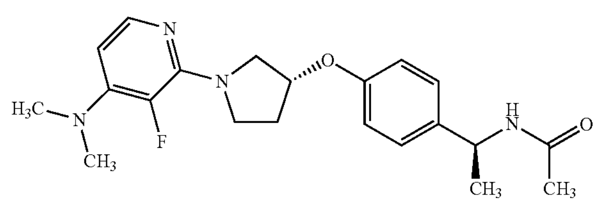 [SMILES: CC(=O)N[C@@H](C)c1ccc(O[C@@H]2CCN(c3nccc(N(C)C)c3F)C2)cc1] | A | 387 [M + H]+ | 1.09 (C) |
| 1.99 | XX.5 + pyrrolidine | 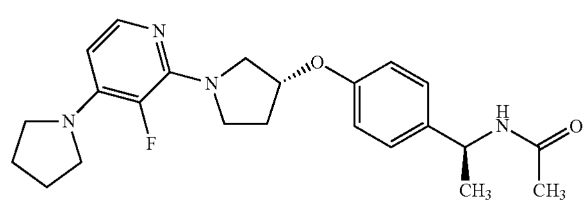 [SMILES: CC(=O)N[C@@H](C)c1ccc(O[C@@H]2CCN(c3nccc(N4CCCC4)c3F)C2)cc1] | A | 413 [M + H]+ | 1.19 (C) |
| 1.100 | XX.5 + cyclo-propyl-N-methyl-methan-amine | 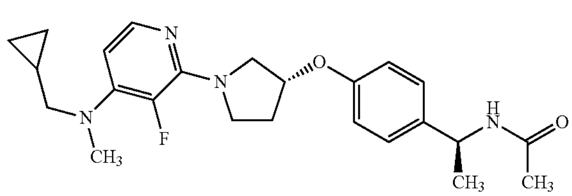 [SMILES: CC(=O)N[C@@H](C)c1ccc(O[C@@H]2CCN(c3nccc(N(C)CC4CC4)c3F)C2)cc1] | A | 427 [M + H]+ | 1.30 (Q) |

-continued

| Ex. | Starting material(s) | Structure | Method | Mass spec result | HPLC retention time (method) |
|---|---|---|---|---|---|
| 1.101 | XX.1 + azetidine | 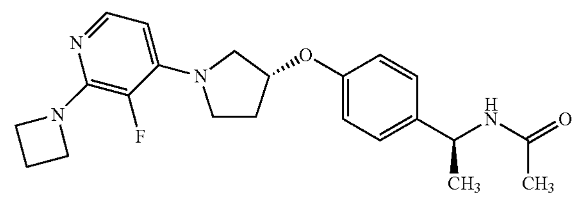 [SMILES: CC(=O)N[C@@H](C)c1ccc(O[C@@H]2CCN(c3ccnc(N4CCC4)c3F)C2)cc1] | A | 399 [M + H]+ | 0.84 (M) |
| 1.102 | XX.1 + piperidine | 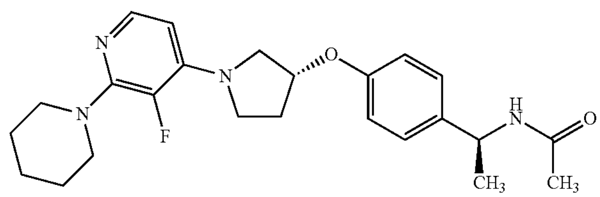 [SMILES: CC(=O)N[C@@H](C)c1ccc(O[C@@H]2CCN(c3ccnc(N4CCCCC4)c3F)C2)cc1] | A | 427 [M + H]+ | 0.89 (M) |
| 1.103 | XX.1 + N-methyl-propan-1-amine | 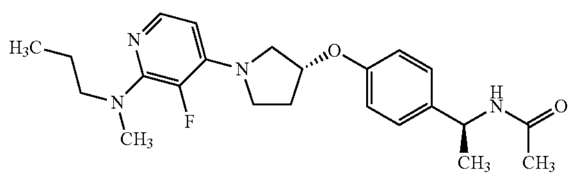 [SMILES: CCCN(C)c1nccc(N2CC[C@@H](Oc3ccc([C@H](C)NC(C)=O)cc3)C2)c1F] | A | 415 [M + H]+ | 0.89 (M) |
| 1.104 | XX.1 + 5-azaspiro-[2.4]heptane | 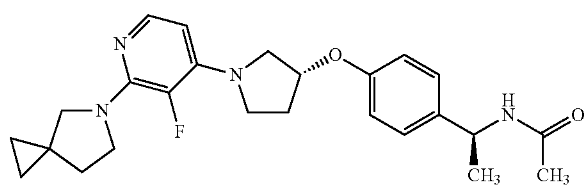 [SMILES: CC(=O)N[C@@H](C)c1ccc(O[C@@H]2CCN(c3ccnc(N4CCC5(CC5)C4)c3F)C2)cc1] | A | 439 [M + H]+ | 0.92 (M) |
| 1.105 | XX.1 + 3,3-difluoro-azetidine | 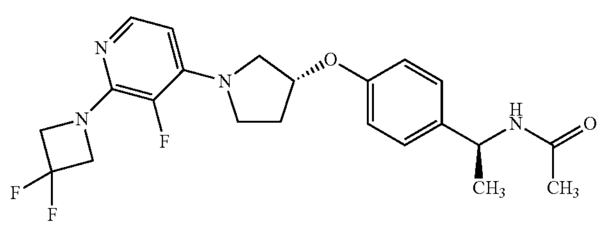 [SMILES: CC(=O)N[C@@H](C)c1ccc(O[C@@H]2CCN(c3ccnc(N4CC(F)(F)C4)c3F)C2)cc1] | A | 435 [M + H]+ | 0.83 (M) |
| 1.106 | XX.1 + 1-methoxy-N-methyl-methanamine | 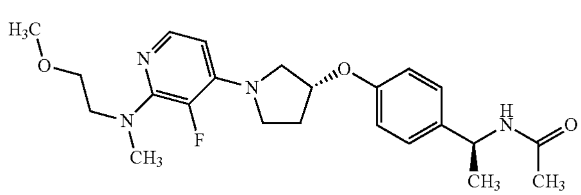 [SMILES: COCCN(C)c1nccc(N2CC[C@@H](Oc3ccc([C@H](C)NC(C)=O)cc3)C2)c1F] | A | 431 [M + H]+ | 0.84 (M) |
| 1.107 | XX.1 + n-propyl-amine | 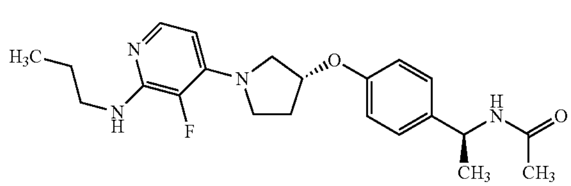 [SMILES: CCCNc1nccc(N2CC[C@@H](Oc3ccc([C@H](C)NC(C)=O)cc3)C2)c1F] | A | 401 [M + H]+ | 0.83 (M) |

| Ex. | Starting material(s) | Structure | Method | Mass spec result | HPLC retention time (method) |
|---|---|---|---|---|---|
| 1.108 | XX.1 + 2,2-difluoro-N-methyl-ethan-amine | 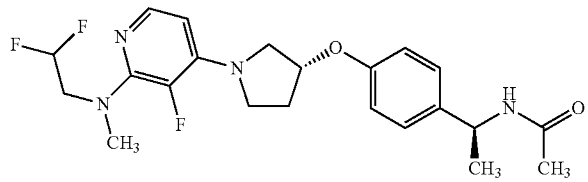 [SMILES: CC(=O)N[C@@H](C)c1ccc(O[C@@H]2CCN(c3ccnc(N(C)CC(F)F)c3F)C2)cc1] | A | 437 [M + H]+ | 0.83 (M) |
| 1.109 | XX.1 + 3-methoxy-azetidine | 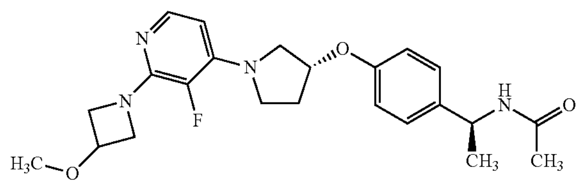 [SMILES: COC1CN(c2nccc(N3CC[C@@H](Oc4ccc([C@H](C)NC(C)=O)cc4)C3)c2F)C1] | A | 429 [M + H]+ | 0.82 (M) |
| 1.110 | XX.1 + 3,3-difluoro-pyrrolidine | 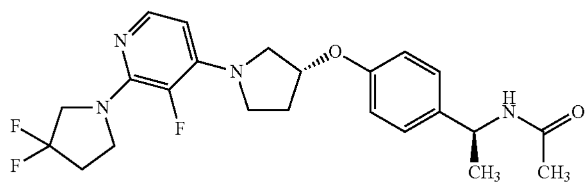 [SMILES: CC(=O)N[C@@H](C)c1ccc(O[C@@H]2CCN(c3ccnc(N4CCC(F)(F)C4)c3F)C2)cc1] | A | 449 [M + H]+ | 0.85 (M) |
| 1.111 | XX.1 + N-methyl-propan-2-amine | 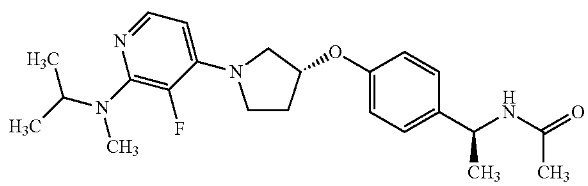 | A | 415 [M + H]+ | 0.87 (M) |
| 1.112 | XX.1 + 2,2,2-trifluoro-N-methyl-ethan-amine | 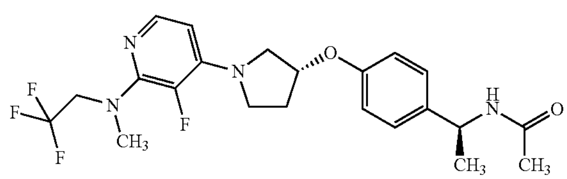 [SMILES: CC(=O)N[C@@H](C)c1ccc(O[C@@H]2CCN(c3ccnc(N(C)CC(F)(F)F)c3F)C2)cc1] | A | 455 [M + H]+ | 0.85 (M) |
| 1.113 | XX.1 + cyclo-pentyl-amine | 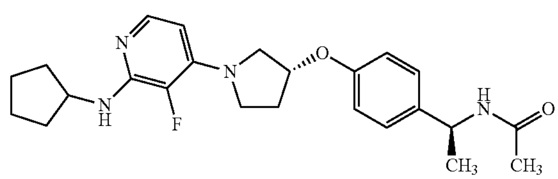 [SMILES: CC(=O)N[C@@H](C)c1ccc(O[C@@H]2CCN(c3ccnc(NC4CCCC4)c3F)C2)cc1] | A | 427 [M + H]+ | 0.92 (K) |
| 1.114 | XX.1 + cyclo-propyl-methan-amine | 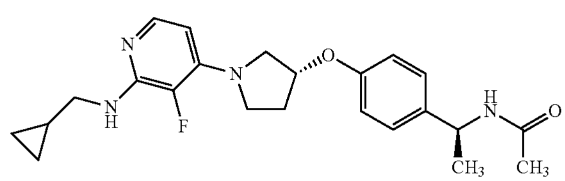 [SMILES: CC(=O)N[C@@H](C)c1ccc(O[C@@H]2CCN(c3ccnc(NCC4CC4)c3F)C2)cc1] | A | 413 [M + H]+ | 0.87 (K) |
| 1.115 | XX.1 + ethan-amine | 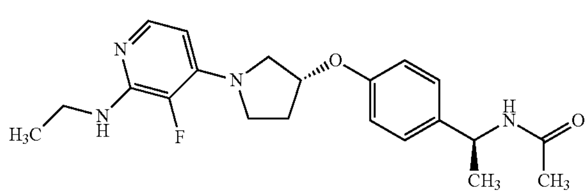 | A | 387 [M + H]+ | 0.81 (K) |

-continued

| Ex. | Starting material(s) | Structure | Method | Mass spec result | HPLC retention time (method) |
|---|---|---|---|---|---|
| 1.116 | XX.1 + 2,2-difluoro-ethan-amine | 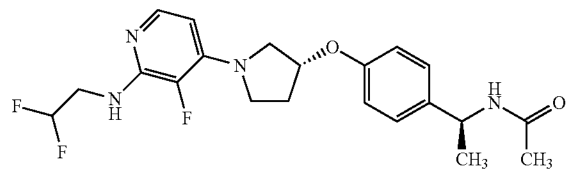 [SMILES: CC(=O)N[C@@H](C)c1ccc(O[C@@H]2CCN(c3ccnc(NCC(F)F)c3F)C2)cc1] | A | 423 [M + H]+ | 0.81 (K) |
| 1.117 | XIII.1 + XXIV.28 | 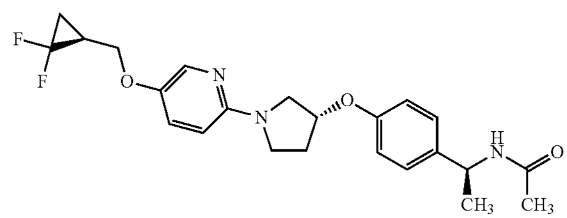 [SMILES: CC(=O)N[C@@H](C)c1ccc(O[C@@H]2CCN(c3ccc(OC[C@@H]4CC4(F)F)cn3)C2)cc1] | A | 432 [M + H]+ | 0.96 (E) |
| 1.118 | XIII.1 + XXIV.27 | 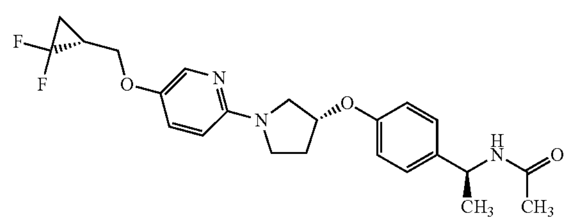 [SMILES: CC(=O)N[C@@H](C)c1ccc(O[C@@H]2CCN(c3ccc(OC[C@H]4CC4(F)F)cn3)C2)cc1] | A | 432 [M + H]+ | 0.85 (M) |
| 1.119 | XX.1 + 2-methoxy-ethan-amine | 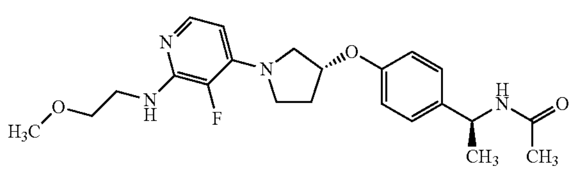 [SMILES: COCCNc1nccc(N2CC[C@@H](Oc3ccc([C@H](C)NC(C)=O)cc3)C2)c1F] | A | 417 [M + H]+ | 0.80 (M) |
| 1.120 | XIII.1 + XXXIII.2 | 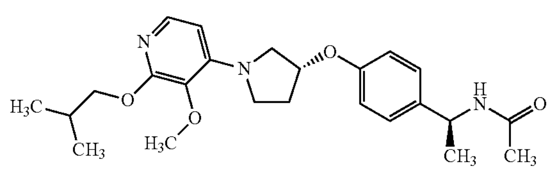 [SMILES: COc1c(N2CC[C@@H](Oc3ccc([C@H](C)NC(C)=O)cc3)C2)ccnc1OCC(C)C] | C | 428 [M + H]+ | 0.84 (W) |
| 1.121 | XIII.1 + XXXIII.1 | 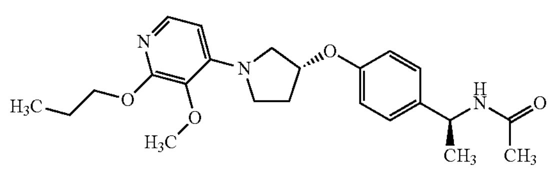 [SMILES: CCCOc1nccc(N2CC[C@@H](Oc3ccc([C@H](C)NC(C)=O)cc3)C2)c1OC] | C | 414 [M + H]+ | 1.08 (Y) |
| 1.122 | XIII.1 + XXV.21 | 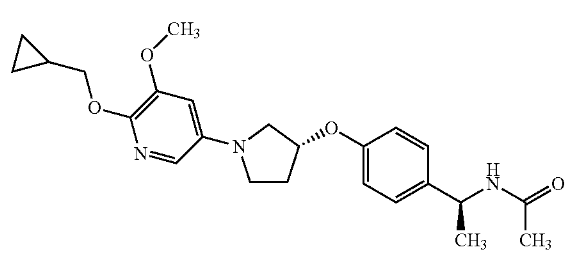 [SMILES: COc1cc(N2CC[C@@H](Oc3ccc([C@H](C)NC(C)=O)cc3)C2)cnc1OCC1CC1] | C | 426 [M + H]+ | 1.07 (Y) |

-continued

| Ex. | Starting material(s) | Structure | Method | Mass spec result | HPLC retention time (method) |
|---|---|---|---|---|---|
| 1.123 | XIII.1 + XXIV.29 | 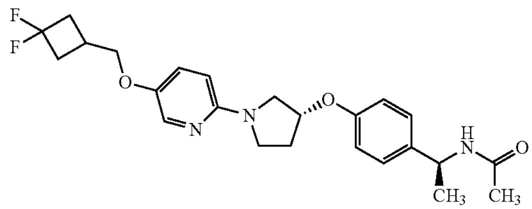 [SMILES: CC(=O)N[C@@H](C)c1ccc(O[C@@H]2CCN(c3ccc(OCC4CC(F)(F)C4)cn3)C2)cc1] | A | 446 [M + H]⁺ | 1.09 (Y) |
| 1.124 | XXI.1 + 3,3-difluoro-pyrrolidine | 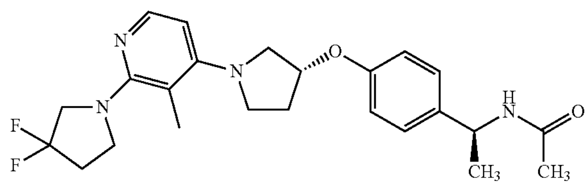 | A | 445 [M + H]⁺ | 1.08 (Y) |
| 1.125 | XXI.1 + pyrrolidine | 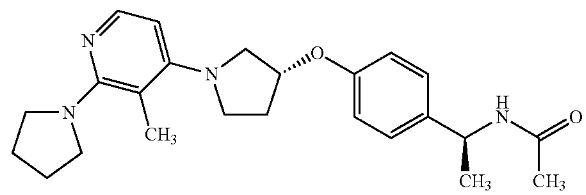 [SMILES: CC(=O)N[C@@H](C)c1ccc(O[C@@H]2CCN(c3ccnc(N4CCCC4)c3C)C2)cc1] | A | 409 [M + H]⁺ | 1.06 (Y) |
| 1.126 | XXI.1 + azetidine | 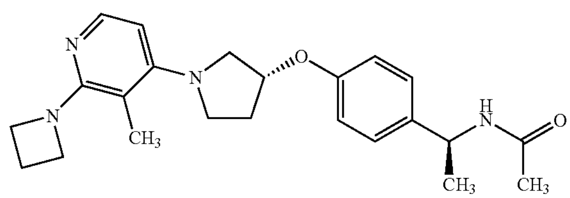 [SMILES: CC(=O)N[C@@H](C)c1ccc(O[C@@H]2CCN(c3ccnc(N4CCC4)c3C)C2)cc1] | A | 395 [M + H]⁺ | 0.93 (Y) |
| 1.127 | XIII.1 + XXXIII.4 | 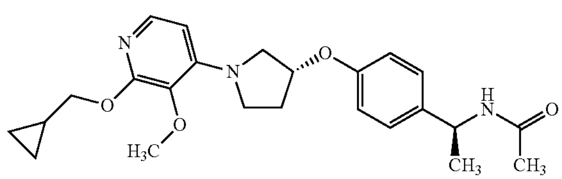 [SMILES: COc1c(N2CC[C@@H](Oc3ccc([C@H](C)NC(C)=O)cc3)C2)ccnc1OCC1CC1] | C | 426 [M + H]⁺ | 1.09 (Y) |
| 1.128 | XIII.1 + V.1 | 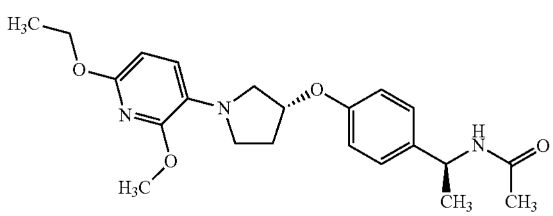 [SMILES: CCOc1ccc(N2CC[C@@H](Oc3ccc([C@H](C)NC(C)=O)cc3)C2)c(OC)n1] | C | 400 [M + H]⁺ | 1.15 (Y) |
| 1.129 | XIII.1 + IV.1 | 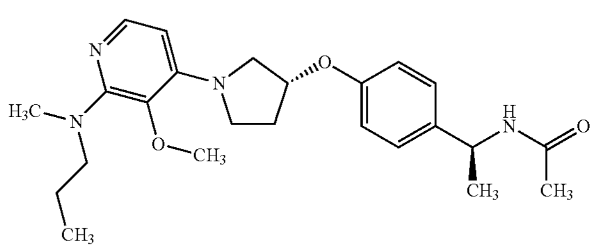 [SMILES: CCCN(C)c1nccc(N2CC[C@@H](Oc3ccc([C@H](C)NC(C)=O)cc3)C2)c1OC] | C | 427 [M + H]⁺ | 0.90 (M) |

| Ex. | Starting material(s) | Structure | Method | Mass spec result | HPLC retention time (method) |
|---|---|---|---|---|---|
| 1.130 | XIII.1 + V.2 | 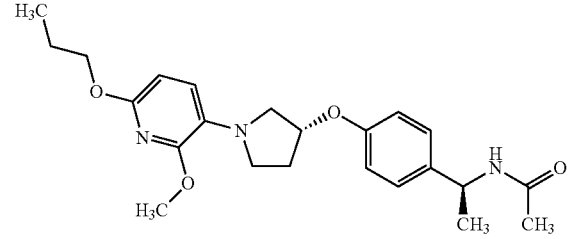 [SMILES: CCCOc1ccc(N2CC[C@@H](Oc3ccc([C@H](C)NC(C)=O)cc3)C2)c(OC)n1] | A | 414 [M + H]+ | 1.25 (Y) |
| 1.131 | XXI.9 + azetidine | 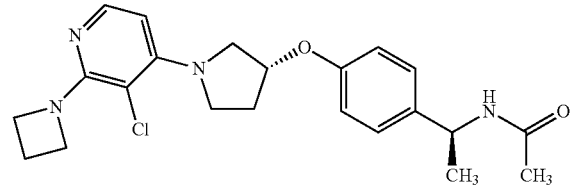 [SMILES: CC(=O)N[C@@H](C)c1ccc(O[C@@H]2CCN(c3ccnc(N4CCC4)c3Cl)C2)cc1] | A | 415 [M + H]+ | 0.84 (M) |
| 1.132 | XXI.9 + 3,3-difluoro-pyrrolidine | 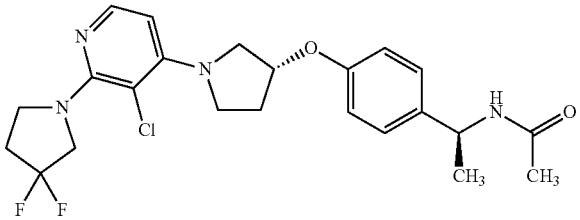 [SMILES: CC(=O)N[C@@H](C)c1ccc(O[C@@H]2CCN(c3ccnc(N4CCC(F)(F)C4)c3Cl)C2)cc1] | A | 465 [M + H]+ | 0.88 (M) |
| 1.133 | XIII.1 + VI.1A | 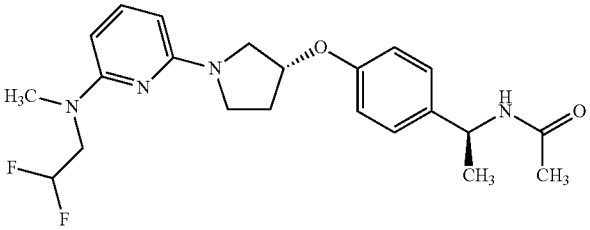 [SMILES: CC(=O)N[C@@H](C)c1ccc(O[C@@H]2CCN(c3cccc(N(C)CC(F)F)n3)C2)cc1] | A | 419 [M + H]+ | 0.96 (K) |
| 1.134 | XIII.1 + VI.2 | 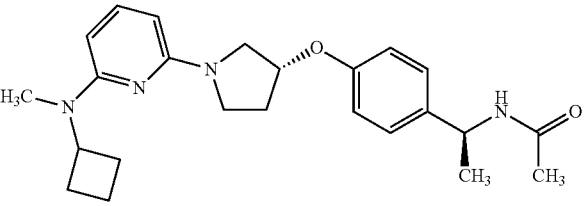 [SMILES: CC(=O)N[C@@H](C)c1ccc(O[C@@H]2CCN(c3cccc(N(C)C4CCC4)n3)C2)cc1] | A | 409 [M + H]+ | 1.04 (K) |
| 1.135 | XXI.9 + propan-amine | 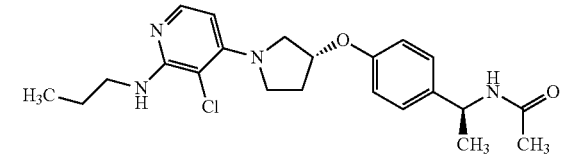 [SMILES: CCCNc1nccc(N2CC[C@@H](Oc3ccc([C@H](C)NC(C)=O)cc3)C2)c1Cl] | A | 417 [M + H]+ | 0.85 (M) |
| 1.136 | XIII.1 + IV.2 | 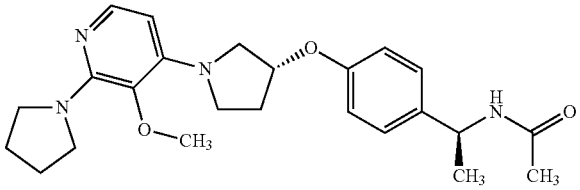 [SMILES: COc1c(N2CC[C@@H](Oc3ccc([C@H](C)NC(C)=O)cc3)C2)ccnc1N1CCCC1] | A | 425 [M + H]+ | 0.89 (K) |

-continued

| Ex. | Starting material(s) | Structure | Method | Mass spec result | HPLC retention time (method) |
|---|---|---|---|---|---|
| 1.137 | XIII.1 + IV.3 | 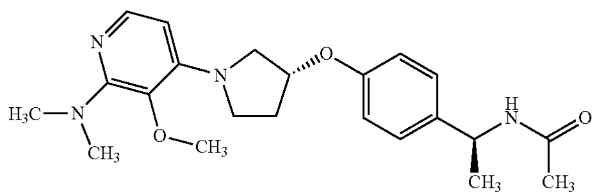 [SMILES: COc1c(N2CC[C@@H](Oc3ccc([C@H](C)NC(C)=O)cc3)C2)ccnc1N(C)C] | A | 399 [M + H]+ | 0.85 (K) |
| 1.138 | XXI.9 + cyclo-propyl-methan-amine | 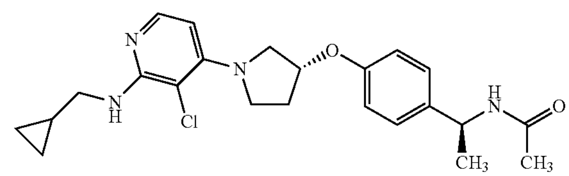 | A | 429 [M + H]+ | 0.87 (M) |
| 1.139 | XIII.1 + XXXIII.5 | 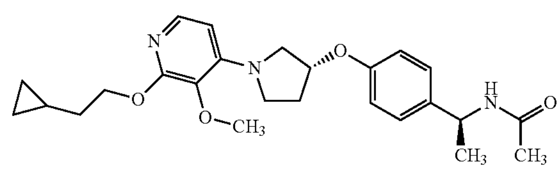 [SMILES: COc1c(N2CC[C@@H](Oc3ccc([C@H](C)NC(C)=O)cc3)C2)ccnc1OCCC1CC1] | A | 440 [M + H]+ | 0.95 (K) |
| 1.140 | XXI.11 + cyclo-propyl-methan-amine | 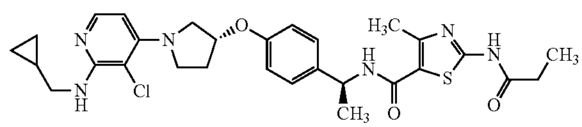 [SMILES: CCC(=O)Nc1nc(C)c(C(=O)N[C@@H](C)c2ccc(O[C@@H]3CCN(c4ccnc(NCC5CC5)c4Cl)C3)cc2)s1] | A | 583 [M + H]+ | 0.87 (D) |
| 1.141 | XXI.12 + 2,2-difluoro-ethyamine | 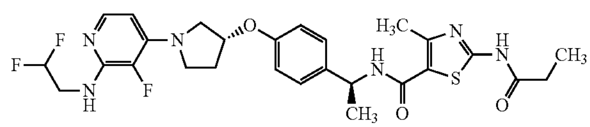 [SMILES: CCC(=O)Nc1nc(C)c(C(=O)N[C@@H](C)c2ccc(O[C@@H]3CCN(c4ccnc(NCC(F)F)c4F)C3)cc2)s1] | A | 577 [M + H]+ | 0.87 (K) |
| 1.142 | XXI.12 + cyclo-propyl-methan-amine | 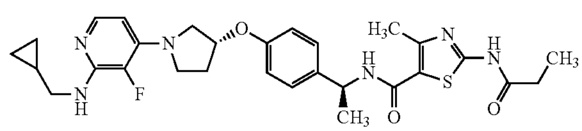 | A | 567 [M + H]+ | 0.86 (D) |
| 1.143 | XXI.11 + 2,2-difluoro-ethan-amine | 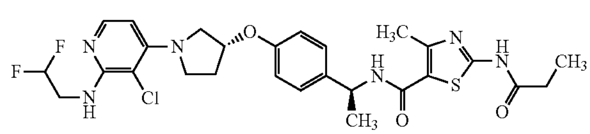 [SMILES: CCC(=O)Nc1nc(C)c(C(=O)N[C@@H](C)c2ccc(O[C@@H]3CCN(c4ccnc(NCC(F)F)c4Cl)C3)cc2)s1] | A | 593 [M + H]+ | 0.92 (K) |
| 1.144 | XIX.3 + XXIV.27 | 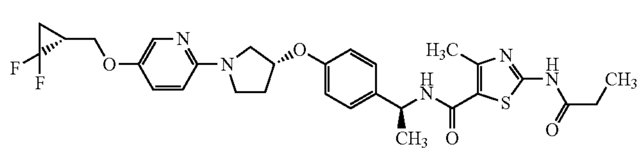 [SMILES: CCC(=O)Nc1nc(C)c(C(=O)N[C@@H](C)c2ccc(O[C@@H]3CCN(c4ccc(OC[C@H]5CC5(F)F)cn4)C3)cc2)s1] | A | 586 [M + H]+ | 0.86 (AB) |
| 1.145 | XIX.3 + XXIV.28 | 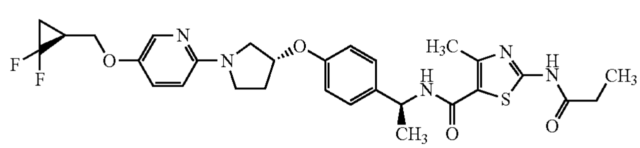 [SMILES: CCC(=O)Nc1nc(C)c(C(=O)N[C@@H](C)c2ccc(O[C@@H]3CCN(c4ccc(OC[C@@H]5CC5(F)F)cn4)C3)cc2)s1] | A | 586 [M + H]+ | 0.86 (AB) |

-continued

| Ex. | Starting material(s) | Structure | Method | Mass spec result | HPLC retention time (method) |
|---|---|---|---|---|---|
| 1.146 | XXI.10 + 3,3-difluoro-pyrrolidine | 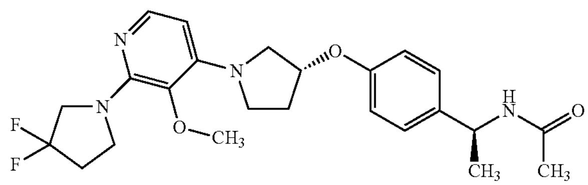 [SMILES: COc1c(N2CC[C@@H](Oc3ccc([C@H](C)NC(C)=O)cc3)C2)ccnc1N1CCC(F)(F)C1] | A | 461 [M + H]⁺ | 0.85 (M) |
| 1.147 | XX.14 + cyclo-propyl-methan-amine | 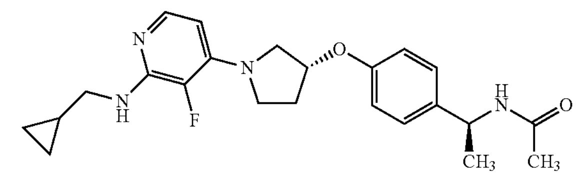 | A | 442 [M + H]⁺ | 0.76 (AC) |
| 1.148 | XXI.9 + pyrrolidine | 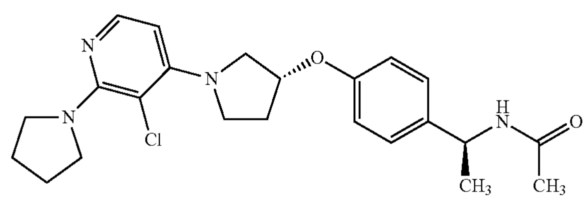 | A | 429 [M + H]⁺ | 0.87 (M) |
| 1.149 | XIII.1 + XXXIII.6 | 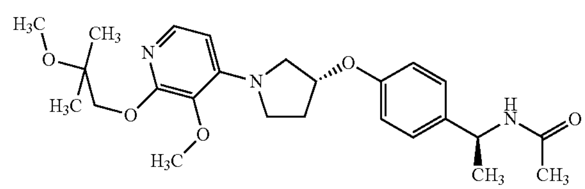 [SMILES: COc1c(N2CC[C@@H](Oc3ccc([C@H](C)NC(C)=O)cc3)C2)ccnc1OCC(C)(C)OC] | A | 458 [M + H]⁺ | 0.72 (AC) |
| 1.150 | XIII.1 + XXXIII.7 | 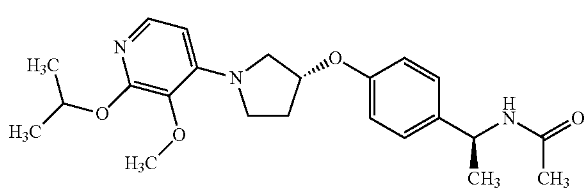 | A | 414 [M + H]⁺ | 0.90 (K) |
| 1.151 | XIII.1 + XXXIII.8 | 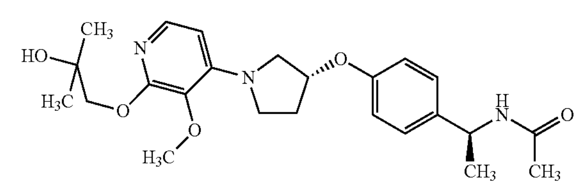 [SMILES: COc1c(N2CC[C@@H](Oc3ccc([C@H](C)NC(C)=O)cc3)C2)ccnc1OCC(C)(C)O] | A | 444 [M + H]⁺ | 0.82 (M) |

Example 2

Example 2.1

General Route

2-Acetamido-N—((1S)-1-(4-((3R)-1-(5-((2,2-difluorocyclopropyl)methoxy)pyridin-2-yl)pyrrolidin-3-yloxy)phenyl)ethyl)-4-methylthiazole-5-carboxamide

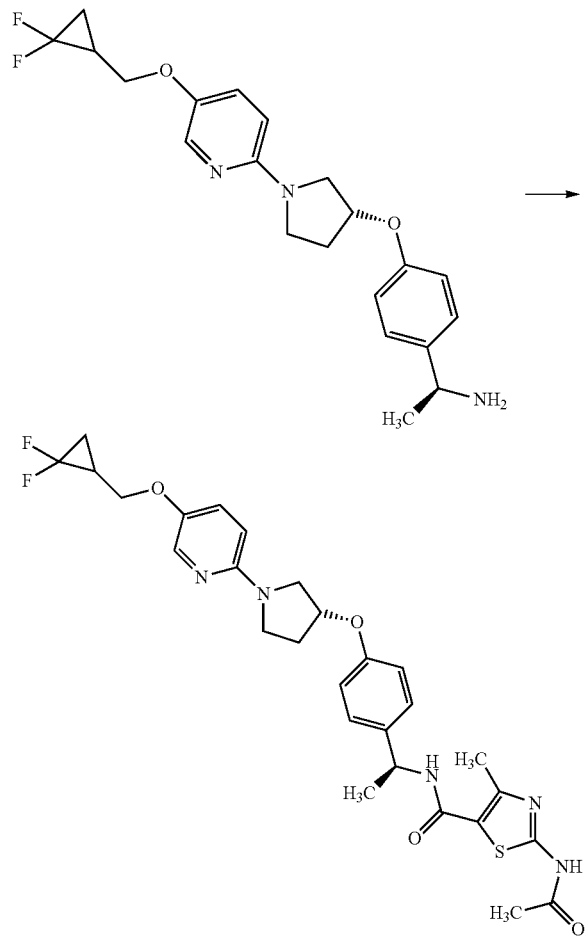

25.7 mg (0.13 mmol) 2-acetylamino-4-methyl-thiazole-5-carboxylic acid, 43.9 µl (0.26 mmol) DIPEA and 45.3 mg (0.14 mmol) TBTU are added to 3 mL DMF and stirred for 10 min. Then 50.0 mg (0.13 mmol) of the amine XXII.1 are added and the resulting mixture is stirred at r.t. over night. Afterwards the mixture is directly purified by HPLC (MeOH/H$_2$O/TFA).

$C_{28}H_{31}F_2N_5O_4S$ (M=571.6 g/mol)

ESI-MS: 572 [M+H]$^+$

R$_t$(HPLC):1.11 min (method C)

The following compounds are prepared analogously to example 2.1:

For the examples CIP is used as coupling reagent ACN is used as solvent. For the examples 2.3-2.8, 2.122 and 2.125 the reaction time is 2 h.

For the examples 2.69-2.93 and 2.99-2.121 TEA is used as base.

For example 2.55 the product is added to TFA/H$_2$O (95/5) and stirred at r.t. 3 h to cleave the tert-butyl group.

For example 2.64 the product is added to methanol and treated with aq. HCl solution (c=1 mol/L) to cleave the THP protecting group.

For the examples where 1-chloro-N,N-2-trimethylpropenylamine is used, the reagent is added to the a mixture of the appropiate acid in DCM and stirred at r.t. for 30 min.

Then the appropriate amine and DIPEA are added and the resulting mixture is stirred at r.t. for 1 h. After aq. work up the crude product is purified by HPLC.

| Ex. | Starting material | Coupling reagent | Structure | Mass spec result | HPLC retention time (method) |
|---|---|---|---|---|---|
| 2.1 | XXII.1 | TBTU | 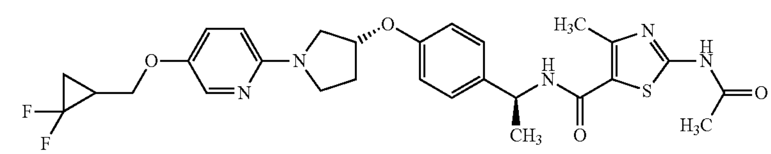 | 572 [M + H]$^+$ | 1.11 (C) |

-continued
| Ex. | Starting material | Coupling reagent | Structure | Mass spec result | HPLC retention time (method) |
|---|---|---|---|---|---|
| 2.2 | XXII.4 | TBTU | 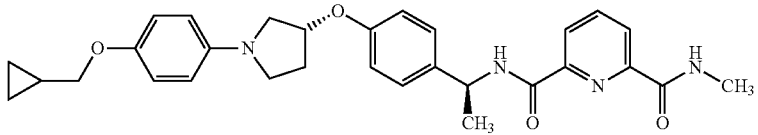 | 515 [M + H]⁺ | 0.63 (O) |
| 2.3 | XXIII | TBTU | 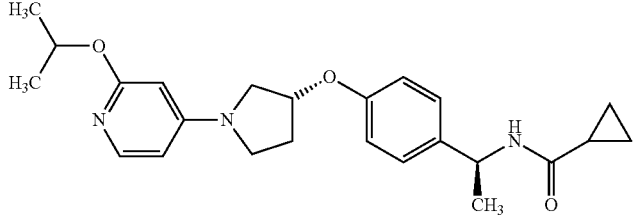 | 410 [M + H]⁺ | 1.10 (C) |
| 2.4 | XXIII | TBTU | 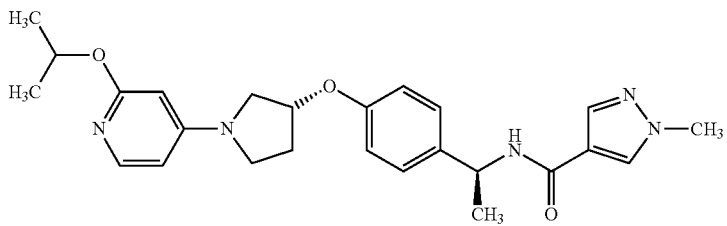 | 450 [M + H]⁺ | 1.07 (C) |
| 2.5 | XXIII | TBTU | 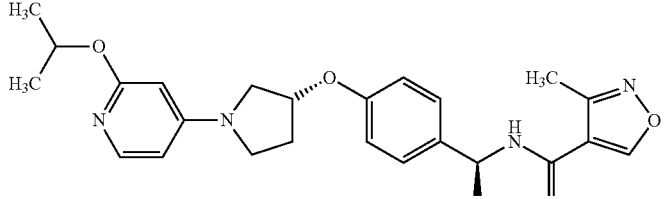 | 451 [M + H]⁺ | 1.11 (C) |
| 2.6 | XXIII | TBTU | 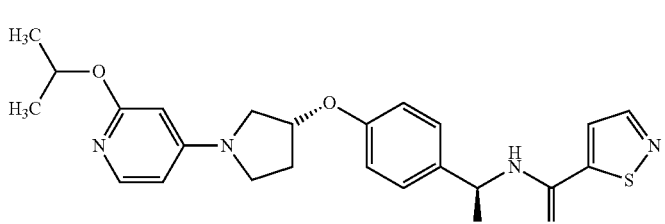 | 453 [M + H]⁺ | 1.12 (C) |
| 2.7 | XXIII | TBTU | 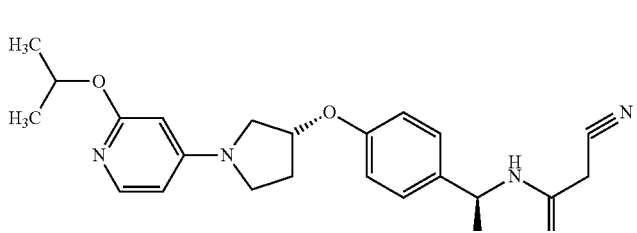 | 409 [M + H]⁺ | 1.05 (C) |

| Ex. | Starting material | Coupling reagent | Structure | Mass spec result | HPLC retention time (method) |
|---|---|---|---|---|---|
| 2.8 | XXIII | TBTU | 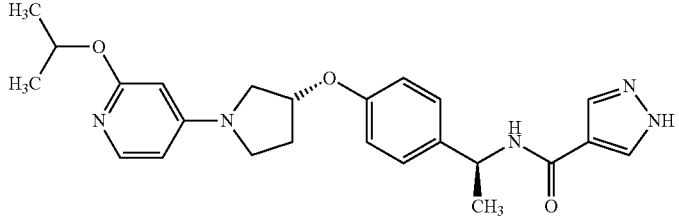 | 436 [M + H]+ | 1.05 (C) |
| 2.9 | XXIII | CIP | 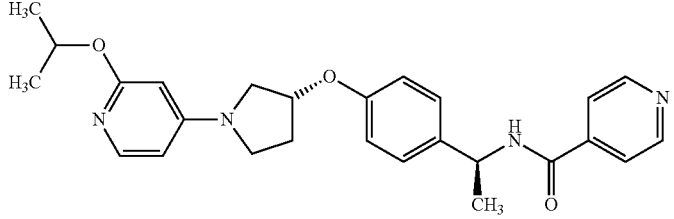 | 447 [M + H]+ | 1.13 (V) |
| 2.10 | XXIII | CIP | 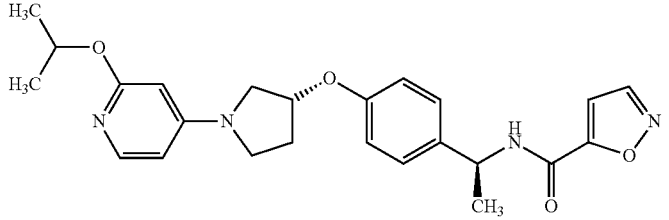 | 437 [M + H]+ | 1.28 (V) |
| 2.11 | XXIII | CIP | 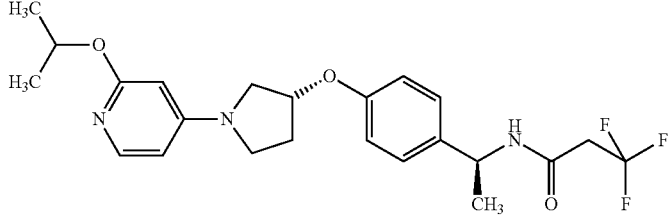 | 452 [M + H]+ | 1.31 (V) |
| 2.12 | XXIII | CIP | 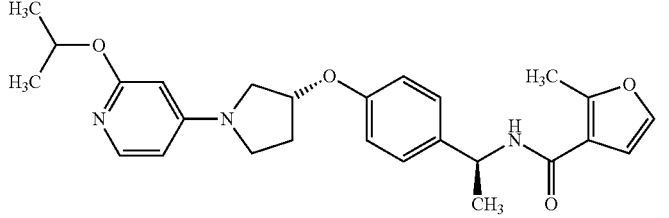 | 450 [M + H]+ | 1.39 (V) |
| 2.13 | XXIII | CIP | 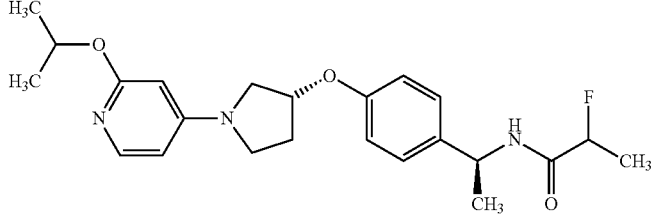 | 416 [M + H]+ | 1.27 (V) |

-continued
| Ex. | Starting material | Coupling reagent | Structure | Mass spec result | HPLC retention time (method) |
|---|---|---|---|---|---|
| 2.14 | XXIII | CIP | 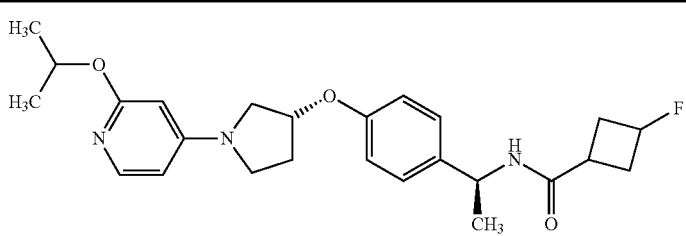 | 442 [M + H]+ | 1.31 (V) |
| 2.15 | XXIII | CIP | 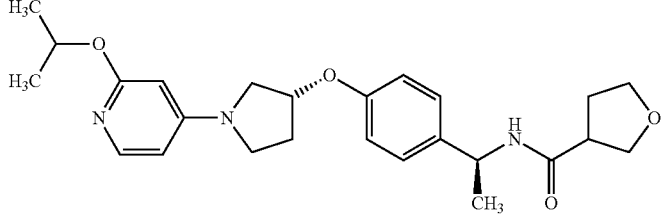 | 440 [M + H]+ | 1.22 (V) |
| 2.16 | XXIII | CIP | 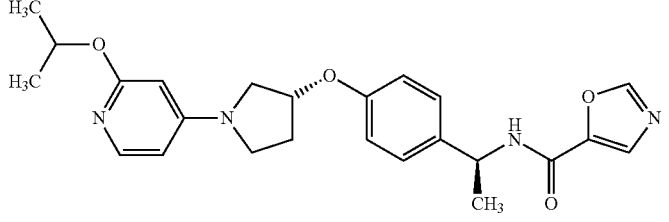 | 436 [M + H]+ | 1.25 (V) |
| 2.17 | XXIII | CIP | 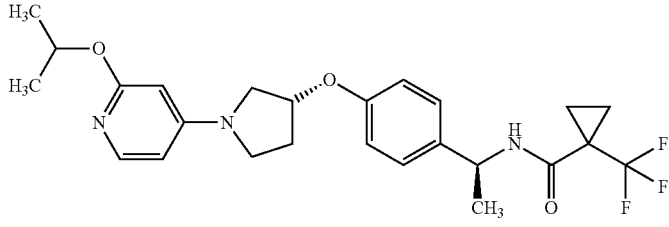 | 478 [M + H]+ | 1.42 (V) |
| 2.18 | XXIII | CIP | 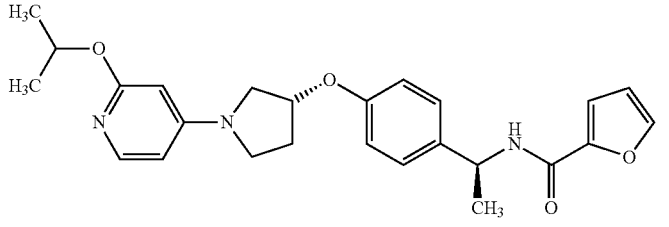 | 436 [M + H]+ | 1.31 (V) |
| 2.19 | XXIII | CIP | 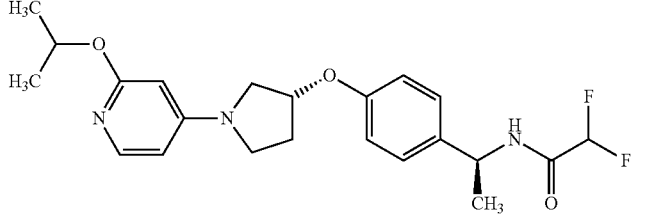 | 420 [M + H]+ | 1.26 (V) |

-continued

| Ex. | Starting material | Coupling reagent | Structure | Mass spec result | HPLC retention time (method) |
|---|---|---|---|---|---|
| 2.20 | XXIII | CIP | 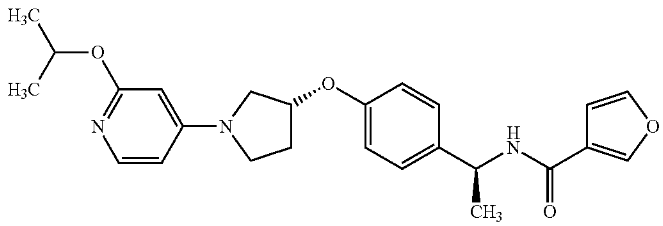 | 436 [M + H]+ | 1.32 (V) |
| 2.21 | XXIII | CIP | 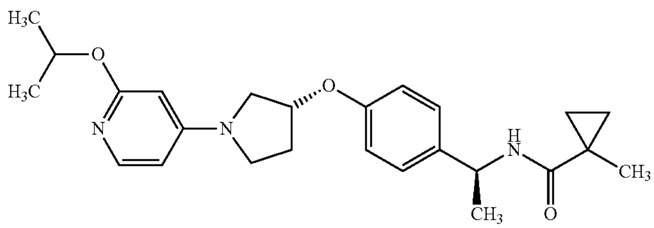 | 424 [M + H]+ | 1.34 (V) |
| 2.22 | XXIII | CIP | 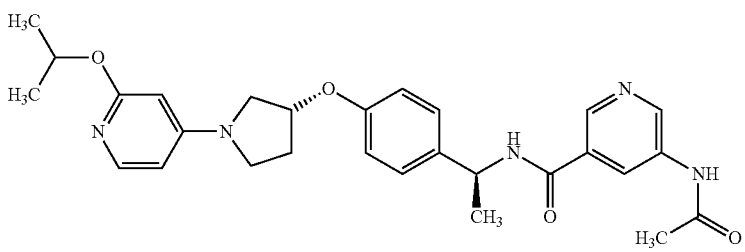 | 504 [M + H]+ | 1.23 (V) |
| 2.23 | XXIII | CIP | 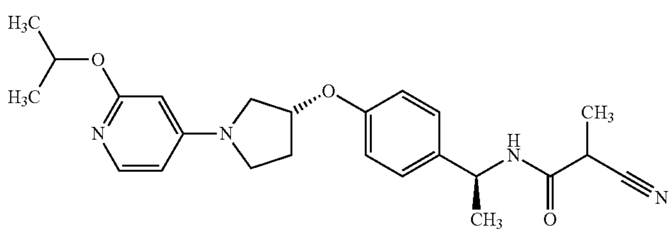 | 423 [M + H]+ | 1.25 (V) |
| 2.24 | XXIII | CIP | 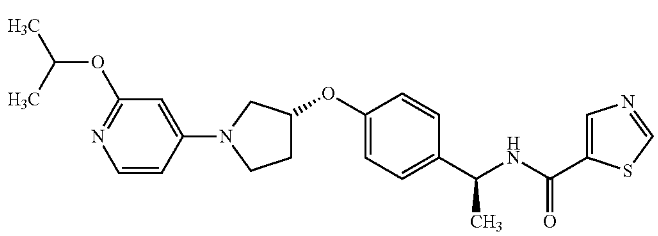 | 453 [M + H]+ | 1.27 (V) |
| 2.25 | XXIII | CIP | 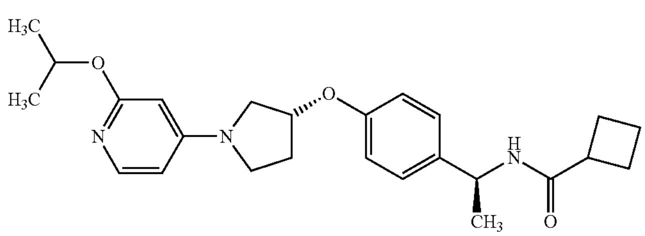 | 424 [M + H]+ | 1.33 (V) |

-continued

| Ex. | Starting material | Coupling reagent | Structure | Mass spec result | HPLC retention time (method) |
|---|---|---|---|---|---|
| 2.26 | XXIII | CIP | 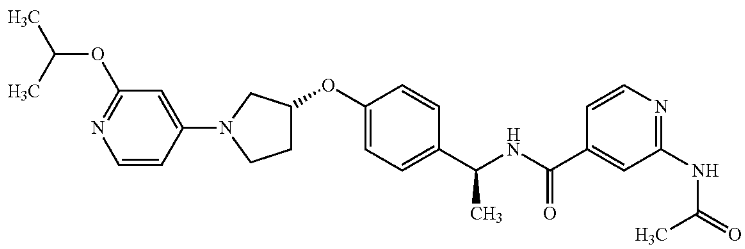 | 504 [M + H]+ | 1.28 (V) |
| 2.27 | XXIII | CIP | 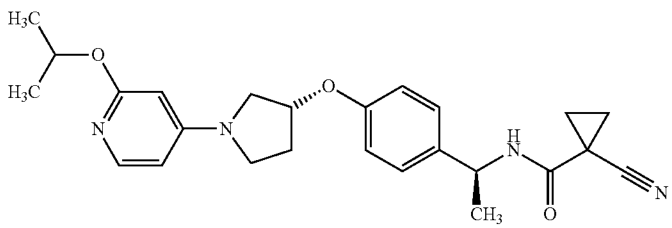 | 435 [M + H]+ | 1.30 (V) |
| 2.28 | XXIII | CIP | 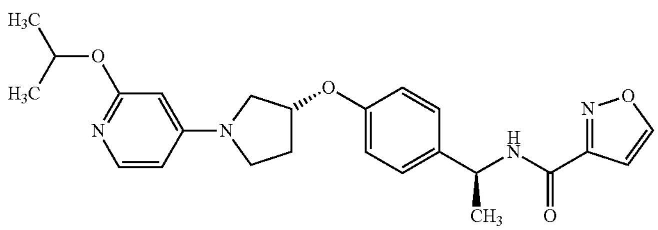 | 437 [M + H]+ | 1.29 (V) |
| 2.29 | XXIII | CIP | 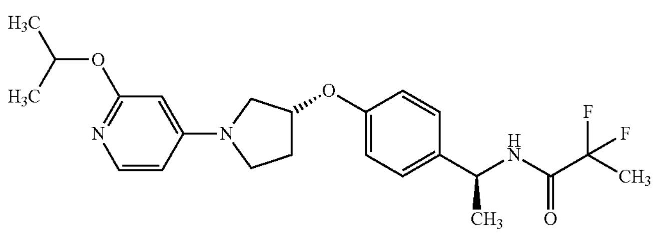 | 434 [M + H]+ | 1.30 (V) |
| 2.30 | XXIII | CIP | 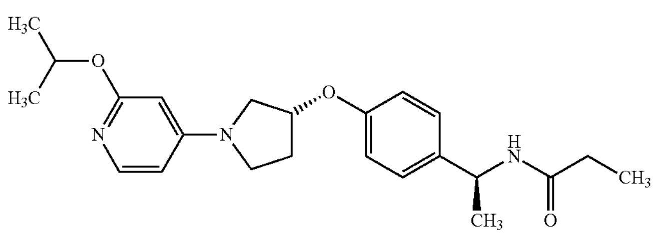 | 398 [M + H]+ | 1.26 (V) |
| 2.31 | XXIII | CIP | 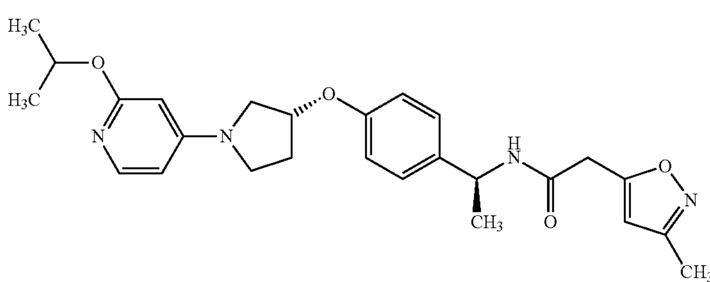 | 465 [M + H]+ | 1.28 (V) |

-continued

| Ex. | Starting material | Coupling reagent | Structure | Mass spec result | HPLC retention time (method) |
|---|---|---|---|---|---|
| 2.32 | XXII.3 | TBTU | 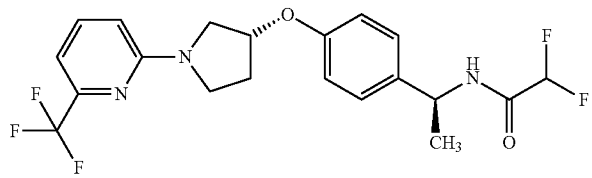 | 430 [M + H]+ | 1.54 (P) |
| 2.33 | XXII.1 | TBTU | 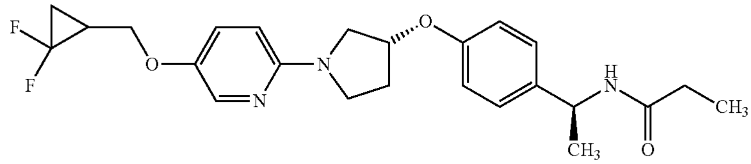 | 446 [M + H]+ | 0.99 (E) |
| 2.34 | XXII.1 | TBTU | 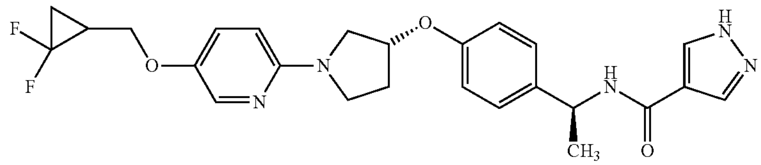 | 484 [M + H]+ | 0.95 (E) |
| 2.35 | XXII.1 | TBTU | 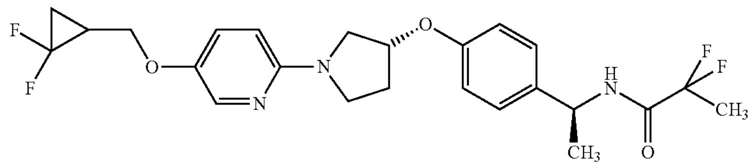 | 482 [M + H]+ | 1.11 (C) |
| 2.36 | XXII.3 | TBTU | 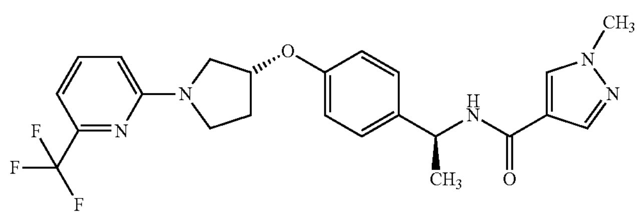 | 460 [M + H]+ | 1.97 (V) |
| 2.37 | XXII.3 | TBTU | 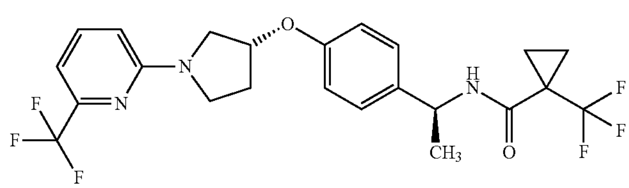 | 488 [M + H]+ | 2.07 (V) |
| 2.38 | XXII.3 | TBTU | 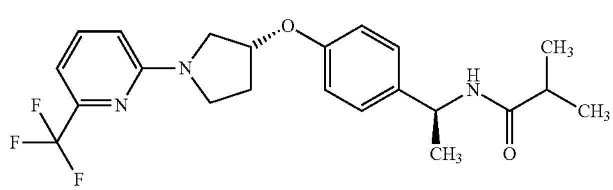 | 422 [M + H]+ | 2.02 (V) |
| 2.39 | XXII.3 | TBTU | 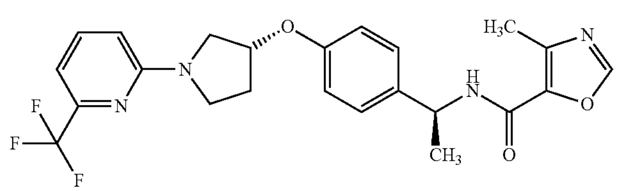 | 461 [M + H]+ | 2.01 (V) |

-continued
| Ex. | Starting material | Coupling reagent | Structure | Mass spec result | HPLC retention time (method) |
|---|---|---|---|---|---|
| 2.40 | XXII.3 | TBTU | 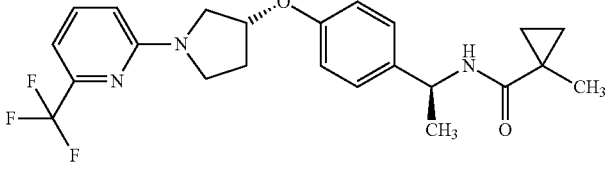 | 434 [M + H]+ | 2.04 (V) |
| 2.41 | XXII.3 | TBTU | 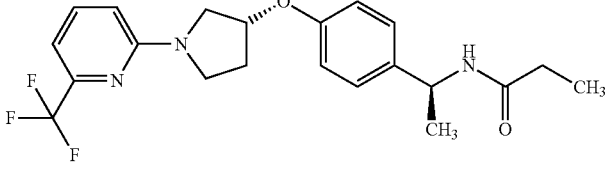 | 408 [M + H]+ | 1.99 (V) |
| 2.42 | XXII.3 | TBTU | 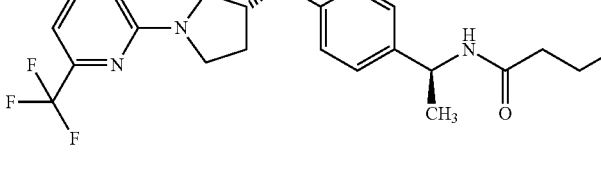 | 433 [M + H]+ | 1.94 (V) |
| 2.43 | XXII.3 | TBTU | 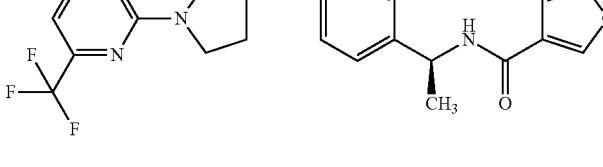 | 461 [M + H]+ | 2.02 (V) |
| 2.44 | XXII.3 | TBTU | 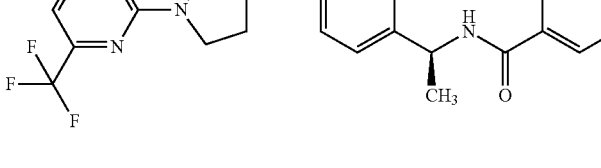 | 475 [M + H]+ | 2.01 (V) |
| 2.45 | XXII.3 | TBTU | 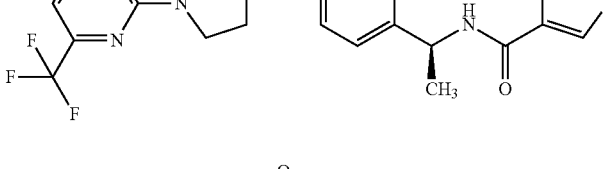 | 463 [M + H]+ | 2.04 (V) |
| 2.45 | XXII.3 | CIP | 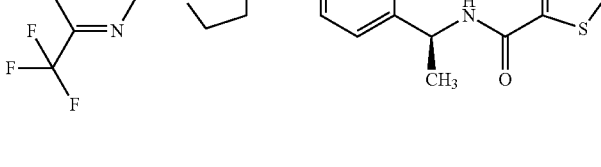 | 463 [M + H]+ | 0.95 (K) |

-continued

| Ex. | Starting material | Coupling reagent | Structure | Mass spec result | HPLC retention time (method) |
|---|---|---|---|---|---|
| 2.47 | XXII.3 | TBTU | 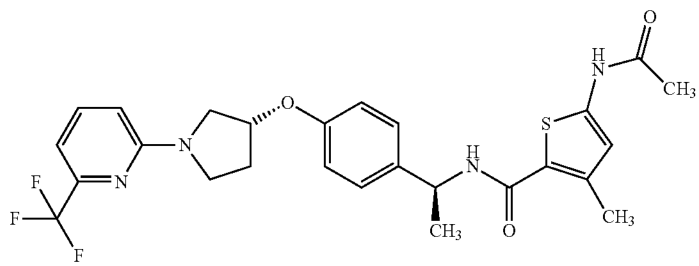 | 548 [M + H]⁺ | 1.96 (V) |
| 2.48 | XXII.3 | TBTU | 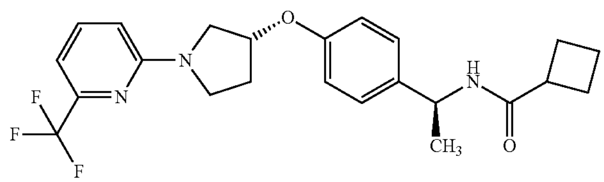 | 434 [M + H]⁺ | 2.04 (V) |
| 2.49 | XXII.3 | TBTU | 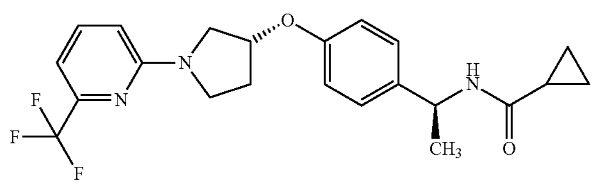 | 420 [M + H]⁺ | 2.00 (V) |
| 2.50 | XXII.3 | TBTU | 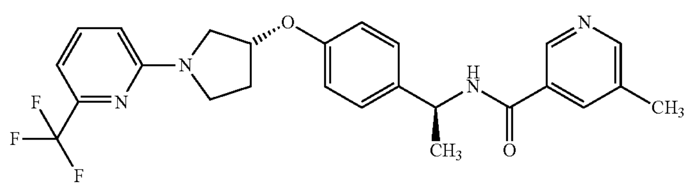 | 471 [M + H]⁺ | 1.94 (V) |
| 2.51 | XXII.3 | CIP | 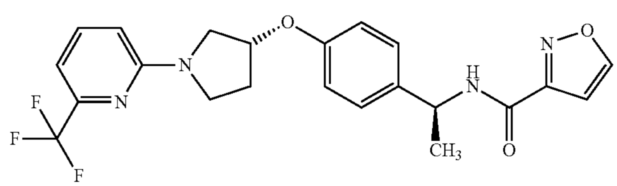 | 447 [M + H]⁺ | 1.02 (K) |
| 2.52 | XXII.3 | TBTU | 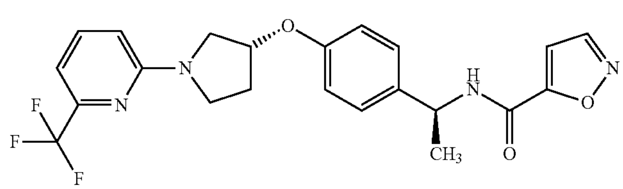 | 447 [M + H]⁺ | 1.99 (V) |
| 2.53 | XXII.3 | TBTU | 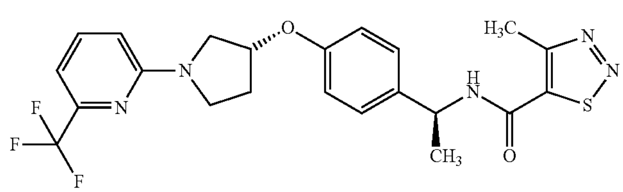 | 478 [M + H]⁺ | 2.04 (V) |

-continued

| Ex. | Starting material | Coupling reagent | Structure | Mass spec result | HPLC retention time (method) |
|---|---|---|---|---|---|
| 2.54 | XXII.3 | TBTU | 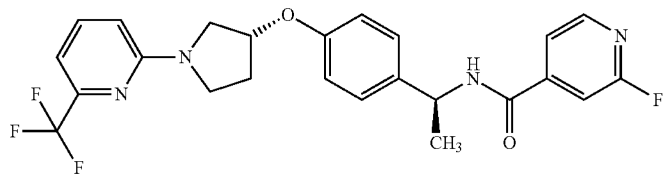 | 475 [M + H]+ | 2.04 (V) |
| 2.55 | XXII.3 | TBTU | 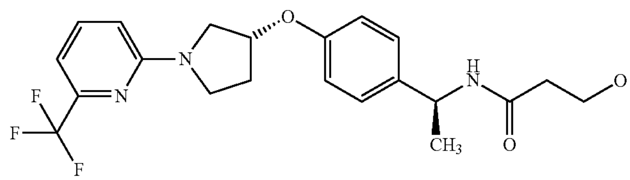 | 424 [M + H]+ | 1.49 (R) |
| 2.56 | XXII.1 | TBTU | 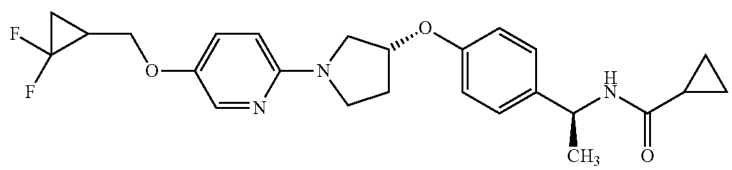 | 458 [M + H]+ | 1.16 (C) |
| 2.57 | XXII.1 | TBTU | 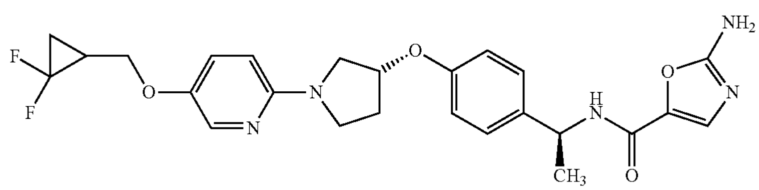 | 500 [M + H]+ | 1.11 (C) |
| 2.58 | XXIII | CIP | 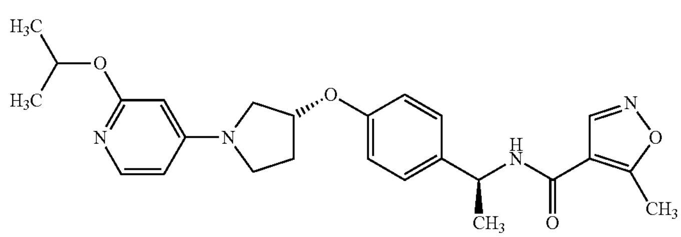 | 451 [M + H]+ | 0.94 (K) |
| 2.59 | XXII.1 | 1-chloro-N,N-2-tri-methyl-propenyl amine | 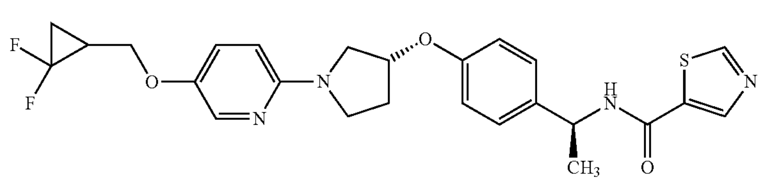 | 501 [M + H]+ | 0.99 (E) |
| 2.60 | XXII.1 | 1-chloro-N,N-2-tri-methyl-propenyl amine | 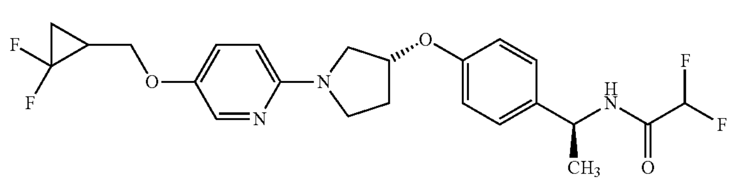 | 468 [M + H]+ | 0.99 (E) |

-continued

| Ex. | Starting material | Coupling reagent | Structure | Mass spec result | HPLC retention time (method) |
|---|---|---|---|---|---|
| 2.61 | XXII.3 | TBTU and CIP | 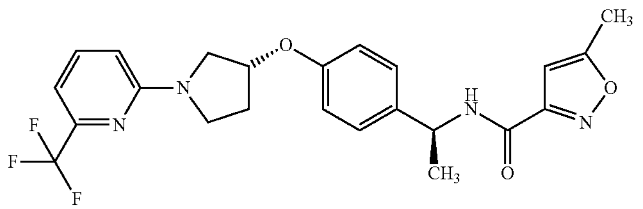 | 461 [M + H]+ | 0.99 (K) |
| 2.62 | XXII.3 | TBTU | 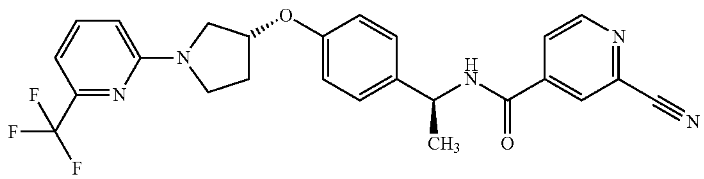 | 482 [M + H]+ | 1.06 (D) |
| 2.63 | XXII.3 | TBTU and CIP | 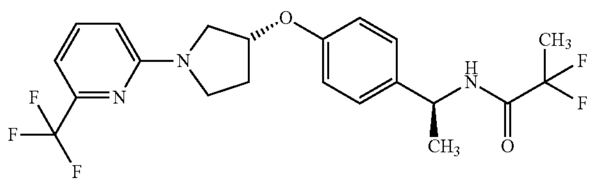 | 444 [M + H]+ | 1.06 (D) |
| 2.64 | XXII.3 | TBTU | 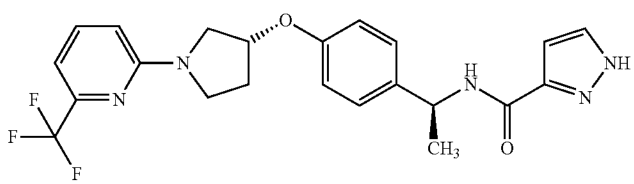 | 446 [M + H]+ | 0.91 (K) |
| 2.65 | XXII.5 | TBTU | 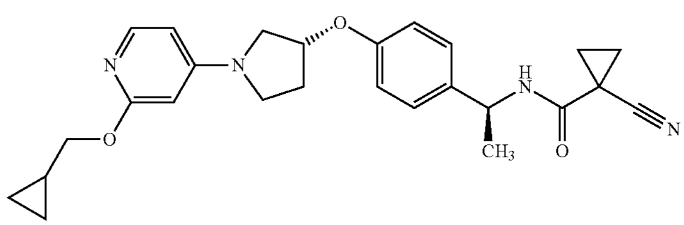 | 447 [M + H]+ | 0.84 (W) |
| 2.66 | XXII.5 | TBTU | 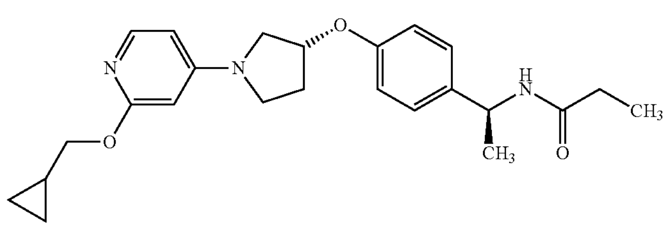 | 410 [M + H]+ | 0.78 (W) |
| 2.67 | XXII.5 | TBTU | 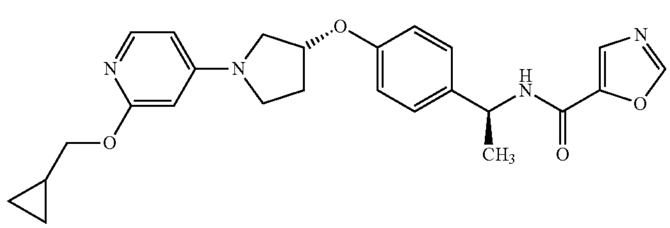 | 449 [M + H]+ | 0.77 (W) |

-continued
| Ex. | Starting material | Coupling reagent | Structure | Mass spec result | HPLC retention time (method) |
|---|---|---|---|---|---|
| 2.68 | XXII.5 | PyBop | 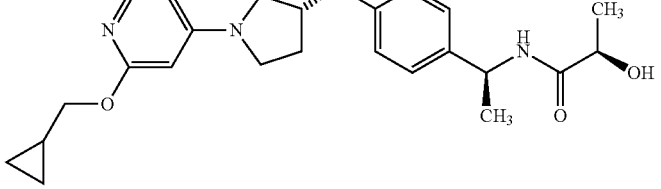 | 426 [M + H]⁺ | 0.74 (W) |
| 2.69 | XXII.5 | TBTU | 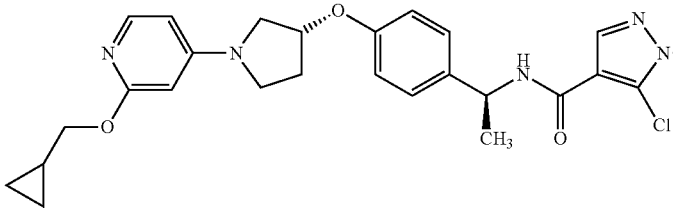 | 496 [M + H]⁺ | 0.81 (W) |
| 2.70 | XXII.5 | TBTU | 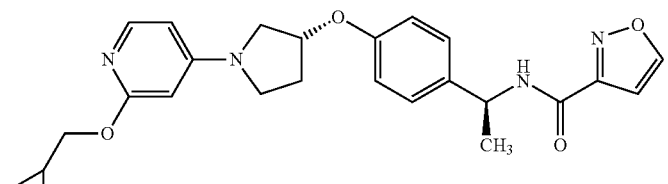 | 449 [M + H]⁺ | 0.83 (W) |
| 2.71 | XXII.5 | TBTU | 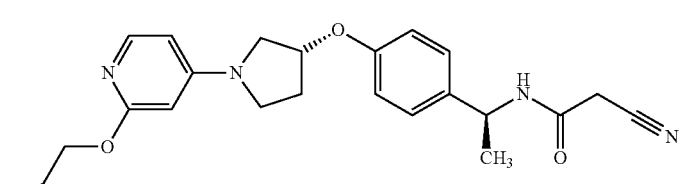 | 421 [M + H]⁺ | 0.76 (W) |
| 2.72 | XXII.5 | PyBop | 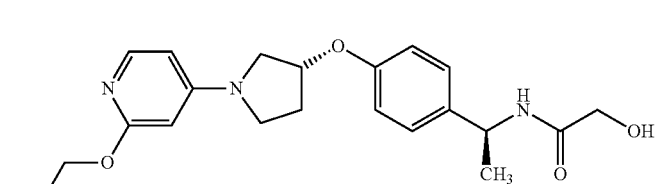 | 412 [M + H]⁺ | 0.72 (W) |
| 2.73 | XXII.5 | TBTU | 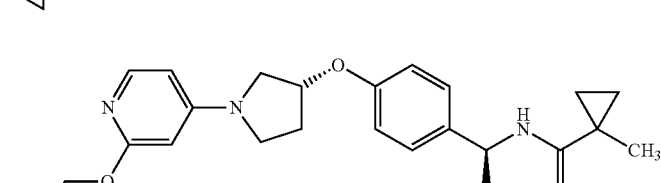 | 436 [M + H]⁺ | 0.85 (W) |

-continued

| Ex. | Starting material | Coupling reagent | Structure | Mass spec result | HPLC retention time (method) |
|---|---|---|---|---|---|
| 2.74 | XXII.5 | TBTU | 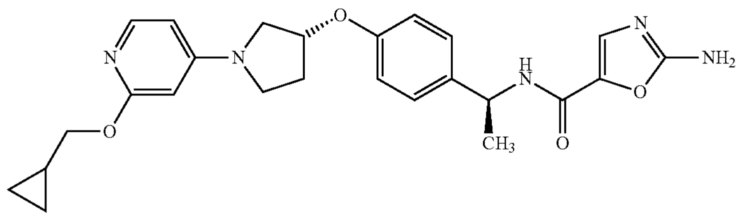 | 464 [M + H]⁺ | 0.69 (W) |
| 2.75 | XXII.5 | TBTU | 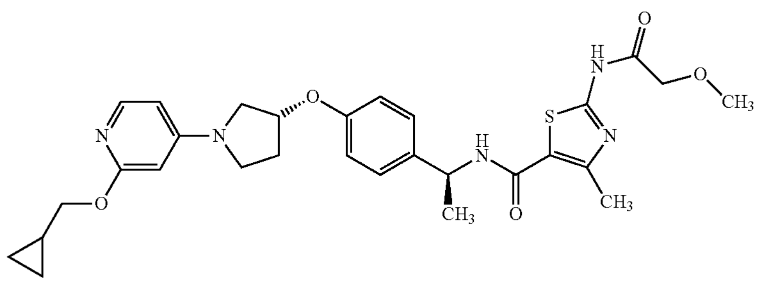 | 566 [M + H]⁺ | 0.83 (W) |
| 2.76 | XXII.5 | TBTU | 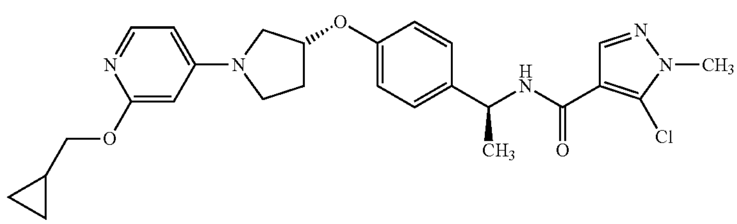 | 463 [M + H]⁺ | 0.83 (W) |
| 2.77 | XXII.5 | TBTU | 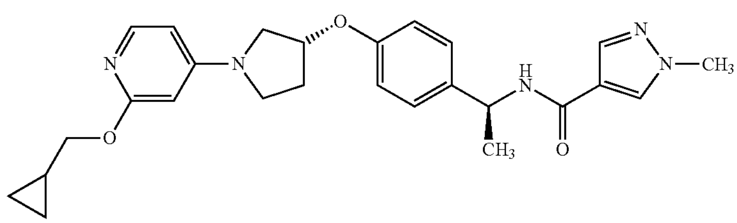 | 462 [M + H]⁺ | 0.76 (W) |
| 2.78 | XXII.5 | PyBop | 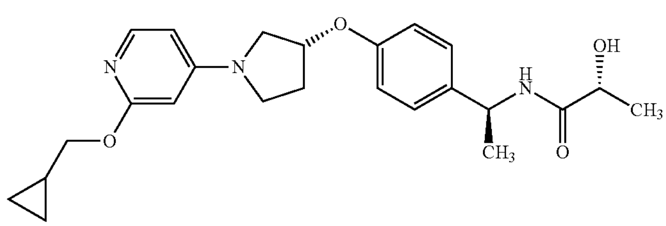 | 426 [M + H]⁺ | 0.74 (W) |
| 2.79 | XXII.5 | TBTU | 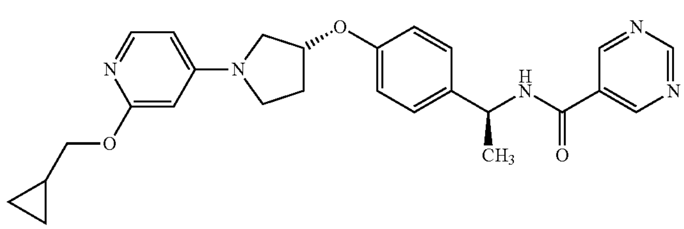 | 460 [M + H]⁺ | 0.76 (W) |

-continued
| Ex. | Starting material | Coupling reagent | Structure | Mass spec result | HPLC retention time (method) |
|---|---|---|---|---|---|
| 2.80 | XXII.5 | TBTU | 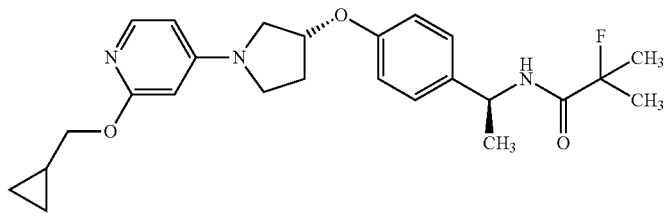 | 442 [M + H]⁺ | 0.86 (W) |
| 2.81 | XXII.5 | TBTU | 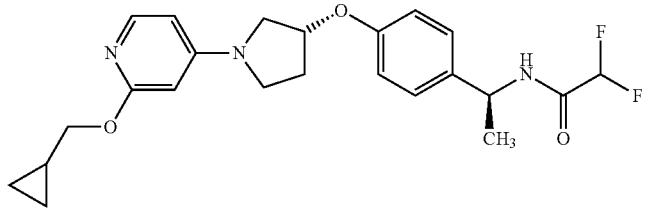 | 432 [M + H]⁺ | 0.82 (W) |
| 2.82 | XXII.5 | TBTU | 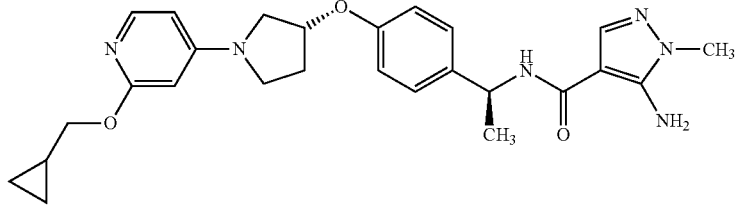 | 477 [M + H]⁺ | 0.75 (W) |
| 2.83 | XXII.5 | TBTU | 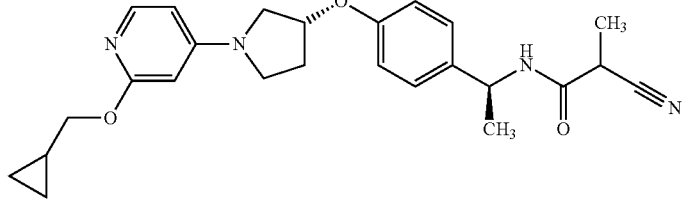 | 435 [M + H]⁺ | 0.81 (W) |
| 2.84 | XXII.5 | TBTU | 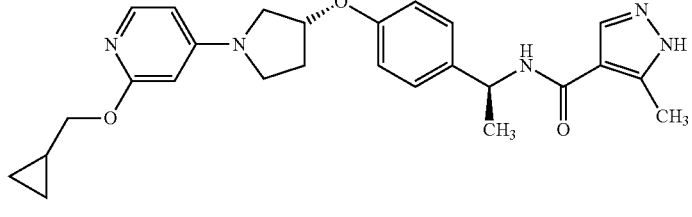 | 462 [M + H]⁺ | 0.76 (W) |
| 2.85 | XXII.5 | TBTU | 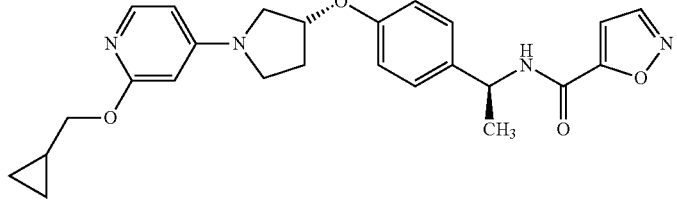 | 449 [M + H]⁺ | 0.81 (W) |

-continued

| Ex. | Starting material | Coupling reagent | Structure | Mass spec result | HPLC retention time (method) |
|---|---|---|---|---|---|
| 2.86 | XXII.5 | TBTU | 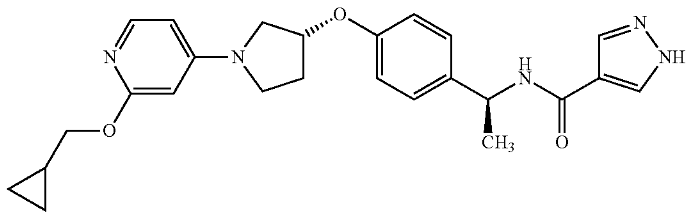 | 448 [M + H]+ | 0.74 (W) |
| 2.87 | XXII.5 | TBTU | 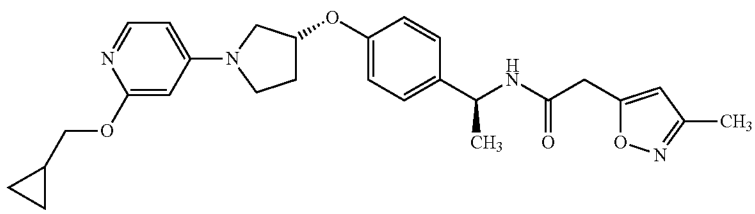 | 477 [M + H]+ | 0.80 (W) |
| 2.88 | XXII.5 | TBTU | 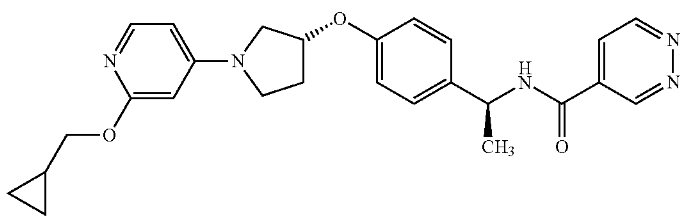 | 460 [M + H]+ | 0.75 (W) |
| 2.89 | XXII.5 | TBTU | 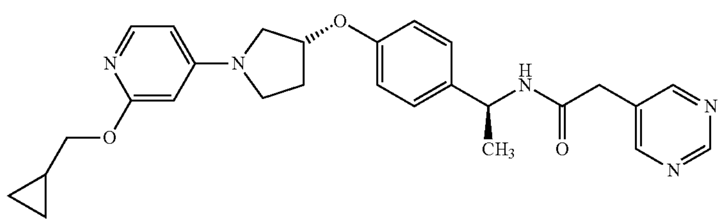 | 475 [M + H]+ | 0.74 (W) |
| 2.90 | XXII.2 | 1-chloro-N,N-2-tri-methyl-propenyl amine | 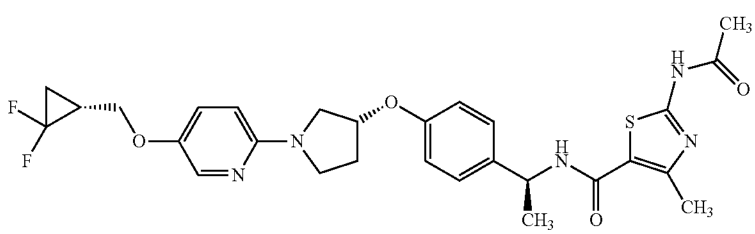 | 572 [M + H]+ | 0.84 (K) |
| 2.91 | XXII.2 | 1-chloro-N,N-2-tri-methyl-propenyl amine | 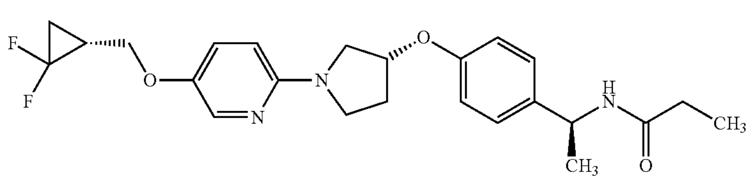 | 446 [M + H]+ | 0.90 (K) |
| 2.92 | XXII.2 | 1-chloro-N,N-2-tri-methyl-propenyl amine | 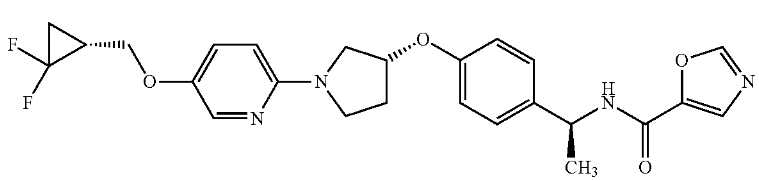 | 485 [M + H]+ | 0.89 (K) |

-continued
| Ex. | Starting material | Coupling reagent | Structure | Mass spec result | HPLC retention time (method) |
|---|---|---|---|---|---|
| 2.93 | XXII.2 | TBTU | 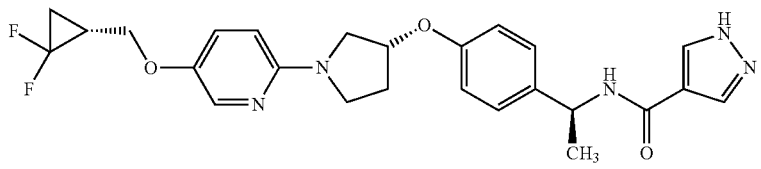 | 484 [M + H]+ | 0.85 (K) |
| 2.94 | XXII.2 | 1-chloro-N,N-2-tri-methyl-propenyl amine | 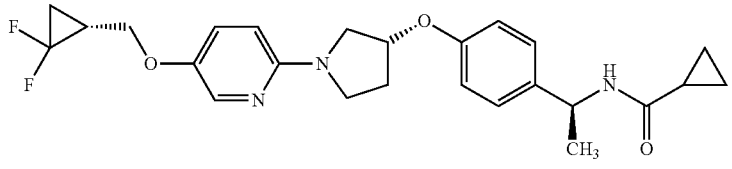 | 458 [M + H]+ | 0.91 (K) |
| 2.95 | XXXI.1 | TBTU | 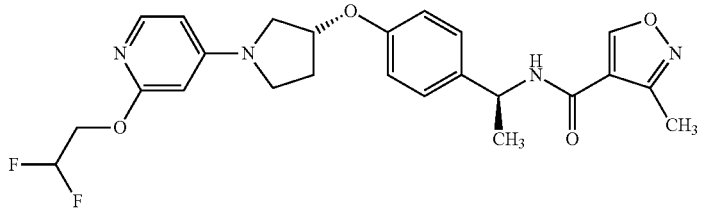 | 473 [M + H]+ | 0.49 (AC) |
| 2.96 | XXXI.1 | TBTU | 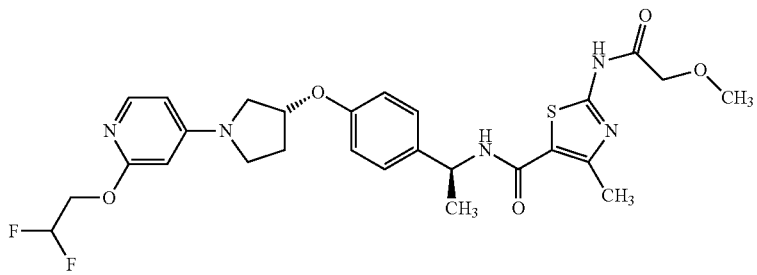 | 576 [M + H]+ | 0.36 (X) |
| 2.97 | XXXI.1 | TBTU | 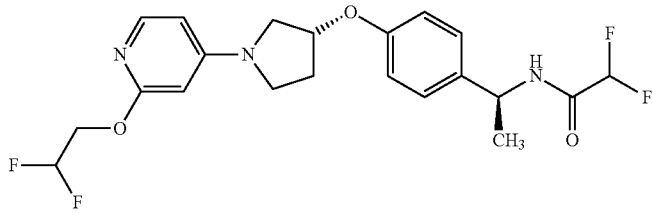 | 442 [M + H]+ | 0.48 (X) |
| 2.98 | XXXI.1 | TBTU | 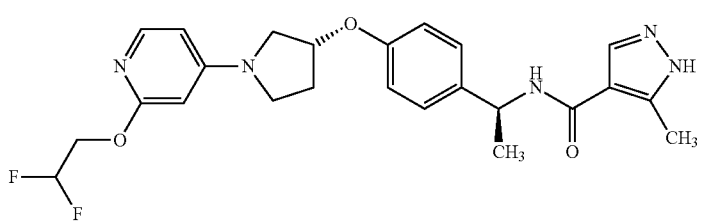 | 472 [M + H]+ | 0.44 ( ) |

-continued

| Ex. | Starting material | Coupling reagent | Structure | Mass spec result | HPLC retention time (method) |
|---|---|---|---|---|---|
| 2.99 | XXXI.1 | TBTU | 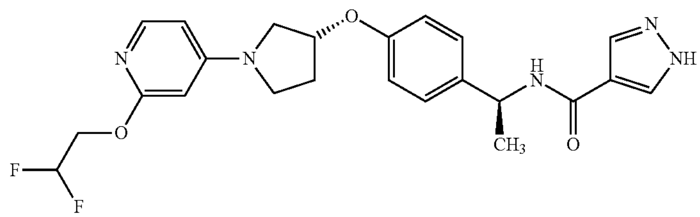 | 458 [M + H]+ | 0.42 (X) |
| 2.100 | XXXI.1 | TBTU | 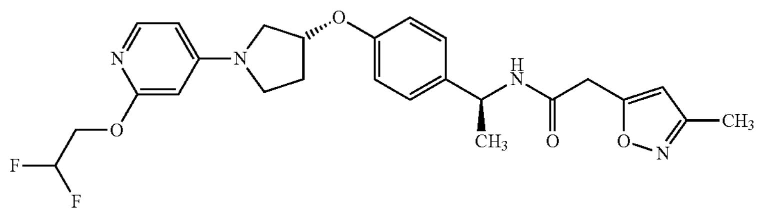 | 487 [M + H]+ | 0.47 (X) |
| 2.101 | XXXI.1 | TBTU | 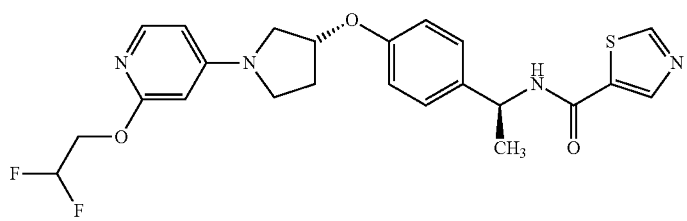 | 475 [M + H]+ | 0.47 (X) |
| 2.102 | XXXI.1 | TBTU | 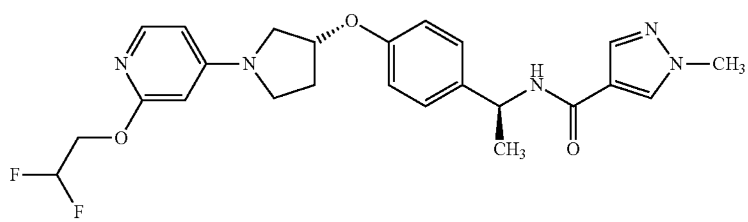 | 472 [M + H]+ | 0.44 (X) |
| 2.103 | XXXI.1 | TBTU | 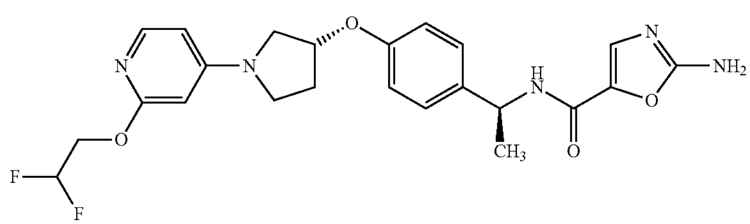 | 474 [M + H]+ | 0.42 (X) |
| 2.104 | XXXI.1 | TBTU | 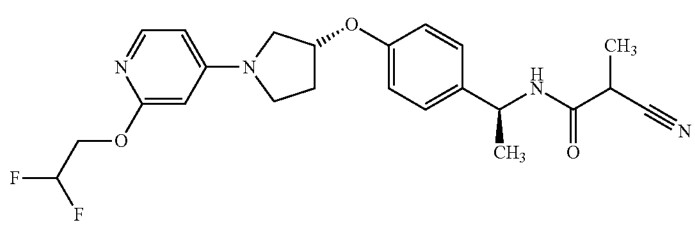 | 445 [M + H]+ | 0.47 (X) |

-continued
| Ex. | Starting material | Coupling reagent | Structure | Mass spec result | HPLC retention time (method) |
|---|---|---|---|---|---|
| 2.105 | XXXI.1 | PyBop | 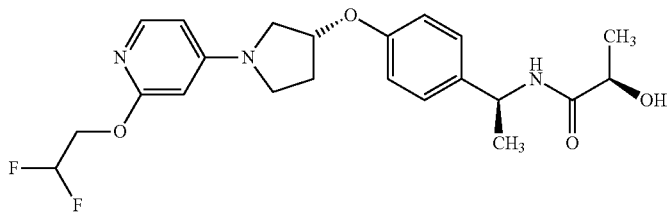 | 436 [M + H]+ | 0.43 (X) |
| 2.106 | XXXI.1 | TBTU | 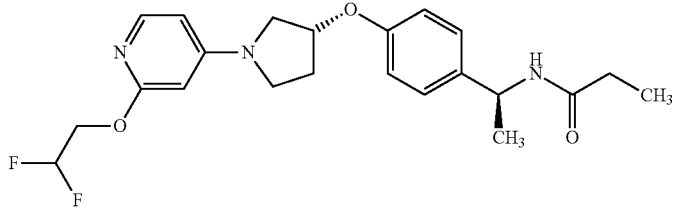 | 420 [M + H]+ | 0.46 (X) |
| 2.107 | XXXI.1 | TBTU | 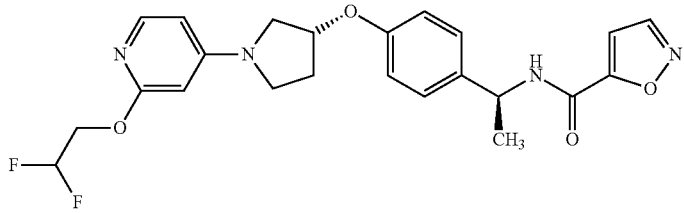 | 459 [M + H]+ | 0.48 (X) |
| 2.108 | XXXI.1 | TBTU | 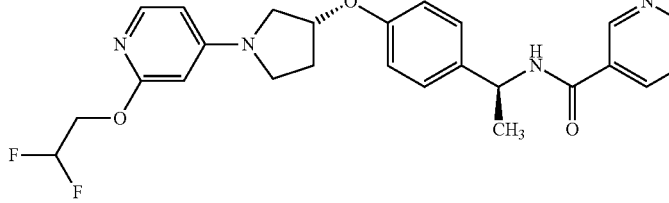 | 470 [M + H]+ | 0.44 (X) |
| 2.109 | XXXI.1 | TBTU | 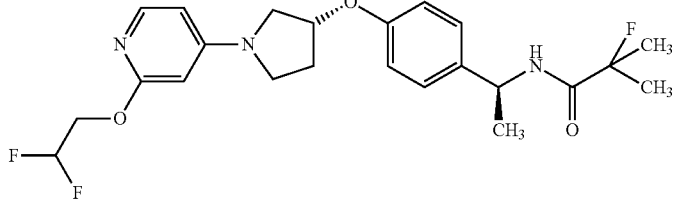 | 452 [M + H]+ | 0.52 (X) |
| 2.110 | XXXI.1 | TBTU | 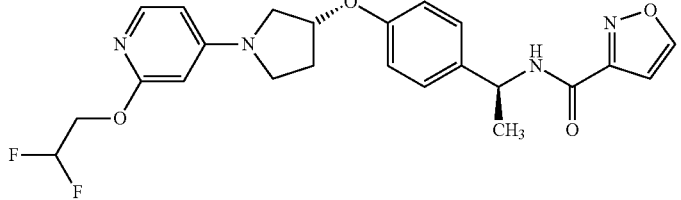 | 459 [M + H]+ | 0.49 (X) |

-continued

| Ex. | Starting material | Coupling reagent | Structure | Mass spec result | HPLC retention time (method) |
|---|---|---|---|---|---|
| 2.111 | XXXI.1 | TBTU | 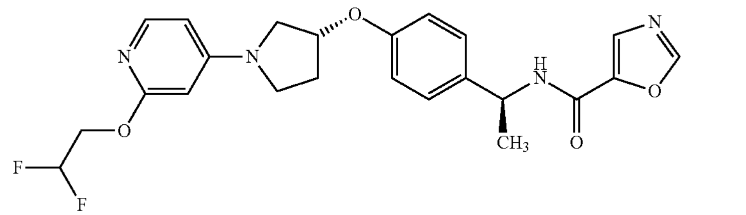 | 459 [M + H]+ | 0.45 (X) |
| 2.112 | XXXI.1 | TBTU | 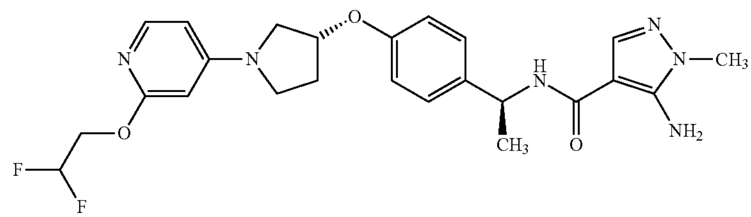 | 487 [M + H]+ | 0.44 (X) |
| 2.113 | XXXI.1 | TBTU | 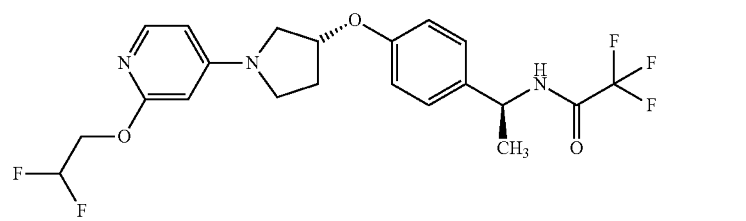 | 460 [M + H]+ | 0.52 (X) |
| 2.114 | XXXI.1 | TBTU | 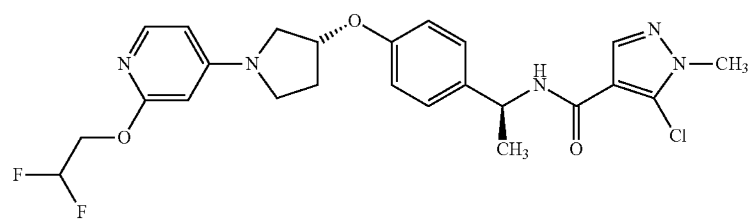 | 506 [M + H]+ | 0.48 (X) |
| 2.115 | XXXI.1 | PyBop | 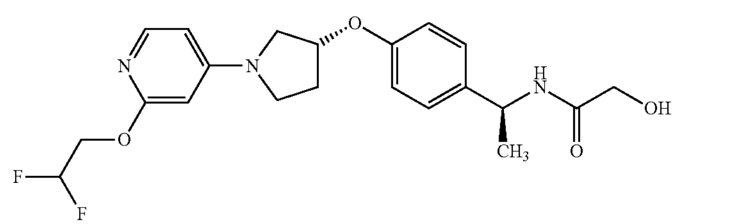 | 422 [M + H]+ | 0.42 (X) |
| 2.116 | XXXI.1 | TBTU | 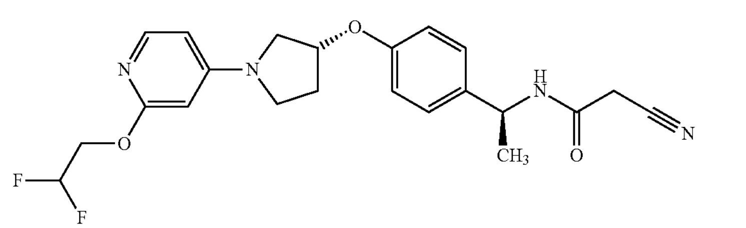 | 431 [M + H]+ | 0.45 (X) |

-continued

| Ex. | Starting material | Coupling reagent | Structure | Mass spec result | HPLC retention time (method) |
|---|---|---|---|---|---|
| 2.117 | XXXI.1 | TBTU | 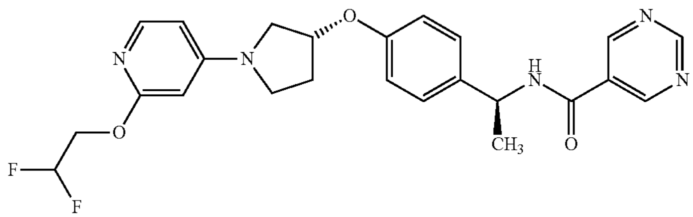 | 484 [M + H]+ | 0.43 (X) |
| 2.118 | XXII.1 | TBTU | 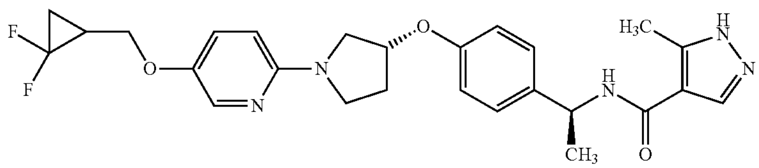 | 498 [M + H]+ | 0.85 (M) |
| 2.119 | XXII.1 | 1-chloro-N,N-2-tri-methyl-propenyl amine | 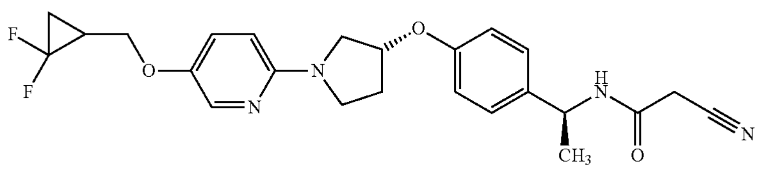 | 457 [M + H]+ | 0.85 (M) |
| 2.120 | XXII.1 | 1-chloro-N,N-2-tri-methyl-propenyl amine | 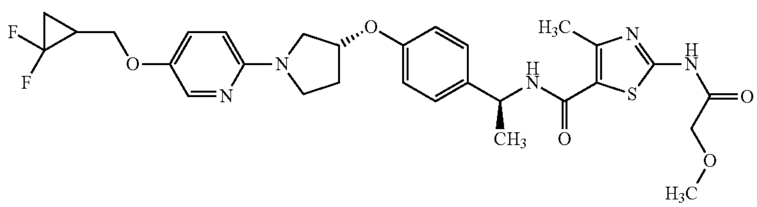 | 602 [M + H]+ | 0.90 (M) |
| 2.121 | XXII.1 | 1-chloro-N,N-2-tri-methyl-propenyl amine | 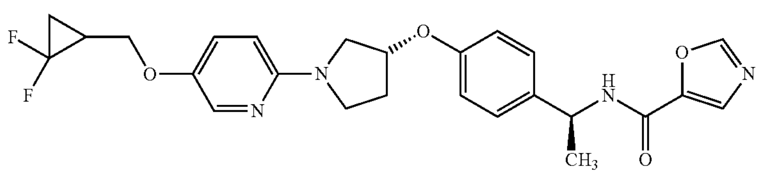 | 485 [M + H]+ | 0.85 (M) |
| 2.122 | XXII.3 | CIP | 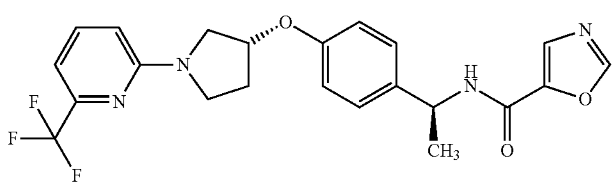 | 447 [M + H]+ | 0.94 (K) |
| 2.123 | XXXII.1 | 1-chloro-N,N-2-tri-methyl-propenyl amine | 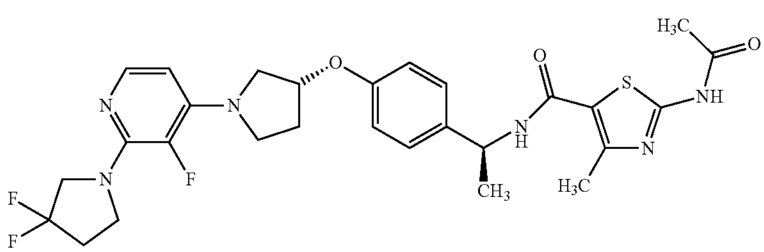 | 589 [M + H]+ | 0.88 (K) |

| Ex. | Starting material | Coupling reagent | Structure | Mass spec result | HPLC retention time (method) |
|---|---|---|---|---|---|
| 2.124 | XXXII.1 | 1-chloro-N,N-2-tri-methyl-propenyl amine | 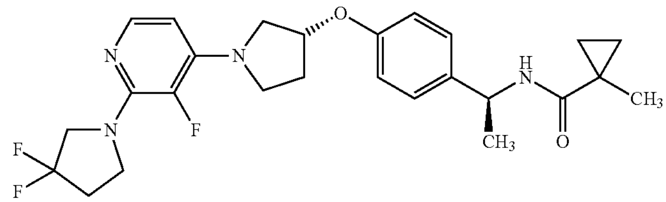 | 489 [M + H]⁺ | 0.45 (AA) |
| 2.125 | XXXII.1 | TBTU | 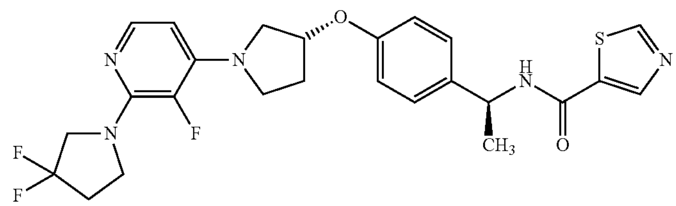 | 518 [M + H]⁺ | 0.42 (AA) |
| 2.126 | XXXII.1 | TBTU | 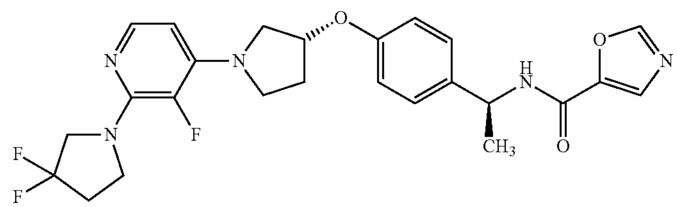 | 502 [M + H]⁺ | 0.41 (AA) |

Example 3

Example 3.1

General Route 1-((1S)-1-(4-((3R)-1-(5-((2,2-Difluorocyclopropyl)methoxy)pyridin-2-yl)pyrrolidin-3-yloxy)phenyl)ethyl)-3-(isoxazol-3-yl)urea

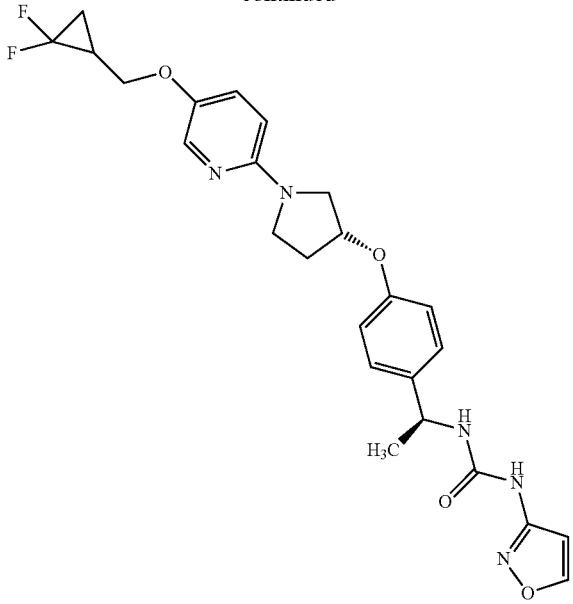

Method A)

To 45.0 mg (0.12 mmol) of amine XXII.1 and 39.0 µL (0.23 mmol) DIPEA in 3 mL THF are added 38.8 mg (0.23 mmol) CDT and the resulting mixture is stirred at r.t for 15 min. Then 19.0 mg (0.23 mmol) of 3-aminoisoxazole are added and the resulting mixture is stirred at r.t over night. Afterwards some DMF is added and the mixture is directly purified by HPLC (MeOH/H₂O/NH₄OH).

Method B)

To 45.0 mg (0.12 mmol) of amine XX11.1 in 3 mL dioxane are added 38.8 mg (0.23 mmol) CDT and 35.05 mg (0.23 mmol) DBU and the resulting mixture is stirred at r.t. for 30 min. Then 19.0 mg (0.23 mmol) of 3-aminoisoxazole are added and stirring is continued over night. The mixture is purified by HPLC (ACN/H$_2$O/NH$_4$OH).

C$_{25}$H$_{27}$F$_2$N$_5$O$_4$ (M=499.5 g/mol)
ESI-MS: 500 [M+H]$^+$
R$_t$(HPLC):0.89 min (method M)

The following compounds are prepared analogously to example 3.1:

For example 3.3 TEA is used as base, DCM as solvent and the reaction is stirred at 35° C. over night.

For the examples 3.4-3.21 TEA as base is used.

For the examples 3.19, 3.20 and 3.24-3.25 the reaction conditions are 45° C. over night.

For example 3.21 the reaction conditions are 40° C. for 2 h.

| Ex. | Starting material | Structure | Method | Mass spec result | HPLC retention time (method) |
|---|---|---|---|---|---|
| 3.1 | XXII.1 | 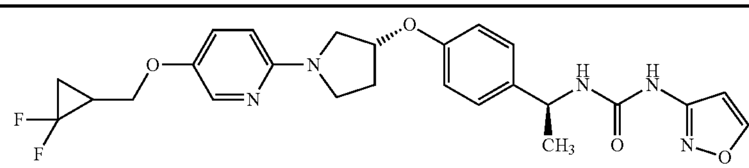 | B | 500 [M + H]$^+$ | 0.89 (M) |
| 3.2 | XXIII | 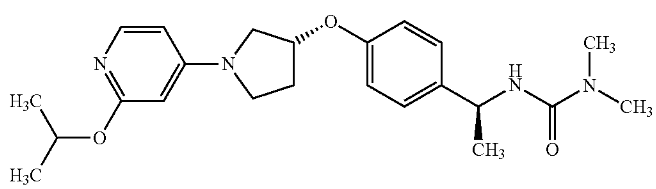 | A | 413 [M + H]$^+$ | 1.09 (C) |
| 3.3 | XXII.1 | 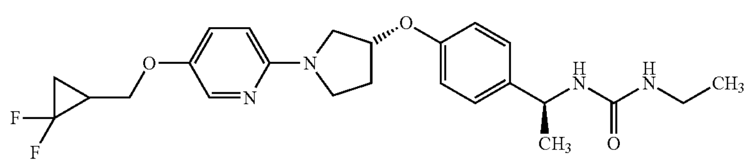 | A | 461 [M + H]$^+$ | 1.08 (C) |
| 3.4 | XXII.5 | 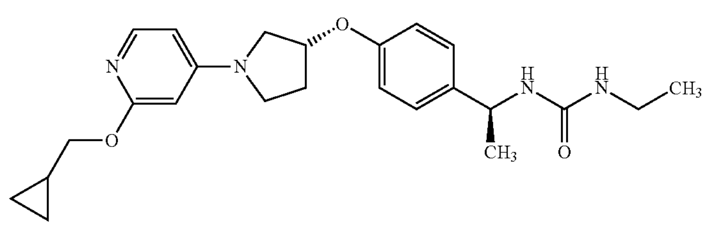 | A | 425 [M + H]$^+$ | 0.77 (W) |
| 3.5 | XXII.5 | 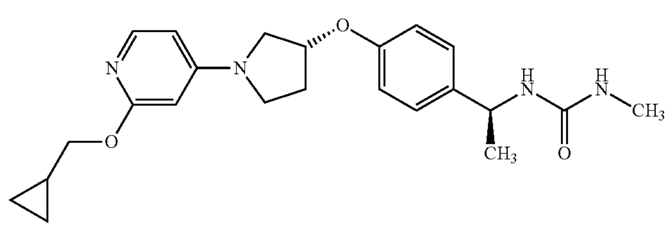 | A | 411 [M + H]$^+$ | 0.74 (W) |
| 3.6 | XXII.5 | 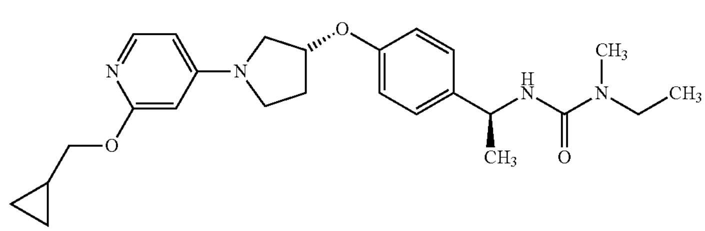 | A | 439 [M + H]$^+$ | 0.81 (W) |
| 3.7 | XXII.1 | 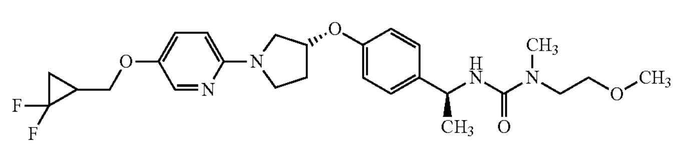 | A | 505 [M + H]$^+$ | 0.90 (M) |

-continued

| Ex. | Starting material | Structure | Method | Mass spec result | HPLC retention time (method) |
|---|---|---|---|---|---|
| 3.8 | XXII.1 | 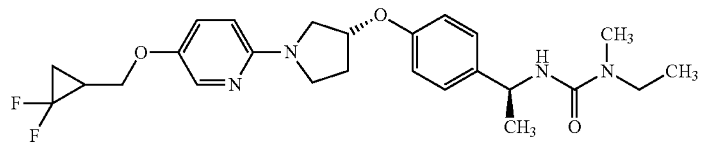 | A | 475 [M + H]+ | 0.89 (M) |
| 3.9 | XXII.1 | 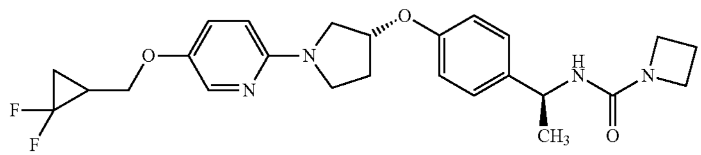 | A | 473 [M + H]+ | 0.87 (M) |
| 3.10 | XXII.1 | 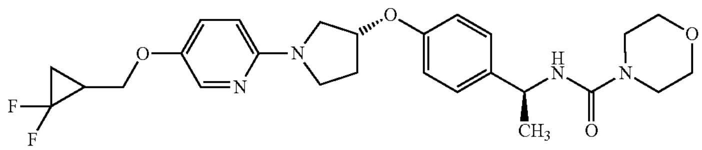 | A | 503 [M + H]+ | 0.89 (M) |
| 3.11 | XXII.1 | 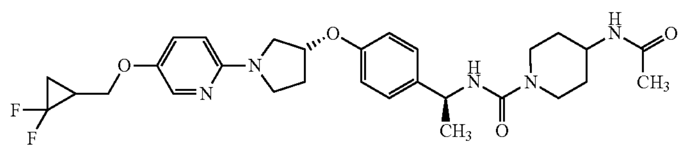 | A | 558 [M + H]+ | 0.83 (M) |
| 3.12 | XXII.5 | 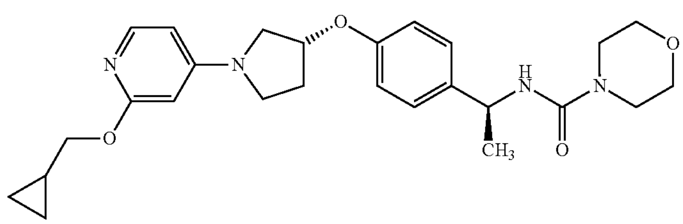 | A | 467 [M + H]+ | 0.77 (W) |
| 3.13 | XXXI.1 | 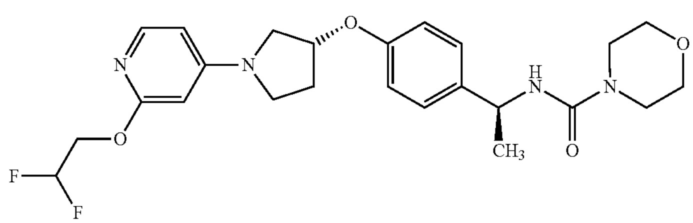 | A | 477 [M + H]+ | 0.45 (X) |
| 3.14 | XXXI.1 | 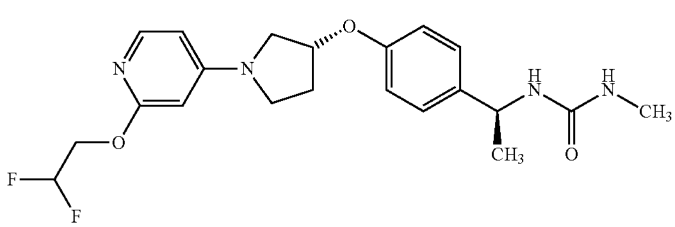 | A | 421 [M + H]+ | 0.43 (X) |
| 3.15 | XXXI.1 | 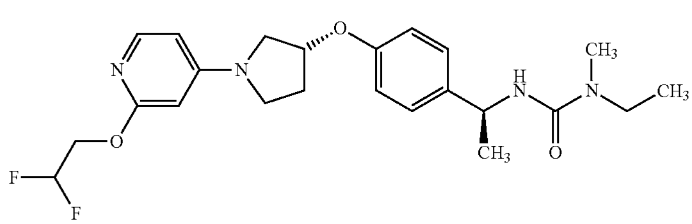 | A | 449 [M + H]+ | 0.48 (X) |

-continued

| Ex. | Starting material | Structure | Method | Mass spec result | HPLC retention time (method) |
|---|---|---|---|---|---|
| 3.16 | XXXI.1 | 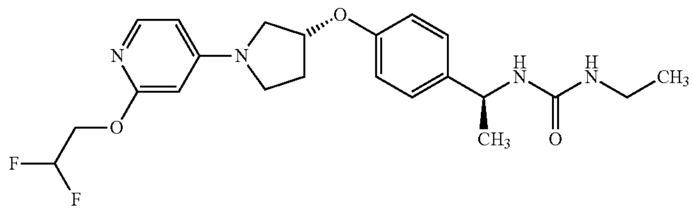 | A | 435 [M + H]⁺ | 0.45 (X) |
| 3.17 | XXXI.1 | 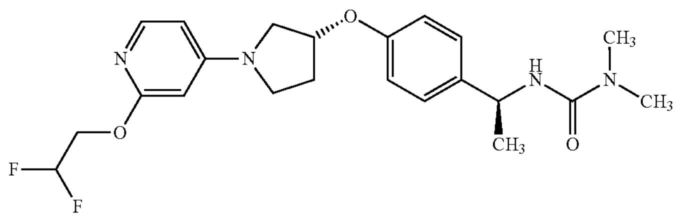 | A | 435 [M + H]⁺ | 0.46 (X) |
| 3.18 | XXII.1 | 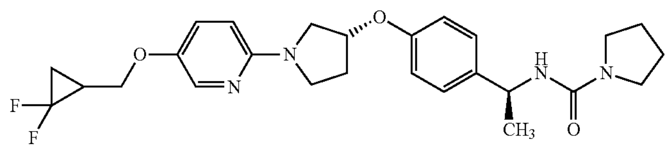 | A | 487 [M + H]⁺ | 0.89 (M) |
| 3.19 | XXII.1 | 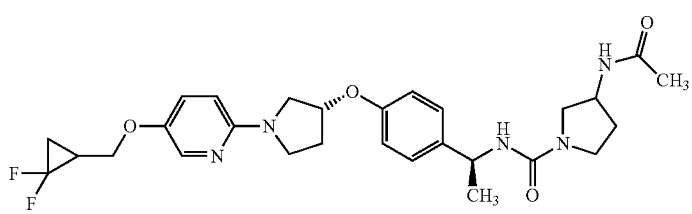 | A | 544 [M + H]⁺ | 0.82 (M) |
| 3.20 | XXII.1 | 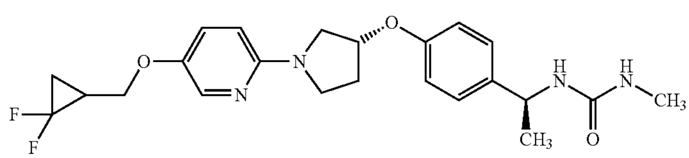 | A | 447 [M + H]⁺ | 0.83 (M) |
| 3.21 | XXII.1 | 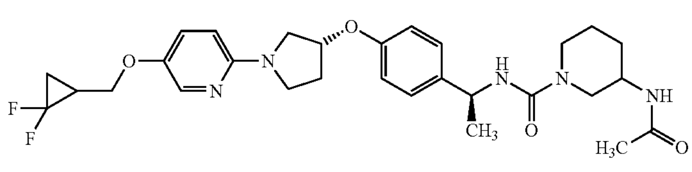 | A | 558 [M + H]⁺ | 0.85 (M) |
| 3.22 | XXXII | 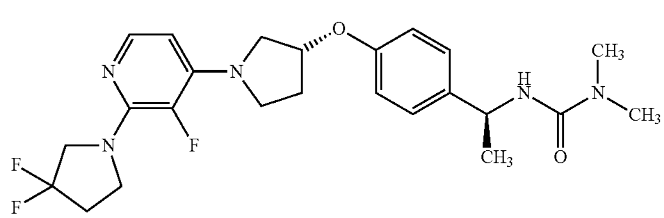 | A | 478 [M + H]⁺ | 1.14 (Y) |

| Ex. | Starting material | Structure | Method | Mass spec result | HPLC retention time (method) |
|---|---|---|---|---|---|
| 3.23 | XXXII | 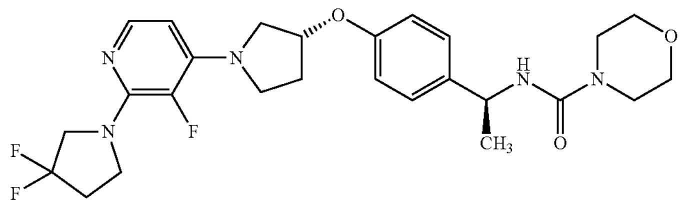 | A | 520 [M + H]+ | 0.75 (Z) |

Example 4

Example 4.1

General Route

Methyl (S)-1-(4-((R)-1-(5-(((R)-2,2-difluorocyclopropyl)methoxy)pyridin-2-yl)pyrrolidin-3-yloxy)phenyl)ethylcarbamate

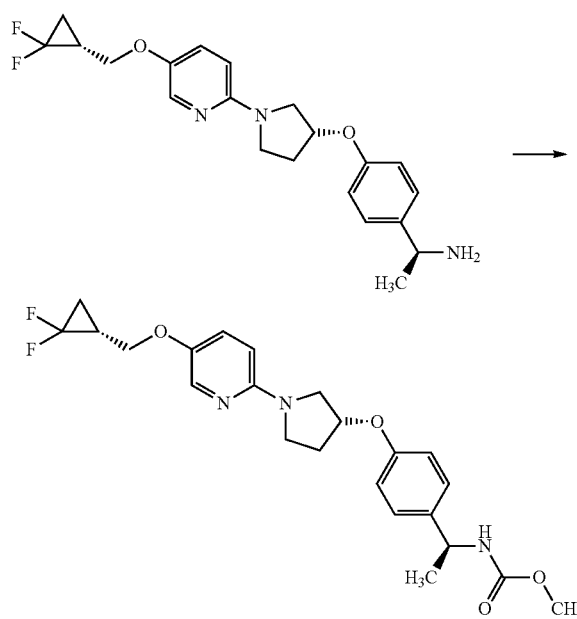

Method A)

25.0 mg (0.06 mmol) of amine XXII.2 in 0.5 mL ACN are chilled to 5° C. in a ice-water bath. Then 35.0 µL (0.26 mmol) TEA and 5.5 µL (0.07 mmol) methyl chloroformate are added and the resulting mixture is stirred at 5° C. for 2 h and at r.t. over night. The crude mixture is directly purified by HPLC (MeOH/H$_2$O/NH$_4$OH).

Method B)

To 50.0 mg (0.13 mmol) of amine XX11.2 in 2 mL DCM are added 25.3 mg (0.15 mmol) CDT and 21.6 µL (0.15 mmol) TEA and stirred at r.t. for 1 h. Then 7.81 µL (0.19 mmol) methanol is added and stirred at 35° C. over night. The crude mixture is directly purified by HPLC (MeOH/H$_2$O/NH$_4$OH).

$C_{23}H_{27}F_2N_3O_4$ (M=447.5 g/mol)

ESI-MS: 448 [M+H]+

$R_t$(HPLC):0.93 min (method K)

The following compounds are prepared analogously to example 4.1:

For example 4.2 the reaction temperature is r.t.

For example 4.4 THF is uses as solvent.

For example 4.6 and 4.9 THF is used as solvent and DIPEA as base.

For example 4.7 the reaction conditions are 70° C. over night.

| Ex. | Starting material | Structure | Method | Mass spec result | HPLC retention time (method) |
|---|---|---|---|---|---|
| 4.1 | XXII.2 | 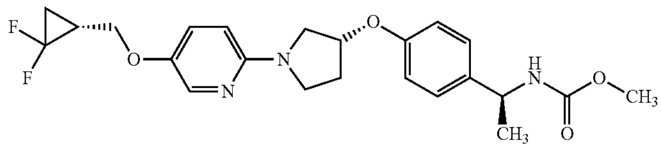 | A | 448 [M + H]+ | 0.93 (K) |

-continued

| Ex. | Starting material | Structure | Method | Mass spec result | HPLC retention time (method) |
|---|---|---|---|---|---|
| 4.2 | XXII.3 | 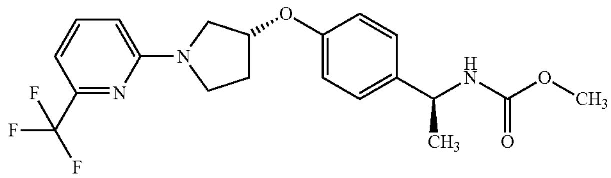 | A | 410 [M + H]⁺ | 1.58 (P) |
| 4.3 | XXII.1 | 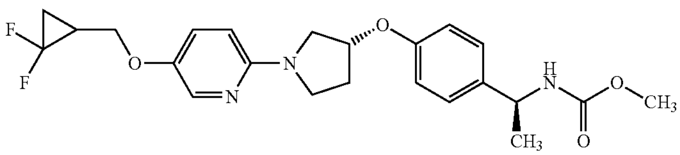 | B | 448 [M + H]⁺ | 1.11 (C) |
| 4.4 | XXII.5 | 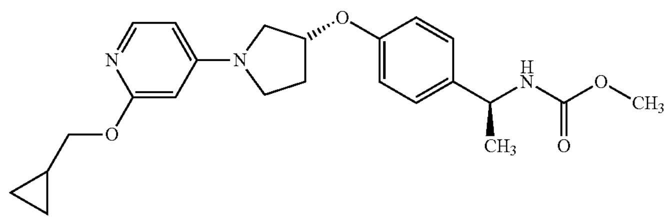 | A | 412 [M + H]⁺ | 0.82 (W) |
| 4.5 | XXXI.1 | 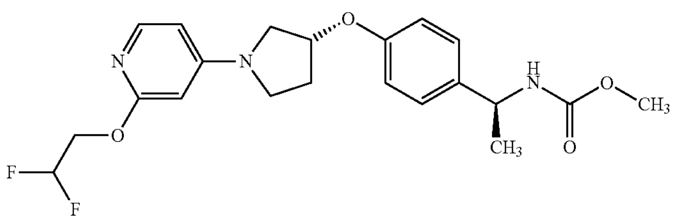 | A | 422 [M + H]⁺ | 0.49 (X) |
| 4.6 | XXXI.2 | 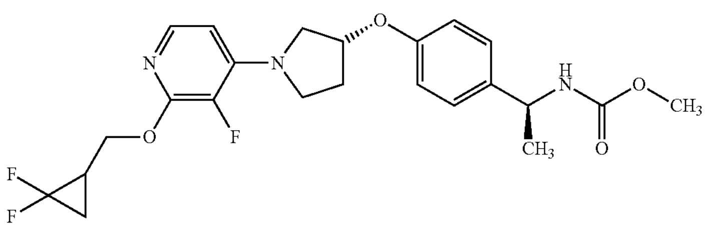 | A | 466 [M + H]⁺ | 1.02 (M) |
| 4.7 | XXXII | 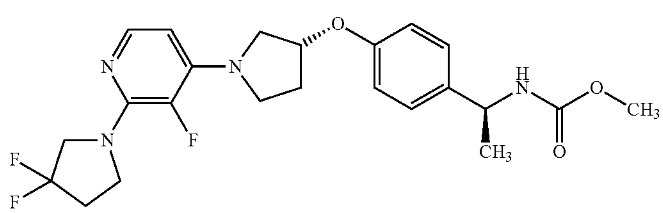 | A | 465 [M + H]⁺ | 0.44 (AA) |
| 4.8 | XXXII.2 | 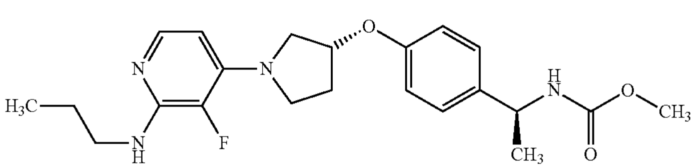 | A | 417 [M + H]⁺ | 0.83 (D) |

| Ex. | Starting material | Structure | Method | Mass spec result | HPLC retention time (method) |
|---|---|---|---|---|---|
| 4.9 | XXXI.3 | ![structure] | A | 417 [M + H]⁺ | 0.83 (D) |

Example 5

Example 5.1

General Route

N—((S)-1-(4-((R)-1-(6-(Trifluoromethyl)pyridin-2-yl)pyrrolidin-3-yloxy)phenyl)ethyl) pivalamide

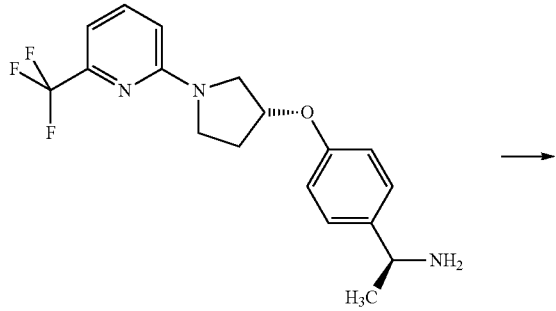

→

To 35.1 mg (0.10 mmol) of amine XX11.3 and 51.6 μL (0.30 mmol) DIPEA in 2 mL DCM are added 14.5 mg (0.12 mmol) trimethylacetyl chloride and the mixture is stirred at r.t. over night. The solvent is removed in vacuo, some DMF is added and the mixture is purified by HPLC (MeOH/H₂O/TFA).

$C_{23}H_{28}F_3N_3O_2$ (M=435.5 g/mol)

ESI-MS: 436 [M+H]⁺

$R_f$(HPLC):1.65 min (method P)

The following compounds are prepared analogously to example 5.1:

For the examples 5.3-5.8 THF is used as solvent.

For example 5.3 the reaction conditions are r.t. for 30 min.

| Ex. | Starting material | Structure | Mass spec result | HPLC retention time (method) |
|---|---|---|---|---|
| 5.1 | XXII.3 | 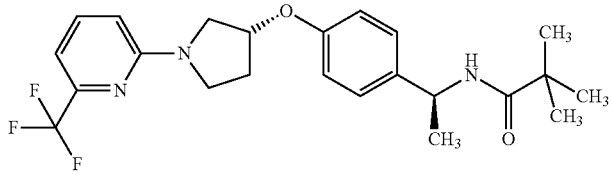 | 436 [M + H]⁺ | 1.65 (P) |

-continued
| Ex. | Starting material | Structure | Mass spec result | HPLC retention time (method) |
|---|---|---|---|---|
| 5.2 | XXII.3 | 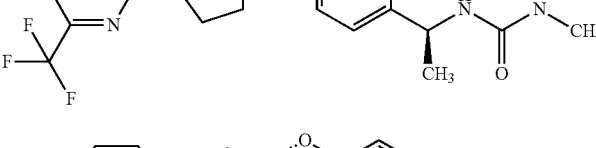 | 423 [M + H]+ | 1.54 (P) |
| 5.3 | XXXII | 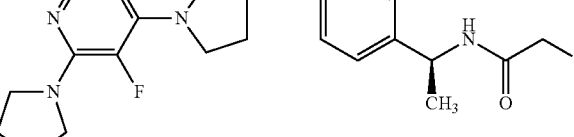 | 463 [M + H]+ | 0.41 (AA) |
| 5.4 | XXXI.2 | 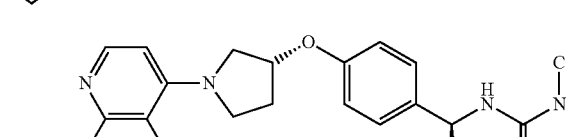 | 479 [M + H]+ | 0.99 (M) |
| 5.5 | XXXI.2 | 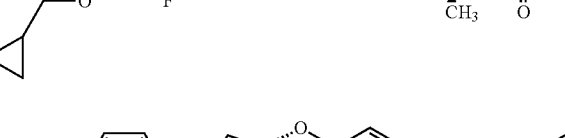 | 521 [M + H]+ | 0.97 (M) |
| 5.6 | XXXII.2 | 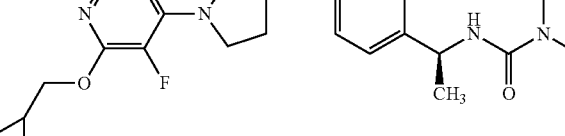 | 430 [M + H]+ | 0.40 (AA) |
| 5.7 | XXXII.2 | 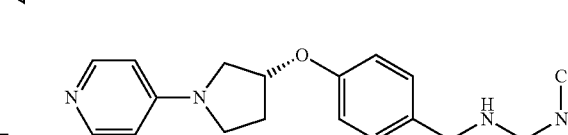 | 430 [M + H]+ | 0.39 (AA) |
| 5.8 | XXXII.2 | 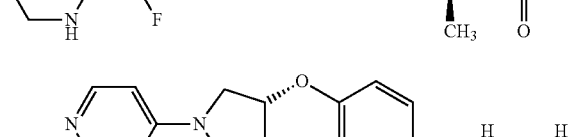 | 472 [M + H]+ | 0.39 (AA) |
| 5.9 | XXXI.3 | 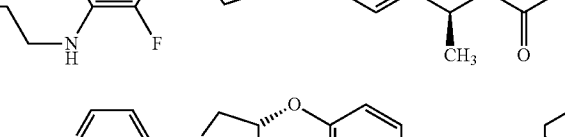 | 453 [M + H]+ | 0.56 (AA) |

Example 6

Example 6.1

General Route

2-Hydroxy-N—((S)-1-(4-((R)-1-(6-(trifluoromethyl)pyridin-2-yl)pyrrolidin-3-yloxy)phenyl)ethyl)propanamide

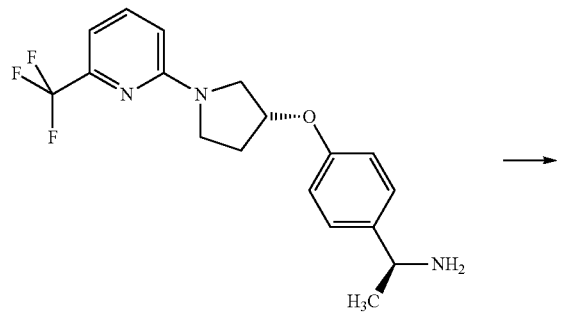

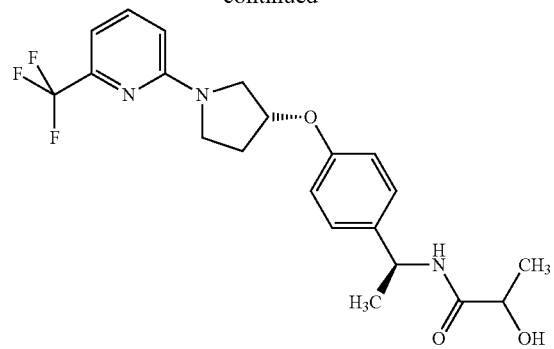

13.2 mg (0.10 mmol) 2-acetoxy-propionic acid, 51.6 μl (0.30 mmol) DIPEA and 32.1 mg (0.10 mmol) TBTU are added to 2 mL DMF and stirred for 10 min. Then 35.1 mg (0.10 mmol) of the amine XXII.3 are added and the resulting mixture is stirred at r.t. over night. The solvent is removed and the resulting product is added to 2 mL methanol and treated with 500 mg aq. NaOH solution (c=1 mol/L) and stirred at r.t for 2 h. The reaction mixture is set to a mild acid pH value with aq. HCl solution (c=1 mol/IL) and is directly purified by HPLC (MeOH/H$_2$O/TFA).

$C_{21}H_{24}F_3N_3O_3$ (M=423.4 g/mol)
ESI-MS: 424 [M+H]$^+$
R$_t$(HPLC):1.52 min (method P)

The following compounds are prepared analogously to example 6.1:

| Ex. | Starting material | Structure | Mass spec result | HPLC retention time (method) |
|---|---|---|---|---|
| 6.1 | XXII.3 | 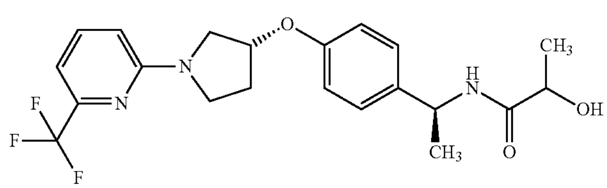 | 424 [M + H]$^+$ | 1.52 (P) |
| 6.2 | XXII.3 | 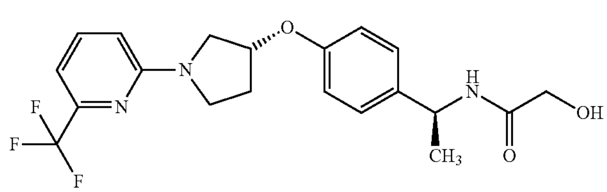 | 410 [M + H]$^+$ | 1.49 (P) |

Example 7

Example 7.1

General Route 2,2,3,3,3-Pentafluoro-N—((S)-1-(4-((R)-1-(6-(trifluoromethyl)pyridin-2-yl)pyrrolidin-3-yloxy)phenyl)ethyl)propanamide

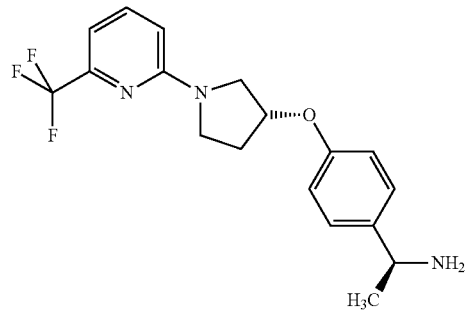

→

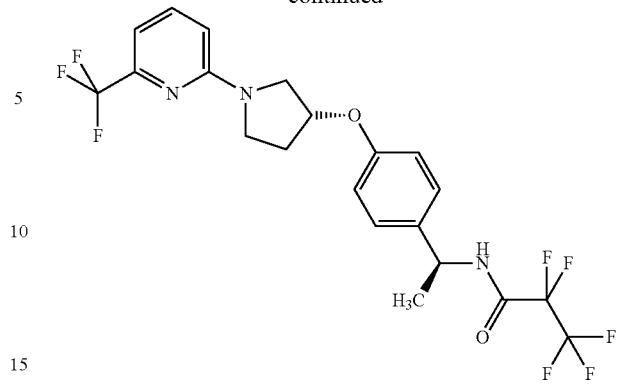

To 35.1 mg (0.10 mmol) of amine XXII.3 and 40.1 μL (0.30 mmol) TEA in 2 mL DCM are added 29.6 μL (0.15 mmol) pentafluoropropionic anhydride and the mixture is stirred at r.t. over night. The solvent is removed, some DMF is added and the mixture is purified by HPLC (MeOH/H$_2$O/TFA).
$C_{21}H_{19}F_8N_3O_2$ (M=497.4 g/mol)
ESI-MS: 498 [M+H]$^+$
R$_f$(HPLC):1.61 min (method R)

The following compounds are prepared analogously to example 7.1:

For example 7.3 the reaction time is 1 h.

| Ex. | Starting material | Structure | Mass spec result | HPLC retention time (method) |
|---|---|---|---|---|
| 7.1 | XXII.3 | 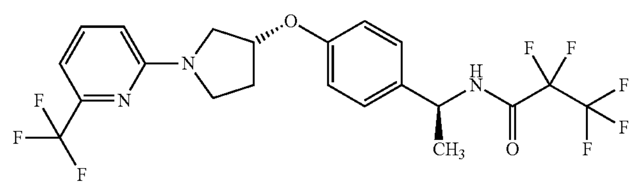 | 498 [M + H]$^+$ | 1.61 (R) |
| 7.2 | XXII.3 | 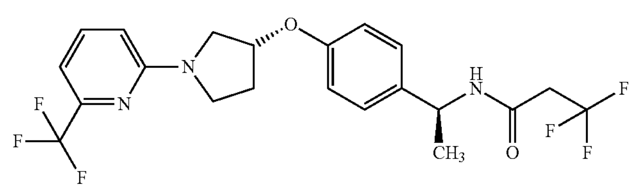 | 448 [M + H]$^+$ | 1.61 (P) |
| 7.3 | XXII.5 | 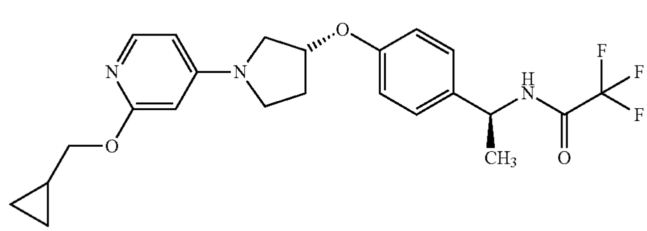 | 450 [M + H]$^+$ | 0.76 (D) |

Example 8

Example 8.1

General Route

N—((S)-1-(4-((R)-1-(6-(Trifluoromethyl)pyridin-2-yl)pyrrolidin-3-yloxy)phenyl)ethyl)acetamide

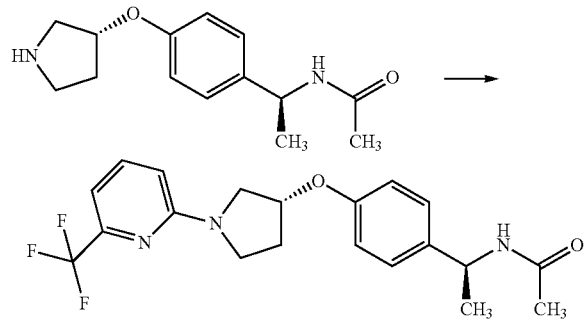

50.0 mg (0.20 mmol) of amine XIII.3, 36.5 mg (0.20 mmol) 2-chloro-6-(trifluoro-methyl)pyridine and 51.8 µL (0.30 mmol) DIPEA in 1 mL DMSO are stirred at 35° C. over night. The reaction mixture is directly purified by HPLC (MeOH/H$_2$O/NH$_4$OH).

$C_{20}H_{22}F_3N_3O_2$ (M=393.4 g/mol)

ESI-MS: 394 [M+H]$^+$

R$_t$(HPLC):1.13 min (method C)

The following compounds are prepared analogously to example 8.1:

For the examples 8.2-8.7, 8.9-8.11 and 8.14-8.15 the reaction is done in NMP at 130° C. for 72 h.

For example 8.8 the reaction is done in NMP at 130° C. for 3 h.

For example 8.12 the reaction is done in THF at 70° C. over night.

For example 8.13 the reaction conditions are 100° C. for two weeks.

| Ex. | Starting material | Structure | Mass spec result | HPLC retention time (method) |
|---|---|---|---|---|
| 8.1 | XIII.3 + 2-chloro-6-(trifluoro-methyl)-pyridinetrifluoromethyl)pyridine | 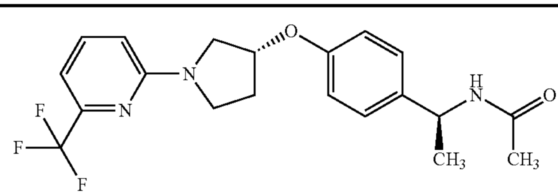 | 394 [M + H]$^+$ | 1.13 (C) |
| 8.2 | XIII.1 + 2,4-dichloro-5-methylpyridine | 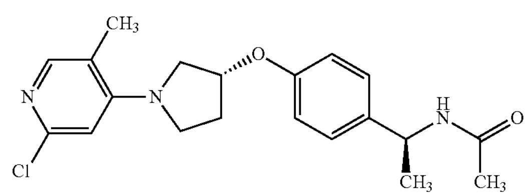 [SMILES: CC(=O)N[C@@H](C)c1ccc(O[C@@H]2CCN(c3cc(Cl)ncc3C)C2)cc1] | 374 [M + H]$^+$ | 0.29 (O) |
| 8.3 | XIII.1 + 2-2,3-difluoro-5-(trifluoromethyltrifluoromethyl)-pyridine | 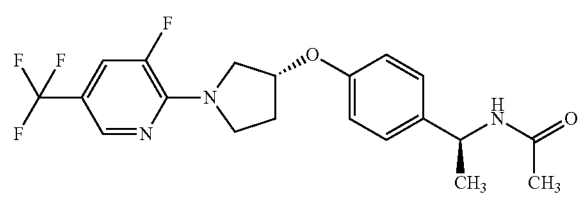 [SMILES: CC(=O)N[C@@H](C)c1ccc(O[C@@H]2CCN(c3ncc(C(F)(F)F)cc3F)C2)cc1] | 412 [M + H]$^+$ | 0.46 (O) |
| 8.4 | XIII.1 + 4-chloro-2-(trifluoromethyltrifluoromethyl)pyridine | 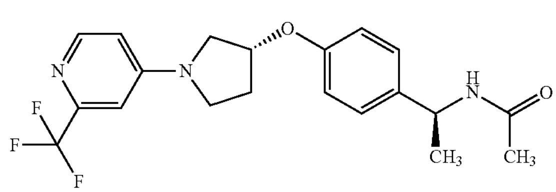 [SMILES: CC(=O)N[C@@H](C)c1ccc(O[C@@H]2CCN(c3ccnc(C(F)(F)F)c3)C2)cc1] | 394 [M + H]$^+$ | 0.29 (O) |

-continued

| Ex. | Starting material | Structure | Mass spec result | HPLC retention time (method) |
|---|---|---|---|---|
| 8.5 | XIII.1 + (4-chloro-pyridin-2-yl)-(4,5-difluoro-2,3-dihydro-indol-1-yl)-methanone | 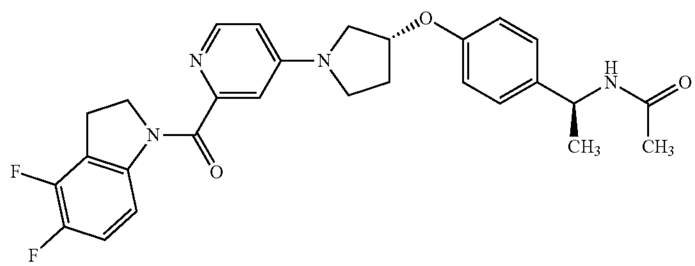 [SMILES: CC(=O)N[C@@H](C)c1ccc(O[C@@H]2CCN(c3ccnc(C(=O)N4CCc5c4ccc(F)c5F)c3)C2)cc1] | 507 [M + H]+ | 0.35 (O) |
| 8.6 | XIII.1 + 6-3,6-difluoro-2-(trifluoromethyltrifluoromethyl)-pyridine | 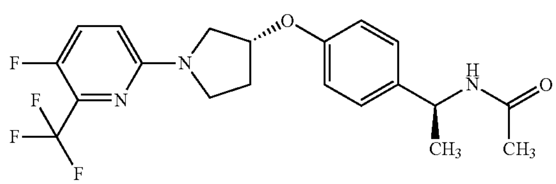 [SMILES: CC(=O)N[C@@H](C)c1ccc(O[C@@H]2CCN(c3ccc(F)c(C(F)(F)F)n3)C2)cc1] | 410 [M + H]+ | 1.51 (B) |
| 8.7 | XIII.1 + 2-chloro-4-(trifluoromethyltrifluoromethyl) pyridine | 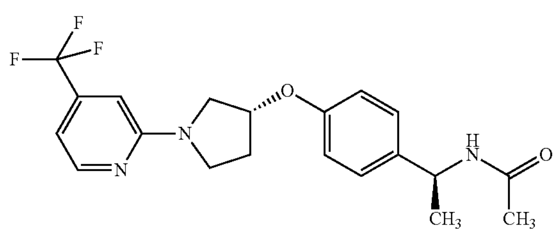 [SMILES: CC(=O)N[C@@H](C)c1ccc(O[C@@H]2CCN(c3cc(C(F)(F)F)ccn3)C2)cc1] | 394 [M + H]+ | 0.30 (O) |
| 8.8 | XIII.1 + 3,6-dichloro-2-(trifluoromethyltrifluoromethyl) pyridine | 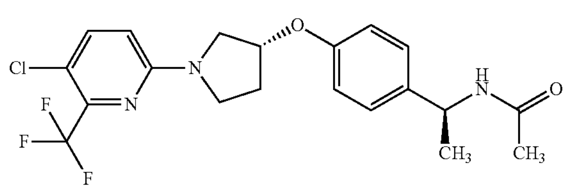 [SMILES: CC(=O)N[C@@H](C)c1ccc(O[C@@H]2CCN(c3ccc(Cl)c(C(F)(F)F)n3)C2)cc1] | 428 [M + H]+ | 0.49 (O) |
| 8.9 | XIII.5 + 2-fluoro-6-(trifluoromethyltrifluoromethyl) pyridine | 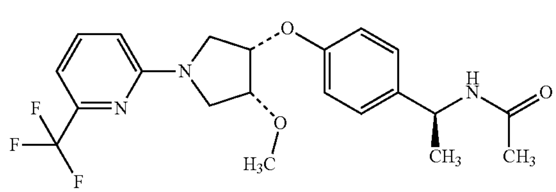 [SMILES: CO[C@@H]1CN(c2cccc(C(F)(F)F)n2)C[C@@H]1Oc1ccc([C@H](C)NC(C)=O)cc1] | 424 [M + H]+ | 1.12 (C) |
| 8.10 | XIII.1 and XXIV.22 | 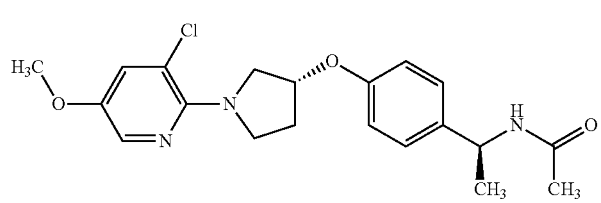 [SMILES: COc1cnc(N2CC[C@@H](Oc3ccc([C@H](C)NC(C)=O)cc3)C2)c(Cl)c1] | 390 [M + H]+ | 1.17 (C) |

| Ex. | Starting material | Structure | Mass spec result | HPLC retention time (method) |
|---|---|---|---|---|
| 8.11 | XIII.1 + 4-chloro-pyridine-2-carboxylic acid(4-chloro-phenyl)-amide | 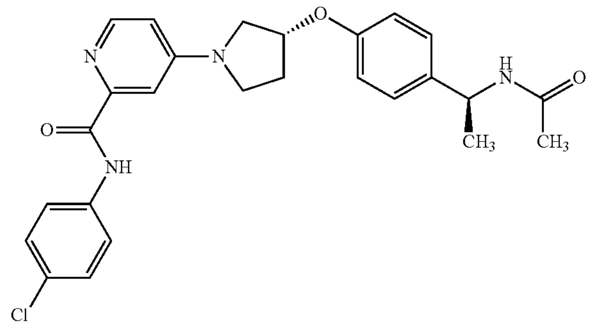 [SMILES: CC(=O)N[C@@H](C)c1ccc(O[C@@H]2CCN(c3ccnc(C(=O)Nc4ccc(Cl)cc4)c3)C2)cc1] | 479 [M + H]⁺ | 0.36 (O) |

Example 9

Example 9.1

General Route

N—((S)-1-(4-((R)-1-(2-Cyclobutoxypyridin-4-yl)pyrrolidin-3-yloxy)phenyl)ethyl-acetamide

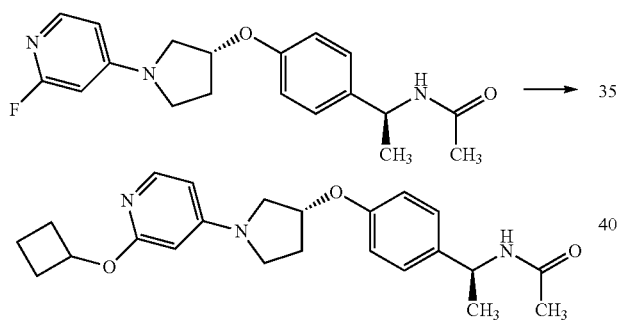

25.0 mg (0.07 mmol) of example XX.7 and 26.8 µL (0.07 mmol) cyclobutanol are added to 2 mL dioxane. Then 14.6 mg (0.36 mmol) NaH (60% suspension in mineral oil) are added and the reaction mixture is stirred at 130° C. over night. The solvent is removed in vacuo. A small amount DMF is added and the mixture is purified by HPLC (MeOH/H$_2$O/TFA).

$C_{23}H_{29}N_3O_3$ (M=395.5 g/mol)

ESI-MS: 396 [M+H]⁺

R$_t$(HPLC):1.43 min (method J)

The following compounds are prepared analogously to example 9.1:

For example 9.2 the reaction time is 3 h.

For example 9.39 the reaction conditions are DMSO as solvent and 50° C. over night.

For the examples 9.52 and 9.54 the reaction time is 3 d.

For the examples 9.68-9.70 the reaction conditions are THF as solvent and 70° C. over night.

For the examples 9.71-9.82 and 9.84-9.88 the reaction conditions are 80-100° C. for 3-16 h.

For the example 9.83 propanol is used as solvent.

| Ex. | Starting material | Structure | Mass spec result | HPLC retention time (method) |
|---|---|---|---|---|
| 9.1 | XX.7 | 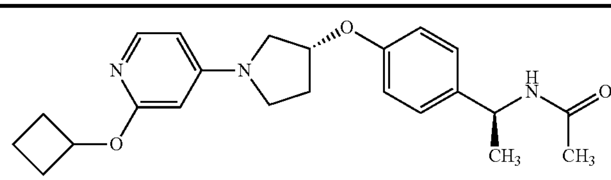 | 396 [M + H]⁺ | 1.43 (S) |
| 9.2 | XX.7 | 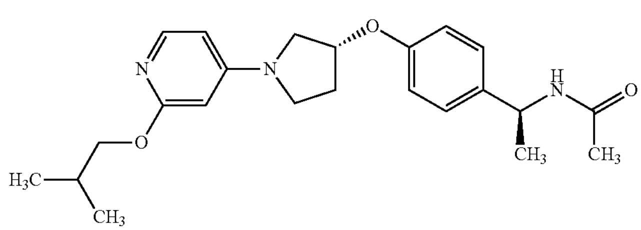 [SMILES: CC(=O)N[C@@H](C)c1ccc(O[C@@H]2CCN(c3ccnc(OCC(C)C)c3)C2)cc1] | 398 [M + H]⁺ | 1.10 (R) |

-continued

| Ex. | Starting material | Structure | Mass spec result | HPLC retention time (method) |
|---|---|---|---|---|
| 9.3 | XX.7 | 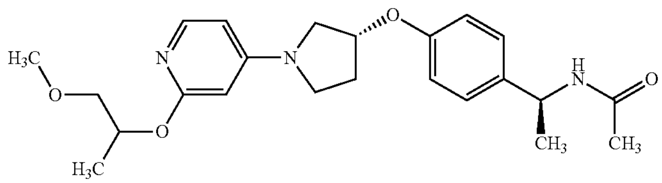 [SMILES: COCC(C)Oc1cc(N2CC[C@@H](Oc3ccc([C@H](C)NC(C)=O)cc3)C2)ccn1] | 414 [M + H]+ | 1.05 (V) |
| 9.4 | XX.7 | 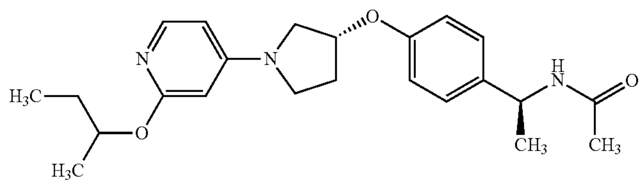 [SMILES: CCC(C)Oc1cc(N2CC[C@@H](Oc3ccc([C@H](C)NC(C)=O)cc3)C2)ccn1] | 398 [M + H]+ | 1.15 (V) |
| 9.5 | XX.7 | 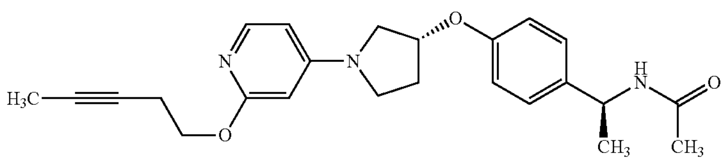 [SMILES: CC#CCCOc1cc(N2CC[C@@H](Oc3ccc([C@H](C)NC(C)=O)cc3)C2)ccn1] | 408 [M + H]+ | 1.12 (V) |
| 9.6 | XX.7 | 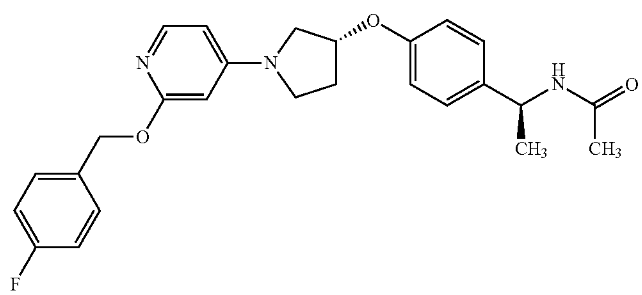 [SMILES: CC(=O)N[C@@H](C)c1ccc(O[C@@H]2CCN(c3ccnc(OCc4ccc(F)cc4)c3)C2)cc1] | 450 [M + H]+ | 1.21 (V) |
| 9.7 | XX.7 | 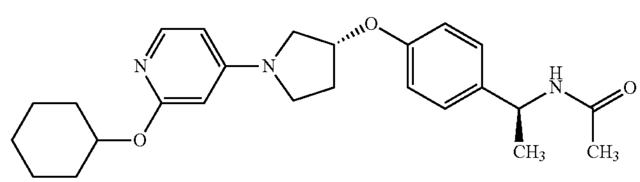 [SMILES: CC(=O)N[C@@H](C)c1ccc(O[C@@H]2CCN(c3ccnc(OC4CCCCC4)c3)C2)cc1] | 424 [M + H]+ | 1.26 (V) |
| 9.8 | XX.7 | 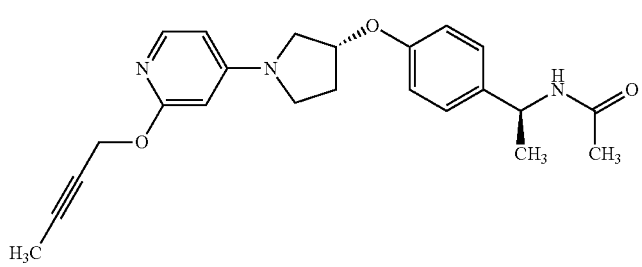 [SMILES: CC#CCOc1cc(N2CC[C@@H](Oc3ccc([C@H](C)NC(C)=O)cc3)C2)ccn1] | 394 [M + H]+ | 1.06 (V) |

-continued

| Ex. | Starting material | Structure | Mass spec result | HPLC retention time (method) |
|---|---|---|---|---|
| 9.9 | XX.7 | 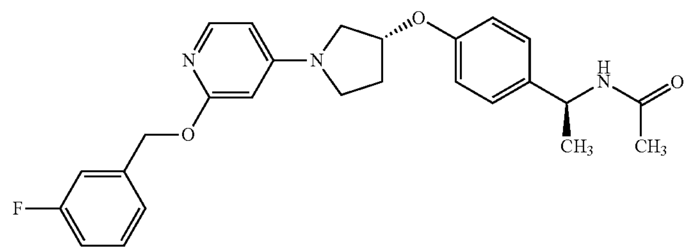 [SMILES: CC(=O)N[C@@H](C)c1ccc(O[C@@H]2CCN(c3ccnc(OCc4cccc(F)c4)c3)C2)cc1] | 450 [M + H]+ | 1.22 (V) |
| 9.10 | XX.7 | 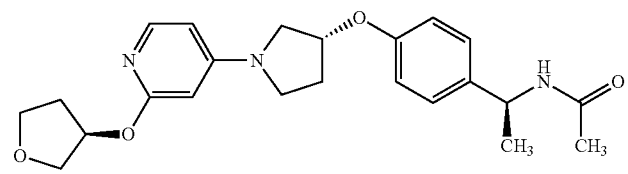 [SMILES: CC(=O)N[C@@H](C)c1ccc(O[C@@H]2CCN(c3ccnc(O[C@@H]4CCOC4)c3)C2)cc1] | 412 [M + H]+ | 0.96 (V) |
| 9.11 | XX.7 | 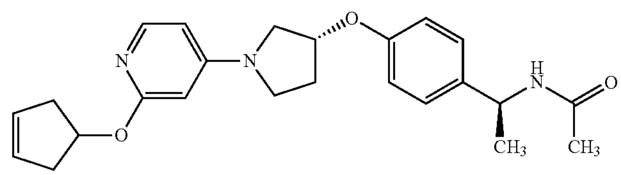 [SMILES: CC(=O)N[C@@H](C)c1ccc(O[C@@H]2CCN(c3ccnc(OC4CC=CC4)c3)C2)cc1] | 408 [M + H]+ | 1.15 (V) |
| 9.12 | XX.7 | 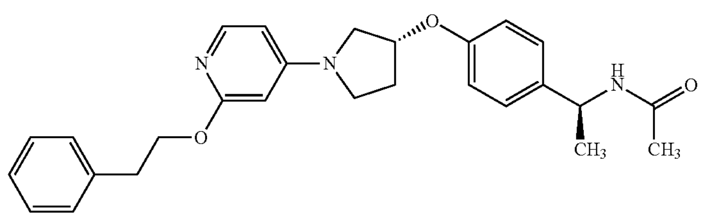 [SMILES: CC(=O)N[C@@H](C)c1ccc(O[C@@H]2CCN(c3ccnc(OCCc4ccccc4)c3)C2)cc1] | 446 [M + H]+ | 1.24 (V) |
| 9.13 | XX.7 | 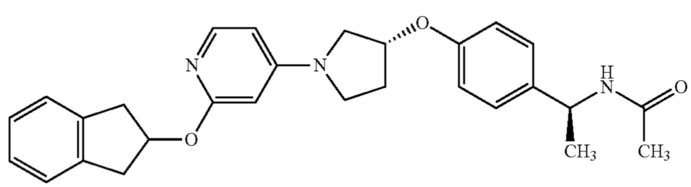 [SMILES: CC(=O)N[C@@H](C)c1ccc(O[C@@H]2CCN(c3ccnc(OC4Cc5ccccc5C4)c3)C2)cc1] | 458 [M + H]+ | 1.27 (V) |
| 9.14 | XX.7 | 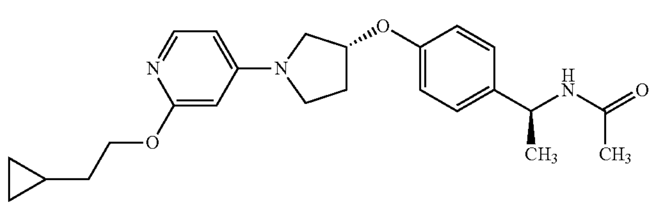 [SMILES: CC(=O)N[C@@H](C)c1ccc(O[C@@H]2CCN(c3ccnc(OCCC4CC4)c3)C2)cc1] | 410 [M + H]+ | 1.21 (V) |
| 9.15 | XX.7 | 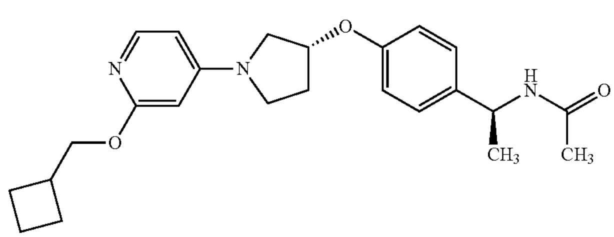 [SMILES: CC(=O)N[C@@H](C)c1ccc(O[C@@H]2CCN(c3ccnc(OCC4CCC4)c3)C2)cc1] | 410 [M + H]+ | 1.22 (V) |

-continued

| Ex. | Starting material | Structure | Mass spec result | HPLC retention time (method) |
|---|---|---|---|---|
| 9.16 | XX.7 | 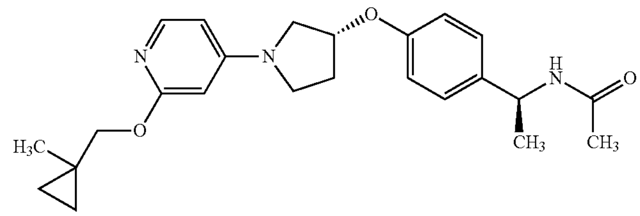 [SMILES: CC(=O)N[C@@H](C)c1ccc(O[C@@H]2CCN(c3ccnc(OCC4(C)CC4)c3)C2)cc1] | 410 [M + H]+ | 1.20 (V) |
| 9.17 | XX.7 | 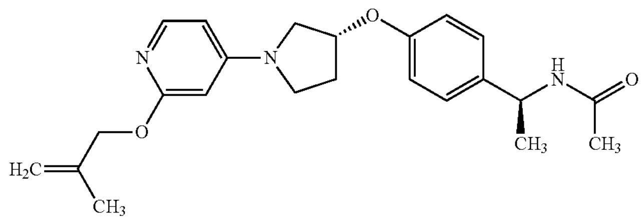 [SMILES: C=C(C)COc1cc(N2CC[C@@H](Oc3ccc([C@H](C)NC(C)=O)cc3)C2)ccn1] | 396 [M + H]+ | 1.12 (V) |
| 9.18 | XX.7 | 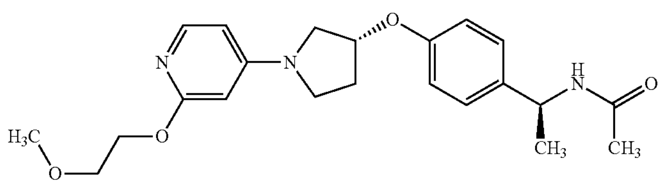 [SMILES: COCCOc1cc(N2CC[C@@H](Oc3ccc([C@H](C)NC(C)=O)cc3)C2)ccn1] | 400 [M + H]+ | 0.94 (V) |
| 9.19 | XX.7 | 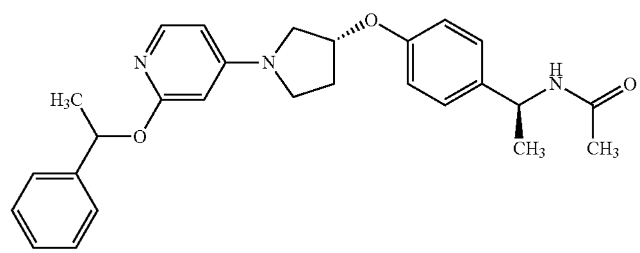 [SMILES: CC(=O)N[C@@H](C)c1ccc(O[C@@H]2CCN(c3ccnc(OC(C)c4ccccc4)c3)C2)cc1] | 446 [M + H]+ | 1.24 (V) |
| 9.20 | XX.7 | 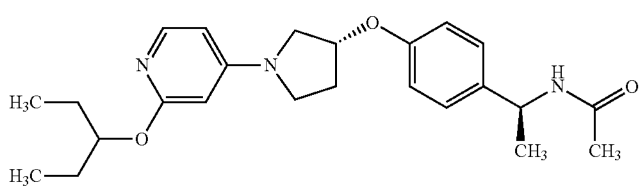 [SMILES: CCC(CC)Oc1cc(N2CC[C@@H](Oc3ccc([C@H](C)NC(C)=O)cc3)C2)ccn1] | 412 [M + H]+ | 1.22 (V) |
| 9.21 | XX.7 | 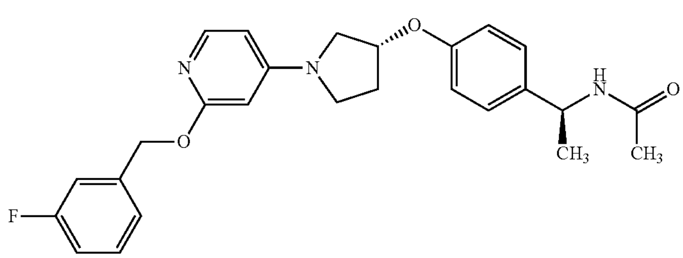 [SMILES: CC(=O)N[C@@H](C)c1ccc(O[C@@H]2CCN(c3ccnc(OCc4cccc(F)c4)c3)C2)cc1] | 450 [M + H]+ | 1.20 (V) |
| 9.22 | XX.7 | 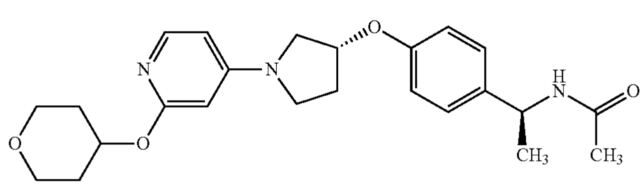 [SMILES: CC(=O)N[C@@H](C)c1ccc(O[C@@H]2CCN(c3ccnc(OC4CCOCC4)c3)C2)cc1] | 426 [M + H]+ | 1.01 (V) |

-continued
| Ex. | Starting material | Structure | Mass spec result | HPLC retention time (method) |
|---|---|---|---|---|
| 9.23 | XX.7 | 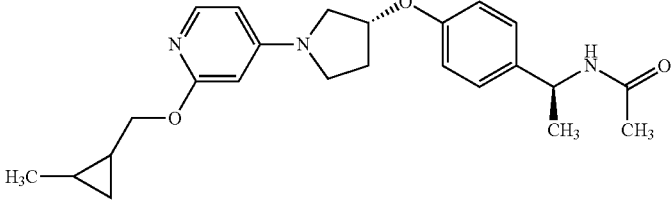 | 410 [M + H]+ | 1.22 (V) |
| 9.24 | XX.7 | 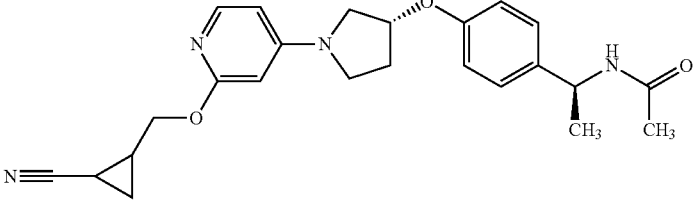 | 421 [M + H]+ | 0.99 (V) |
| 9.25 | XX.7 | 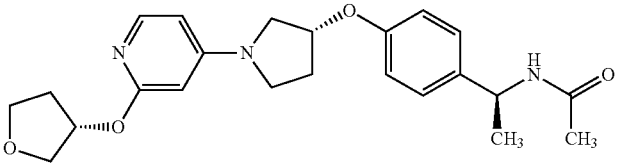 [SMILES: CC(=O)N[C@@H](C)c1ccc(O[C@@H]2CCN(c3ccnc(O[C@H]4CCOC4)c3)C2)cc1] | 412 [M + H]+ | 0.96 (V) |
| 9.26 | XX.7 | 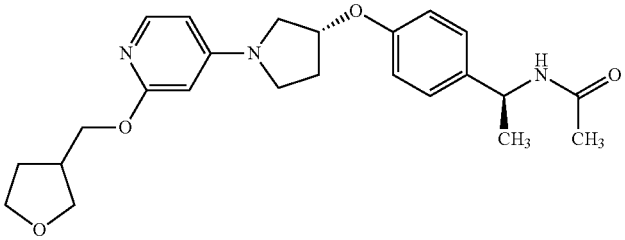 [SMILES: CC(=O)N[C@@H](C)c1ccc(O[C@@H]2CCN(c3ccnc(OCC4CCOC4)c3)C2)cc1] | 426 [M + H]+ | 1.03 (V) |
| 9.27 | XX.7 | 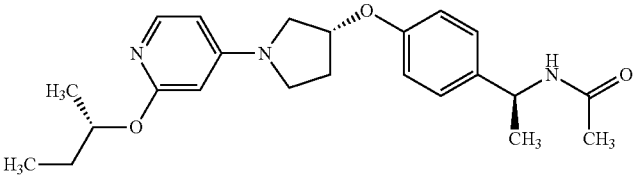 [SMILES: CC[C@H](C)Oc1cc(N2CC[C@@H](Oc3ccc([C@H](C)NC(C)=O)cc3)C2)ccn1] | 398 [M + H]+ | 1.17 (V) |
| 9.28 | XX.7 | 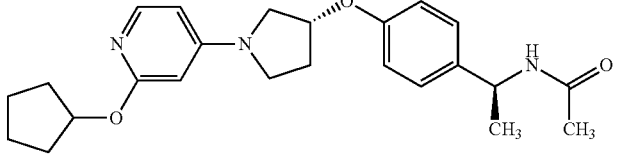 | 410 [M + H]+ | 1.20 (V) |
| 9.29 | XX.7 | 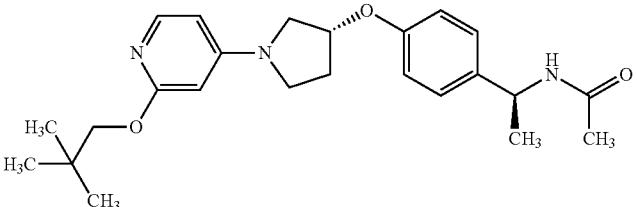 | 412 [M + H]+ | 1.25 (V) |

-continued

| Ex. | Starting material | Structure | Mass spec result | HPLC retention time (method) |
|---|---|---|---|---|
| 9.30 | XX.7 | 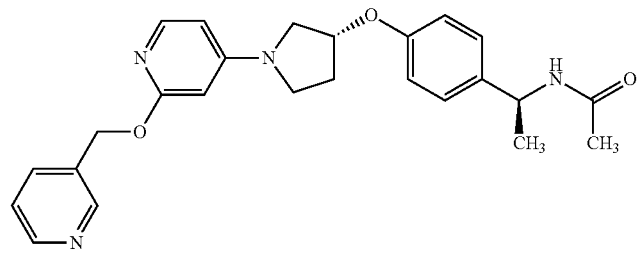 [SMILES: CC(=O)N[C@@H](C)c1ccc(O[C@@H]2CCN(c3ccnc(OCc4cccnc4)c3)C2)cc1] | 433 [M + H]+ | 0.80 (V) |
| 9.31 | XX.7 | 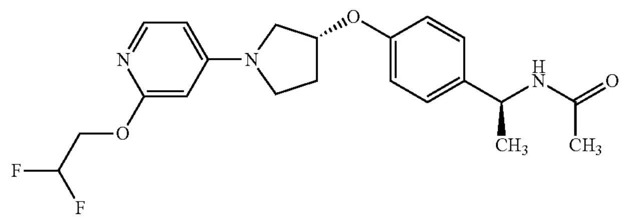 [SMILES: CC(=O)N[C@@H](C)c1ccc(O[C@@H]2CCN(c3ccnc(OCC(F)F)c3)C2)cc1] | 406 [M + H]+ | 1.19 (H) |
| 9.32 | XX.7 | 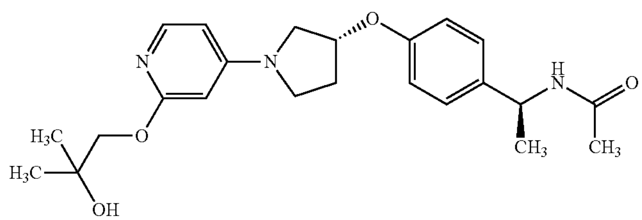 [SMILES: CC(=O)N[C@@H](C)c1ccc(O[C@@H]2CCN(c3ccnc(OCC(C)(C)O)c3)C2)cc1] | 414 [M + H]+ | 0.64 (D) |
| 9.33 | XX.7 | 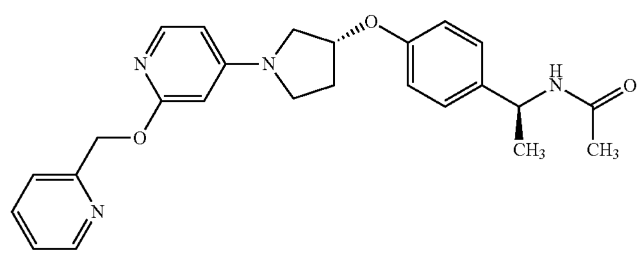 [SMILES: CC(=O)N[C@@H](C)c1ccc(O[C@@H]2CCN(c3ccnc(OCc4ccccn4)c3)C2)cc1] | 433 [M + H]+ | 0.98 (V) |
| 9.34 | XX.7 | 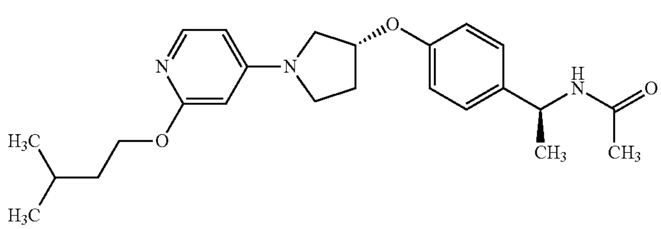 [SMILES: CC(=O)N[C@@H](C)c1ccc(O[C@@H]2CCN(c3ccnc(OCCC(C)C)c3)C2)cc1] | 412 [M + H]+ | 1.27 (V) |
| 9.35 | XX.7 | 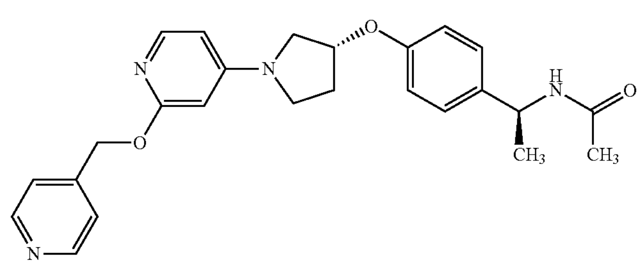 [SMILES: CC(=O)N[C@@H](C)c1ccc(O[C@@H]2CCN(c3ccnc(OCc4ccncc4)c3)C2)cc1] | 433 [M + H]+ | 0.76 (V) |

-continued
| Ex. | Starting material | Structure | Mass spec result | HPLC retention time (method) |
|---|---|---|---|---|
| 9.36 | XX.10 | 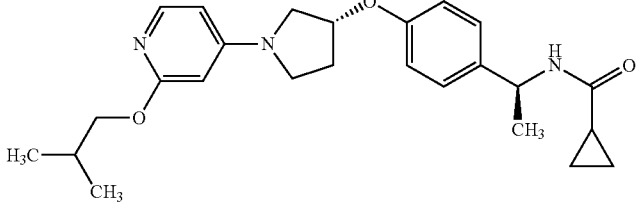 | 424 [M + H]⁺ | 1.07 (E) |
| 9.37 | XX.10 | 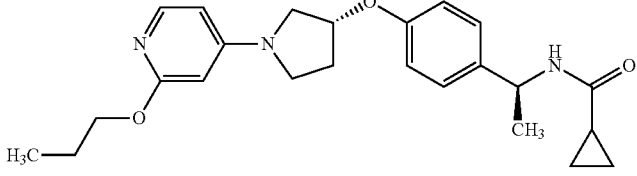 | 410 [M + H]⁺ | 1.01 (E) |
| 9.38 | XX.10 | 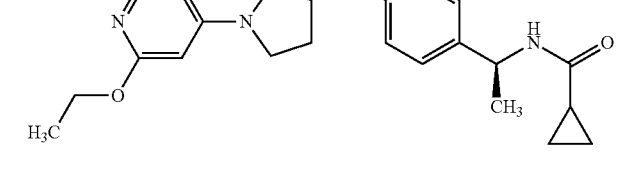 | 396 [M + H]⁺ | 0.96 (E) |
| 9.39 | XX.10 | 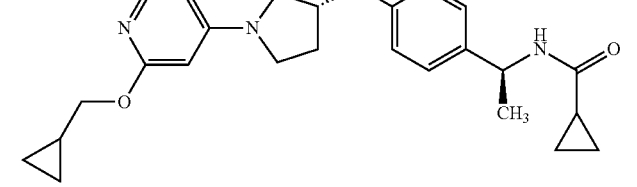 | 422 [M + H]⁺ | 0.96 (B) |
| 9.40 | XX.10 | 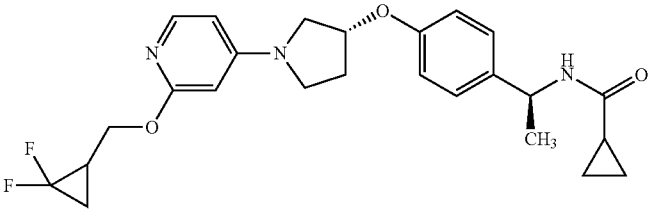 [SMILES: C[C@H](NC(=O)C1CC1)c1ccc(O[C@@H]2CCN(c3ccnc(OCC4CC4(F)F)c3)C2)cc1] | 458 [M + H]⁺ | 1.00 (E) |
| 9.41 | XX.10 | 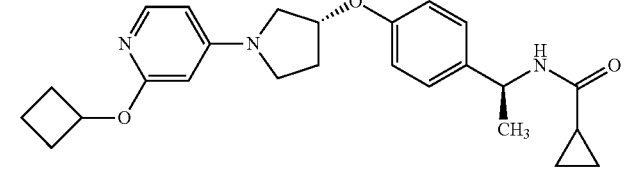 | 422 [M + H]⁺ | 1.03 (E) |
| 9.42 | XX.10 | 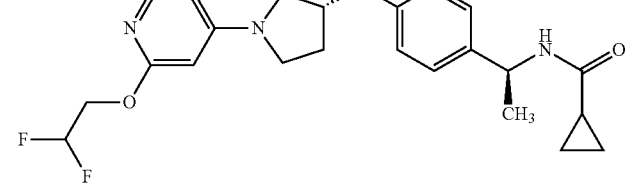 | 432 [M + H]⁺ | 0.93 (E) |

-continued

| Ex. | Starting material | Structure | Mass spec result | HPLC retention time (method) |
|---|---|---|---|---|
| 9.43 | XX.10 | 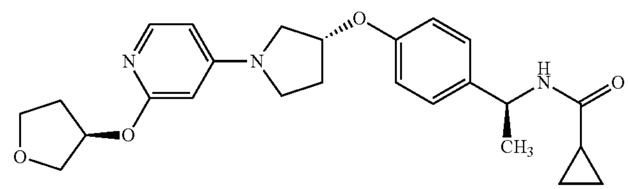 [SMILES: C[C@H](NC(=O)C1CC1)c1ccc(O[C@@H]2CCN(c3ccnc(O[C@@H]4CCOC4)c3)C2)cc1] | 438 [M + H]+ | 0.90 (E) |
| 9.44 | XX.7 | 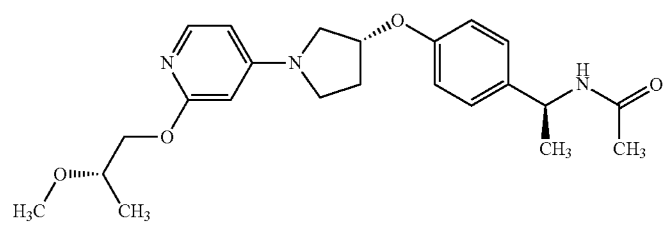 [SMILES: CO[C@@H](C)COc1cc(N2CC[C@@H](Oc3ccc([C@H](C)NC(C)=O)cc3)C2)ccn1] | 414 [M + H]+ | 1.15 (V) |
| 9.45 | XX.7 | 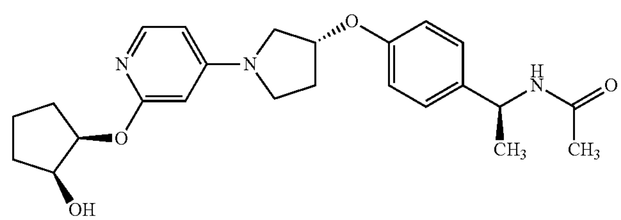 [SMILES: CC(=O)N[C@@H](C)c1ccc(O[C@@H]2CCN(c3ccnc(O[C@@H]4CCC[C@@H]4O)c3)C2)cc1] | 426 [M + H]+ | 1.15 (V) |
| 9.46 | XX.7 | 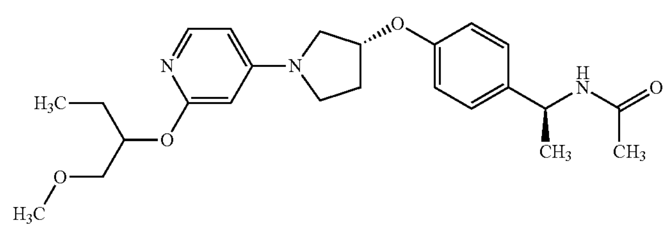 [SMILES: CCC(COC)Oc1cc(N2CC[C@@H](Oc3ccc([C@H](C)NC(C)=O)cc3)C2)ccn1] | 428 [M + H]+ | 1.22 (V) |
| 9.47 | XX.7 | 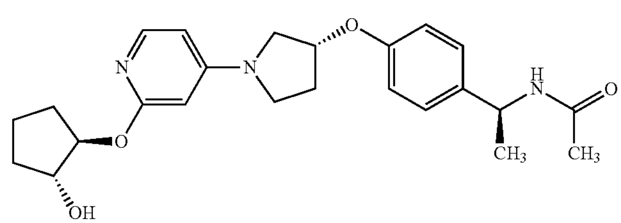 [SMILES: CC(=O)N[C@@H](C)c1ccc(O[C@@H]2CCN(c3ccnc(O[C@@H]4CCC[C@H]4O)c3)C2)cc1] | 426 [M + H]+ | 1.15 (V) |
| 9.48 | XX.7 | 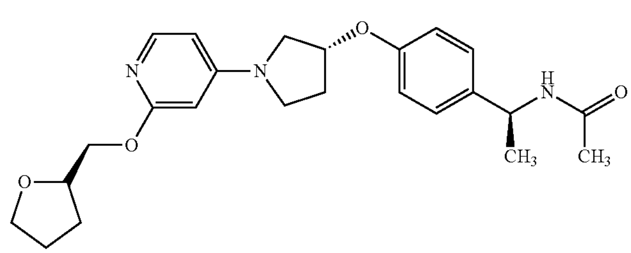 | 426 [M + H]+ | 1.16 (V) |

-continued

| Ex. | Starting material | Structure | Mass spec result | HPLC retention time (method) |
|---|---|---|---|---|
| 9.49 | XX.7 | 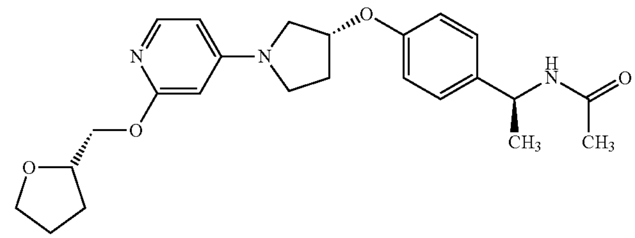 | 426 [M + H]+ | 1.14 (V) |
| 9.50 | XX.1 | 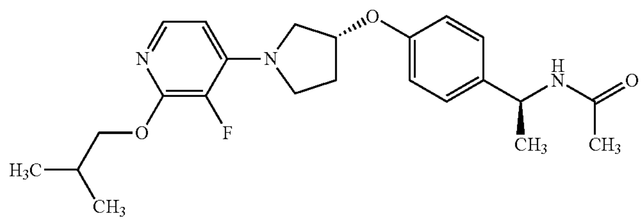 | 416 [M + H]+ | 1.18 (E) |
| 9.51 | XX.1 | 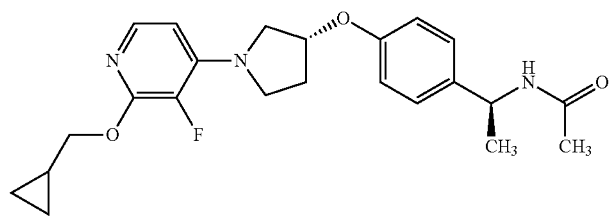 [SMILES: CC(=O)N[C@@H](C)c1ccc(O[C@@H]2CCN(c3ccnc(OCC4CC4)c3F)C2)cc1] | 414 [M + H]+ | 0.92 (K) |
| 9.52 | XX.1 | 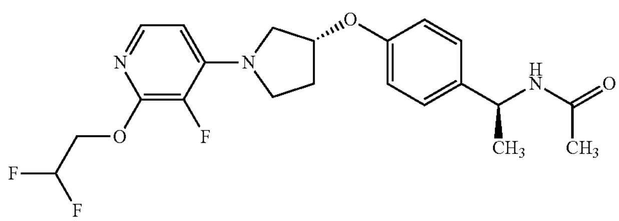 [SMILES: CC(=O)N[C@@H](C)c1ccc(O[C@@H]2CCN(c3ccnc(OCC(F)F)c3F)C2)cc1] | 424 [M + H]+ | 1.19 (E) |
| 9.53 | XX.1 | 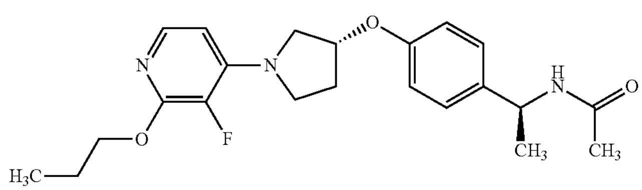 | 402 [M + H]+ | 1.11 (E) |
| 9.54 | XXI.1 | 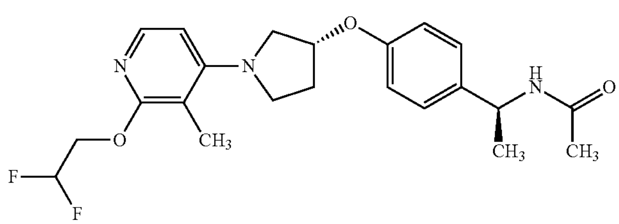 [SMILES: CC(=O)N[C@@H](C)c1ccc(O[C@@H]2CCN(c3ccnc(OCC(F)F)c3C)C2)cc1] | 420 [M + H]+ | 0.99 (E) |
| 9.55 | XXI.1 | 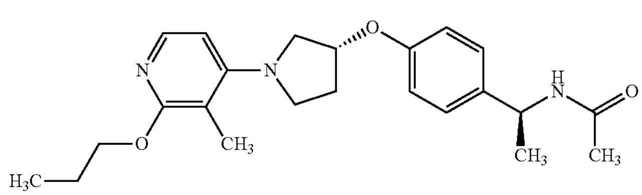 [SMILES: CCCOc1nccc(N2CC[C@@H](Oc3ccc([C@H](C)NC(C)=O)cc3)C2)c1C] | 398 [M + H]+ | 1.04 (E) |

-continued

| Ex. | Starting material | Structure | Mass spec result | HPLC retention time (method) |
|---|---|---|---|---|
| 9.56 | XX.2 | 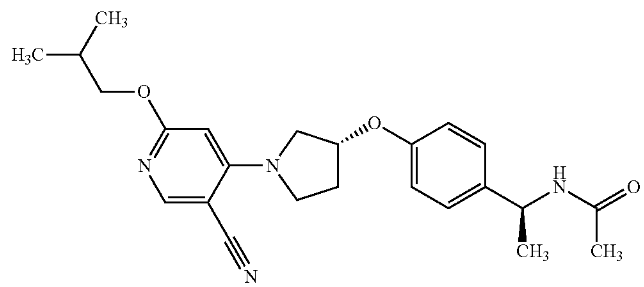 [SMILES: CC(=O)N[C@@H](C)c1ccc(O[C@@H]2CCN(c3cc(OCC(C)C)ncc3C#N)C2)cc1] | 423 [M + H]+ | 1.27 (E) |
| 9.57 | XXI.1 | 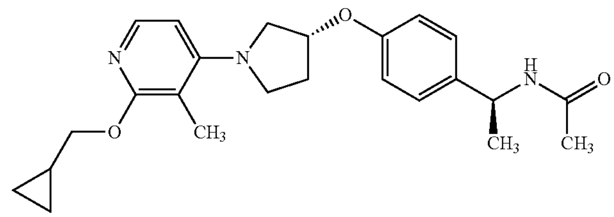 [SMILES: CC(=O)N[C@@H](C)c1ccc(O[C@@H]2CCN(c3ccnc(OCC4CC4)c3C)C2)cc1] | 410 [M + H]+ | 1.23 (C) |
| 9.58 | XXI.1 | 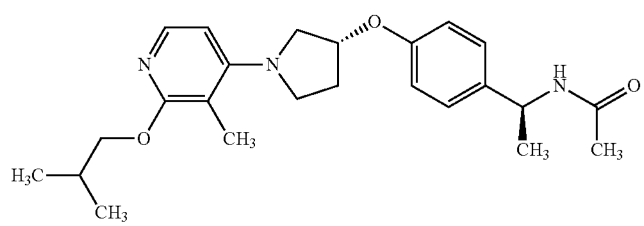 [SMILES: CC(=O)N[C@@H](C)c1ccc(O[C@@H]2CCN(c3ccnc(OCC(C)C)c3C)C2)cc1] | 412 [M + H]+ | 1.08 (C) |
| 9.59 | XXI.1 | 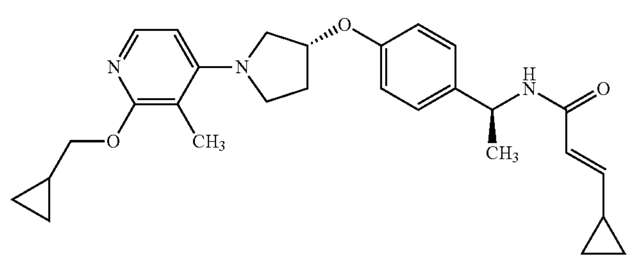 [SMILES: Cc1c(N2CC[C@@H](Oc3ccc([C@H](C)NC(=O)/C=C/C4CC4)cc3)C2)ccnc1OCC1CC1] | 462 [M + H]+ | 1.23 (C) |
| 9.60 | XXI.1 | 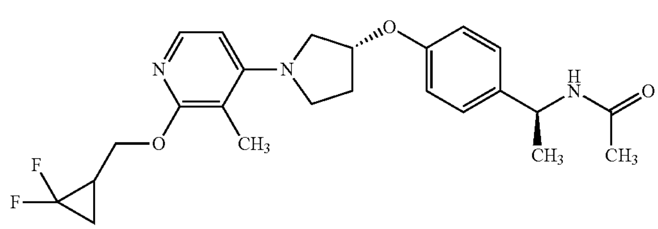 [SMILES: CC(=O)N[C@@H](C)c1ccc(O[C@@H]2CCN(c3ccnc(OCC4CC4(F)F)c3C)C2)cc1] | 446 [M + H]+ | 0.88 (M) |
| 9.61 | XX.7 | 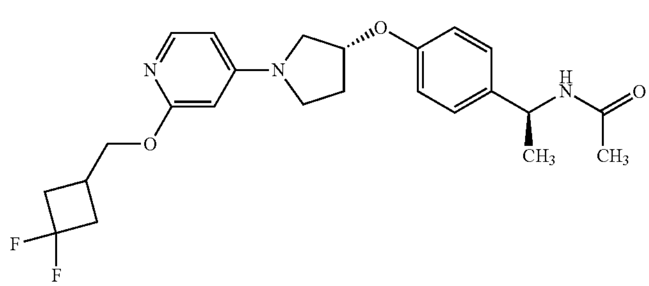 [SMILES: CC(=O)N[C@@H](C)c1ccc(O[C@@H]2CCN(c3ccnc(OCC4CC(F)(F)C4)c3)C2)cc1] | 446 [M + H]+ | 0.85 (M) |

-continued

| Ex. | Starting material | Structure | Mass spec result | HPLC retention time (method) |
|---|---|---|---|---|
| 9.62 | XX.1 | 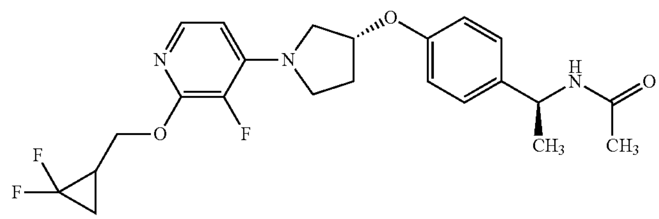 [SMILES: CC(=O)N[C@@H](C)c1ccc(O[C@@H]2CCN(c3ccnc(OCC4CC4(F)F)c3F)C2)cc1] | 450 [M + H]+ | 0.96 (M) |
| 9.63 | XX.12 | 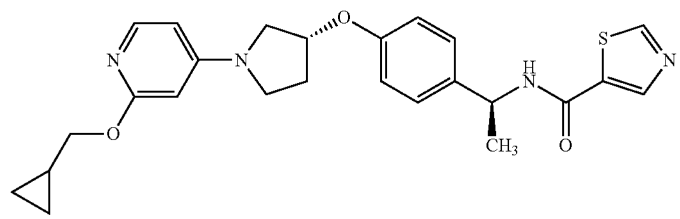 [SMILES: C[C@H](NC(=O)c1cncs1)c1ccc(O[C@@H]2CCN(c3ccnc(OCC4CC4)c3)C2)cc1] | 465 [M + H]+ | 0.87 (M) |
| 9.64 | XX.12 | 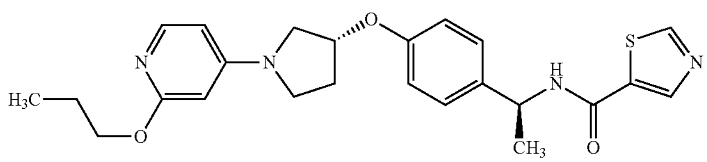 [SMILES: CCCOc1cc(N2CC[C@@H](Oc3ccc([C@H](C)NC(=O)c4cncs4)cc3)C2)ccn1] | 453 [M + H]+ | 0.87 (M) |
| 9.65 | XX.12 | 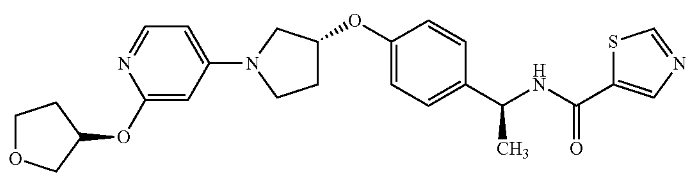 | 481 [M + H]+ | 0.81 (M) |
| 9.66 | XX.1 | 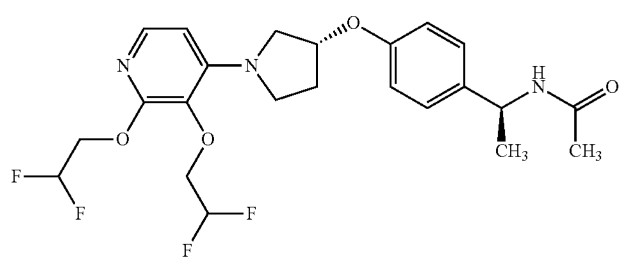 [SMILES: CC(=O)N[C@@H](C)c1ccc(O[C@@H]2CCN(c3ccnc(OCC(F)F)c3OCC(F)F)C2)cc1] | 486 [M + H]+ | 0.96 (M) |
| 9.67 | XX.6 | 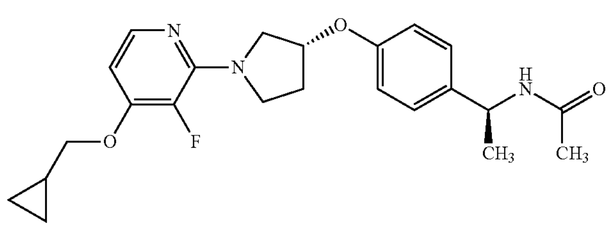 [SMILES: CC(=O)N[C@@H](C)c1ccc(O[C@@H]2CCN(c3nccc(OCC4CC4)c3F)C2)cc1] | 414 [M + H]+ | 0.87 (M) |
| 9.68 | XX.6 | 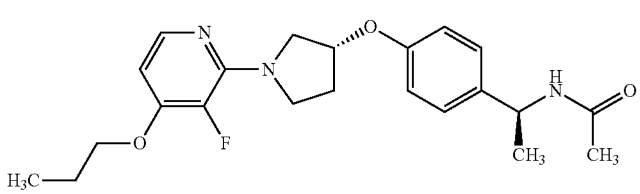 [SMILES: CCCOc1ccnc(N2CC[C@@H](Oc3ccc([C@H](C)NC(C)=O)cc3)C2)c1F] | 402 [M + H]+ | 0.87 (M) |

-continued

| Ex. | Starting material | Structure | Mass spec result | HPLC retention time (method) |
|---|---|---|---|---|
| 9.69 | XX.6 | 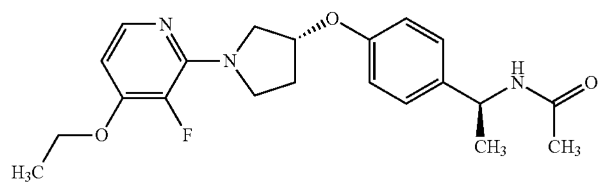 [SMILES: CCOc1ccnc(N2CC[C@@H](Oc3ccc([C@H](C)NC(C)=O)cc3)C2)c1F] | 388 [M + H]+ | 0.86 (M) |
| 9.70 | XXI.3 | 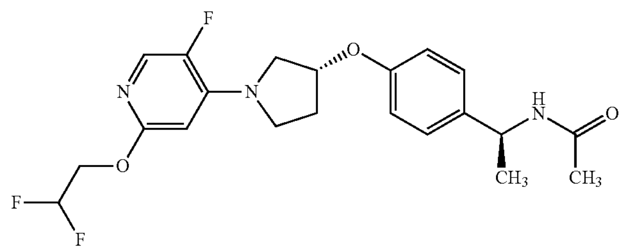 [SMILES: CC(=O)N[C@@H](C)c1ccc(O[C@@H]2CCN(c3cc(OCC(F)F)ncc3F)C2)cc1] | 424 [M + H]+ | 0.92 (K) |
| 9.71 | XXI.9 | 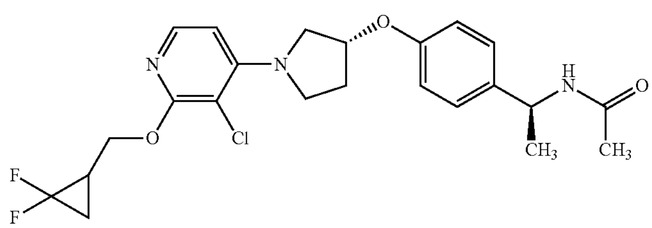 [SMILES: CC(=O)N[C@@H](C)c1ccc(O[C@@H]2CCN(c3ccnc(OCC4CC4(F)F)c3Cl)C2)cc1] | 466 [M + H]+ | 1.02 (M) |
| 9.72 | XXI.9 | 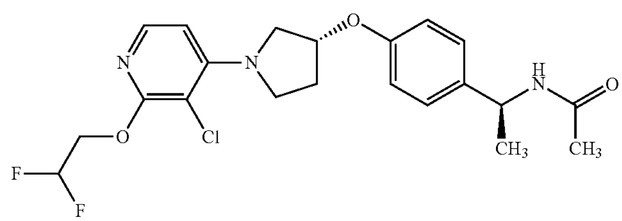 | 440 [M + H]+ | 1.04 (M) |
| 9.73 | XXI.11 | 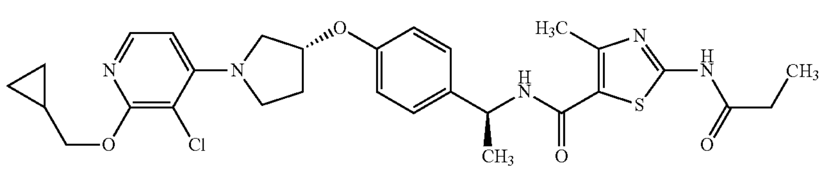 [SMILES: CCC(=O)Nc1nc(C)c(C(=O)N[C@@H](C)c2ccc(O[C@@H]3CCN(c4ccnc(OCC5CC5)c4Cl)C3)cc2)s1] | 584 [M + H]+ | 1.02 (D) |
| 9.74 | XX.1 | 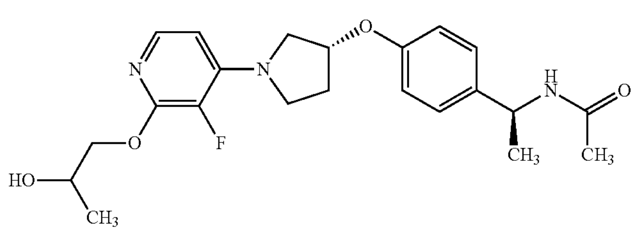 [SMILES: CC(=O)N[C@@H](C)c1ccc(O[C@@H]2CCN(c3ccnc(OCC(C)O)c3F)C2)cc1] | 418 [M + H]+ | 0.78 (M) |
| 9.75 | XX.1 | 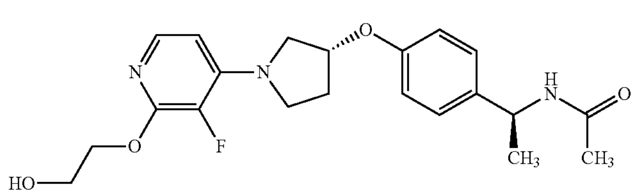 [SMILES: CC(=O)N[C@@H](C)c1ccc(O[C@@H]2CCN(c3ccnc(OCCO)c3F)C2)cc1] | 404 [M + H]+ | 0.91 (M) |

-continued

| Ex. | Starting material | Structure | Mass spec result | HPLC retention time (method) |
|---|---|---|---|---|
| 9.76 | XXI.9 | 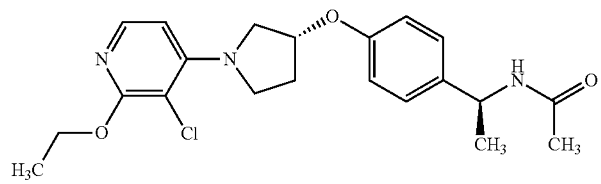 | 404 [M + H]+ | 0.64 (AD) |
| 9.77 | XXI.9 | 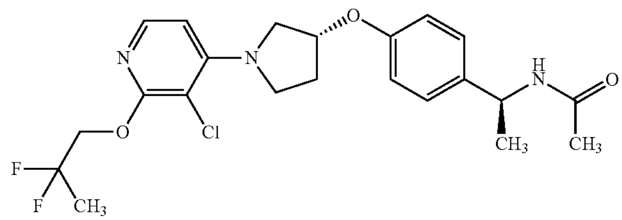 [SMILES: CC(=O)N[C@@H](C)c1ccc(O[C@@H]2CCN(c3ccnc(OCC(C)(F)F)c3Cl)C2)cc1] | 454 [M + H]+ | 0.88 (AD) |
| 9.78 | XXI.9 | 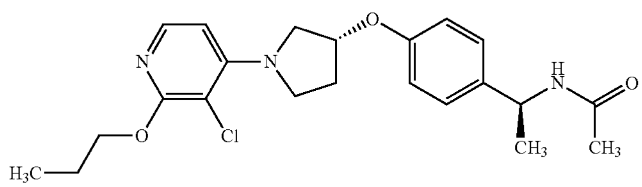 | 418 [M + H]+ | 0.70 (AD) |
| 9.79 | XXI.9 | 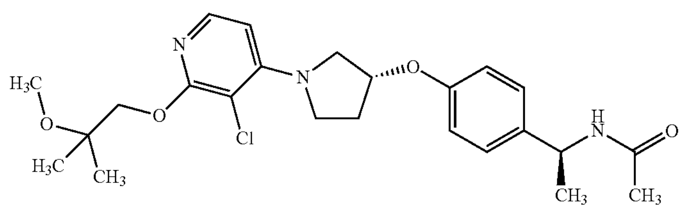 [SMILES: COC(C)(C)COc1nccc(N2CC[C@@H](Oc3ccc([C@H](C)NC(C)=O)cc3)C2)c1Cl] | 462 [M + H]+ | 0.72 (AD) |
| 9.80 | XXI.9 | 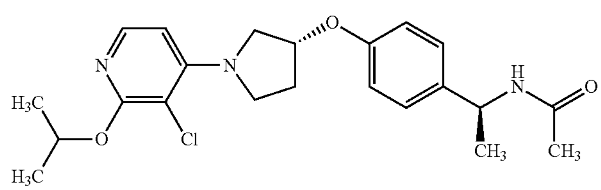 | 418 [M + H]+ | 0.67 (AD) |
| 9.81 | XXI.9 | 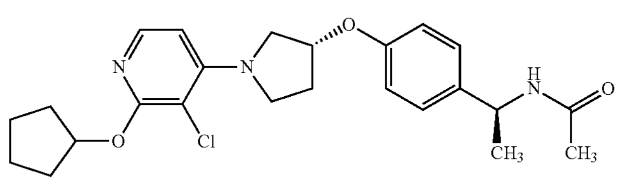 | 444 [M + H]+ | 0.73 (AD) |
| 9.82 | XXI.9 | 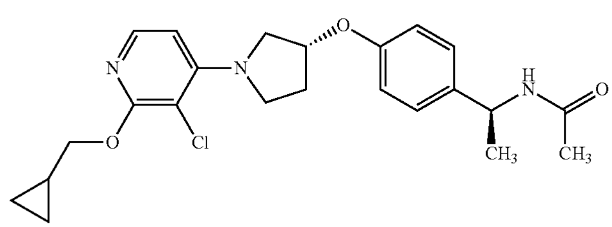 | 430 [M + H]+ | 0.93 (K) |

-continued

| Ex. | Starting material | Structure | Mass spec result | HPLC retention time (method) |
|---|---|---|---|---|
| 9.83 | XX.1 | 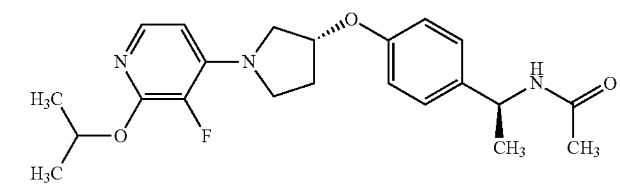 [SMILES: CC(=O)N[C@@H](C)c1ccc(O[C@@H]2CCN(c3ccnc(OC(C)C)c3F)C2)cc1] | 402 [M + H]+ | 0.42 (AA) |
| 9.84 | XX.1 | 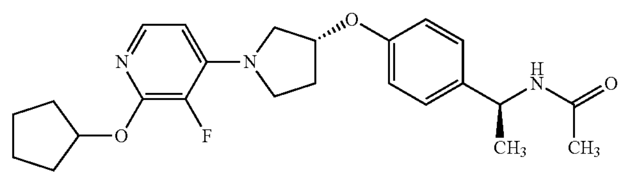 [SMILES: CC(=O)N[C@@H](C)c1ccc(O[C@@H]2CCN(c3ccnc(OC4CCCC4)c3F)C2)cc1] | 428 [M + H]+ | 1.18 (Y) |
| 9.85 | XX.1 | 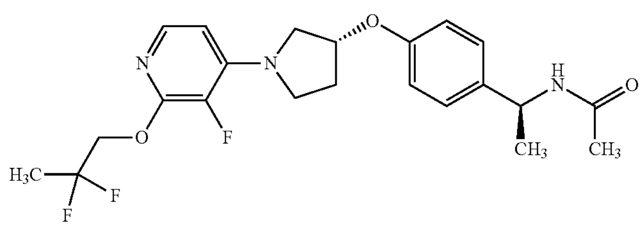 [SMILES: CC(=O)N[C@@H](C)c1ccc(O[C@@H]2CCN(c3ccnc(OCC(C)(F)F)c3F)C2)cc1] | 438 [M + H]+ | 1.33 (W) |
| 9.86 | XX.1 | 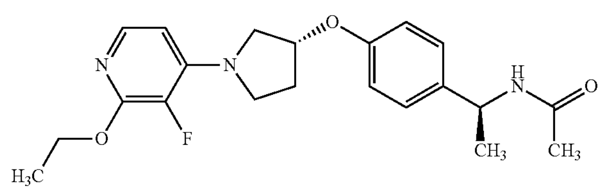 [SMILES: CCOc1nccc(N2CC[C@@H](Oc3ccc([C@H](C)NC(C)=O)cc3)C2)c1F] | 388 [M + H]+ | 0.96 (W) |
| 9.87 | XX.1 | 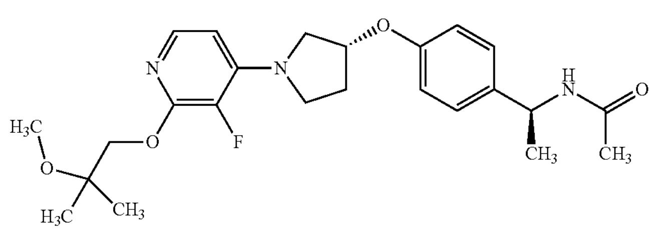 [SMILES: COC(C)(C)COc1nccc(N2CC[C@@H](Oc3ccc([C@H](C)NC(C)=O)cc3)C2)c1F] | 446 [M + H]+ | 0.44 (AA) |
| 9.88 | XX.1 | 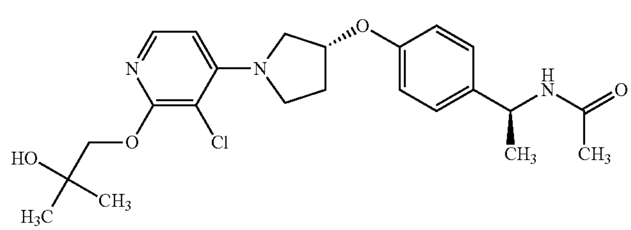 [SMILES: CC(=O)N[C@@H](C)c1ccc(O[C@@H]2CCN(c3ccnc(OCC(C)(C)O)c3Cl)C2)cc1] | 448 [M + H]+ | 0.95 (M) |

Example 10

Example 10.1

General Route

N—((S)-1-(4-((R)-1-(6-(Dimethylamino)pyridin-2-yl)pyrrolidin-3-yloxy)phenyl)ethyl)acetamide

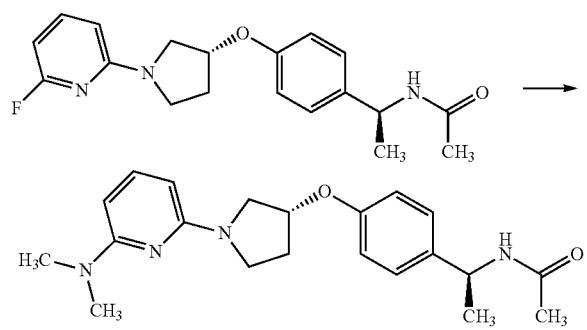

35.0 mg (0.19 mmol) of example XX.3 and 27.1 mg (0.60 mmol) dimethanamine are added to 1 mL NMP and stirred at 220° C. for 3 h in a microwave oven. Afterwards the reaction mixture is directly purified by HPLC (MeOH/H$_2$O/TFA).

$C_{21}H_{28}N_4O_2$ (M=368.5 g/mol)

ESI-MS: 369 [M+H]$^+$

R$_t$(HPLC):0.90 min (method E)

The following compounds are prepared analogously to example 10.1:

For the examples 10.2, 10.12, 10.14-10.17 and 10.19 3 eq. DIPEA are added.

For example 10.13 the reaction conditions are 190° C. for 2 days.

For the examples 10.18 and 10.20 the reaction conditions are 150° C. over night.

For the examples 10.22-10.24, 10.27, 10.51, 10.53 and 10.55 the reaction is done without solvent at 110° C.-150° C.

For example 10.26 the reaction is stirred over night.

For the examples 10.28-10.50 DIPEA (4 eq) as base is added and the reaction conditions are 220° C. for 72 h.

For the example 10.52 and 10.54 the reaction is done in dioxane at 120° C. over night.

| Ex. | Starting material | Structure | Mass spec result | HPLC retention time (method) |
|---|---|---|---|---|
| 10.1 | XX.3 + dimethanamine | 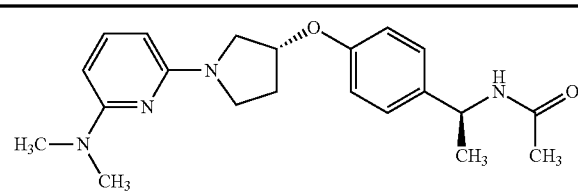 | 359 [M + H]$^+$ | 0.90 (E) |
| 10.2 | XX.3 + 1-cyclopropyl-N-methyl-methanamine | 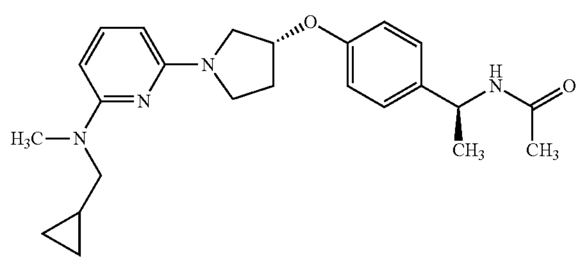 [SMILES: CC(=O)N[C@@H](C)c1ccc(O[C@@H]2CCN(c3cccc(N(C)CC4CC4)n3)C2)cc1] | 409 [M + H]$^+$ | 1.00 (E) |
| 10.3 | XX.3 + pyrrolidine | 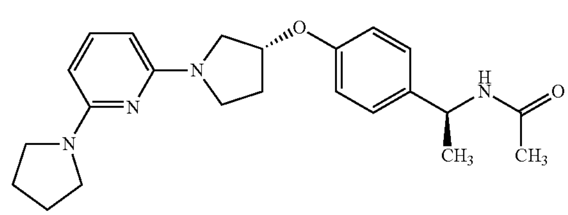 [SMILES: CC(=O)N[C@@H](C)c1ccc(O[C@@H]2CCN(c3cccc(N4CCCC4)n3)C2)cc1] | 395 [M + H]$^+$ | 1.00 (E) |
| 10.4 | XX.3 + piperidine | 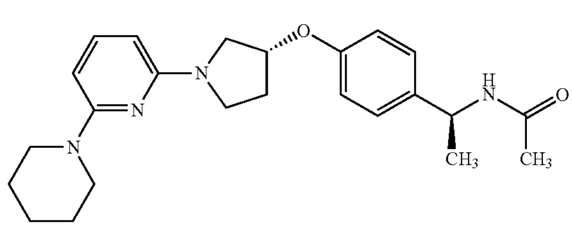 [SMILES: CC(=O)N[C@@H](C)c1ccc(O[C@@H]2CCN(c3cccc(N4CCCCC4)n3)C2)cc1] | 409 [M + H]$^+$ | 1.00 (E) |

-continued

| Ex. | Starting material | Structure | Mass spec result | HPLC retention time (method) |
|---|---|---|---|---|
| 10.5 | XX.3 + N-methyl-propan-1-amine | 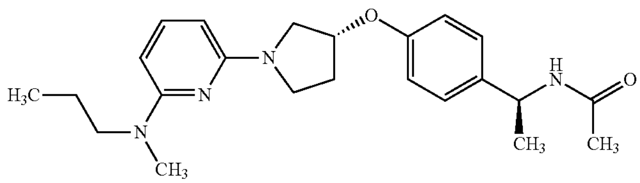 [SMILES: CCCN(C)c1cccc(N2CC[C@@H](Oc3ccc([C@H](C)NC(C)=O)cc3)C2)n1] | 397 [M + H]⁺ | 1.00 (E) |
| 10.6 | XX.8 + piperidine | 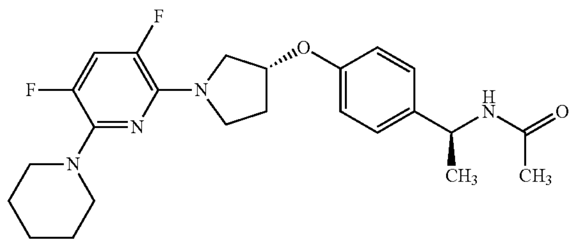 [SMILES: CC(=O)N[C@@H](C)c1ccc(O[C@@H]2CCN(c3nc(N4CCCCC4)c(F)cc3F)C2)cc1] | 445 [M + H]⁺ | 1.40 (E) |
| 10.7 | XX.8 + N-methyl-propan-1-amine | 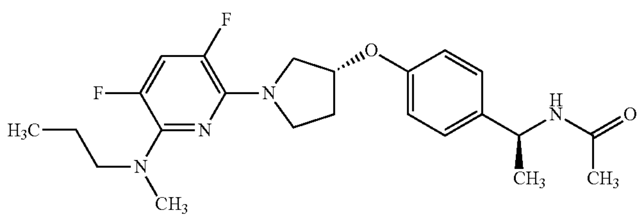 [SMILES: CCCN(C)c1nc(N2CC[C@@H](Oc3ccc([C@H](C)NC(C)=O)cc3)C2)c(F)cc1F] | 433 [M + H]⁺ | 1.40 (E) |
| 10.8 | XX.8 + pyrrolidine | 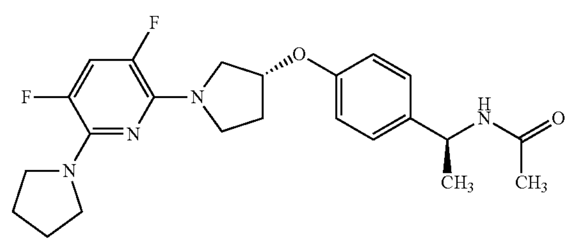 [SMILES: CC(=O)N[C@@H](C)c1ccc(O[C@@H]2CCN(c3nc(N4CCCC4)c(F)cc3F)C2)cc1] | 431 [M + H]⁺ | 1.40 (E) |
| 10.9 | XX.7 + N-methyl-cyclo-pentan-amine | 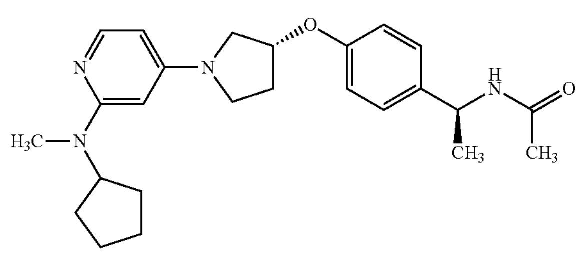 [SMILES: CC(=O)N[C@@H](C)c1ccc(O[C@@H]2CCN(c3ccnc(N(C)C4CCCC4)c3)C2)cc1] | 423 [M + H]⁺ | 1.17 (C) |
| 10.10 | XX.3 +− 3-methyl-pyrrolidine | 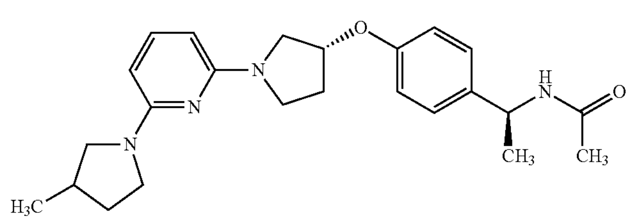 [SMILES: CC(=O)N[C@@H](C)c1ccc(O[C@@H]2CCN(c3cccc(N4CCC(C)C4)n3)C2)cc1] | 409 [M + H]⁺ | 0.88 (M) |

-continued

| Ex. | Starting material | Structure | Mass spec result | HPLC retention time (method) |
|---|---|---|---|---|
| 10.11 | XX.3 + azetidine | 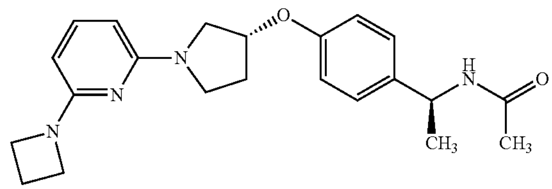 [SMILES: CC(=O)N[C@@H](C)c1ccc(O[C@@H]2CCN(c3cccc(N4CCC4)n3)C2)cc1] | 381 [M + H]+ | 0.82 (M) |
| 10.12 | XX.3 + ethanamine | 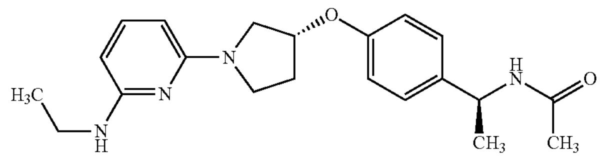 [SMILES: CCNc1cccc(N2CC[C@@H](Oc3ccc([C@H](C)NC(C)=O)cc3)C2)n1] | 369 [M + H]+ | 0.83 (M) |
| 10.13 | XX.3 + morpholine | 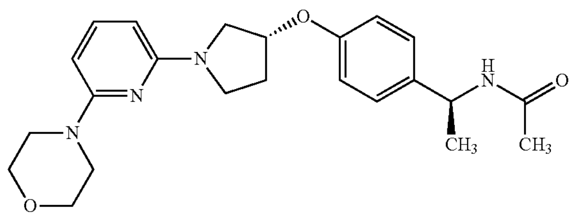 [SMILES: CC(=O)N[C@@H](C)c1ccc(O[C@@H]2CCN(c3cccc(N4CCOCC4)n3)C2)cc1] | 411 [M + H]+ | 1.17 (C) |
| 10.14 | XX.1 + N-methyl-ethanamine | 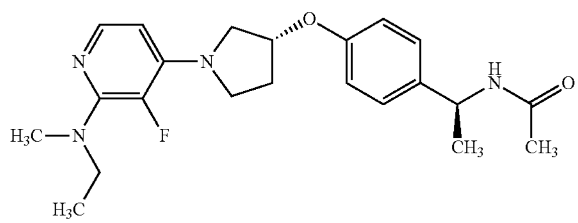 [SMILES: CCN(C)c1nccc(N2CC[C@@H](Oc3ccc([C@H](C)NC(C)=O)cc3)C2)c1F] | 401 [M + H]+ | 0.84 (M) |
| 10.15 | XX.1 + morpholine | 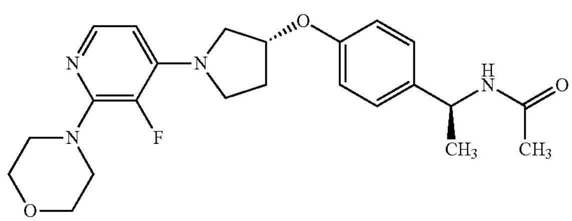 [SMILES: CC(=O)N[C@@H](C)c1ccc(O[C@@H]2CCN(c3ccnc(N4CCOCC4)c3F)C2)cc1] | 429 [M + H]+ | 0.79 (M) |
| 10.16 | XX.1 + pyrrolidine | 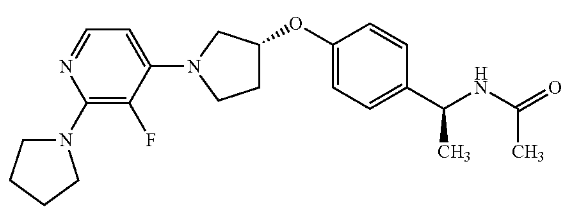 [SMILES: CC(=O)N[C@@H](C)c1ccc(O[C@@H]2CCN(c3ccnc(N4CCCC4)c3F)C2)cc1] | 413 [M + H]+ | 0.84 (M) |
| 10.17 | XX.1 + dimethan-amine | 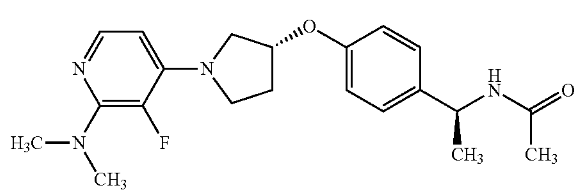 [SMILES: CC(=O)N[C@@H](C)c1ccc(O[C@@H]2CCN(c3ccnc(N(C)C)c3F)C2)cc1] | 387 [M + H]+ | 0.81 (M) |

-continued

| Ex. | Starting material | Structure | Mass spec result | HPLC retention time (method) |
|---|---|---|---|---|
| 10.18 | XX.4 + dimethanamine | 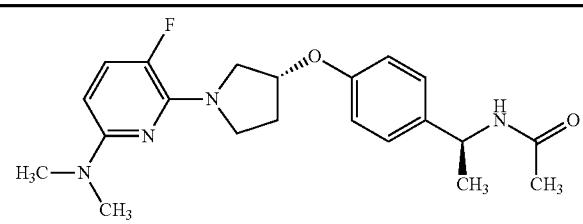 | 387 [M + H]⁺ | 0.97 (K) |
| 10.19 | XX.1 + diethanamine | 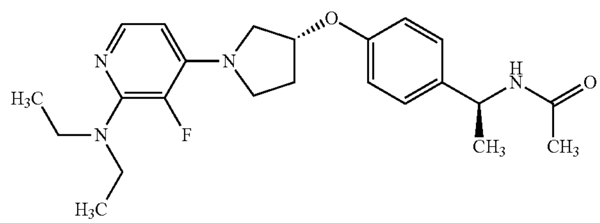 [SMILES: CCN(CC)c1nccc(N2CC[C@@H](Oc3ccc([C@H](C)NC(C)=O)cc3)C2)c1F] | 415 [M + H]⁺ | 0.87 (M) |
| 10.20 | XXI.3 + pyrrolidine | 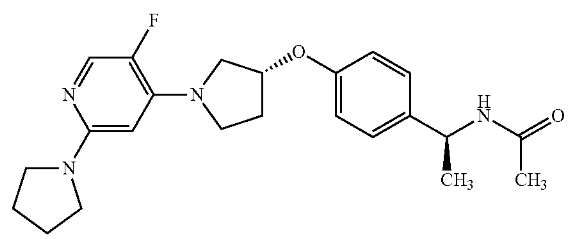 [SMILES: CC(=O)N[C@@H](C)c1ccc(O[C@@H]2CCN(c3cc(N4CCCC4)ncc3F)C2)cc1] | 413 [M + H]⁺ | 0.97 (K) |
| 10.21 | XX.3 + methanamine | 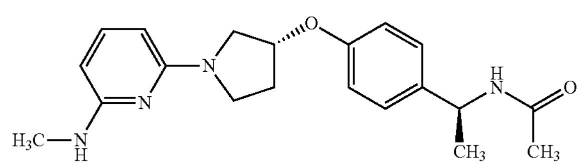 [SMILES: CNc1cccc(N2CC[C@@H](Oc3ccc([C@H](C)NC(C)=O)cc3)C2)n1] | 355 [M + H]⁺ | 0.80 (M) |
| 10.22 | XXI.3 + morpholine | 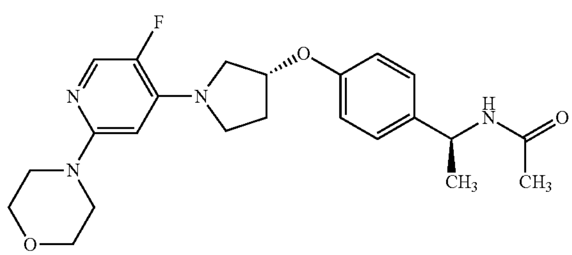 [SMILES: CC(=O)N[C@@H](C)c1ccc(O[C@@H]2CCN(c3cc(N4CCOCC4)ncc3F)C2)cc1] | 429 [M + H]⁺ | 0.80 (M) |
| 10.23 | XXI.3 + N-methylethanamine | 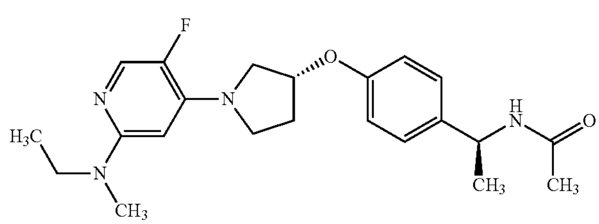 [SMILES: CCN(C)c1cc(N2CC[C@@H](Oc3ccc([C@H](C)NC(C)=O)cc3)C2)c(F)cn1] | 401 [M + H]⁺ | 0.88 (M) |
| 10.24 | XXI.3 + dimethylamine | 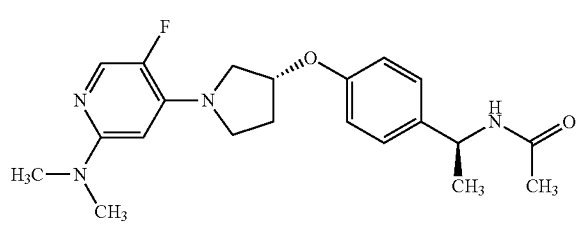 | 387 [M + H]⁺ | 0.83 (M) |

-continued

| Ex. | Starting material | Structure | Mass spec result | HPLC retention time (method) |
|---|---|---|---|---|
| 10.25 | XX.3 + N-methyl-1-(tetrahydro-furan-3-yl)-methan-amine | 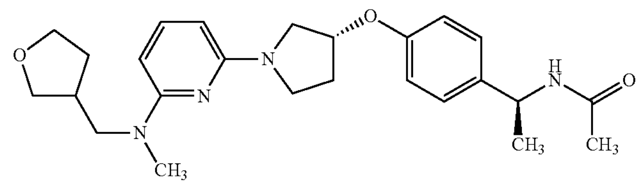 [SMILES: CC(=O)N[C@@H](C)c1ccc(O[C@@H]2CCN(c3cccc(N(C)CC4CCOC4)n3)C2)cc1] | 439 [M + H]⁺ | 0.68 (D) |
| 10.26 | XXI.3 + cyclopro-pylmethan--aminecyclopropylmethan-amine | 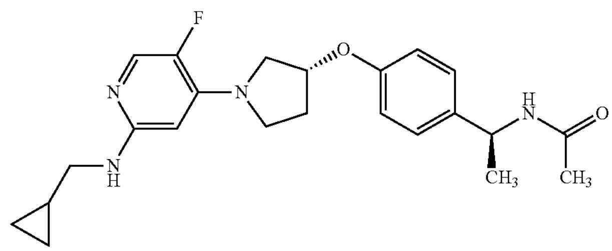 [SMILES: CC(=O)N[C@@H](C)c1ccc(O[C@@H]2CCN(c3cc(NCC4CC4)ncc3F)C2)cc1] | 413 [M + H]⁺ | 0.85 (K) |
| 10.27 | XX.3 diethan-amine | 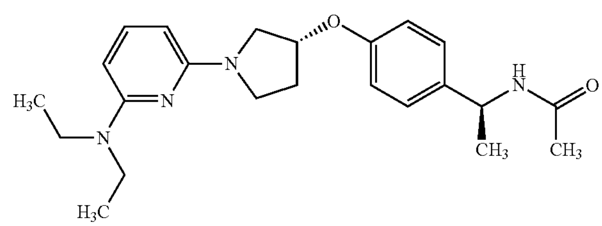 [SMILES: CCN(CC)c1cccc(N2CC[C@@H](Oc3ccc([C@H](C)NC(C)=O)cc3)C2)n1] | 397 [M + H]⁺ | 0.75 (Y) |
| 10.28 | XX.3 + 2-methoxy-N-methyl-ethan-aminemethylethanaime | 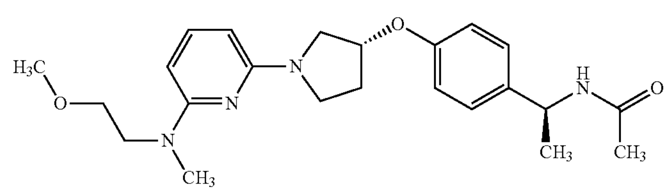 [SMILES: COCCN(C)c1cccc(N2CC[C@@H](Oc3ccc([C@H](C)NC(C)=O)cc3)C2)n1] | 413 [M + H]⁺ | 0.70 (Y) |
| 10.29 | XX.3 + N-methyl-cyclopen-tanamine-cyclo-petanamine | 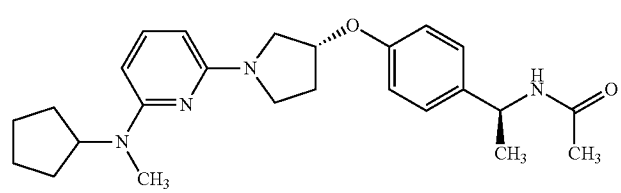 [SMILES: CC(=O)N[C@@H](C)c1ccc(O[C@@H]2CCN(c3cccc(N(C)C4CCCC4)n3)C2)cc1] | 423 [M + H]⁺ | 0.80 (Y) |
| 10.30 | XX.3 + N-methyl-ethanamine | 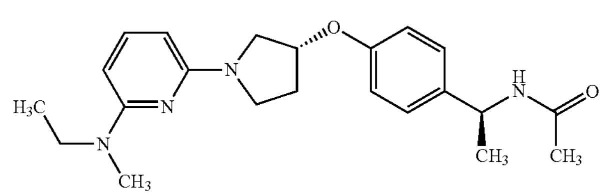 [SMILES: CCN(C)c1cccc(N2CC[C@@H](Oc3ccc([C@H](C)NC(C)=O)cc3)C2)n1] | 383 [M + H]⁺ | 0.70 (Y) |
| 10.31 | XX.3 + N-methyl-propan-2-amine | 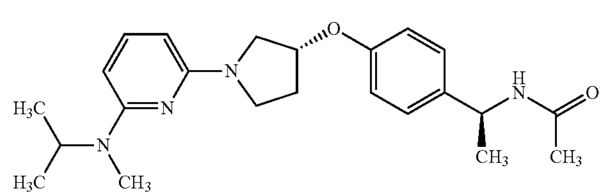 [SMILES: CC(=O)N[C@@H](C)c1ccc(O[C@@H]2CCN(c3cccc(N(C)C(C)C)n3)C2)cc1] | 397 [M + H]⁺ | 0.75 (Y) |

-continued

| Ex. | Starting material | Structure | Mass spec result | HPLC retention time (method) |
|---|---|---|---|---|
| 10.32 | XX.3 + 5-azaspiro-[2.4]heptane | 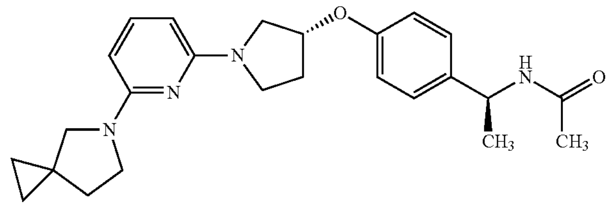 [SMILES: CC(=O)N[C@@H](C)c1ccc(O[C@@H]2CCN(c3cccc(N4CCC5(CC5)C4)n3)C2)cc1] | 421 [M + H]⁺ | 0.85 (W) |
| 10.33 | XX.3 + 2-methyl-pyrrolidine | 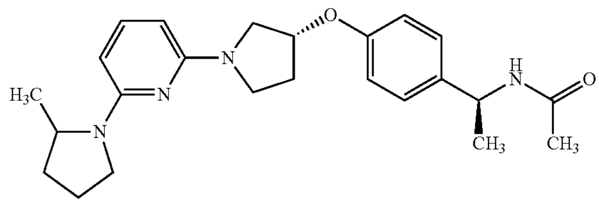 [SMILES: CC(=O)N[C@@H](C)c1ccc(O[C@@H]2CCN(c3cccc(N4CCCC4C)n3)C2)cc1] | 409 [M + H]⁺ | 0.82 (W) |
| 10.34 | XX.3 + 4,4-difluoro-piperidine | 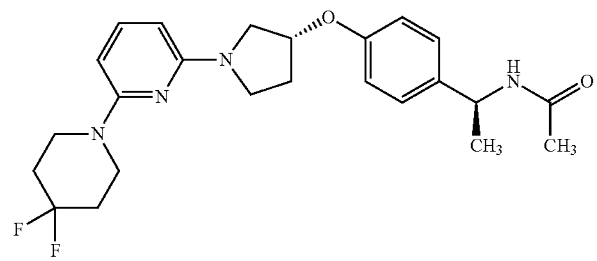 [SMILES: CC(=O)N[C@@H](C)c1ccc(O[C@@H]2CCN(c3cccc(N4CCC(F)(F)CC4)n3)C2)cc1] | 445 [M + H]⁺ | 0.98 (W) |
| 10.35 | XX.3 + 1-(methyl-amino)-propan-2-ol | 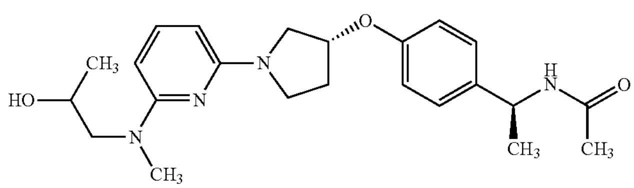 [SMILES: CC(=O)N[C@@H](C)c1ccc(O[C@@H]2CCN(c3cccc(N(C)CC(C)O)n3)C2)cc1] | 413 [M + H]⁺ | 0.76 (W) |
| 10.36 | XX.3 + N, 2-dimethyl-propan-1-amine | 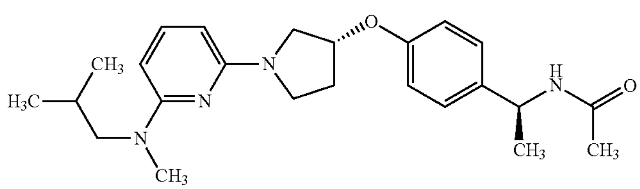 [SMILES: CC(=O)N[C@@H](C)c1ccc(O[C@@H]2CCN(c3cccc(N(C)CC(C)C)n3)C2)cc1] | 411 [M + H]⁺ | 0.89 (W) |
| 10.37 | XX.3 + 3-methoxy-piperidine | 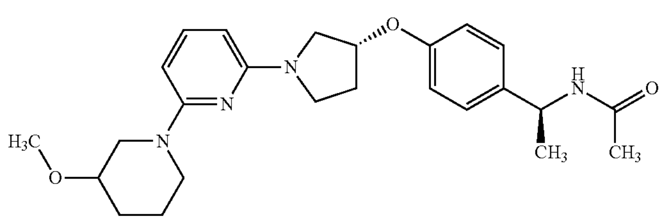 [SMILES: COC1CCCN(c2cccc(N3CC[C@@H](Oc4ccc([C@H](C)NC(C)=O)cc4)C3)n2)C1] | 439 [M + H]⁺ | 0.81 (W) |
| 10.38 | XX.3 + 2,2-dimethyl-morpholine | 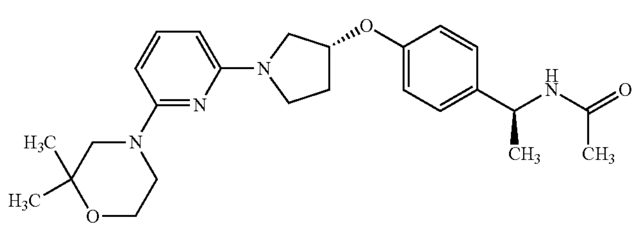 [SMILES: CC(=O)N[C@@H](C)c1ccc(O[C@@H]2CCN(c3cccc(N4CCOC(C)(C)C4)n3)C2)cc1] | 439 [M + H]⁺ | 0.87 (W) |

| Ex. | Starting material | Structure | Mass spec result | HPLC retention time (method) |
|---|---|---|---|---|
| 10.39 | XX.3 + N-methyl-tetrahydro-2H-pyran-4-amine | 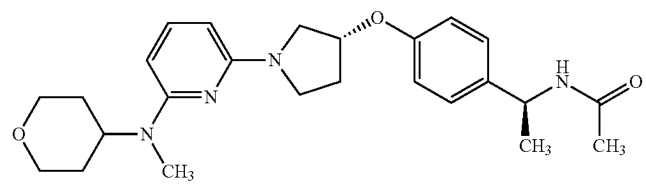 [SMILES: CC(=O)N[C@@H](C)c1ccc(O[C@@H]2CCN(c3cccc(N(C)C4CCOCC4)n3)C2)cc1] | 439 [M + H]+ | 0.79 (W) |
| 10.40 | XX.3 + 1,4-oxaze-pane | 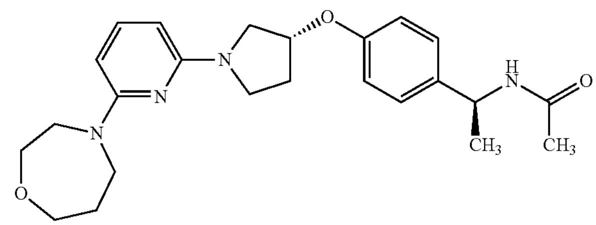 [SMILES: CC(=O)N[C@@H](C)c1ccc(O[C@@H]2CCN(c3cccc(N4CCCOCC4)n3)C2)cc1] | 425 [M + H]+ | 0.78 (W) |
| 10.41 | XX.3 + (R)-2-(methoxy-methyl)-pyrrolidine | 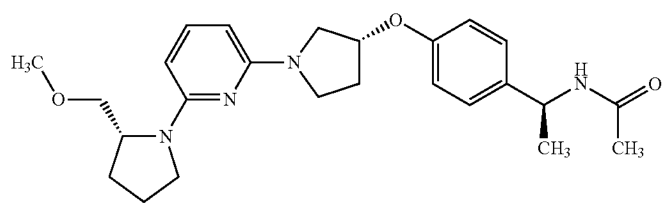 [SMILES: COC[C@H]1CCCN1c1cccc(N2CC[C@@H](Oc3ccc([C@H](C)NC(C)=O)cc3)C2)n1] | 439 [M + H]+ | 0.82 (W) |
| 10.42 | XX.3 + 4-methoxy-piperidine | 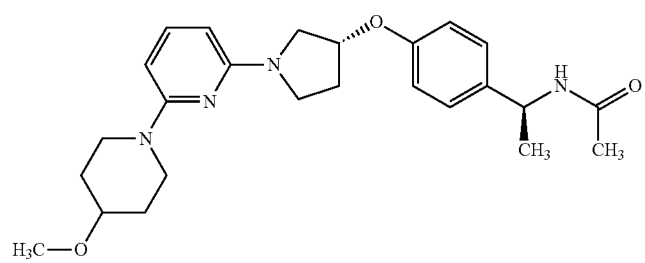 [SMILES: COC1CCN(c2cccc(N3CC[C@@H](Oc4ccc([C@H](C)NC(C)=O)cc4)C3)n2)CC1] | 439 [M + H]+ | 0.79 (W) |
| 10.43 | XX.3 + 2-(ethyl-amino)-ethanol | 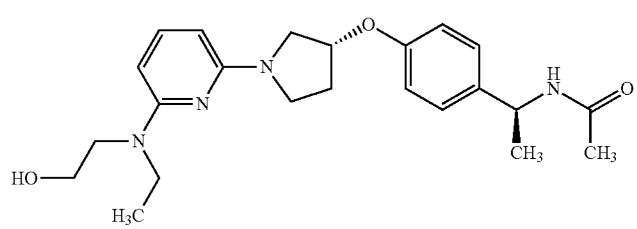 [SMILES: CCN(CCO)c1cccc(N2CC[C@@H](Oc3ccc([C@H](C)NC(C)=O)cc3)C2)n1] | 413 [M + H]+ | 0.77 (W) |
| 10.44 | XX.3 + 2,5-dihydro-1H-pyrrol | 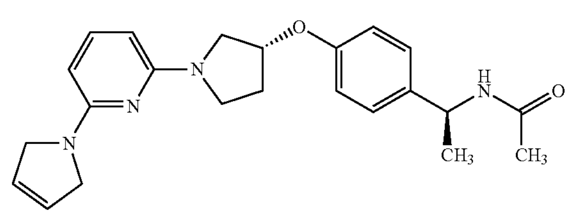 [SMILES: CC(=O)N[C@@H](C)c1ccc(O[C@@H]2CCN(c3cccc(N4CC=CC4)n3)C2)cc1] | 393 [M + H]+ | 0.78 (W) |

-continued

| Ex. | Starting material | Structure | Mass spec result | HPLC retention time (method) |
|---|---|---|---|---|
| 10.45 | XX.3 + (R)-N-methyl-1-(tetra-hydrotetrahydro-furan-2-yl)methan-amine | 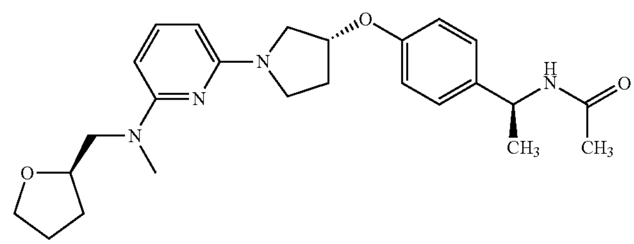 [SMILES: CC(=O)N[C@@H](C)c1ccc(O[C@@H]2CCN(c3cccc(N(C)C[C@H]4CCCO4)n3)C2)cc1] | 439 [M + H]+ | 0.80 (W) |
| 10.46 | XX.3 + (S)-2-(methoxy-methyl)-pyrrolidine | 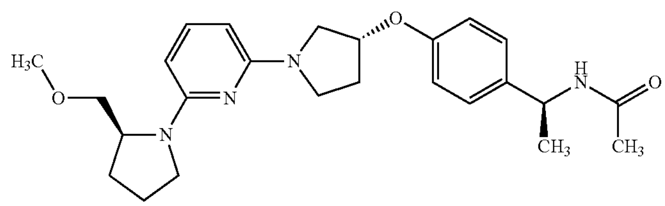 [SMILES: COC[C@@H]1CCCN1c1cccc(N2CC[C@@H](Oc3ccc([C@H](C)NC(C)=O)cc3)C2)n1] | 439 [M + H]+ | 0.82 (W) |
| 10.47 | XX.3 + 3-methyl-pyrrolidin-3-ol | 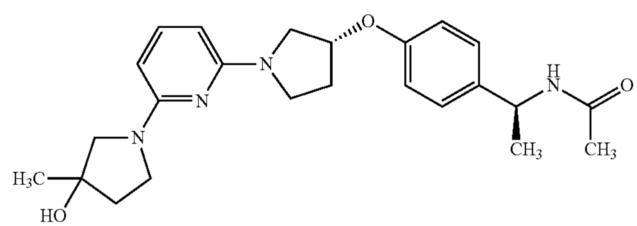 [SMILES: CC(=O)N[C@@H](C)c1ccc(O[C@@H]2CCN(c3cccc(N4CCC(C)(O)C4)n3)C2)cc1] | 425 [M + H]+ | 0.72 (W) |
| 10.48 | XX.3 + 3,3-dimethyl-pyrrolidine | 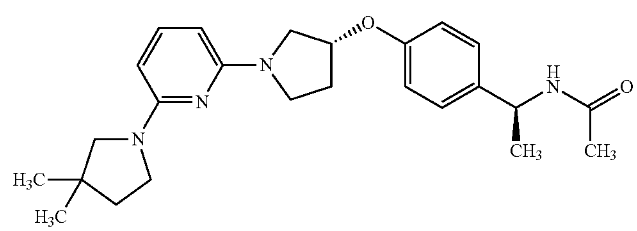 [SMILES: CC(=O)N[C@@H](C)c1ccc(O[C@@H]2CCN(c3cccc(N4CCC(C)(C)C4)n3)C2)cc1] | 423 [M + H]+ | 0.86 (W) |
| 10.49 | XX.3 + 3-methyl-morpho-line-3-methyl-morpholine | 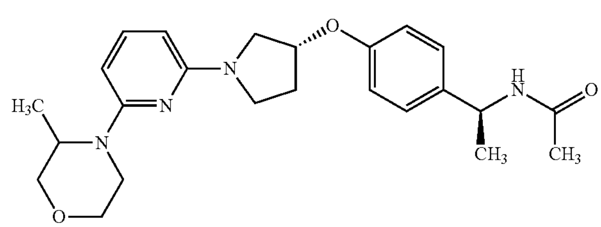 [SMILES: CC(=O)N[C@@H](C)c1ccc(O[C@@H]2CCN(c3cccc(N4CCOCC4C)n3)C2)cc1] | 425 [M + H]+ | 0.81 (W) |
| 10.50 | XX.1 + 1-amino-methyl-cyclobutanol | 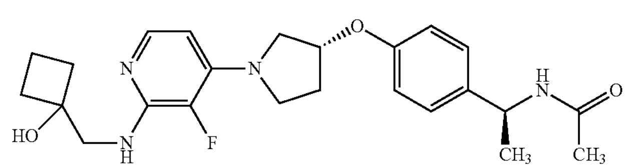 [SMILES: CC(=O)N[C@@H](C)c1ccc(O[C@@H]2CCN(c3ccnc(NCC4(O)CCC4)c3F)C2)cc1] | 443 [M + H]+ | 0.83 (M) |
| 10.51 | XXI.9 + 1-amino-2-methyl-propan-2-ol | 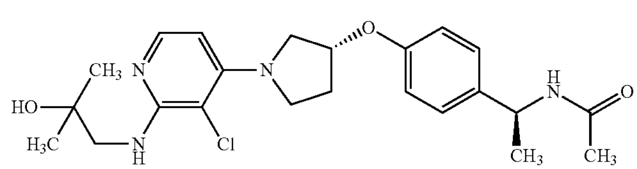 [SMILES: CC(=O)N[C@@H](C)c1ccc(O[C@@H]2CCN(c3ccnc(NCC(C)(C)O)c3Cl)C2)cc1] | 447 [M + H]+ | 0.82 (K) |

-continued

| Ex. | Starting material | Structure | Mass spec result | HPLC retention time (method) |
|---|---|---|---|---|
| 10.52 | XX.1 + 3-methyl-pyrrolidin-3-ol | 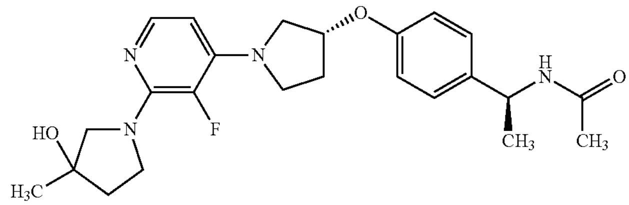 [SMILES: CC(=O)N[C@@H](C)c1ccc(O[C@@H]2CCN(c3ccnc(N4CCC(C)(O)C4)c3F)C2)cc1] | 443 [M + H]⁺ | 0.70 (w) |
| 10.53 | XX.1 + 1-amino-2-methyl-propan-2-ol | 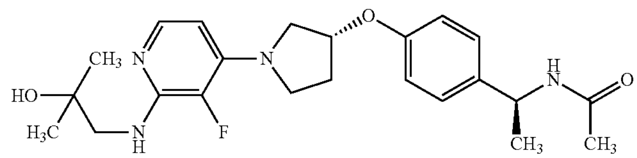 [SMILES: CC(=O)N[C@@H](C)c1ccc(O[C@@H]2CCN(c3ccnc(NCC(C)(C)O)c3F)C2)cc1] | 431 [M + H]⁺ | 0.62 (AC) |
| 10.54 | XXI.9 + 3-methyl-pyrrolidin-3-ol | 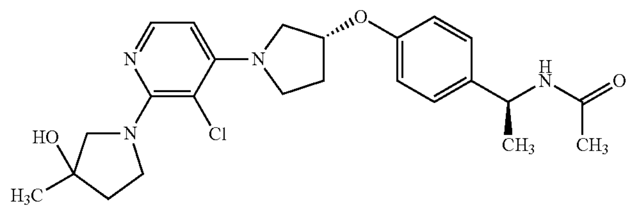 [SMILES: CC(=O)N[C@@H](C)c1ccc(O[C@@H]2CCN(c3ccnc(N4CCC(C)(O)C4)c3Cl)C2)cc1] | 459 [M + H]⁺ | 0.78 (D) |
| 10.55 | XXI.9 + 1-amino-methyl-cyclobutanol | 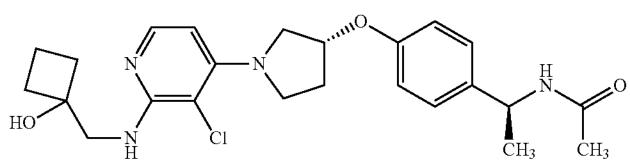 [SMILES: CC(=O)N[C@@H](C)c1ccc(O[C@@H]2CCN(c3ccnc(NCC4(O)CCC4)c3Cl)C2)cc1] | 459 [M + H]⁺ | 0.85 (K) |

Example 11

Example 11.1

General Route

N—((S)-1-(4-((R)-1-(5-(2,2-Difluoroethoxy)pyridin-2-yl)pyrrolidin-3-yloxy)phenyl)ethyl)acetamide

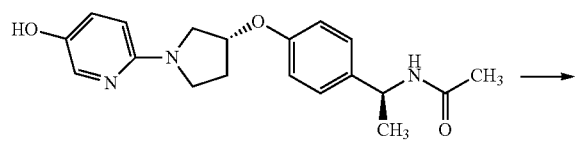

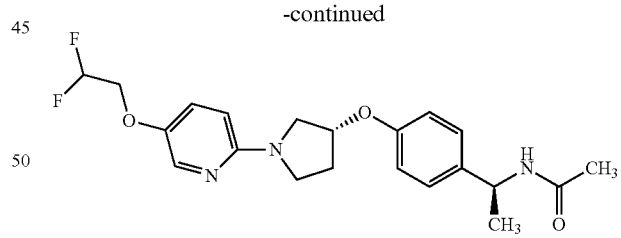

60.0 mg (0.18 mmol) of example XXI.2, 50.6 mg (0.26 mmol) 2-iodo-1,1-difluoroethane and 72.9 mg (0.53 mmol) K$_2$CO$_3$ in 2 mL ACN are stirred at 80° C. over night. A small amount of water is added, the reaction mixture is filtered and the filtrate is directly purified by HPLC (MeOH/H$_2$O/NH$_4$OH).

C$_{21}$H$_{25}$F$_2$N$_3$O$_3$ (M=405.4 g/mol)

ESI-MS: 406 [M+H]⁺

R$_t$(HPLC):1.46 min (method J)

The following compounds are prepared analogously to example 11.1:

| Ex. | Starting material | Structure | Mass spec result | HPLC retention time (method) |
|---|---|---|---|---|
| 11.1 | XXI.2 | (structure) | 406 [M + H]⁺ | 1.46 (J) |
| 11.2 | XXI.2 | (structure) | 456 [M + H]⁺ | 1.50 (L) |
| 11.3 | XXI.2 | (structure) | 402 [M + H]⁺ | 1.02 (C) |

Example 12

N—((S)-1-(4-((R)-1-(6-(Trifluoromethyl)pyridin-2-yl)pyrrolidin-3-yloxy)phenyl)ethyl) formamide 35.1 mg (0.10 mmol) of example XXII.3 in 2 mL (24.8 mmol) ethyl formate is stirred at r.t. over night. Then the solvent is removed in vacuo and the crude product is purified by HPLC (MeOH/H₂O/TFA).

$C_{19}H_{20}F_3N_3O_2$ (M=379.4 g/mol)
ESI-MS: 380 [m+H]⁺
$R_t$(HPLC):1.50 min (method P)

Example 13

2-Amino-N—((1S)-1-(4-((3R)-1-(5-((2,2-difluorocyclopropyl)methoxy)pyridin-2-yl)pyrrolidin-3-yloxy)phenyl)ethyl)-4-methylthiazole-5-carboxamide

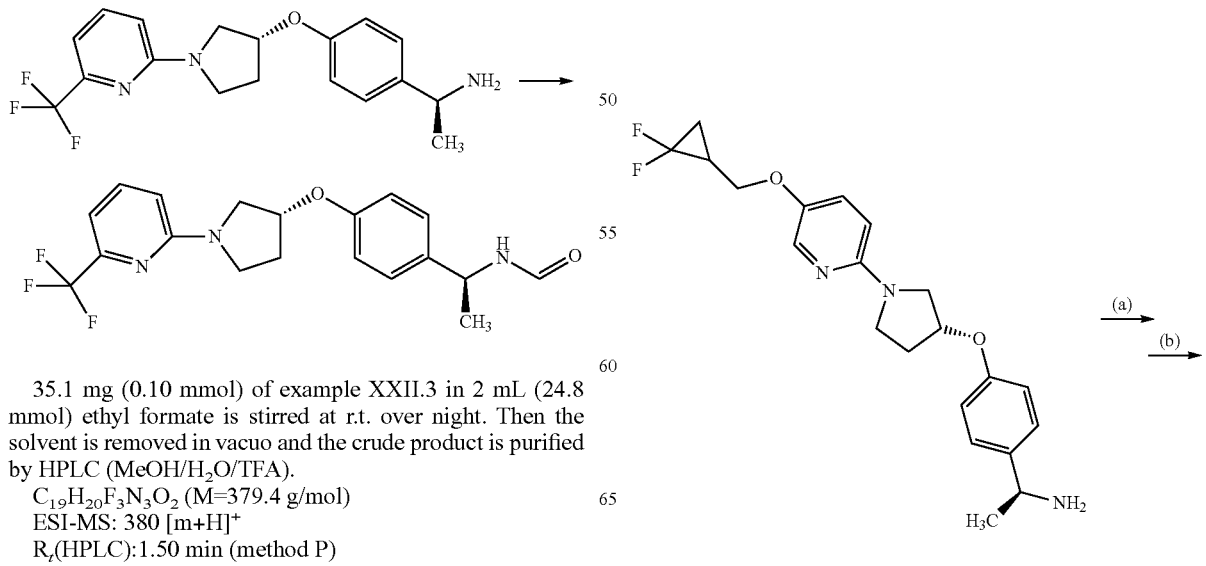

-continued

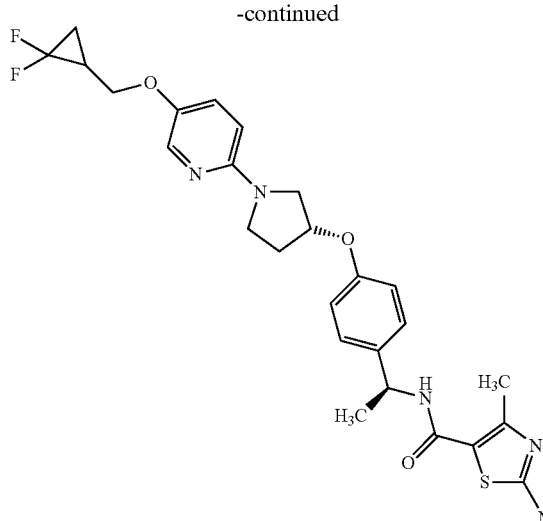

a) To 113 mg (0.42 mmol) N-Boc-amino-4-methylthiazole-5-carboxylic acid in 2 mL DCM are added 55.6 µL (0.42 mmol) 1-chloro-N,N,2-trimethylpropenylamine and the resulting mixture is stirred at r.t. for 30 min. 150 mg (0.39 mmol) of product XXII.1 and 137 µL (0.80 mmol) DIPEA in 2 mL DCM are added and stirring is continued for 1 h. The solvent is removed in vacuo and the crude product is purified by HPLC (ACN/H$_2$O/TFA).
$C_{31}H_{37}F_2N_5O_5S$ (M=629.7 g/mol)
ESI-MS: 630 [M+H]$^+$
R$_t$(HPLC):0.99 min (method M)

b) To 340 mg (0.54 mmol) of the above mentioned product in 10 mL DCM are added 0.42 mL (5.40 mmol) TFA and the mixture is stirred at reflux for 4 h. The solvent is removed in vacuo and to the residue is added water and aq. 4N NaOH solution. The precipitation is filtered and washed with water. The crude product is dissolved in DMF and purified by HPLC (ACN/H$_2$O/TFA).
$C_{26}H_{29}F_2N_5O_3S$ (M=529.6 g/mol)
ESI-MS: 530 [M+H]$^+$
R$_t$(HPLC):0.81 min (method M)

Example 14

Example 14.1

General Route

N—((S)-1-(4-((R)-1-(2-(2,2-Difluoroethoxy)-3-methoxypyridin-4-yl)pyrrolidin-3-yloxy)phenyl)ethyl)acetamide

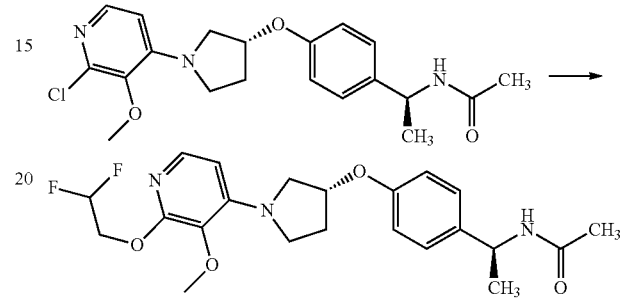

To 100 mg (0.25 mmol) of example XXI.10 in 1 mL dioxane are added 23.5 mg (0.28 mmol) 2,2-difluoroethanol, 101 mg (1.03 mmol) NaOtBu and 9.47 mg (0.01 mmol) chloro(2-dicyclohexyl-phosphino-2',4',6'-triisopropyl-1,1'-biphenyl)(2-(2-aminoethyl)-phenyl)-palladium (II). The mixture is degassed thoroughly and stirred at 70° C. over night. Water is added and the resulting mixture is extracted with DCM. The solvent is removed and the residue is purified by HPLC (ACN/H$_2$O/NH$_3$).
$C_{22}H_{27}F_2N_3O_4$ (M=435.5 g/mol)
ESI-MS: 436 [M+H]$^+$
R$_t$(HPLC):0.87 min (method M)

The following compounds are prepared analogously to example 14.1:

For example 14.2 the solvent is NMP.

| Ex. | Starting material | Structure | Mass spec result | HPLC retention time (method) |
|---|---|---|---|---|
| 14.1 | XXI.10 + 2,2-difluoro-ethanol | 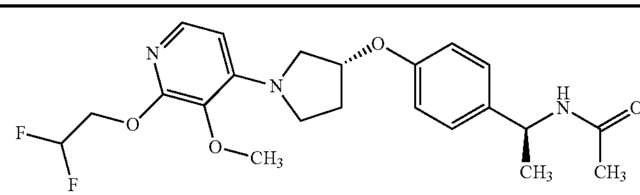 | 436 [M + H]$^+$ | 0.87 (M) |
| 14.2 | XXI.10 + difluoro-cyclopropyl-methanol | 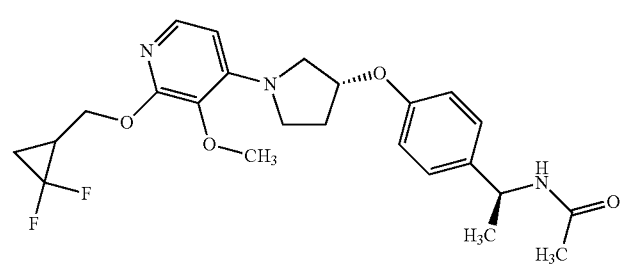 [SMILES: COc1c(N2CC[C@@H](Oc3ccc([C@H](C)NC(C)=O)cc3)C2)ccnc1OCC1CC1(F)F] | 462 [M + H]$^+$ | 0.76 (AC) |

Example 15

N—((S)-1-(4-((R)-1-(2-cyclopropyl-fluoropyridin-4-yl)pyrrolidin-3-yloxy)phenyl)-ethyl)-acetamide

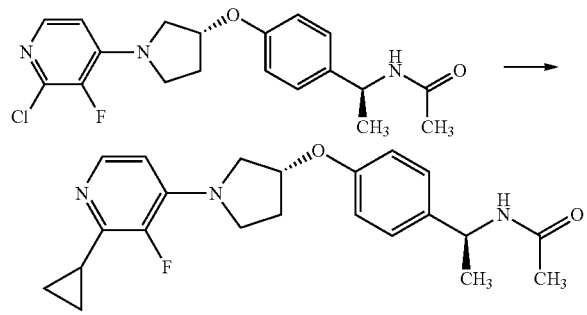

To 70.0 mg (0.19 mmol) of example XXI in 5 mL dioxane are added 20.0 mg (0.23 mmol) cyclopropylboronic acid, 8 mg (0.01 mmol) 1,1-bis(diphenylphosphino)-ferrocene-dichloropalladium (II) and 85.0 mg (0.39 mmol) $K_3PO_4$. The mixture is stirred at 110° C. over night. After cooling down to r.t. etOAc is added together with Celite® and activated charcoal. After stirring for a short period of time the mixture is filtered, the solvent is removed in vacuo and the residue is purified by HPLC.

$C_{22}H_{26}FN_3O_2$ (M=383.5 g/mol)
ESI-MS: 384 $[M+H]^+$
$R_f$(HPLC):0.51 min (method AD)

Analytic Methods

| Method A | | |
|---|---|---|
| time (min) | Vol % water (incl. 0.2% $NH_4OH$) | Vol % MeOH |
| 0.00 | 95 | 5 |
| 0.20 | 95 | 5 |
| 2.20 | 5 | 95 |
| 2.30 | 5 | 95 |
| 2.40 | 0 | 100 |
| 2.60 | 0 | 100 |

Analytical column: XBridge C18 (Waters); 2.5 μm; 3.0 × 30 mm;
column temperature: 40° C.; flow: 1.3 mL/min;

| Method B | | |
|---|---|---|
| time (min) | Vol % water (incl. 0.1% TFA) | Vol % MeOH |
| 0.00 | 95 | 5 |
| 0.05 | 95 | 5 |
| 1.40 | 0 | 100 |
| 1.80 | 0 | 100 |

Analytical column: Sunfire C18 (Waters) 2.5 μm 3.0 × 30 mm;
column temperature: 60° C.; flow: 2.2 mL/min.

| Method C | | |
|---|---|---|
| time (min) | Vol % water (incl. 0.1% $NH_4OH$) | Vol % MeOH |
| 0.00 | 95 | 5 |
| 0.05 | 95 | 5 |
| 1.40 | 0 | 100 |
| 1.80 | 0 | 100 |

Analytical column: XBridge C18 (Waters) 2.5 um; 3.0 × 30 mm;
column temperature: 60° C.; flow: 2.2 mL/min.

| Method D | | | |
|---|---|---|---|
| time (min) | Vol % water (incl. 0.1% TFA) | Vol % ACN | Flow [mL/min] |
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: Sunfire C18 (Waters) 2.5 μm; 3.0 × 30 mm;
column temperature: 60° C.

| Method E | | |
|---|---|---|
| time (min) | Vol % water (incl. 0.1% TFA) | Vol % MeOH |
| 0.00 | 95 | 5 |
| 0.05 | 95 | 5 |
| 1.40 | 0 | 100 |
| 1.80 | 0 | 100 |

Analytical column: Stablebond C18 (Waters) 1.8 μm; 3.0 × 30 mm;
column temperature: 60° C.; flow: 2.2 mL/min.

| Method F | | |
|---|---|---|
| time (min) | Vol % water (incl. 0.1% FA) | Vol % ACN (incl. 0.1% FA) |
| 0.00 | 95 | 5 |
| 3.50 | 2 | 98 |
| 6.00 | 2 | 98 |

Analytical column: XBridge C18 (Waters) 3.5 μm; 2.1 × 50 mm;
column temperature: 35° C.; flow: 0.8 mL/min.

| Method G | | |
|---|---|---|
| time (min) | Vol % water (incl. 0.1% FA) | Vol % ACN (incl. 0.1% FA) |
| 0.00 | 95 | 5 |
| 1.60 | 2 | 98 |
| 3.00 | 2 | 98 |

Analytical column: XBridge C18 (Waters) 3.5 μm; 2.1 × 30 mm;
column temperature: 35° C.; flow: 1.0 mL/min.

Method H

| time (min) | Vol % water (incl. 0.1% NH₄OH) | Vol % MeOH | Flow [mL/min] |
|---|---|---|---|
| 0.00 | 95 | 5 | 2.2 |
| 0.30 | 95 | 5 | 2.2 |
| 1.50 | 0 | 100 | 2.2 |
| 1.55 | 0 | 100 | 2.9 |
| 1.70 | 0 | 100 | 2.9 |

Analytical column: XBridge C18 (Waters) 2.5 μm; 3.0 × 30 mm; column temperature: 60° C.

Method I

| time (min) | Vol % water (incl. 0.1% TFA) | Vol % ACN |
|---|---|---|
| 0.00 | 95 | 5 |
| 0.05 | 95 | 5 |
| 1.40 | 0 | 100 |
| 1.80 | 0 | 100 |

Analytical column: Stablebond C18 (Agilent) 1.8 μm; 3.0 × 30 mm; column temperature: 60° C.; flow: 2.2 mL/min.

Method J

| time (min) | Vol % water (incl. 0.1% NH₄OH) | Vol % MeOH |
|---|---|---|
| 0.00 | 95 | 5 |
| 0.15 | 95 | 5 |
| 1.70 | 0 | 100 |
| 2.25 | 0 | 100 |

Analytical column: XBridge C18 (Waters) 3.5 μm; 4.6 × 30 mm; column temperature: 60° C.; flow: 4.0 mL/min.

Method K

| time (min) | Vol % water (incl. 0.1% NH₄OH) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 μm; 3.0 × 30 mm; column temperature: 60° C.

Method L

| time (min) | Vol % water (incl. 0.1% NH₄OH) | Vol % MeOH |
|---|---|---|
| 0.00 | 95 | 5 |
| 0.15 | 95 | 5 |
| 1.70 | 0 | 100 |
| 2.10 | 0 | 100 |

Analytical column: XBridge C18 (Waters) 3.5 μm; 4.6 × 30 mm; column temperature: 60° C.; flow: 4 mL/min

Method M

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stablebond C18 (Agilent) 1.8 μm; 3.0 × 30 mm; column temperature: 60° C.

Method N

| time (min) | Vol % water (incl. 0.1% TFA) | Vol % MeOH (incl. 0.1% TFA) | Flow [mL/min] |
|---|---|---|---|
| 0.00 | 95 | 5 | 4.0 |
| 0.15 | 95 | 5 | 4.0 |
| 1.70 | 0 | 100 | 4.0 |
| 2.25 | 0 | 100 | 4.0 |

Analytical column: Sunfire C18 (Waters) 3.5 μm; 4.6 × 30 mm; column temperature: 60° C.

Method O

| time (min) | Vol % water (incl. 0.1% TFA) | Vol % ACN (incl. 0.08% TFA) |
|---|---|---|
| 0.00 | 95.0 | 5.0 |
| 0.70 | 1.0 | 99.0 |
| 0.80 | 1.0 | 99.0 |
| 0.81 | 95.0 | 5.0 |

Analytical column: Ascentis Express C18; 2.7 μm; 2.1 × 50 mm; column temperature: 60° C.; flow: 1.5 mL/min;

Method P

| time (min) | Vol % water (incl. 0.1% NH₄OH) | Vol % MeOH |
|---|---|---|
| 0.00 | 80 | 20 |
| 1.70 | 0.0 | 100.0 |
| 2.50 | 0.0 | 100.0 |

Analytical column: XBridge C18 (Waters) 3.5 μm; 4.6 × 30 mm; column temperature: 60° C.; flow: 2.0 mL/min.

Method Q

| time (min) | Vol % water (incl. 0.1% TFA) | Vol % MeOH | Flow [mL/min] |
|---|---|---|---|
| 0.00 | 95 | 5 | 1.9 |
| 0.20 | 95 | 5 | 1.9 |
| 1.55 | 0 | 100 | 1.9 |
| 1.60 | 0 | 100 | 2.4 |
| 1.80 | 0 | 100 | 2.4 |

Analytical column: Sunfire C18 (Waters) 2.5 μm; 3.0 × 30 mm; column temperature: 60° C.

Method R

| time (min) | Vol % water (incl. 0.1% TFA) | Vol % MeOH | Flow [mL/min] |
|---|---|---|---|
| 0.00 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Analytical column: Sunfire C18 (Waters) 2.5 µm; 3.0 × 30 mm; column temperature: 60° C.

Method S

| time (min) | Vol % water (incl. 0.1% TFA) | Vol % MeOH | Flow [mL/min] |
|---|---|---|---|
| 0.00 | 95 | 5 | 4.0 |
| 0.05 | 95 | 5 | 3.0 |
| 2.05 | 0 | 100 | 3.0 |
| 2.10 | 0 | 100 | 4.5 |
| 2.40 | 0 | 100 | 4.5 |

Analytical column: Sunfire C18 (Waters) 2.5 µm; 4.6 × 30 mm; column temperature: 60° C.

Method T

| time (min) | Vol % water (incl. 0.1% FA) | Vol % MeOH | Flow [mL/min] |
|---|---|---|---|
| 0.00 | 95 | 5 | 2.2 |
| 0.05 | 95 | 5 | 2.2 |
| 1.40 | 0 | 100 | 2.2 |
| 1.80 | 0 | 100 | 2.2 |

Analytical column: Sunfire C18 (Waters) 2.5 µm; 3.0 × 30 mm; column temperature: 60° C.

Method U

| time (min) | Vol % water (incl. 0.1% TFA) | Vol % ACN | Flow [mL/min] |
|---|---|---|---|
| 0.00 | 50 | 50 | 2.2 |
| 0.20 | 50 | 50 | 2.2 |
| 1.20 | 0 | 100 | 2.2 |
| 1.25 | 0 | 100 | 3.0 |
| 1.40 | 0 | 100 | 3.0 |

Analytical column: Stablebond C18 (Agilent) 1.8 µm; 3.0 × 30 mm; column temperature: 60° C.

Method V

| time (min) | Vol % water (incl. 0.1% TFA) | Vol % MeOH |
|---|---|---|
| 0.00 | 80 | 20 |
| 1.70 | 0 | 100 |
| 2.50 | 0 | 100 |
| 2.60 | 80 | 20 |

Analytical column: Sunfire C18 (Waters) 3.5 µm; 4.6 × 50 mm; column temperature: 60° C.; flow: 2.0 mL/min.

Method W

| time (min) | Vol % water (incl. 0.1% TFA) | Vol % ACN |
|---|---|---|
| 0.00 | 98 | 2 |
| 1.50 | 0 | 100 |
| 1.80 | 0 | 100 |

Analytical column: Sunfire C18 (Waters) 3.5 µm; 4.6 × 30 mm; column temperature: 60° C.; flow: 2.5 mL/min.

Method X

| time (min) | Vol % water (incl. 0.1% NH$_4$OH) | Vol % ACN |
|---|---|---|
| 0.00 | 95 | 5 |
| 0.80 | 0.1 | 99.9 |
| 0.90 | 0.1 | 99.9 |

Analytical column: BEH C18 (Waters) 1.7 µm; 2.1 × 30 mm; column temperature: 60° C.; flow: 1.5 mL/min.

Method Y

| time (min) | Vol % water (incl. 0.1% NH$_4$OH) | Vol % ACN |
|---|---|---|
| 0.00 | 98 | 2 |
| 1.50 | 0.0 | 100.0 |
| 1.80 | 0.0 | 100.0 |

Analytical column: XBridge C18 (Waters) 3.5 µm; 4.6 × 30 mm; column temperature: 60° C.; flow: 2.5 mL/min.

Method Z

| time (min) | Vol % water (incl. 0.1% TFA) | Vol % ACN |
|---|---|---|
| 0.00 | 98 | 2 |
| 1.50 | 0 | 100 |
| 1.80 | 0 | 100 |

Analytical column: Sunfire C18 (Waters) 3.5 µm; 4.6 × 30 mm; column temperature: 60° C.; flow: 2.5 mL/min.

Method AA

| time (min) | Vol % water (incl. 0.1% TFA) | Vol % ACN (incl. 0.08% TFA) |
|---|---|---|
| 0.00 | 95 | 5 |
| 0.75 | 0 | 100 |
| 0.85 | 0 | 100 |

Analytical column: Sunfire C18 (Waters) 2.5 µm; 2.1 × 50 mm; column temperature: 60° C.; flow: 1.5 mL/min.

Method AB

| time (min) | Vol % water (incl. 0.1% TFA) | Vol % ACN (incl. 0.08% TFA) |
|---|---|---|
| 0.00 | 98 | 2 |
| 1.20 | 0 | 100 |
| 1.40 | 0 | 100 |

Analytical column: XBridge C18 (Waters) 2.5 µm; 3.0 × 30 mm; column temperature: 60° C.; flow: 2.0 mL/min.

| Methode AC | | |
|---|---|---|
| time (min) | Vol % water (incl. 0.1% NH₄OH) | Vol % ACN |
| 0.00 | 98 | 2 |
| 1.20 | 0 | 100 |
| 1.40 | 0 | 100 |

Analytical column: XBridge C18 (Waters) 2.5 μm; 3.0 × 30 mm;
column temperature: 60° C.; flow: 2.0 mL/min.

| Methode AD | | |
|---|---|---|
| time (min) | Vol % water (incl. 0.1% TFA) | Vol % ACN |
| 0.00 | 98 | 2 |
| 1.20 | 0 | 100 |
| 1.40 | 0 | 100 |

Analytical column: Sunfire C18 (Waters) 2.5 μm; 3.0 × 30 mm;
column temperature: 60° C.; flow: 2.0 mL/min.

The invention claimed is:
1. A compound of formula I

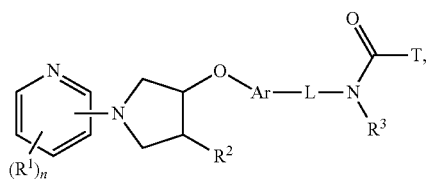

(I)

wherein
Ar is selected from a group consisting of phenylene and pyridinylene, which are each optionally substituted with one or two substituents independently selected from F, Cl, —O—CH₃ and CH₃;
$R^1$ independently of one another are selected from a group consisting of halogen, CN, $C_{1-6}$-alkyl, $C_{3-6}$-cycloalkyl, —O—($C_{1-6}$-alkyl), —S—($C_{1-3}$-alkyl), —O—($C_{3-6}$-cycloalkyl), —O—($C_{5-6}$-cycloalkenyl), —O—$(CH_2)_{1-2}$-($C_{3-6}$-cycloalkyl), —O—($C_{1-3}$-alkyl)-aryl, —O—$CH_2$—($C_{2-4}$-alkenyl), —O—$CH_2$—($C_{2-4}$-alkinyl), —O—$CH_2$-tetrahydrofuranyl, —O—$CH_2$-heteroaryl, —O-heterocyclyl, —O-aryl, —O-heteroaryl, —(C=O)—NH-aryl, —$NR^{N1}R^{N2}$,

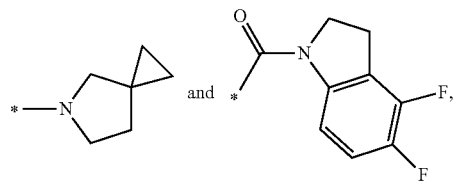

wherein $R^{N1}$ is H or $C_{1-3}$-alkyl, and
$R^{N2}$ is H, $C_{1-4}$-alkyl, $C_{3-6}$-cycloalkyl, —$CH_2$—($C_{3-6}$-cycloalkyl), heterocyclyl or —$CH_2$-heterocyclyl,
or wherein $R^{N1}$ and $R^{N2}$ are connected and together with the N-atom to which they are attached form an azetidinyl, pyrrolidinyl, piperidinyl, 2,5-dihydro-1H-pyrrolyl, morpholinyl or [1,4]oxazepanyl ring, wherein each of said rings is optionally substituted with one or two F, OH, $C_{1-3}$-alkyl, —O—$C_{1-3}$-alkyl or —($C_{1-3}$-alkyl)-O—($C_{1-3}$-alkyl), said substituents being the same or different,
wherein heterocyclyl is tetrahydrofuranyl or tetrahydropyranyl,
wherein heteroaryl is selected from the group consisting of pyridinyl, pyrimidinyl, pyridazinyl and pyrazinyl,
wherein aryl is selected from the group consisting of phenyl, indanyl and naphthyl,
wherein each alkyl is linear or branched and is optionally substituted with 1 to 6 F or with one —OH or —O—($C_{1-3}$-alkyl),
wherein each cycloalkyl is optionally substituted with 1 to 4 F or with one CN, OH, $CH_3$, $CF_3$ or —$SO_2$—($C_{1-3}$-alkyl), and wherein each aryl or heteroaryl is optionally substituted with one or two substituents independently selected from F, Cl, $C_{1-3}$alkyl or —O—$CH_3$;
n is 1, 2 or 3;
$R^2$ is H, F, Cl, CN or —O—($C_{1-3}$-alkyl);
$R^3$ is H or $C_{1-3}$-alkyl;
L is straight-chain $C_{1-3}$-alkylene, which is optionally substituted with one or two $C_{1-3}$-alkyl groups; and
T is selected from a group consisting of H,
linear or branched $C_{1-6}$-alkyl which is optionally substituted with one to six F, with one CN, OH, —O—$CH_3$ or —O—C(=O)—$CH_3$, or with a heteroaryl group preferably selected from the group consisting of: oxazolyl, thiazolyl, pyrrolyl, isoxazolyl, pyrimidinyl and pyrazinyl,
wherein each of said heteroaryl groups is optionally substituted with one or two substituents, which are independently of each other selected from the group consisting of $C_{1-3}$-alkyl, —($C_{1-3}$-alkyl)-O—$CH_3$ and —NH—(C=O)—($C_{1-3}$-alkyl);
($C_{2-4}$-alkenyl)-($C_{3-7}$-cycloalkyl);
$C_{3-6}$-cycloalkyl which is optionally substituted with one or two F, CN, $CH_3$, $CF_3$, OH, —O—($C_{1-3}$-alkyl), $NH_2$, —NH—(C=O)$CH_3$, —C(=O)—$NH_2$, —C(=O)—NH($C_{1-3}$-alkyl) or —C(=O)—N($C_{1-3}$-alkyl)₂, wherein the substituents are identical of different;
—O—($C_{1-2}$-alkyl);
tetrahydrofuranyl;
—$NR^4R^5$, wherein $R^4$ is H or $C_{1-3}$-alkyl, and $R^5$ is H, $C_{1-3}$-alkyl, —($C_{1-3}$-alkyl)-O—$CH_3$ or a 5-membered heteroaryl group containing 1 to 3 heteroatoms selected independently from O, S, N and NH, wherein said heteroaryl group is optionally substituted with $C_{1-3}$-alkyl; or wherein $R^4$ and $R^5$ are connected and together with the N to which they are attached form an azetidinyl, pyrrolidinyl, piperidinyl, piperazinyl or morpholinyl ring that is optionally substituted with one or two $C_{1-3}$-alkyl or with one —NH—(C=O)—$CH_3$;
a 5-membered heteroaryl group containing one to three heteroatoms selected independently from O, S, N and NH, which is optionally substituted with one or two substituents selected independently from the group consisting of:
Cl, $C_{1-3}$-alkyl, —NH—C(=O)—($C_{1-3}$-alkyl)-O—$CH_3$, $NH_2$, —NH—C(=O)—$C_{1-3}$-alkyl, —NH—C(=O)—$CH_2OH$, —NH—C(=O)—$CH_2O$—C(=O)$CH_3$, —NH—C(=O)—$CH_2OCH_2$-Ph and —O—($C_{1-2}$-alkyl), wherein each alkyl group is optionally substituted with one to three F or with one OH;

a 6-membered heteroaryl group containing 1 or 2 N, which is optionally substituted with F, CN, —CH₃, —C(=O)—NH—(CH₃) or —NH—C(=O)—(CH₃); and phenyl optionally substituted with F, Cl, CN or —OCH₃;

or a tautomer or salt thereof.

2. A compound according to claim 1, wherein
Ar is

wherein the before mentioned group is optionally monosubstituted with F;
R² is H, F or —O—CH₃; and
R³ is H.

3. A compound according to claim 1, wherein
L is —CH(CH₃)—; and
R² is H.

4. A compound according to claim 1, wherein R¹ is selected from a group consisting of:
F, Cl, CN, C₁₋₄-alkyl, C₃₋₅-cycloalkyl, —O—(C₁₋₅-alkyl), —O—(C₃₋₆-cycloalkyl), —O-cyclopentenyl, —O-tetrahydrofuranyl, —O—CH₂—(C₂₋₄-alkenyl), —O—CH₂—(C₃₋₄-cycloalkyl), —O—CH₂-phenyl, —NR^{N1}R^{N2} and

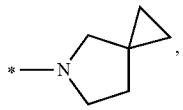

wherein R^{N1} is H or C₁₋₂-alkyl, and
R^{N2} is C₁₋₄-alkyl or —CH₂—(C₃₋₆-cycloalkyl),
or wherein R^{N1} and R^{N2} are connected and together with the N-atom to which they are attached form an azetidinyl, pyrrolidinyl, piperidinyl or morpholin ring, wherein each of said rings is optionally substitued with one or two F or CH₃,
wherein each alkyl is linear or branched and is optionally substituted with 1 to 3 F or with one —O—CH₃ or OH and
wherein each C₃₋₆-cycloalkyl is optionally substituted with 1 to 2 F or with one CN or CH₃,
wherein each phenyl is optionally substituted with one F.

5. A compound according to claim 1, wherein R¹ is selected from a group consisting of:
CF₃, C₁₋₄-alkyl, C₃₋₅-cycloalkyl, —O—(C₁₋₅-alkyl), —O—(C₃₋₆-cycloalkyl), —NH—(C₁₋₃-alkyl), —N(C₁₋₃-alkyl)₂,

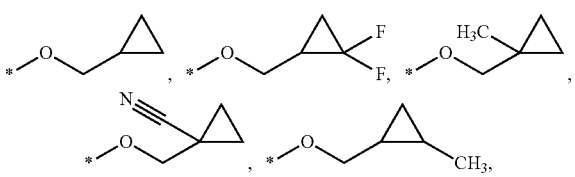

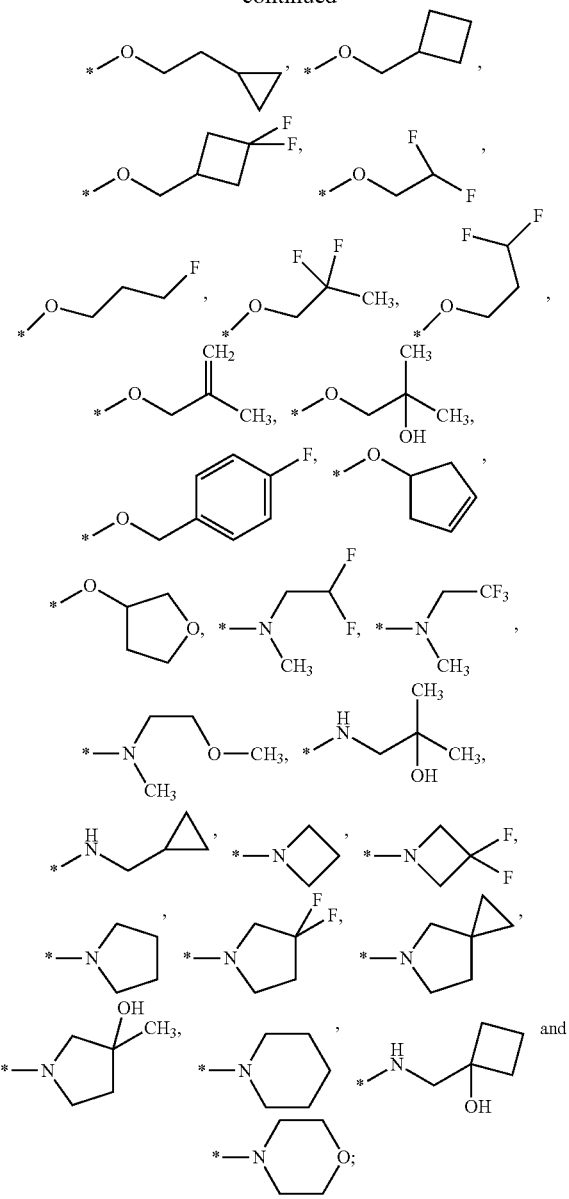

or, if n is 2, the second R¹ group is selected from the group consisting of F, Cl, CN, CH₃, —O—CH₃ and —O—CH₂—CHF₂;
or, if n is 3, the third R¹ group is F.

6. A compound according to claim 1, wherein T is selected from a group consisting of:
linear or branched C₁₋₃-alkyl which is optionally substituted with one to six F, or with one CN, OH or —O—CH₃, or with a heteroaryl group preferably selected from the group consisting of: thiazolyl, isoxazolyl and pyrimidinyl,
wherein each of said heteroaryl groups is optionally substituted with one or two substituents, which are independently of each other selected from the group consisting of C₁₋₃-alkyl, —(C₁₋₃-alkyl)-O—CH₃ and —NH—(C=O)—CH₃;
C₃₋₆-cycloalkyl which is optionally substituted with one or two F or one CN, CH₃ or CF₃;
—O—CH₃;

tetrahydrofuranyl;

—NR⁴R⁵, wherein R⁴ is H or C₁₋₃-alkyl, and R⁵ is H, C₁₋₃-alkyl, —(C₁₋₃-alkyl)-O—CH₃ or isoxazolyl; or wherein R⁴ and R⁵ are connected and together with the N to which they are attached form an azetidinyl, pyrrolidinyl, piperidinyl or morpholinyl ring that is optionally substituted with one or two C₁₋₃-alkyl or with one —NH—C(=O)—CH₃;

a furanyl, thiazolyl, oxazolyl, pyrazolyl, isoxazolyl, isothiazolyl or thiadiazolyl group, each of which is optionally substituted with one or two substituents selected independently from the group consisting of: Cl, C₁₋₃-alkyl, —NH—C(=O)—(C₁₋₃-alkyl)-O—CH₃, NH₂ and —NH—C(=O)—C₁₋₃-alkyl; and a pyridinyl, pyridazinyl or pyrimidinyl group, each of which is optionally substituted with F, CN, —CH₃, —C(=O)—NH—(OH₃) or —NH—C(=O)—(OH₃).

7. A compound according to claim 1, wherein T is selected from a group consisting of:

—CH₃, —CHF₂, —CF₃, —CH₂CH₃, —OCH₃, —NH(CH₃), —N(CH₃)₂, —NH(CH₂CH₃), —N(CH₃)(CH₂CH₃),

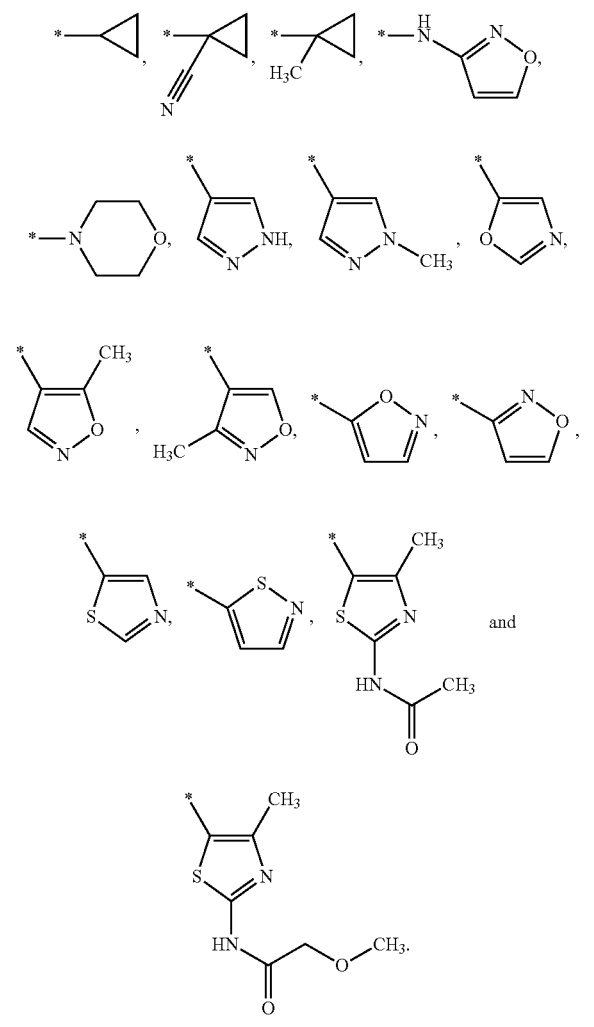

8. A compound according to claim 1 having the formula

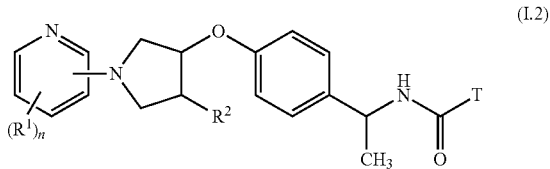

(I.2)

wherein n is 1, 2 or 3;

R¹ is independently selected from a group consisting of F, Cl, CN, CF₃, C₁₋₄-alkyl, C₃₋₅-cycloalkyl, —O—(C₁₋₅-alkyl), —O—(C₃₋₆-cycloalkyl), —NH—(C₁₋₃-alkyl), —N(C₁₋₃-alkyl)₂,

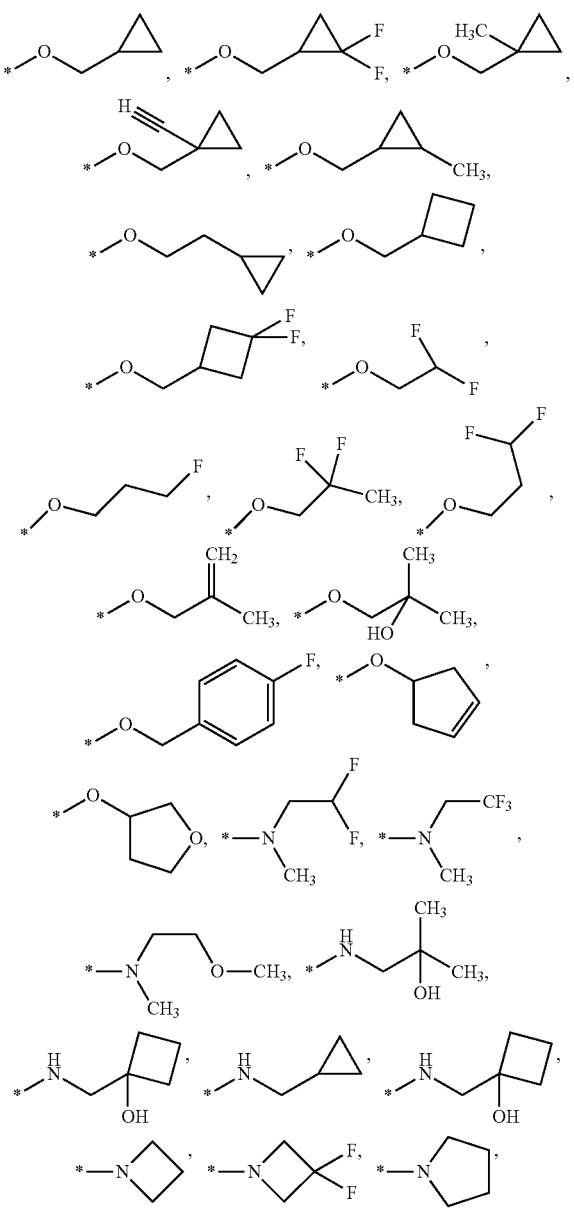

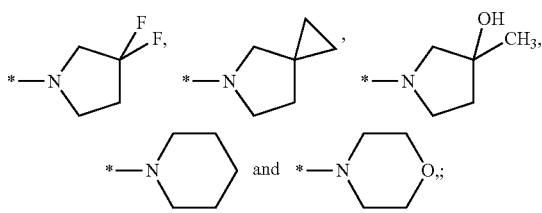

R² is H, F or —O—CH₃; and

T is selected from a group consisting of:

linear or branched $C_{1-3}$-alkyl which is optionally substituted with one to six F, or with one CN, OH or —O—CH₃, or with a heteroaryl group preferably selected from the group consisting of: thiazolyl, isoxazolyl and pyrimidinyl, wherein each of said heteroaryl groups is optionally substituted with one or two substituents, which are independently of each other selected from the group consisting of $C_{1-3}$-alkyl, —($C_{1-3}$-alkyl)-O—OH₃ and —NH—(C=O)—CH₃;

$C_{3-6}$-cycloalkyl which is optionally substituted with one or two F or one CN, CH₃ or CF₃;

—O—CH₃;

tetrahydrofuranyl;

—NR⁴R⁵, wherein R⁴ is H or $C_{1-3}$-alkyl, and R⁵ is H, $C_{1-3}$-alkyl, —($C_{1-3}$-alkyl)-O—CH₃ or isoxazolyl; or wherein R⁴ and R⁵ are connected and together with the N to which they are attached form an azetidinyl, pyrrolidinyl, piperidinyl or morpholinyl ring that is optionally substituted with one or two $C_{1-3}$-alkyl or with one —NH—(C=O)—CH₃;

a furanyl, thiazolyl, oxazolyl, pyrazolyl, isoxazolyl, isothiazolyl or thiadiazolyl group, each of which is optionally substituted with one or two substituents selected independently from the group consisting of: Cl, $C_{1-3}$-alkyl, —NH—C(=O)—($C_{1-3}$-alkyl)-O—CH₃, NH₂ and —NH—C(=O)—$C_{1-3}$-alkyl; and a pyridinyl, pyridazinyl or pyrimidinyl group, each of which is optionally substituted with F, CN, —CH₃, —C(=O)—NH—(OH₃) or —NH—C(=O)—(CH₃);

or a salt thereof.

9. A compound according to claim 1 having the formula

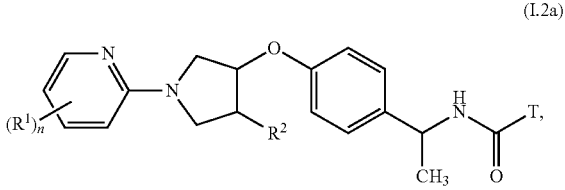

(I.2a)

wherein n is 1, 2 or 3;

R¹ is selected from a group consisting of CF₃, $C_{1-4}$-alkyl, $C_{3-5}$-cycloalkyl, —O—($C_{1-5}$-alkyl), —O—($C_{3-6}$-cycloalkyl),

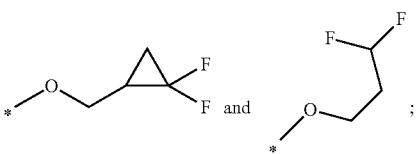

or, if n is 2, the second R¹ group is selected from the group consisting of F and Cl;

or, if n is 3, the third R¹ group is F;

R² is H, F or —O—CH₃; and

T is selected from a group consisting of:

linear or branched $C_{1-3}$-alkyl which is optionally substituted with one to three F, cyclopropyl which is optionally substituted with one CN or CH₃;

—O—CH₃;

—NR⁴R⁵, wherein R⁴ is H or $C_{1-3}$-alkyl, and R⁵ is $C_{1-3}$-alkyl; and a thiazolyl, oxazolyl, pyrazolyl, isoxazolyl or isothiazolyl group, each of which is optionally substituted with one or two substituents selected independently from the group consisting of: CH₃, —NH—C(=O)—CH₂—O—CH₃ and —NH—C(=O)—CH₃;

or a pharmaceutically acceptable salt thereof.

10. A compound according to claim 1 having the formula

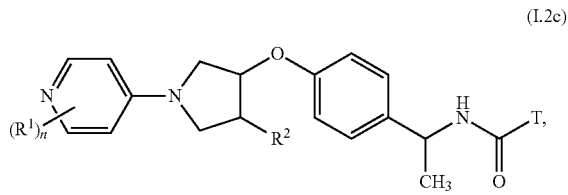

(I.2c)

wherein n is 1, 2 or 3;

R¹ is selected from a group consisting of —O—($C_{1-5}$-alkyl), —O—($C_{3-6}$-cycloalkyl), —NH—($C_{1-3}$-alkyl), —N($C_{1-3}$-alkyl)₂,

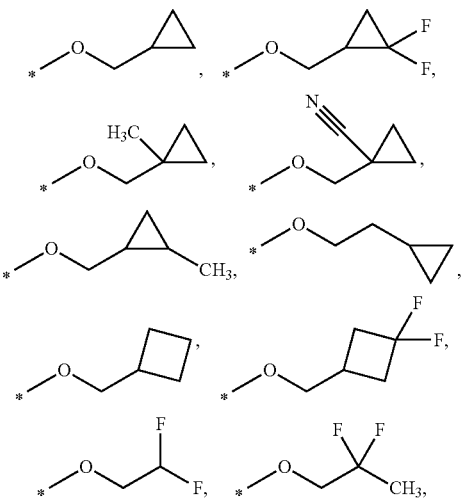

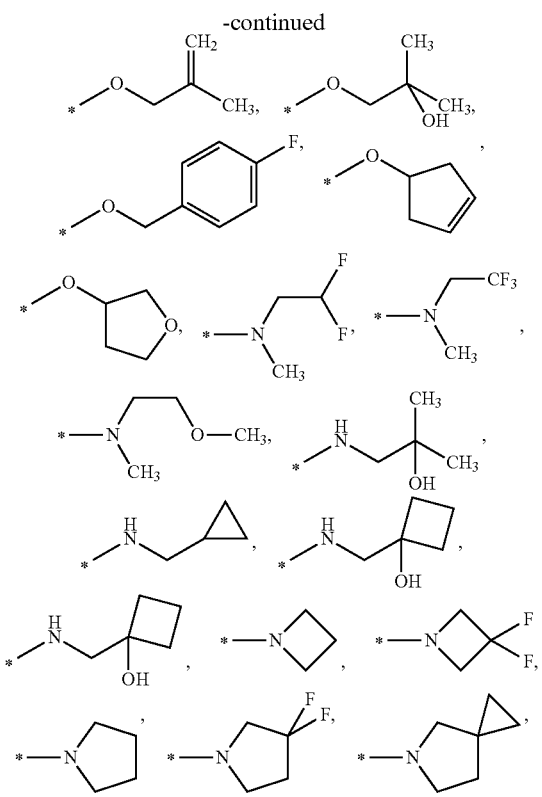
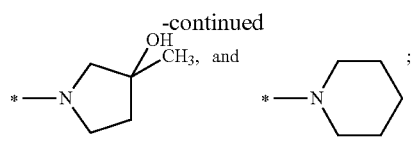

or, if n is 2, the second R$^1$ group is selected from the group consisting of F, Cl, CH$_3$ and —O—CH$_3$;

or, if n is 3, the third R$^1$ group is F;

R$^2$ is H, F or —O—CH$_3$; and

T is selected from a group consisting of:

linear or branched C$_{1-3}$-alkyl which is optionally substituted with one to three F, cyclopropyl which is optionally substituted with one CN or CH$_3$;

—O—CH$_3$;

—NR$^4$R$^5$, wherein R$^4$ is H or C$_{1-3}$-alkyl, and R$^5$ is C$_{1-3}$-alkyl; and a thiazolyl, oxazolyl, pyrazolyl, isoxazolyl or isothiazolyl group, each of which is optionally substituted with one or two substituents selected independently from the group consisting of: CH$_3$, —NH—C(=O)—CH$_2$—O—CH$_3$ and —NH—C(=O)—CH$_3$;

or a pharmaceutically acceptable salt thereof.

11. A compound according to claim 1 selected from the group consisting of:

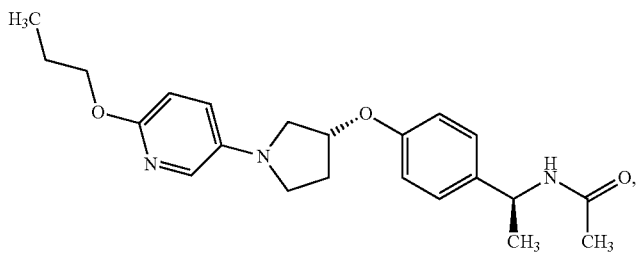

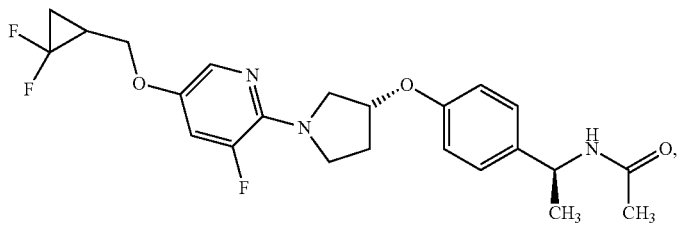

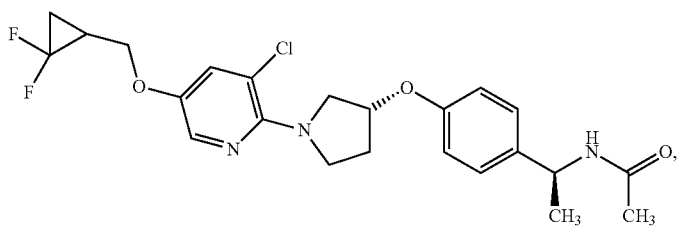

-continued
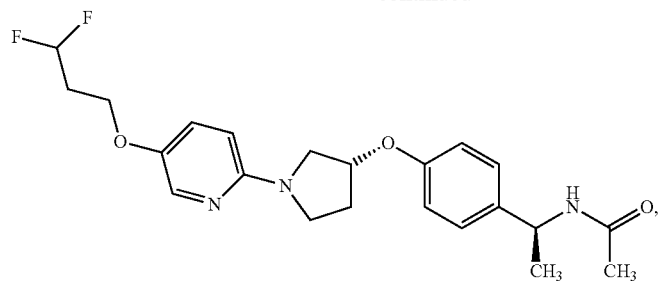
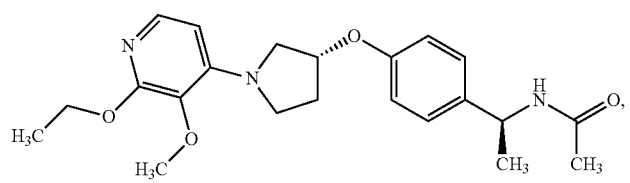
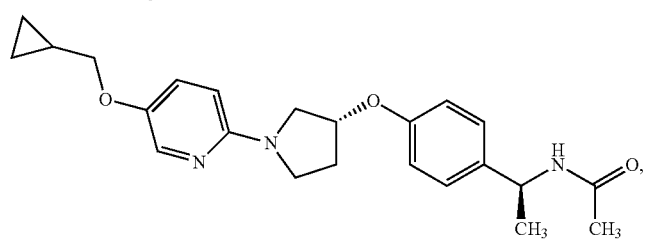
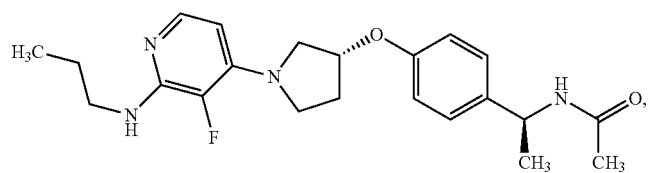
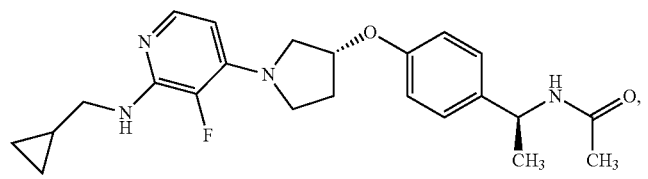
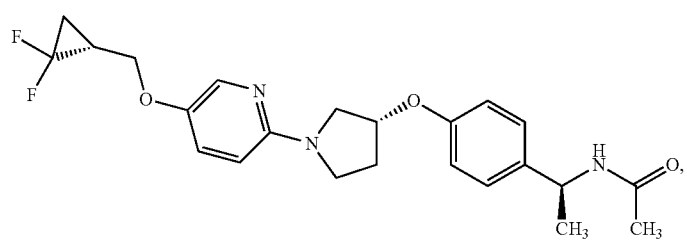
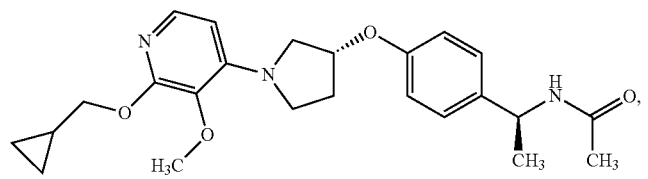
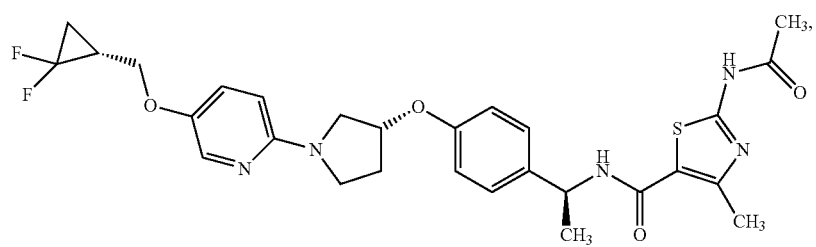

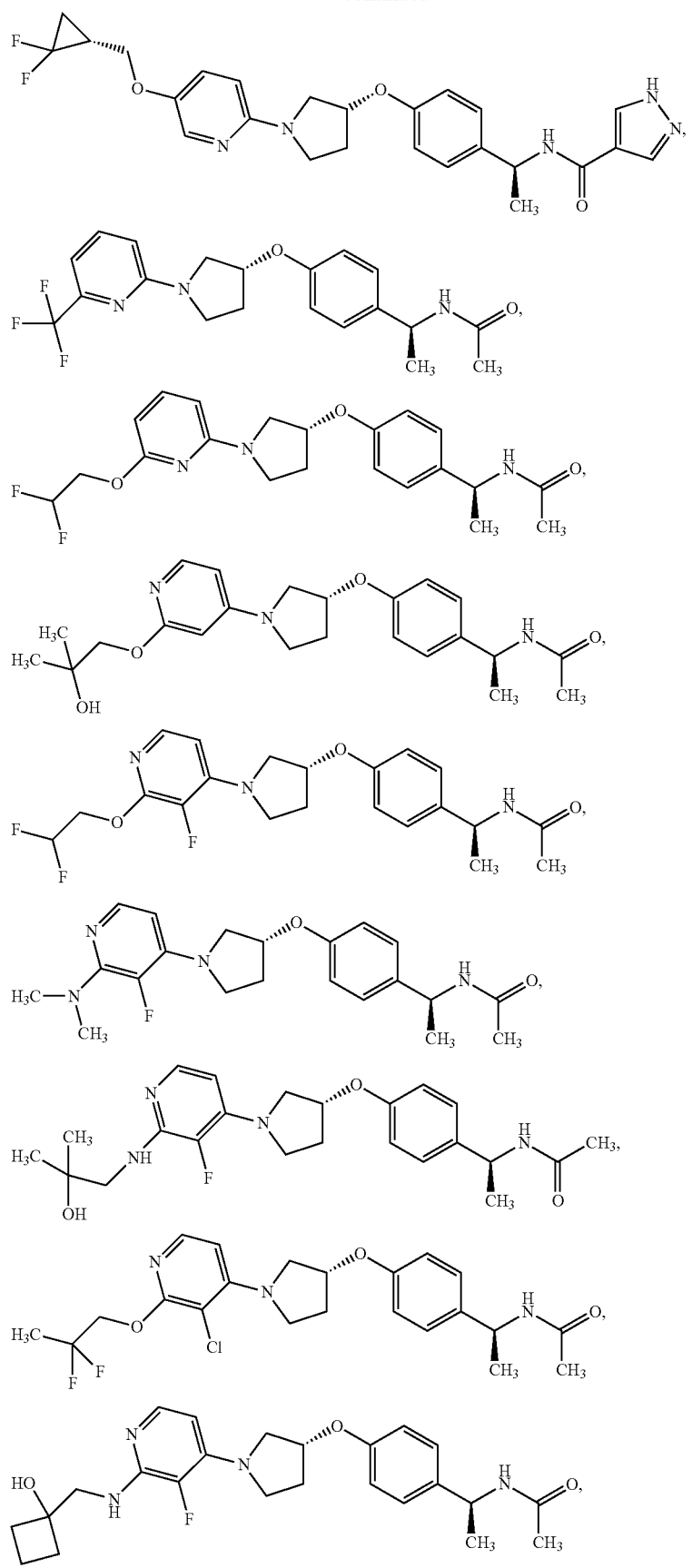

-continued

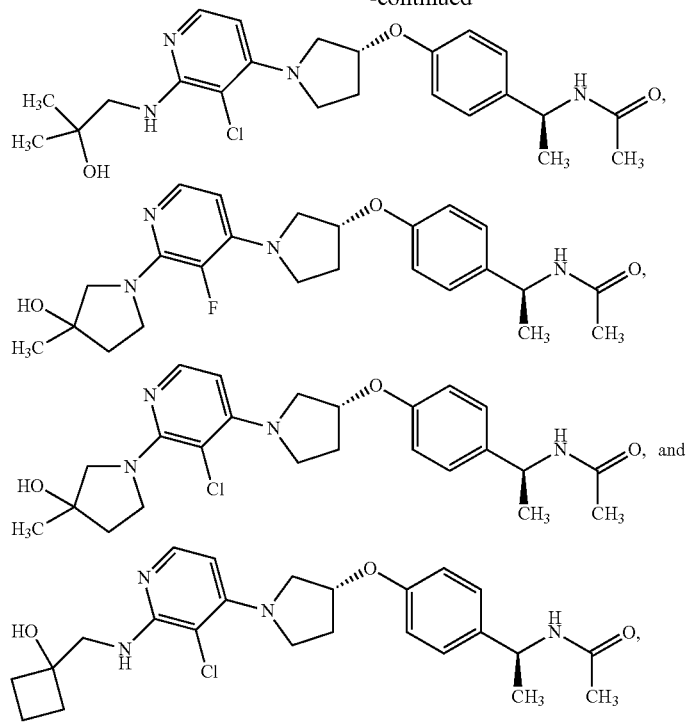

or a pharmaceutically acceptable salt thereof.

12. A pharmaceutically acceptable salt of a compound according to any of claims 1 to 11.

13. A method for treating obesity or type-2 diabetes which comprises administering to a host suffering from one of said conditions a compound according to claim 1 or a pharmaceutically acceptable salt thereof.

14. A pharmaceutical composition comprising a compound according to claim 1, or a pharmaceutically acceptable salt thereof, together with one or more inert carriers and/or diluents.

* * * * *